US012529114B2

(12) United States Patent
Eloit et al.

(10) Patent No.: US 12,529,114 B2
(45) Date of Patent: Jan. 20, 2026

(54) ORTHOBUNYAVIRUS IN HUMAN ENCEPHALITIS AND ITS DIAGNOSTIC AND THERAPEUTIC APPLICATIONS

(71) Applicants: INSTITUT PASTEUR, Paris (FR); ASSISTANCE PUBLIQUE—HOPITAUX DE PARIS, Paris (FR); INSERM (Institut National de la Sante et de la Recherche Medicale), Paris (FR); SORBONNE UNIVERSITE, Paris (FR); INSTITUT DU CERVEAU ET DE LA MOELLE EPINIERE—ICM, Paris (FR); ECOLE NATIONALE VETERINAIRE DE MAISONS ALFORT, Maisons Alfort (FR); CENTRE NATIONAL DE LA RECHERCHE SCIENTIFIQUE—CNRS, Paris (FR)

(72) Inventors: Marc Eloit, Paris (FR); Philippe Perot, Paris (FR); Danielle Seilhean, Paris (FR); Charles Duyckaerts, Saint Mande (FR); Delphine Chretien, Saint Denis (FR)

(73) Assignees: INSTITUT PASTEUR, Paris (FR); ASSISTANCE PUBLIQUE—HOPITAUX DE PARIS, Paris (FR); INSERM (Institut National de la Sante et de la Recherche Medicale), Paris (FR); SORBONNE UNIVERSITE, Paris (FR); INSTITUT DU CERVEAU ET DE LA MOELLE EPINIERE—ICM, Paris (FR); ECOLE NATIONALE VETERINAIRE DE MAISONS ALFORT, Maisons Alfort (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 968 days.

(21) Appl. No.: 17/606,554

(22) PCT Filed: May 7, 2020

(86) PCT No.: PCT/EP2020/062775
§ 371 (c)(1),
(2) Date: Oct. 26, 2021

(87) PCT Pub. No.: WO2020/229315
PCT Pub. Date: Nov. 19, 2020

(65) Prior Publication Data

US 2023/0151439 A1 May 18, 2023

(30) Foreign Application Priority Data

May 10, 2019 (EP) .................................... 19305604

(51) Int. Cl.
*C12Q 1/70* (2006.01)
*C12Q 1/6841* (2018.01)
*C12Q 1/6844* (2018.01)

(52) U.S. Cl.
CPC ........... *C12Q 1/701* (2013.01); *C12Q 1/6841* (2013.01); *C12Q 1/6844* (2013.01)

(58) Field of Classification Search
None
See application file for complete search history.

(56) References Cited

PUBLICATIONS

Perot et al. (GenBank QHA34089.1 deposited in Nov. 2018).*
Perot et al. (GenBank Accession No. MK204830 in Nov. 2018).*
Perot et al., HAL Open Science, Jun. 2020, p. 1701-1708).*
Yadav et al., A mini-review of Bunyaviruses recorded in India, The Indian journal of medical research, 2017, 145(5), 601-610.
Yadav et al., Molecular characterization of Umbre virus (Bunyaviridae), Virology Journal, Oct. 2008, 5, 115.
Sukhralia et al., From dengue to Zika: the wide spread of mosquito-borne arboviruses, Eur J Clin Microbiol Infect Dis. Jan. 2019, 38(1), 3-14.
Hellert et al., Orthobunyavirus spike architecture and recognition by neutralizing antibodies, Nat Commun, Feb. 20, 2019, 10(1), 879.

* cited by examiner

*Primary Examiner* — Agnieszka Boesen
(74) *Attorney, Agent, or Firm* — Arrigo, Lee, Guttman & Mouta-Bellum LLP

(57) ABSTRACT

The invention relates to methods of diagnosis or detection of Moissiacense virus, a novel orthobunyavirus causing human encephalitis, comprising determining the presence of at least one nucleic acid or protein of said virus or antibodies thereto, in a biological sample. The invention also relates to the various diagnostic agents derived from the viral nucleic acids or proteins, in articular nucleic acid primers and probes, antigens and antibodies, and their use for the diagnosis of Moissiacense virus infection and associated disease, in particular encephalitis. The invention further relates to antigens derived from the viral proteins as vaccine for the prevention of Moissiacense virus infection and associated disease, in particular encephalitis.

20 Claims, 11 Drawing Sheets

Specification includes a Sequence Listing.

A

Figure 4:
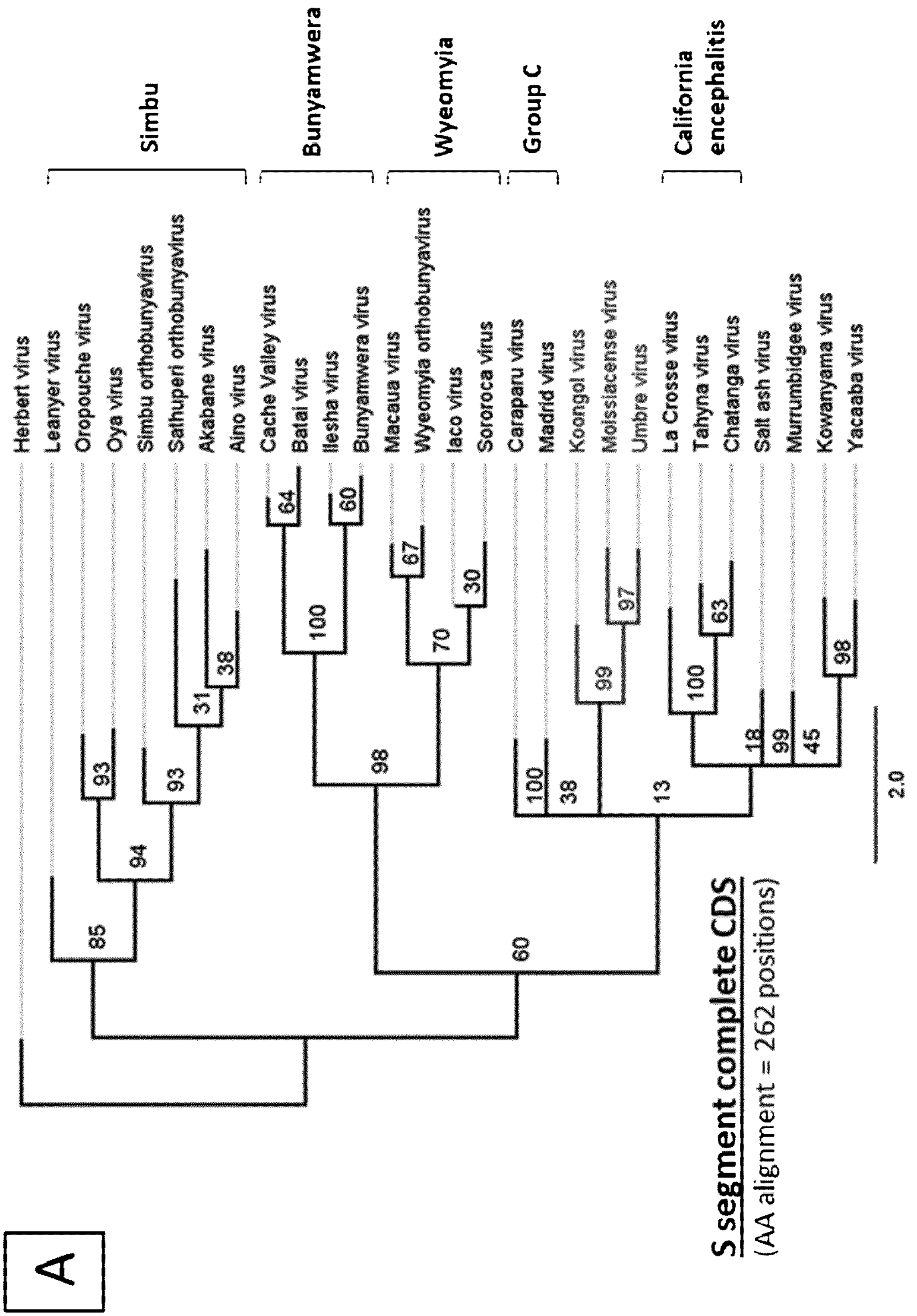

Continuation of Figure 4
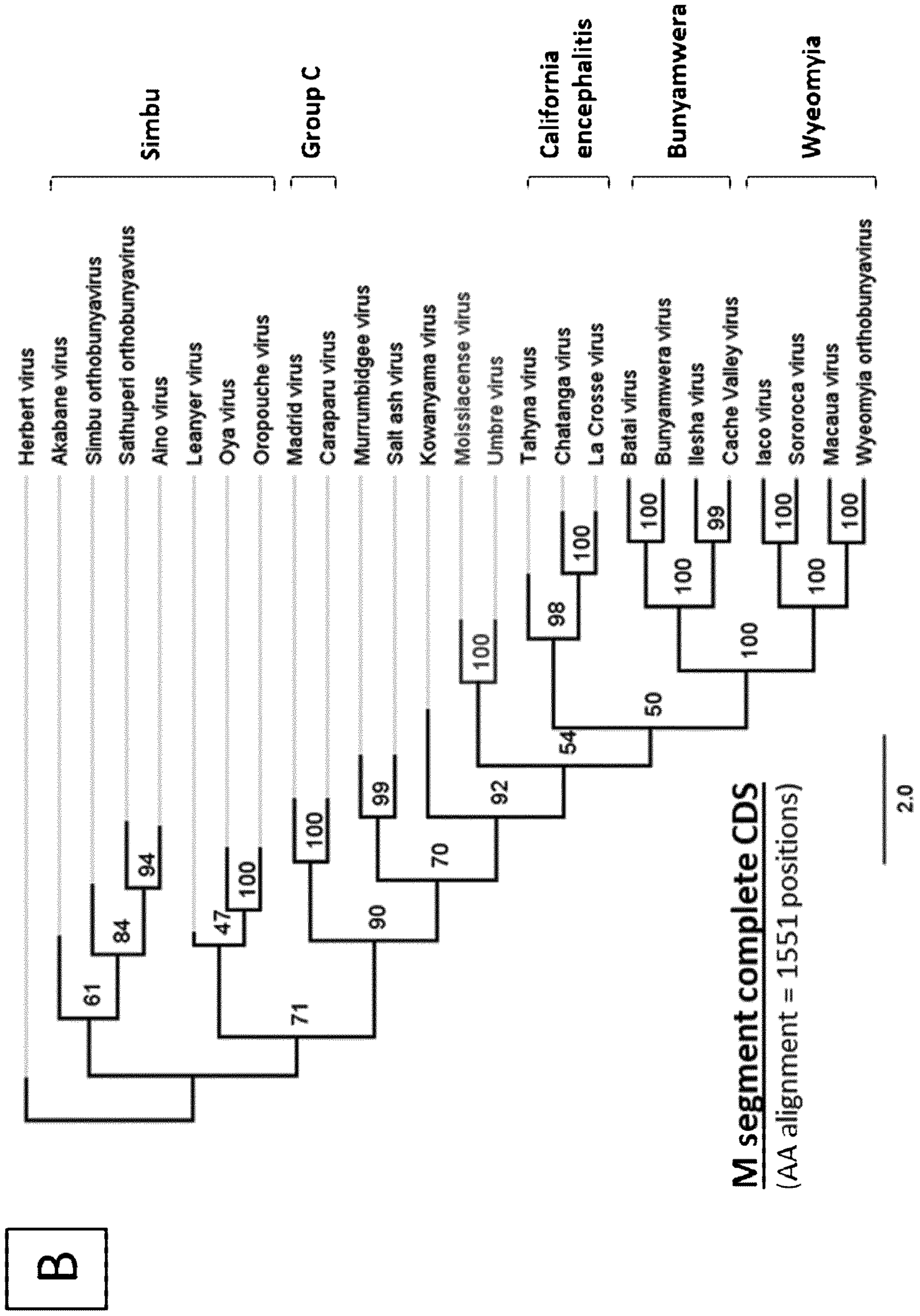

Continuation of Figure 4
C
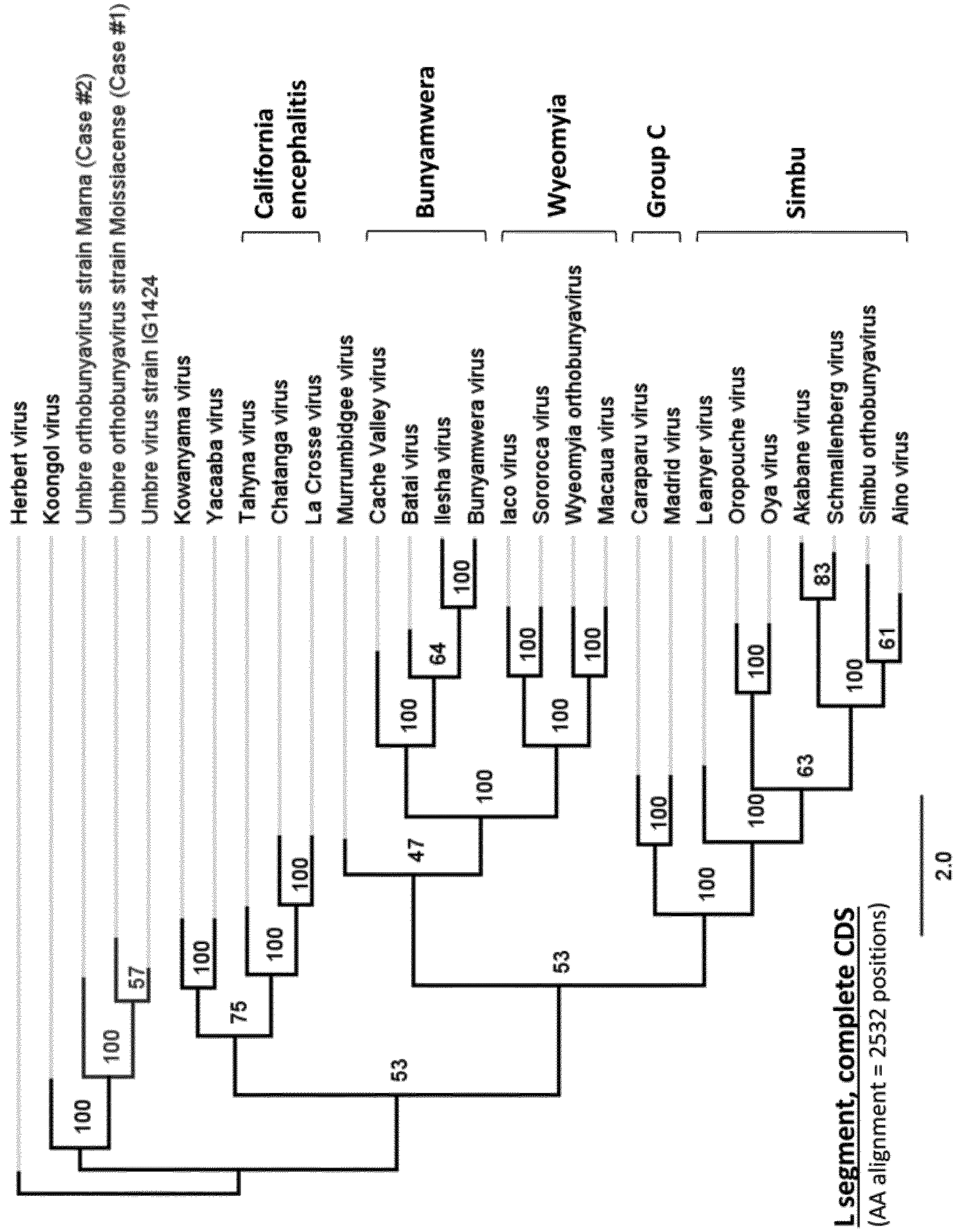

Continuation of Figure 4
D
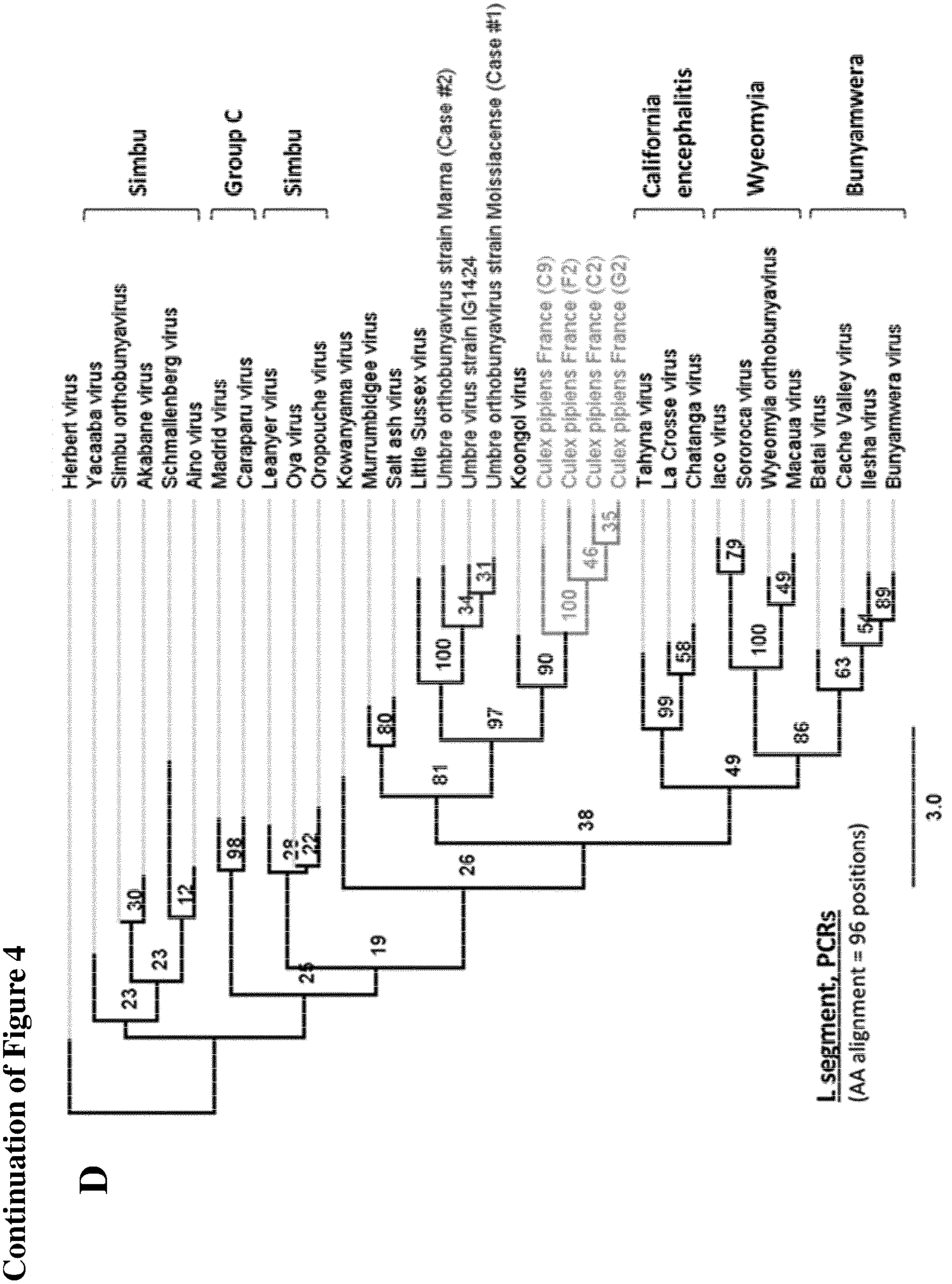

Figure 6

Forward primer

```
Cal/Bwa group         GCAAAUGGAUUUGAUCCUGAUGCAG (SEQ ID NO: 74)
Moissiacense virus    AGAAGUACUUAUAACCCAGCAGAUG (SEQ ID NO: 76)
                      **  * *** * * *  * ** **

Bunyamwera group      CUGCUAACACCAGCAGUACUUUUGAC (SEQ ID NO: 78)
Moissiacense virus    AGGAUGUUAGUAGAAGUACUUAUAAC (SEQ ID NO: 80)
                      ** * *** **  *       * *

Moissiacense virus    GAUUCUAAGCUCACAUACGAGGAUACACA (SEQ ID NO: 84)
Wyeomyia group        AUGUCUGAAAUUGUAUUUGAUGAUAUUGG (SEQ ID NO: 82)
                      ***   * ** ***  **  *    ****

Moissiacense virus    CCGAGACAGUUGAAGUUACAUU (SEQ ID NO: 88)
Oropouche             GGCCCAUGGUUGACCUUACUUU (SEQ ID NO: 86)
                      ***** **     **    *
```

Continuation of Figure 6

Reverse primer

```
Cal/Bwa group        UUGUUCCUGUUUGCUGGAAAAUGAU (SEQ ID NO: 75)
Moissiacense virus   CGCUGAGCCUGUCCAAUUCUAUGGU (SEQ ID NO: 77)
                     *** ***** * * ******    *

Bunyamwera group     UGGAGGGUAAGACCAUCGUCAGGAACUG (SEQ ID NO: 79)
Moissiacense virus   UGAAGAGUUAGCUCAUCGUCCGCAACCU (SEQ ID NO: 81)
                       *  *  *  **       * *   **

Moissiacense virus   GCUGAGCCUGUCCAAUUCUAU (SEQ ID NO: 85)
Wyeomyia group       UAUUUCGAUUCCCCGGAAAGU (SEQ ID NO: 83)
                     ** ***** **  *******

Moissiacense virus   GCCAAUGGGAACAUUUUAAAU (SEQ ID NO: 89)
Oropouche            ACCAAAGGGAAGAAAGUGAAU (SEQ ID NO: 87)
                     *    *     * *** *
```

P value (t test) = 0.0176

P value (F test) = 0.3414

| How big is the difference? | |
|---|---|
| Mean ± SEM of column A | 0.1869 ± 0.02598, n=300 |
| Mean ± SEM of column B | 0.2768 ± 0.02745, n=300 |
| Difference between means | 0.08998 ± 0.03779 |

P value (t test) = 0.0006

P value (F test) < 0.0001

| How big is the difference? | |
|---|---|
| Mean ± SEM of column A | 0.2079 ± 0.05054, n=34 |
| Mean ± SEM of column B | 0.6435 ± 0.1104, n=34 |
| Difference between means | 0.4355 ± 0.1214 |

SEQUENCE LISTING

<160> NUMBER OF SEQ ID NOS: 97

<210> SEQ ID NO 1
<211> LENGTH: 772
<212> TYPE: DNA
<213> ORGANISM: Moissiacense virus (Umbre orthobunyavirus strain Moissiacense)
<220> FEATURE:
<221> NAME/KEY: CDS
<222> LOCATION: (59)..(772)

<400> SEQUENCE: 1
aatcattata tctaaatttg ctaaacgcag aactgggtag cactagcatt tatccagg 58 atg gct gat tct aag ctc aca tac gag gat aca cag gat gtt agt aga 106
Met Ala Asp Ser Lys Leu Thr Tyr Glu Asp Thr Gln Asp Val Ser Arg
1 5 10 15 agt act tat aac cca gca gat gaa tac gat acg ttt gtg ggt gtc tac 154
Ser Thr Tyr Asn Pro Ala Asp Glu Tyr Asp Thr Phe Val Gly Val Tyr
20 25 30 aga gaa ttt ctc aca att gat aac att aga atc ttc ttc atc aac gct 202
Arg Glu Phe Leu Thr Ile Asp Asn Ile Arg Ile Phe Phe Ile Asn Ala
35 40 45 cca aag gcc aaa act gcg atg gct aaa ctc aag acc gag aca gtt gaa 250
Pro Lys Ala Lys Thr Ala Met Ala Lys Leu Lys Thr Glu Thr Val Glu
50 55 60 gtt aca ttt gga aca ctc gtt gtc aag ctg gtt aat aac cat aga att 298
Val Thr Phe Gly Thr Leu Val Val Lys Leu Val Asn Asn His Arg Ile
65 70 75 80 gga cag gct cag cgt gag gtt gcg gac gat gag cta act ctt cac cga 346
Gly Gln Ala Gln Arg Glu Val Ala Asp Asp Glu Leu Thr Leu His Arg
85 90 95 ctt tct ggc tac att gca aag tac act ctt cac cta tac aaa aat gca 394
Leu Ser Gly Tyr Ile Ala Lys Tyr Thr Leu His Leu Tyr Lys Asn Ala
100 105 110 aaa aaa gca gga gag aga gaa gca ata ata acc aag atc gtt aat cca 442
Lys Lys Ala Gly Glu Arg Glu Ala Ile Ile Thr Lys Ile Val Asn Pro
115 120 125 att tct gcc aaa atg ggc ttc caa tgg agt gtt ggg ccg gaa att tat 490
Ile Ser Ala Lys Met Gly Phe Gln Trp Ser Val Gly Pro Glu Ile Tyr
130 135 140 ctc tca acg ctg cca gga acc gaa atg ttt cta gat aca ttt aaa atg 538
Leu Ser Thr Leu Pro Gly Thr Glu Met Phe Leu Asp Thr Phe Lys Met
145 150 155 160 ttc cca ttg gca ttc atc ttg tta aga gtt aaa aga gga gag atc aag 586
Phe Pro Leu Ala Phe Ile Leu Leu Arg Val Lys Arg Gly Glu Ile Lys
165 170 175 gtg gaa atg gca aaa aaa gca atg cgg cag aag tat ggc gac aaa gat 634
Val Glu Met Ala Lys Lys Ala Met Arg Gln Lys Tyr Gly Asp Lys Asp
180 185 190 gcc agt gaa tgg ctg cag gag gac att gag act gta aaa ggg gca ata 682
Ala Ser Glu Trp Leu Gln Glu Asp Ile Glu Thr Val Lys Gly Ala Ile
195 200 205 aaa aca gtt gaa aag ctc aag cca acg ctg aca gga ttg gct gct tca 730
Lys Thr Val Glu Lys Leu Lys Pro Thr Leu Thr Gly Leu Ala Ala Ser
210 215 220 atg act gct ttc ctg caa caa ctt ggt atc aac act aag taa 772
Met Thr Ala Phe Leu Gln Gln Leu Gly Ile Asn Thr Lys
225 230 235

<210> SEQ ID NO 2
<211> LENGTH: 237

<212> TYPE: PRT
<213> ORGANISM: Moissiacense virus (Umbre orthobunyavirus strain Moissiacense)

<400> SEQUENCE: 2

```
Met Ala Asp Ser Lys Leu Thr Tyr Glu Asp Thr Gln Asp Val Ser Arg
1               5                   10                  15

Ser Thr Tyr Asn Pro Ala Asp Glu Tyr Asp Thr Phe Val Gly Val Tyr
            20                  25                  30

Arg Glu Phe Leu Thr Ile Asp Asn Ile Arg Ile Phe Phe Ile Asn Ala
        35                  40                  45

Pro Lys Ala Lys Thr Ala Met Ala Lys Leu Lys Thr Glu Thr Val Glu
    50                  55                  60

Val Thr Phe Gly Thr Leu Val Val Lys Leu Val Asn Asn His Arg Ile
65                  70                  75                  80

Gly Gln Ala Gln Arg Glu Val Ala Asp Asp Glu Leu Thr Leu His Arg
                85                  90                  95

Leu Ser Gly Tyr Ile Ala Lys Tyr Thr Leu His Leu Tyr Lys Asn Ala
            100                 105                 110

Lys Lys Ala Gly Glu Arg Glu Ala Ile Ile Thr Lys Ile Val Asn Pro
        115                 120                 125

Ile Ser Ala Lys Met Gly Phe Gln Trp Ser Val Gly Pro Glu Ile Tyr
    130                 135                 140

Leu Ser Thr Leu Pro Gly Thr Glu Met Phe Leu Asp Thr Phe Lys Met
145                 150                 155                 160

Phe Pro Leu Ala Phe Ile Leu Leu Arg Val Lys Arg Gly Glu Ile Lys
                165                 170                 175

Val Glu Met Ala Lys Lys Ala Met Arg Gln Lys Tyr Gly Asp Lys Asp
            180                 185                 190

Ala Ser Glu Trp Leu Gln Glu Asp Ile Glu Thr Val Lys Gly Ala Ile
        195                 200                 205

Lys Thr Val Glu Lys Leu Lys Pro Thr Leu Thr Gly Leu Ala Ala Ser
    210                 215                 220

Met Thr Ala Phe Leu Gln Gln Leu Gly Ile Asn Thr Lys
225                 230                 235
```

<210> SEQ ID NO 3
<211> LENGTH: 4395
<212> TYPE: DNA
<213> ORGANISM: Moissiacense virus (Umbre orthobunyavirus strain Moissiacense)
<220> FEATURE:
<221> NAME/KEY: CDS
<222> LOCATION: (1)..(4395)
<220> FEATURE:
<221> NAME/KEY: variation
<222> LOCATION: (4114)..(4116)
<223> OTHER INFORMATION: nnn is att or aaa

<400> SEQUENCE: 3

```
atg gtg atc ttt gca ttg ttg tcg ata cta tta gtt ggc ttc agc aat       48
Met Val Ile Phe Ala Leu Leu Ser Ile Leu Leu Val Gly Phe Ser Asn
1               5                   10                  15

caa gcg act att cga tgt ttc tct ggc ggc tcc aaa atc atg gaa aaa       96
Gln Ala Thr Ile Arg Cys Phe Ser Gly Gly Ser Lys Ile Met Glu Lys
            20                  25                  30

aca tcg aat gtc tca ttg agt gaa cta tgc tta aag gat gat gtc agc      144
Thr Ser Asn Val Ser Leu Ser Glu Leu Cys Leu Lys Asp Asp Val Ser
        35                  40                  45
```

-continued

```
cag cta aaa att ata gtt gac cac aca aaa aat gat tca gga tta ttt      192
Gln Leu Lys Ile Ile Val Asp His Thr Lys Asn Asp Ser Gly Leu Phe
    50                  55                  60

tca act gcc agc gtc tgg aga aaa tgg ata gtc tca gat tgg acc aca      240
Ser Thr Ala Ser Val Trp Arg Lys Trp Ile Val Ser Asp Trp Thr Thr
65                  70                  75                  80

tgt aac cct aaa aaa atg gct tta gga aca ata tct gtt ata gat atc      288
Cys Asn Pro Lys Lys Met Ala Leu Gly Thr Ile Ser Val Ile Asp Ile
                85                  90                  95

gat aaa aac ttt atc tta aaa agc tcc agc tat ata tgc aat aaa gag      336
Asp Lys Asn Phe Ile Leu Lys Ser Ser Ser Tyr Ile Cys Asn Lys Glu
            100                 105                 110

tgc acg ata aca gtg gat aaa gaa aga gcc caa gtt ctg cta caa tca      384
Cys Thr Ile Thr Val Asp Lys Glu Arg Ala Gln Val Leu Leu Gln Ser
        115                 120                 125

gat ggc tta aat cac ttt gaa gtt tct gga acc act ttg agt tct gga      432
Asp Gly Leu Asn His Phe Glu Val Ser Gly Thr Thr Leu Ser Ser Gly
    130                 135                 140

tgg ttt aaa tcg aca gcc act gtt acc tta gat caa acc tgc gag cat      480
Trp Phe Lys Ser Thr Ala Thr Val Thr Leu Asp Gln Thr Cys Glu His
145                 150                 155                 160

gtt aaa gtg tct tgt ggc cag aaa tca atg caa ttc cat gcc tgc ttc      528
Val Lys Val Ser Cys Gly Gln Lys Ser Met Gln Phe His Ala Cys Phe
                165                 170                 175

aag aat cat atg tca tgc att aga ttc ttg cat aga agt ata atg cca      576
Lys Asn His Met Ser Cys Ile Arg Phe Leu His Arg Ser Ile Met Pro
            180                 185                 190

gca agc ttt gca gtt tct atc tgc cag aat ata gag ttg ata tta atg      624
Ala Ser Phe Ala Val Ser Ile Cys Gln Asn Ile Glu Leu Ile Leu Met
        195                 200                 205

aca acg ttt aca ttg att ata ttc ttg cta cta agc att tta aca aaa      672
Thr Thr Phe Thr Leu Ile Ile Phe Leu Leu Leu Ser Ile Leu Thr Lys
    210                 215                 220

aca tac ata tgc tat att ttg cta ccc ata ttc ata ccc ttt gcg tac      720
Thr Tyr Ile Cys Tyr Ile Leu Leu Pro Ile Phe Ile Pro Phe Ala Tyr
225                 230                 235                 240

gca tat gga ttt gtt tat gat aaa aca tgc aag aag tgc tca tta tgt      768
Ala Tyr Gly Phe Val Tyr Asp Lys Thr Cys Lys Lys Cys Ser Leu Cys
                245                 250                 255

gga tta gct tac cac cct ttc aca aag tgt ggg ata cat tgt gtt tgt      816
Gly Leu Ala Tyr His Pro Phe Thr Lys Cys Gly Ile His Cys Val Cys
            260                 265                 270

gga tgt aga ttt gaa aat tca gat gca atg aaa acc cac aga gaa aaa      864
Gly Cys Arg Phe Glu Asn Ser Asp Ala Met Lys Thr His Arg Glu Lys
        275                 280                 285

ggg aaa tgt ccg gga ttc aag tca atg aga att gct agg gta ctg tgt      912
Gly Lys Cys Pro Gly Phe Lys Ser Met Arg Ile Ala Arg Val Leu Cys
    290                 295                 300

aag gct aaa ggt tca gct ttc gct tta tct gta cta ttg gcc acg ttg      960
Lys Ala Lys Gly Ser Ala Phe Ala Leu Ser Val Leu Leu Ala Thr Leu
305                 310                 315                 320

gca ttg ggc ttc ttg acg cct gta caa ggg cta gtt cta gat aag acc     1008
Ala Leu Gly Phe Leu Thr Pro Val Gln Gly Leu Val Leu Asp Lys Thr
                325                 330                 335

caa att aac tac aca gaa gat caa tta cca gaa tca ttt cag acg atg     1056
Gln Ile Asn Tyr Thr Glu Asp Gln Leu Pro Glu Ser Phe Gln Thr Met
            340                 345                 350

caa tca aca ata tct ata ttc aaa ttt gca aca gtc atg aat gca ggt     1104
Gln Ser Thr Ile Ser Ile Phe Lys Phe Ala Thr Val Met Asn Ala Gly
        355                 360                 365
```

-continued

```
tgg act tac tgc atg ttc ctt gtt aca ttg gct tta tat atc ata cac      1152
Trp Thr Tyr Cys Met Phe Leu Val Thr Leu Ala Leu Tyr Ile Ile His
    370                 375                 380

aag aag tat gct cac aga tta ctg agc tat tat gta ata cat tgc agg      1200
Lys Lys Tyr Ala His Arg Leu Leu Ser Tyr Tyr Val Ile His Cys Arg
385                 390                 395                 400

gag tgt gac atg ctt cat gac aaa agt ggg ctt aag tat aat ggt gat      1248
Glu Cys Asp Met Leu His Asp Lys Ser Gly Leu Lys Tyr Asn Gly Asp
                405                 410                 415

ttt act aac aaa tgc ggt ttt tgt aca tgt ggg caa gtt gaa gat gca      1296
Phe Thr Asn Lys Cys Gly Phe Cys Thr Cys Gly Gln Val Glu Asp Ala
            420                 425                 430

atg ggg ctg acc gtc cat caa ata cga aat cat tgc tct gcc aac tat      1344
Met Gly Leu Thr Val His Gln Ile Arg Asn His Cys Ser Ala Asn Tyr
        435                 440                 445

aga act aag atg gtg ctg aac tgg atg atc gtg cta tta tta gct act      1392
Arg Thr Lys Met Val Leu Asn Trp Met Ile Val Leu Leu Leu Ala Thr
    450                 455                 460

cta atc aaa gat agc ata atg ctg act gcc gca gca ggg aca gaa ttt      1440
Leu Ile Lys Asp Ser Ile Met Leu Thr Ala Ala Ala Gly Thr Glu Phe
465                 470                 475                 480

gaa aca tgc atc aag aaa gta gaa atg aca ccg gaa tgc aca gga cct      1488
Glu Thr Cys Ile Lys Lys Val Glu Met Thr Pro Glu Cys Thr Gly Pro
                485                 490                 495

ttc atg gaa gtt gga atc tgt gat cac cag cag aag agc cta aga tac      1536
Phe Met Glu Val Gly Ile Cys Asp His Gln Gln Lys Ser Leu Arg Tyr
            500                 505                 510

cat gag ata gct aat atg tta ttg ggt aaa ggg aca atc tca aaa tta      1584
His Glu Ile Ala Asn Met Leu Leu Gly Lys Gly Thr Ile Ser Lys Leu
        515                 520                 525

gat gtg gat att ata gat gca ttg cct gac agg ata gct gga gac ctc      1632
Asp Val Asp Ile Ile Asp Ala Leu Pro Asp Arg Ile Ala Gly Asp Leu
    530                 535                 540

cag ata ata cag tca agc agt gat ttc cac cat caa cag atg ctg gaa      1680
Gln Ile Ile Gln Ser Ser Ser Asp Phe His His Gln Gln Met Leu Glu
545                 550                 555                 560

tat gtg ttt cta ttg cgt cat tgt gat tat tac tca agt ttt gtt tcg      1728
Tyr Val Phe Leu Leu Arg His Cys Asp Tyr Tyr Ser Ser Phe Val Ser
                565                 570                 575

gat aac agc tac tca caa atc ttg tgg caa aca gca gca aag tta aat      1776
Asp Asn Ser Tyr Ser Gln Ile Leu Trp Gln Thr Ala Ala Lys Leu Asn
            580                 585                 590

gaa acc aac ctt tgc aaa cat gag aat tca aag aaa tcc tgc aag tgc      1824
Glu Thr Asn Leu Cys Lys His Glu Asn Ser Lys Lys Ser Cys Lys Cys
        595                 600                 605

tta aaa tca aat gca aat tgt gga gag tca gaa gac atc aac ata gca      1872
Leu Lys Ser Asn Ala Asn Cys Gly Glu Ser Glu Asp Ile Asn Ile Ala
    610                 615                 620

gca cag gca tac tac aaa aat aag gaa tct gag cta gga caa gat cta      1920
Ala Gln Ala Tyr Tyr Lys Asn Lys Glu Ser Glu Leu Gly Gln Asp Leu
625                 630                 635                 640

aca acc ata atg tac ata ctc aaa aaa atg att cca gga tca ggt tat      1968
Thr Thr Ile Met Tyr Ile Leu Lys Lys Met Ile Pro Gly Ser Gly Tyr
                645                 650                 655

agt tat ctg cta aat gca gcc aag cac aac aaa tta gaa ttg ttc aaa      2016
Ser Tyr Leu Leu Asn Ala Ala Lys His Asn Lys Leu Glu Leu Phe Lys
            660                 665                 670

gct tac atg act aat att tcc tca aaa tat tca aat aac aaa aaa tta      2064
Ala Tyr Met Thr Asn Ile Ser Ser Lys Tyr Ser Asn Asn Lys Lys Leu
```

-continued

```
        675                 680                 685

aaa gat ttc atg gcg ata ata aat gct ata cta gca aat ctg tca gct      2112
Lys Asp Phe Met Ala Ile Ile Asn Ala Ile Leu Ala Asn Leu Ser Ala
    690                 695                 700

ctc tca cat agt agt gaa gaa tca atc tca caa tac aaa cag att gat      2160
Leu Ser His Ser Ser Glu Glu Ser Ile Ser Gln Tyr Lys Gln Ile Asp
705                 710                 715                 720

ttt tct tcc cta gta ggc gaa aca aca gac atg ctc gaa gca aat ttt      2208
Phe Ser Ser Leu Val Gly Glu Thr Thr Asp Met Leu Glu Ala Asn Phe
                725                 730                 735

aat caa acg atc agt aca gac aag ata att tgt gaa aat cct aaa gta      2256
Asn Gln Thr Ile Ser Thr Asp Lys Ile Ile Cys Glu Asn Pro Lys Val
            740                 745                 750

atg att tgc att tca ccc agg aca aaa gtt tca tcc ggt gaa ttg tat      2304
Met Ile Cys Ile Ser Pro Arg Thr Lys Val Ser Ser Gly Glu Leu Tyr
        755                 760                 765

gtc tgc caa aga tca gga aag tac tac ata ata gat acc ggc aaa ttc      2352
Val Cys Gln Arg Ser Gly Lys Tyr Tyr Ile Ile Asp Thr Gly Lys Phe
    770                 775                 780

aag cta tat aaa tta att gac gca gac aat ttg tac tgt gca gca gat      2400
Lys Leu Tyr Lys Leu Ile Asp Ala Asp Asn Leu Tyr Cys Ala Ala Asp
785                 790                 795                 800

gct cag tgt agg tat gaa ttt aga att tta acc aca ggg gaa atg cag      2448
Ala Gln Cys Arg Tyr Glu Phe Arg Ile Leu Thr Thr Gly Glu Met Gln
                805                 810                 815

gca act ttt aaa gat aat tgc aaa gca tca gta cat gtt aac acc cca      2496
Ala Thr Phe Lys Asp Asn Cys Lys Ala Ser Val His Val Asn Thr Pro
            820                 825                 830

gga tac caa aat gaa gct ata act cat tgc aaa gtg ctc gcg aat ggt      2544
Gly Tyr Gln Asn Glu Ala Ile Thr His Cys Lys Val Leu Ala Asn Gly
        835                 840                 845

aaa tgt aag tat aat aat caa act tca ata gat ata aca ttg tgt gct      2592
Lys Cys Lys Tyr Asn Asn Gln Thr Ser Ile Asp Ile Thr Leu Cys Ala
    850                 855                 860

aac aac aga tat tat ccc gaa gca aaa ggc agg atc ttt gga gtt gat      2640
Asn Asn Arg Tyr Tyr Pro Glu Ala Lys Gly Arg Ile Phe Gly Val Asp
865                 870                 875                 880

cca gaa gat cta tgc ttt gat aag aca tgt act aaa caa cag act cca      2688
Pro Glu Asp Leu Cys Phe Asp Lys Thr Cys Thr Lys Gln Gln Thr Pro
                885                 890                 895

tac aac gaa gaa cta atc agt atg tgt gtt tgg gaa aat ccg aca ctt      2736
Tyr Asn Glu Glu Leu Ile Ser Met Cys Val Trp Glu Asn Pro Thr Leu
            900                 905                 910

agg cca atc aaa ccc aga act gag gtt tct atg act ttc caa gag tac      2784
Arg Pro Ile Lys Pro Arg Thr Glu Val Ser Met Thr Phe Gln Glu Tyr
        915                 920                 925

aaa gat cag tta tta aag aaa atc aac aca gac ctg gtg ctg cac aaa      2832
Lys Asp Gln Leu Leu Lys Lys Ile Asn Thr Asp Leu Val Leu His Lys
    930                 935                 940

ttt gtt aga aca caa aac tta cct tat ttc ata ccg caa ttc aag tat      2880
Phe Val Arg Thr Gln Asn Leu Pro Tyr Phe Ile Pro Gln Phe Lys Tyr
945                 950                 955                 960

ata act ata caa gga acg tca aca aca gac ggg att act tcc agt ttt      2928
Ile Thr Ile Gln Gly Thr Ser Thr Thr Asp Gly Ile Thr Ser Ser Phe
                965                 970                 975

ata ttc ttt gaa att cct gca ttg aca gga gca tct gct gga tac aaa      2976
Ile Phe Phe Glu Ile Pro Ala Leu Thr Gly Ala Ser Ala Gly Tyr Lys
            980                 985                 990

gtt ata aat agc gaa ggc caa gaa  ttg atg gac atg gta  gtt tat atc    3024
```

-continued

```
Val Ile Asn Ser Glu Gly Gln Glu  Leu Met Asp Met Val  Val Tyr Ile
        995                 1000                 1005

aaa aca  tca aag act agc gca  aag tac aag cgc gtg  tat tat aca      3069
Lys Thr  Ser Lys Thr Ser Ala  Lys Tyr Lys Arg Val  Tyr Tyr Thr
    1010                 1015                 1020

ggc ccc  act ata gct ata aat  aca aaa cat caa gag  cac tgc aca      3114
Gly Pro  Thr Ile Ala Ile Asn  Thr Lys His Gln Glu  His Cys Thr
    1025                 1030                 1035

ggg aca  tgt cct gaa aga ata  gaa cat gat gaa ggt  tgg gca aca      3159
Gly Thr  Cys Pro Glu Arg Ile  Glu His Asp Glu Gly  Trp Ala Thr
    1040                 1045                 1050

ttt tcg  aaa gaa aga acc agc  aat tgg ggc tgt gaa  gaa ttt ggt      3204
Phe Ser  Lys Glu Arg Thr Ser  Asn Trp Gly Cys Glu  Glu Phe Gly
    1055                 1060                 1065

tgt cta  gct gtt gag act ggt  tgt tta ttt ggg tca  tgc cag gat      3249
Cys Leu  Ala Val Glu Thr Gly  Cys Leu Phe Gly Ser  Cys Gln Asp
    1070                 1075                 1080

gta att  aga aga gaa ctt gat  gtt ttt tca aag ttg  gag gaa gat      3294
Val Ile  Arg Arg Glu Leu Asp  Val Phe Ser Lys Leu  Glu Glu Asp
    1085                 1090                 1095

aaa ata  ttg act gaa ctc tgt  ata aca tta agc cat  gac act tac      3339
Lys Ile  Leu Thr Glu Leu Cys  Ile Thr Leu Ser His  Asp Thr Tyr
    1100                 1105                 1110

tgc gtg  aca atc gat tct aca  aca cca aca atc aat  gat tac ttt      3384
Cys Val  Thr Ile Asp Ser Thr  Thr Pro Thr Ile Asn  Asp Tyr Phe
    1115                 1120                 1125

gaa atc  caa tac aaa aca gta  gat gta caa aca ttg  cca aag atg      3429
Glu Ile  Gln Tyr Lys Thr Val  Asp Val Gln Thr Leu  Pro Lys Met
    1130                 1135                 1140

ata gga  gtc act cat cat aag  cta ttg cga ggg cag  ata aac gaa      3474
Ile Gly  Val Thr His His Lys  Leu Leu Arg Gly Gln  Ile Asn Glu
    1145                 1150                 1155

tta gga  tca ttt ggc aaa ttt  tgt ggc aac ata caa  gta gtt ggt      3519
Leu Gly  Ser Phe Gly Lys Phe  Cys Gly Asn Ile Gln  Val Val Gly
    1160                 1165                 1170

aat caa  aca tat ggg cag gct  gca gta aag ttt gat  tac att tgc      3564
Asn Gln  Thr Tyr Gly Gln Ala  Ala Val Lys Phe Asp  Tyr Ile Cys
    1175                 1180                 1185

cat gct  gca caa aga aaa gat  gta gtt ata aga aag  tgc tta gaa      3609
His Ala  Ala Gln Arg Lys Asp  Val Val Ile Arg Lys  Cys Leu Glu
    1190                 1195                 1200

aat aat  tac caa agt tgt aag  cta ctg aca cat gac  aca gac ttg      3654
Asn Asn  Tyr Gln Ser Cys Lys  Leu Leu Thr His Asp  Thr Asp Leu
    1205                 1210                 1215

ata ctt  gaa gaa agt aag acc  agt gtt gaa gtc ata  aac aat aaa      3699
Ile Leu  Glu Glu Ser Lys Thr  Ser Val Glu Val Ile  Asn Asn Lys
    1220                 1225                 1230

agg att  aca gga caa ata gca  cta aag gtc ttg ttg  gga gac ttt      3744
Arg Ile  Thr Gly Gln Ile Ala  Leu Lys Val Leu Leu  Gly Asp Phe
    1235                 1240                 1245

aac tac  aag cag tat gct gca  aat gta gag gct gac  ata gaa gca      3789
Asn Tyr  Lys Gln Tyr Ala Ala  Asn Val Glu Ala Asp  Ile Glu Ala
    1250                 1255                 1260

aat tgc  gtt ggg tgt aca aat  tgt ata aag gga ata  aca tgt gaa      3834
Asn Cys  Val Gly Cys Thr Asn  Cys Ile Lys Gly Ile  Thr Cys Glu
    1265                 1270                 1275

ata aag  gtg aaa aca gaa att  gaa gca tca tgt aag  gta gag ccc      3879
Ile Lys  Val Lys Thr Glu Ile  Glu Ala Ser Cys Lys  Val Glu Pro
    1280                 1285                 1290
```

-continued

```
cca tgc  ccc tct tac aca agt  aga att ata ata aaa  cca ggt aga      3924
Pro Cys  Pro Ser Tyr Thr Ser  Arg Ile Ile Ile Lys  Pro Gly Arg
    1295                 1300                 1305

gac acc  cac aca tta ttg atg  aag tgt gac aaa aaa  ata acg act      3969
Asp Thr  His Thr Leu Leu Met  Lys Cys Asp Lys Lys  Ile Thr Thr
    1310                 1315                 1320

ggt gaa  cta gca ata aaa ata  tgt aat atg caa atc  cag gct cat      4014
Gly Glu  Leu Ala Ile Lys Ile  Cys Asn Met Gln Ile  Gln Ala His
    1325                 1330                 1335

ctt tca  aca ata gag agc aat  gac caa cta gaa ttg  tcg act ggg      4059
Leu Ser  Thr Ile Glu Ser Asn  Asp Gln Leu Glu Leu  Ser Thr Gly
    1340                 1345                 1350

gat caa  tca aca tat ata cat  gaa gaa gac cta agg  tgt tca acc      4104
Asp Gln  Ser Thr Tyr Ile His  Glu Glu Asp Leu Arg  Cys Ser Thr
    1355                 1360                 1365

tgg atc  tgc aww gtg aga gac  gaa ggg ata agc ttc  atc ttt aag      4149
Trp Ile  Cys Xaa Val Arg Asp  Glu Gly Ile Ser Phe  Ile Phe Lys
    1370                 1375                 1380

cca tta  aca gac tgg ctt gga  agc ttc aca aag ccg  ata ctt ata      4194
Pro Leu  Thr Asp Trp Leu Gly  Ser Phe Thr Lys Pro  Ile Leu Ile
    1385                 1390                 1395

gct ggc  tgt atg ata att gtt  gca att att ttg att  tat ata tta      4239
Ala Gly  Cys Met Ile Ile Val  Ala Ile Ile Leu Ile  Tyr Ile Leu
    1400                 1405                 1410

atg cct  atg tgt gct aga ctc  aga gat ttg tta aag  aaa aac gag      4284
Met Pro  Met Cys Ala Arg Leu  Arg Asp Leu Leu Lys  Lys Asn Glu
    1415                 1420                 1425

tat gaa  tat cta caa gat aca  aaa gtg att gta aag  ccc aag ggt      4329
Tyr Glu  Tyr Leu Gln Asp Thr  Lys Val Ile Val Lys  Pro Lys Gly
    1430                 1435                 1440

aca gca  agt tca ata ggc ttg  aga tcg aag aaa ata  aat atc caa      4374
Thr Ala  Ser Ser Ile Gly Leu  Arg Ser Lys Lys Ile  Asn Ile Gln
    1445                 1450                 1455

tcg tct  aag gct gtt gat taa                                       4395
Ser Ser  Lys Ala Val Asp
    1460
```

<210> SEQ ID NO 4
<211> LENGTH: 1464
<212> TYPE: PRT
<213> ORGANISM: Moissiacense virus (Umbre orthobunyavirus strain Moissiacense)
<220> FEATURE:
<221> NAME/KEY: misc_feature
<222> LOCATION: (1372)..(1372)
<223> OTHER INFORMATION: The 'Xaa' at location 1372 stands for Lys, Asn, or Ile.

<400> SEQUENCE: 4

```
Met Val Ile Phe Ala Leu Leu Ser Ile Leu Leu Val Gly Phe Ser Asn
1               5                   10                  15

Gln Ala Thr Ile Arg Cys Phe Ser Gly Gly Ser Lys Ile Met Glu Lys
            20                  25                  30

Thr Ser Asn Val Ser Leu Ser Glu Leu Cys Leu Lys Asp Asp Val Ser
        35                  40                  45

Gln Leu Lys Ile Ile Val Asp His Thr Lys Asn Asp Ser Gly Leu Phe
    50                  55                  60

Ser Thr Ala Ser Val Trp Arg Lys Trp Ile Val Ser Asp Trp Thr Thr
65                  70                  75                  80

Cys Asn Pro Lys Lys Met Ala Leu Gly Thr Ile Ser Val Ile Asp Ile
                85                  90                  95
```

```
Asp Lys Asn Phe Ile Leu Lys Ser Ser Ser Tyr Ile Cys Asn Lys Glu
            100                 105                 110

Cys Thr Ile Thr Val Asp Lys Glu Arg Ala Gln Val Leu Leu Gln Ser
        115                 120                 125

Asp Gly Leu Asn His Phe Glu Val Ser Gly Thr Thr Leu Ser Ser Gly
    130                 135                 140

Trp Phe Lys Ser Thr Ala Thr Val Thr Leu Asp Gln Thr Cys Glu His
145                 150                 155                 160

Val Lys Val Ser Cys Gly Gln Lys Ser Met Gln Phe His Ala Cys Phe
                165                 170                 175

Lys Asn His Met Ser Cys Ile Arg Phe Leu His Arg Ser Ile Met Pro
            180                 185                 190

Ala Ser Phe Ala Val Ser Ile Cys Gln Asn Ile Glu Leu Ile Leu Met
        195                 200                 205

Thr Thr Phe Thr Leu Ile Ile Phe Leu Leu Leu Ser Ile Leu Thr Lys
    210                 215                 220

Thr Tyr Ile Cys Tyr Ile Leu Leu Pro Ile Phe Ile Pro Phe Ala Tyr
225                 230                 235                 240

Ala Tyr Gly Phe Val Tyr Asp Lys Thr Cys Lys Lys Cys Ser Leu Cys
                245                 250                 255

Gly Leu Ala Tyr His Pro Phe Thr Lys Cys Gly Ile His Cys Val Cys
            260                 265                 270

Gly Cys Arg Phe Glu Asn Ser Asp Ala Met Lys Thr His Arg Glu Lys
        275                 280                 285

Gly Lys Cys Pro Gly Phe Lys Ser Met Arg Ile Ala Arg Val Leu Cys
    290                 295                 300

Lys Ala Lys Gly Ser Ala Phe Ala Leu Ser Val Leu Leu Ala Thr Leu
305                 310                 315                 320

Ala Leu Gly Phe Leu Thr Pro Val Gln Gly Leu Val Leu Asp Lys Thr
                325                 330                 335

Gln Ile Asn Tyr Thr Glu Asp Gln Leu Pro Glu Ser Phe Gln Thr Met
            340                 345                 350

Gln Ser Thr Ile Ser Ile Phe Lys Phe Ala Thr Val Met Asn Ala Gly
        355                 360                 365

Trp Thr Tyr Cys Met Phe Leu Val Thr Leu Ala Leu Tyr Ile Ile His
    370                 375                 380

Lys Lys Tyr Ala His Arg Leu Leu Ser Tyr Tyr Val Ile His Cys Arg
385                 390                 395                 400

Glu Cys Asp Met Leu His Asp Lys Ser Gly Leu Lys Tyr Asn Gly Asp
                405                 410                 415

Phe Thr Asn Lys Cys Gly Phe Cys Thr Cys Gly Gln Val Glu Asp Ala
            420                 425                 430

Met Gly Leu Thr Val His Gln Ile Arg Asn His Cys Ser Ala Asn Tyr
        435                 440                 445

Arg Thr Lys Met Val Leu Asn Trp Met Ile Val Leu Leu Leu Ala Thr
    450                 455                 460

Leu Ile Lys Asp Ser Ile Met Leu Thr Ala Ala Ala Gly Thr Glu Phe
465                 470                 475                 480

Glu Thr Cys Ile Lys Lys Val Glu Met Thr Pro Glu Cys Thr Gly Pro
                485                 490                 495

Phe Met Glu Val Gly Ile Cys Asp His Gln Gln Lys Ser Leu Arg Tyr
            500                 505                 510
```

```
His Glu Ile Ala Asn Met Leu Leu Gly Lys Gly Thr Ile Ser Lys Leu
        515                 520                 525

Asp Val Asp Ile Ile Asp Ala Leu Pro Asp Arg Ile Ala Gly Asp Leu
    530                 535                 540

Gln Ile Ile Gln Ser Ser Ser Asp Phe His His Gln Gln Met Leu Glu
545                 550                 555                 560

Tyr Val Phe Leu Leu Arg His Cys Asp Tyr Tyr Ser Ser Phe Val Ser
                565                 570                 575

Asp Asn Ser Tyr Ser Gln Ile Leu Trp Gln Thr Ala Ala Lys Leu Asn
            580                 585                 590

Glu Thr Asn Leu Cys Lys His Glu Asn Ser Lys Lys Ser Cys Lys Cys
        595                 600                 605

Leu Lys Ser Asn Ala Asn Cys Gly Glu Ser Glu Asp Ile Asn Ile Ala
    610                 615                 620

Ala Gln Ala Tyr Tyr Lys Asn Lys Glu Ser Glu Leu Gly Gln Asp Leu
625                 630                 635                 640

Thr Thr Ile Met Tyr Ile Leu Lys Lys Met Ile Pro Gly Ser Gly Tyr
                645                 650                 655

Ser Tyr Leu Leu Asn Ala Ala Lys His Asn Lys Leu Glu Leu Phe Lys
            660                 665                 670

Ala Tyr Met Thr Asn Ile Ser Ser Lys Tyr Ser Asn Asn Lys Lys Leu
        675                 680                 685

Lys Asp Phe Met Ala Ile Ile Asn Ala Ile Leu Ala Asn Leu Ser Ala
    690                 695                 700

Leu Ser His Ser Ser Glu Glu Ser Ile Ser Gln Tyr Lys Gln Ile Asp
705                 710                 715                 720

Phe Ser Ser Leu Val Gly Glu Thr Thr Asp Met Leu Glu Ala Asn Phe
                725                 730                 735

Asn Gln Thr Ile Ser Thr Asp Lys Ile Ile Cys Glu Asn Pro Lys Val
            740                 745                 750

Met Ile Cys Ile Ser Pro Arg Thr Lys Val Ser Ser Gly Glu Leu Tyr
        755                 760                 765

Val Cys Gln Arg Ser Gly Lys Tyr Tyr Ile Ile Asp Thr Gly Lys Phe
    770                 775                 780

Lys Leu Tyr Lys Leu Ile Asp Ala Asp Asn Leu Tyr Cys Ala Ala Asp
785                 790                 795                 800

Ala Gln Cys Arg Tyr Glu Phe Arg Ile Leu Thr Thr Gly Glu Met Gln
                805                 810                 815

Ala Thr Phe Lys Asp Asn Cys Lys Ala Ser Val His Val Asn Thr Pro
            820                 825                 830

Gly Tyr Gln Asn Glu Ala Ile Thr His Cys Lys Val Leu Ala Asn Gly
        835                 840                 845

Lys Cys Lys Tyr Asn Asn Gln Thr Ser Ile Asp Ile Thr Leu Cys Ala
    850                 855                 860

Asn Asn Arg Tyr Tyr Pro Glu Ala Lys Gly Arg Ile Phe Gly Val Asp
865                 870                 875                 880

Pro Glu Asp Leu Cys Phe Asp Lys Thr Cys Thr Lys Gln Gln Thr Pro
                885                 890                 895

Tyr Asn Glu Glu Leu Ile Ser Met Cys Val Trp Glu Asn Pro Thr Leu
            900                 905                 910

Arg Pro Ile Lys Pro Arg Thr Glu Val Ser Met Thr Phe Gln Glu Tyr
        915                 920                 925

Lys Asp Gln Leu Leu Lys Lys Ile Asn Thr Asp Leu Val Leu His Lys
```

-continued

```
    930                 935                 940

Phe Val Arg Thr Gln Asn Leu Pro Tyr Phe Ile Pro Gln Phe Lys Tyr
945                 950                 955                 960

Ile Thr Ile Gln Gly Thr Ser Thr Thr Asp Gly Ile Thr Ser Ser Phe
                965                 970                 975

Ile Phe Phe Glu Ile Pro Ala Leu Thr Gly Ala Ser Ala Gly Tyr Lys
            980                 985                 990

Val Ile Asn Ser Glu Gly Gln Glu  Leu Met Asp Met Val  Val Tyr Ile
        995                 1000                1005

Lys Thr  Ser Lys Thr Ser Ala  Lys Tyr Lys Arg Val  Tyr Tyr Thr
    1010                 1015                1020

Gly Pro  Thr Ile Ala Ile Asn  Thr Lys His Gln Glu  His Cys Thr
    1025                 1030                1035

Gly Thr  Cys Pro Glu Arg Ile  Glu His Asp Glu Gly  Trp Ala Thr
    1040                 1045                1050

Phe Ser  Lys Glu Arg Thr Ser  Asn Trp Gly Cys Glu  Glu Phe Gly
    1055                 1060                1065

Cys Leu  Ala Val Glu Thr Gly  Cys Leu Phe Gly Ser  Cys Gln Asp
    1070                 1075                1080

Val Ile  Arg Arg Glu Leu Asp  Val Phe Ser Lys Leu  Glu Glu Asp
    1085                 1090                1095

Lys Ile  Leu Thr Glu Leu Cys  Ile Thr Leu Ser His  Asp Thr Tyr
    1100                 1105                1110

Cys Val  Thr Ile Asp Ser Thr  Thr Pro Thr Ile Asn  Asp Tyr Phe
    1115                 1120                1125

Glu Ile  Gln Tyr Lys Thr Val  Asp Val Gln Thr Leu  Pro Lys Met
    1130                 1135                1140

Ile Gly  Val Thr His His Lys  Leu Leu Arg Gly Gln  Ile Asn Glu
    1145                 1150                1155

Leu Gly  Ser Phe Gly Lys Phe  Cys Gly Asn Ile Gln  Val Val Gly
    1160                 1165                1170

Asn Gln  Thr Tyr Gly Gln Ala  Ala Val Lys Phe Asp  Tyr Ile Cys
    1175                 1180                1185

His Ala  Ala Gln Arg Lys Asp  Val Val Ile Arg Lys  Cys Leu Glu
    1190                 1195                1200

Asn Asn  Tyr Gln Ser Cys Lys  Leu Leu Thr His Asp  Thr Asp Leu
    1205                 1210                1215

Ile Leu  Glu Glu Ser Lys Thr  Ser Val Glu Val Ile  Asn Asn Lys
    1220                 1225                1230

Arg Ile  Thr Gly Gln Ile Ala  Leu Lys Val Leu Leu  Gly Asp Phe
    1235                 1240                1245

Asn Tyr  Lys Gln Tyr Ala Ala  Asn Val Glu Ala Asp  Ile Glu Ala
    1250                 1255                1260

Asn Cys  Val Gly Cys Thr Asn  Cys Ile Lys Gly Ile  Thr Cys Glu
    1265                 1270                1275

Ile Lys  Val Lys Thr Glu Ile  Glu Ala Ser Cys Lys  Val Glu Pro
    1280                 1285                1290

Pro Cys  Pro Ser Tyr Thr Ser  Arg Ile Ile Ile Lys  Pro Gly Arg
    1295                 1300                1305

Asp Thr  His Thr Leu Leu Met  Lys Cys Asp Lys Lys  Ile Thr Thr
    1310                 1315                1320

Gly Glu  Leu Ala Ile Lys Ile  Cys Asn Met Gln Ile  Gln Ala His
    1325                 1330                1335
```

```
Leu Ser  Thr Ile Glu Ser Asn  Asp Gln Leu Glu Leu  Ser Thr Gly
    1340                 1345                 1350

Asp Gln  Ser Thr Tyr Ile His  Glu Glu Asp Leu Arg  Cys Ser Thr
    1355                 1360                 1365

Trp Ile  Cys Xaa Val Arg Asp  Glu Gly Ile Ser Phe  Ile Phe Lys
    1370                 1375                 1380

Pro Leu  Thr Asp Trp Leu Gly  Ser Phe Thr Lys Pro  Ile Leu Ile
    1385                 1390                 1395

Ala Gly  Cys Met Ile Ile Val  Ala Ile Ile Leu Ile  Tyr Ile Leu
    1400                 1405                 1410

Met Pro  Met Cys Ala Arg Leu  Arg Asp Leu Leu Lys  Lys Asn Glu
    1415                 1420                 1425

Tyr Glu  Tyr Leu Gln Asp Thr  Lys Val Ile Val Lys  Pro Lys Gly
    1430                 1435                 1440

Thr Ala  Ser Ser Ile Gly Leu  Arg Ser Lys Lys Ile  Asn Ile Gln
    1445                 1450                 1455

Ser Ser  Lys Ala Val Asp
    1460


<210> SEQ ID NO 5
<211> LENGTH: 6828
<212> TYPE: DNA
<213> ORGANISM: Moissiacense virus (Umbre orthobunyavirus strain
      Moissiasence)
<220> FEATURE:
<221> NAME/KEY: CDS
<222> LOCATION: (1)..(6828)

<400> SEQUENCE: 5

atg ctg gac caa gaa aat gag caa gct tta aat aga ctt gca gcc gca       48
Met Leu Asp Gln Glu Asn Glu Gln Ala Leu Asn Arg Leu Ala Ala Ala
1               5                   10                  15

gtt gcg aga gca aat gag cct gcc gaa ggc aaa gaa gca tat aat gct       96
Val Ala Arg Ala Asn Glu Pro Ala Glu Gly Lys Glu Ala Tyr Asn Ala
            20                  25                  30

ata ctg agt aga agg cat gat tac ttt ggg caa gtt ttt tgt gag acc      144
Ile Leu Ser Arg Arg His Asp Tyr Phe Gly Gln Val Phe Cys Glu Thr
        35                  40                  45

ata ggc ata cca tac agg aac gat gtt cgg cta gag gat atc cta cat      192
Ile Gly Ile Pro Tyr Arg Asn Asp Val Arg Leu Glu Asp Ile Leu His
    50                  55                  60

gaa tgt gac caa aca gtc gac act cta aca aat aag ata cca aac ata      240
Glu Cys Asp Gln Thr Val Asp Thr Leu Thr Asn Lys Ile Pro Asn Ile
65                  70                  75                  80

act cca gac aac ttt gag ttt aga gac aat atc cta act ata ata gat      288
Thr Pro Asp Asn Phe Glu Phe Arg Asp Asn Ile Leu Thr Ile Ile Asp
                85                  90                  95

tat aaa gta gca gtt agt gat gaa agt gct gac tat act cgt gaa aag      336
Tyr Lys Val Ala Val Ser Asp Glu Ser Ala Asp Tyr Thr Arg Glu Lys
            100                 105                 110

tat gaa aat gct gtt gat gcc ata aag cat ttg gtt gac ttt cct att      384
Tyr Glu Asn Ala Val Asp Ala Ile Lys His Leu Val Asp Phe Pro Ile
        115                 120                 125

aga gtg tgt ata gtt agg ata cac cca tac act aga caa gtt act tac      432
Arg Val Cys Ile Val Arg Ile His Pro Tyr Thr Arg Gln Val Thr Tyr
    130                 135                 140

tct gat gac aat ttt atg aga cga ttt gcc cat gtg gta tac cct gtt      480
Ser Asp Asp Asn Phe Met Arg Arg Phe Ala His Val Val Tyr Pro Val
145                 150                 155                 160
```

```
gat ttt aca agg tat act caa tta act gaa gaa ctc aag gaa aaa ttt      528
Asp Phe Thr Arg Tyr Thr Gln Leu Thr Glu Glu Leu Lys Glu Lys Phe
                165                 170                 175

gca gat agc cct gaa ttt atg gat atg ata gca tat ggc gat gtc act      576
Ala Asp Ser Pro Glu Phe Met Asp Met Ile Ala Tyr Gly Asp Val Thr
            180                 185                 190

ttt act gca aac tgg tgt caa aat gga tgc cct gag cta tat ggg cat      624
Phe Thr Ala Asn Trp Cys Gln Asn Gly Cys Pro Glu Leu Tyr Gly His
        195                 200                 205

ccg ata ttc aaa gaa ttt tta gaa agc atg cca ttg aaa tac cag aaa      672
Pro Ile Phe Lys Glu Phe Leu Glu Ser Met Pro Leu Lys Tyr Gln Lys
    210                 215                 220

ttg ttt gaa aag tct tta ctg agt tct tgc tat act tct gag aga tgg      720
Leu Phe Glu Lys Ser Leu Leu Ser Ser Cys Tyr Thr Ser Glu Arg Trp
225                 230                 235                 240

gat tcc aat ctt aaa gaa gtc aag ggt gca act aaa gat gag tat gaa      768
Asp Ser Asn Leu Lys Glu Val Lys Gly Ala Thr Lys Asp Glu Tyr Glu
                245                 250                 255

gat ttt ata tct cga tct gca aga gag ctc tat aca aca tct cct gac      816
Asp Phe Ile Ser Arg Ser Ala Arg Glu Leu Tyr Thr Thr Ser Pro Asp
            260                 265                 270

tat tca gaa cct agt cga gag gaa att cta aaa ggg tgg gaa gaa atg      864
Tyr Ser Glu Pro Ser Arg Glu Glu Ile Leu Lys Gly Trp Glu Glu Met
        275                 280                 285

aca gaa cga gtg aaa gaa caa agg gaa gtg tcc tca aat att aat gac      912
Thr Glu Arg Val Lys Glu Gln Arg Glu Val Ser Ser Asn Ile Asn Asp
    290                 295                 300

caa aag cca agt gct cac ttc ata tgg gct gaa aac aat cct gaa cta      960
Gln Lys Pro Ser Ala His Phe Ile Trp Ala Glu Asn Asn Pro Glu Leu
305                 310                 315                 320

ccg act gca aat tct gct aag ata tgt gca att tca aaa ctt tta cag     1008
Pro Thr Ala Asn Ser Ala Lys Ile Cys Ala Ile Ser Lys Leu Leu Gln
                325                 330                 335

tcc att aac ata gaa agc tct ttt gct gag gat ttt aaa aga cta ggc     1056
Ser Ile Asn Ile Glu Ser Ser Phe Ala Glu Asp Phe Lys Arg Leu Gly
            340                 345                 350

aaa tta ttc gac ttt tct gaa gat atc cct gga tat gag cga cat tgc     1104
Lys Leu Phe Asp Phe Ser Glu Asp Ile Pro Gly Tyr Glu Arg His Cys
        355                 360                 365

gaa caa ctt aaa agg cag gct aga tca aat cca gga caa ata aaa aac     1152
Glu Gln Leu Lys Arg Gln Ala Arg Ser Asn Pro Gly Gln Ile Lys Asn
    370                 375                 380

aaa aaa cta gac cca aag aaa att ggg aat gca tta gtt tta tgg gag     1200
Lys Lys Leu Asp Pro Lys Lys Ile Gly Asn Ala Leu Val Leu Trp Glu
385                 390                 395                 400

caa caa ttt tta tta tct gca gat gaa atg ggg aaa gag aat aaa cta     1248
Gln Gln Phe Leu Leu Ser Ala Asp Glu Met Gly Lys Glu Asn Lys Leu
                405                 410                 415

cac tta ctt aaa gac ttc ttt ggc ata ggg aaa cac aaa caa ttt gca     1296
His Leu Leu Lys Asp Phe Phe Gly Ile Gly Lys His Lys Gln Phe Ala
            420                 425                 430

aaa aaa ggc tta gat gac act gaa aca gat aaa ccg aca atc tta gat     1344
Lys Lys Gly Leu Asp Asp Thr Glu Thr Asp Lys Pro Thr Ile Leu Asp
        435                 440                 445

ttt aat gat aca gaa gtc aaa aga tca gca gag ttg atg atg caa aga     1392
Phe Asn Asp Thr Glu Val Lys Arg Ser Ala Glu Leu Met Met Gln Arg
    450                 455                 460

aca aaa ctc tac tta tct ggc agg tcg tca ctc aat aaa gaa cat cct     1440
Thr Lys Leu Tyr Leu Ser Gly Arg Ser Ser Leu Asn Lys Glu His Pro
```

-continued

```
465                 470                 475                 480

gta gca tca gaa tat cta aat gaa ata aaa aag tgt aat gat gag aca     1488
Val Ala Ser Glu Tyr Leu Asn Glu Ile Lys Lys Cys Asn Asp Glu Thr
                485                 490                 495

cat aat gtt ctg aat gca atc ttt cag aca aaa tat tgg caa tgt atc     1536
His Asn Val Leu Asn Ala Ile Phe Gln Thr Lys Tyr Trp Gln Cys Ile
            500                 505                 510

aca gat att agc atg cta atg aaa aat atg ctt tct gtg tcg cag tat     1584
Thr Asp Ile Ser Met Leu Met Lys Asn Met Leu Ser Val Ser Gln Tyr
        515                 520                 525

aat aga aac aat act ttc aga att gca aca tgt gct aat aat gca cta     1632
Asn Arg Asn Asn Thr Phe Arg Ile Ala Thr Cys Ala Asn Asn Ala Leu
    530                 535                 540

tat gga ctt atc ttt ccg tcg gca gat att aaa aca aag gat gca agc     1680
Tyr Gly Leu Ile Phe Pro Ser Ala Asp Ile Lys Thr Lys Asp Ala Ser
545                 550                 555                 560

att gta tat tgc att att gca att cat aaa gat gag aag tct tta ttc     1728
Ile Val Tyr Cys Ile Ile Ala Ile His Lys Asp Glu Lys Ser Leu Phe
                565                 570                 575

aat cca gga gct cta cat gca act ttc aaa gtg cca ggt ggc ttt tta     1776
Asn Pro Gly Ala Leu His Ala Thr Phe Lys Val Pro Gly Gly Phe Leu
            580                 585                 590

tct ata tct aaa tca atg cga ctt gac aag aag cgc tgt cac aga ata     1824
Ser Ile Ser Lys Ser Met Arg Leu Asp Lys Lys Arg Cys His Arg Ile
        595                 600                 605

gtt act agt cca ggc ata ttc tta aca att gcc acc atg ttg aaa gga     1872
Val Thr Ser Pro Gly Ile Phe Leu Thr Ile Ala Thr Met Leu Lys Gly
    610                 615                 620

gat aat cca act att agt ttg aat gat gtt tta aat ttt agc att ttt     1920
Asp Asn Pro Thr Ile Ser Leu Asn Asp Val Leu Asn Phe Ser Ile Phe
625                 630                 635                 640

gcg agc ttg aac ata act aag agc atg cta tca tta aca gag cct tct     1968
Ala Ser Leu Asn Ile Thr Lys Ser Met Leu Ser Leu Thr Glu Pro Ser
                645                 650                 655

agg tat atg atc atg aac tca tta gca gtc tcc agt cat gta cgc gaa     2016
Arg Tyr Met Ile Met Asn Ser Leu Ala Val Ser Ser His Val Arg Glu
            660                 665                 670

tac atc tct gag aaa ttt tcg cca tat act aaa act ctc ttt agt gtc     2064
Tyr Ile Ser Glu Lys Phe Ser Pro Tyr Thr Lys Thr Leu Phe Ser Val
        675                 680                 685

cat atg gtt gag aaa ata aaa gca ggc tgt cta aat gca ttc aaa caa     2112
His Met Val Glu Lys Ile Lys Ala Gly Cys Leu Asn Ala Phe Lys Gln
    690                 695                 700

aga gaa aaa atc aag act cgc gac ata tac ttg aca gac ata gat ata     2160
Arg Glu Lys Ile Lys Thr Arg Asp Ile Tyr Leu Thr Asp Ile Asp Ile
705                 710                 715                 720

act caa aaa ggg ata caa gat aac aga gac cta tgt agc ata tgg ttt     2208
Thr Gln Lys Gly Ile Gln Asp Asn Arg Asp Leu Cys Ser Ile Trp Phe
                725                 730                 735

gat ggt aat gtc act ttg aaa gaa tat cta aac cag att tat att gtc     2256
Asp Gly Asn Val Thr Leu Lys Glu Tyr Leu Asn Gln Ile Tyr Ile Val
            740                 745                 750

ttt tat ctg aat cca aaa gca tta cat gaa aag cat cat gta atg ata     2304
Phe Tyr Leu Asn Pro Lys Ala Leu His Glu Lys His His Val Met Ile
        755                 760                 765

gat tta ctc aaa aca gtg ata gaa ata gaa ctc gat caa agg gag aat     2352
Asp Leu Leu Lys Thr Val Ile Glu Ile Glu Leu Asp Gln Arg Glu Asn
    770                 775                 780

gtc cct caa cca tgg tct gac gtc cca aaa aag cag act gtc aat ttg     2400
```

-continued

```
Val Pro Gln Pro Trp Ser Asp Val Pro Lys Lys Gln Thr Val Asn Leu
785                 790                 795                 800

ccc att ctt gtt cat agc cta gca aag aat cta ctt cta gac act tca      2448
Pro Ile Leu Val His Ser Leu Ala Lys Asn Leu Leu Leu Asp Thr Ser
                805                 810                 815

ttc gcg cat ttc tta agg tct aga att gaa agc cgc aat aat ttt aga      2496
Phe Ala His Phe Leu Arg Ser Arg Ile Glu Ser Arg Asn Asn Phe Arg
            820                 825                 830

cgc acg ttt gca aca att tca act ttt aca agt agt aag agt tgc tta      2544
Arg Thr Phe Ala Thr Ile Ser Thr Phe Thr Ser Ser Lys Ser Cys Leu
        835                 840                 845

aaa aca ggc aat ttc cat gag ttc aag att aag caa tgt caa cgg ctc      2592
Lys Thr Gly Asn Phe His Glu Phe Lys Ile Lys Gln Cys Gln Arg Leu
    850                 855                 860

aaa aaa gtg aat aca agt gaa gca aaa aaa cat aga ata gca aat gcc      2640
Lys Lys Val Asn Thr Ser Glu Ala Lys Lys His Arg Ile Ala Asn Ala
865                 870                 875                 880

atg ttt gtt gag gaa caa gac caa cat tta gag gtg gag cat gca aac      2688
Met Phe Val Glu Glu Gln Asp Gln His Leu Glu Val Glu His Ala Asn
                885                 890                 895

tac gaa tta atg agg aag gca atc ccg gat tat gtg gat gtc tta tcg      2736
Tyr Glu Leu Met Arg Lys Ala Ile Pro Asp Tyr Val Asp Val Leu Ser
            900                 905                 910

acc aaa gta ttc gat aga tta tat gag cta tat aaa act gga gag att      2784
Thr Lys Val Phe Asp Arg Leu Tyr Glu Leu Tyr Lys Thr Gly Glu Ile
        915                 920                 925

gat gac agt cct gtt atc cat cag att ttt gcg acc atg aaa agc cac      2832
Asp Asp Ser Pro Val Ile His Gln Ile Phe Ala Thr Met Lys Ser His
    930                 935                 940

act aaa ttc tat ttt act tat ttt aat aaa ggc caa aaa aca gca aaa      2880
Thr Lys Phe Tyr Phe Thr Tyr Phe Asn Lys Gly Gln Lys Thr Ala Lys
945                 950                 955                 960

gac cga gaa ata ttt gta ggg gaa tac gag gcc aaa atg tgt atg tat      2928
Asp Arg Glu Ile Phe Val Gly Glu Tyr Glu Ala Lys Met Cys Met Tyr
                965                 970                 975

ctg gta gaa aga ata tat aaa gag aga tcg aaa gtc aat cca gac gaa      2976
Leu Val Glu Arg Ile Tyr Lys Glu Arg Ser Lys Val Asn Pro Asp Glu
            980                 985                 990

atg atc agt gaa cca gga gat ggg  aaa ctc aga gtg cta  gag cgc aaa    3024
Met Ile Ser Glu Pro Gly Asp Gly  Lys Leu Arg Val Leu  Glu Arg Lys
        995                 1000                1005

gca gag  caa gag ata aga ttc  atg gtt gaa aaa atg  aaa gca aag      3069
Ala Glu  Gln Glu Ile Arg Phe  Met Val Glu Lys Met  Lys Ala Lys
    1010                 1015                 1020

aat gat  gaa ata aat aag gaa  atc gag gat gca aaa  gac aat tat      3114
Asn Asp  Glu Ile Asn Lys Glu  Ile Glu Asp Ala Lys  Asp Asn Tyr
    1025                 1030                 1035

gtc cta  aat tta ggg aaa ata  gca gca ctg caa gca  caa aaa tat      3159
Val Leu  Asn Leu Gly Lys Ile  Ala Ala Leu Gln Ala  Gln Lys Tyr
    1040                 1045                 1050

aaa gct  tta aaa ttg gaa atc  aat gca gac atg tca  aag tgg agt      3204
Lys Ala  Leu Lys Leu Glu Ile  Asn Ala Asp Met Ser  Lys Trp Ser
    1055                 1060                 1065

gct caa  gac gtg ttc ttt aaa  tac ttt tgg tct gtc  tgt ctt gac      3249
Ala Gln  Asp Val Phe Phe Lys  Tyr Phe Trp Ser Val  Cys Leu Asp
    1070                 1075                 1080

cca att  ctc tat cct gaa gaa  aaa gaa cac att tta  tat ttt ttt      3294
Pro Ile  Leu Tyr Pro Glu Glu  Lys Glu His Ile Leu  Tyr Phe Phe
    1085                 1090                 1095
```

```
tgt aac  tat atg caa aaa gaa  ttg gtt atc cca gat  gag gtt atc      3339
Cys Asn  Tyr Met Gln Lys Glu  Leu Val Ile Pro Asp  Glu Val Ile
    1100                 1105                 1110

tgc aat  atc cta gat cag agg  aaa gca tac cct aat  gac ata att      3384
Cys Asn  Ile Leu Asp Gln Arg  Lys Ala Tyr Pro Asn  Asp Ile Ile
    1115                 1120                 1125

agt cag  atc aca aat ggc ttg  aca acc aac cat ttc  aat gta aag      3429
Ser Gln  Ile Thr Asn Gly Leu  Thr Thr Asn His Phe  Asn Val Lys
    1130                 1135                 1140

aga aac  tgg cta caa ggc aac  ttc aat tac atg tcc  agc tat gct      3474
Arg Asn  Trp Leu Gln Gly Asn  Phe Asn Tyr Met Ser  Ser Tyr Ala
    1145                 1150                 1155

cac agt  aca gca atg tct gtc  ttt aaa gat gtg ata  aag cgt gct      3519
His Ser  Thr Ala Met Ser Val  Phe Lys Asp Val Ile  Lys Arg Ala
    1160                 1165                 1170

gca gat  tta cta gaa gct gaa  gtt ctg att cat tct  atg gtt cac      3564
Ala Asp  Leu Leu Glu Ala Glu  Val Leu Ile His Ser  Met Val His
    1175                 1180                 1185

tct gat  gat aac cag acc tct  gta aca ttg gtc gac  aac agg ata      3609
Ser Asp  Asp Asn Gln Thr Ser  Val Thr Leu Val Asp  Asn Arg Ile
    1190                 1195                 1200

tgc cca  aag caa ttc aca gca  ttt gta atc aat aca  ttt gaa aag      3654
Cys Pro  Lys Gln Phe Thr Ala  Phe Val Ile Asn Thr  Phe Glu Lys
    1205                 1210                 1215

atc tgc  cta aca ttc ggc tgt  caa gct aat atg aaa  aaa acc tat      3699
Ile Cys  Leu Thr Phe Gly Cys  Gln Ala Asn Met Lys  Lys Thr Tyr
    1220                 1225                 1230

atc acc  aac cat ata aaa gaa  ttt gtt tca cta ttc  aat tta tat      3744
Ile Thr  Asn His Ile Lys Glu  Phe Val Ser Leu Phe  Asn Leu Tyr
    1235                 1240                 1245

gga gaa  cca ttt tca att tat  ggc aga ttc aca tta  aca tct gtt      3789
Gly Glu  Pro Phe Ser Ile Tyr  Gly Arg Phe Thr Leu  Thr Ser Val
    1250                 1255                 1260

gga gac  tgc gca tac atc gga  cca tac gaa gat ctc  gca agc agg      3834
Gly Asp  Cys Ala Tyr Ile Gly  Pro Tyr Glu Asp Leu  Ala Ser Arg
    1265                 1270                 1275

ata tca  gca aca caa acc ggg  ata aag cat gga tgc  cca gct agc      3879
Ile Ser  Ala Thr Gln Thr Gly  Ile Lys His Gly Cys  Pro Ala Ser
    1280                 1285                 1290

caa gcc  tgg tta tcg att act  atc gcc caa tgg atg  act tac ttg      3924
Gln Ala  Trp Leu Ser Ile Thr  Ile Ala Gln Trp Met  Thr Tyr Leu
    1295                 1300                 1305

aca tat  aat atg ttg cca ggc  caa caa aat gac ccc  tgg cca ata      3969
Thr Tyr  Asn Met Leu Pro Gly  Gln Gln Asn Asp Pro  Trp Pro Ile
    1310                 1315                 1320

ttg gaa  atc gat aga aag caa  ttg cca ctt gag ttg  ggt gga tac      4014
Leu Glu  Ile Asp Arg Lys Gln  Leu Pro Leu Glu Leu  Gly Gly Tyr
    1325                 1330                 1335

atc tct  tgt cct cta tcc tta  ata gct tta gct ggg  cta gaa tcc      4059
Ile Ser  Cys Pro Leu Ser Leu  Ile Ala Leu Ala Gly  Leu Glu Ser
    1340                 1345                 1350

ggg aac  att gat ttc ctg atc  aaa ttg gta aac aaa  tat gtt gac      4104
Gly Asn  Ile Asp Phe Leu Ile  Lys Leu Val Asn Lys  Tyr Val Asp
    1355                 1360                 1365

ccc aga  ctt caa cgt gaa cct  atc cag gat caa tgc  act gat ata      4149
Pro Arg  Leu Gln Arg Glu Pro  Ile Gln Asp Gln Cys  Thr Asp Ile
    1370                 1375                 1380

aaa aac  tgg gac att tca agg  ctt agc aaa gtt gaa  ata ttt aag      4194
Lys Asn  Trp Asp Ile Ser Arg  Leu Ser Lys Val Glu  Ile Phe Lys
    1385                 1390                 1395
```

```
cta aaa  gtg ctg cgt tat tta  gtt tta gat gca gag  atg gat aat      4239
Leu Lys  Val Leu Arg Tyr Leu  Val Leu Asp Ala Glu  Met Asp Asn
    1400                1405                1410

act gac  att atg gga gaa acc  agc gaa atg aga gga  aga tcc tta      4284
Thr Asp  Ile Met Gly Glu Thr  Ser Glu Met Arg Gly  Arg Ser Leu
    1415                1420                1425

cta aca  ccc agg aag ttc aca  aca gct ggc tcc ttg  aga aaa ttg      4329
Leu Thr  Pro Arg Lys Phe Thr  Thr Ala Gly Ser Leu  Arg Lys Leu
    1430                1435                1440

gta tct  ttt gaa gat ttc caa  gcg gtg caa gat act  gaa caa ggt      4374
Val Ser  Phe Glu Asp Phe Gln  Ala Val Gln Asp Thr  Glu Gln Gly
    1445                1450                1455

gtg gat  gtt ata gtt gag tac  atg ctg caa aac cca  gca ttg ctc      4419
Val Asp  Val Ile Val Glu Tyr  Met Leu Gln Asn Pro  Ala Leu Leu
    1460                1465                1470

gtg aca  aag gga gaa aca aaa  gat gac tat atg aac  aca gtg ctc      4464
Val Thr  Lys Gly Glu Thr Lys  Asp Asp Tyr Met Asn  Thr Val Leu
    1475                1480                1485

tat aga  tat aac tca aag aaa  ttt aaa gaa tca tta  tcc att cag      4509
Tyr Arg  Tyr Asn Ser Lys Lys  Phe Lys Glu Ser Leu  Ser Ile Gln
    1490                1495                1500

aat cct  act cag ctc ttt ttg  gag caa atc cta ttc  tct cac aag      4554
Asn Pro  Thr Gln Leu Phe Leu  Glu Gln Ile Leu Phe  Ser His Lys
    1505                1510                1515

cct att  gtt gat tat aca ggt  atc gca gaa aag ttc  tca aat ctt      4599
Pro Ile  Val Asp Tyr Thr Gly  Ile Ala Glu Lys Phe  Ser Asn Leu
    1520                1525                1530

aat gat  gga acc atg ctt gaa  gat aat ccg aca ata  aaa ggt agg      4644
Asn Asp  Gly Thr Met Leu Glu  Asp Asn Pro Thr Ile  Lys Gly Arg
    1535                1540                1545

atg acc  ttt aca gat gct ttc  gca atg atc aag aaa  gat cta tca      4689
Met Thr  Phe Thr Asp Ala Phe  Ala Met Ile Lys Lys  Asp Leu Ser
    1550                1555                1560

aca ctc  aaa atc acc aat gag  gac ctt gaa att gtg  cta aaa ttt      4734
Thr Leu  Lys Ile Thr Asn Glu  Asp Leu Glu Ile Val  Leu Lys Phe
    1565                1570                1575

ata att  ttg aat gac cct ttg  act gtg act gct gcc  aac gcc cat      4779
Ile Ile  Leu Asn Asp Pro Leu  Thr Val Thr Ala Ala  Asn Ala His
    1580                1585                1590

atc ttg  cat gta ata ggt cat  tca caa cct agg ctt  gga tca aca      4824
Ile Leu  His Val Ile Gly His  Ser Gln Pro Arg Leu  Gly Ser Thr
    1595                1600                1605

gct tgt  gtt atg cct gaa ttt  agg aat ttg aga atg  ata aaa cat      4869
Ala Cys  Val Met Pro Glu Phe  Arg Asn Leu Arg Met  Ile Lys His
    1610                1615                1620

tca cct  gca cta gtc tta aag  tgt tat agt aaa aac  act ttg ttg      4914
Ser Pro  Ala Leu Val Leu Lys  Cys Tyr Ser Lys Asn  Thr Leu Leu
    1625                1630                1635

ctg ccc  ggg gtg caa gaa aga  gac atg gaa agg gac  ctt aac cat      4959
Leu Pro  Gly Val Gln Glu Arg  Asp Met Glu Arg Asp  Leu Asn His
    1640                1645                1650

ctc aaa  aca ttt att gag act  aca aga tta gag cat  aaa atg caa      5004
Leu Lys  Thr Phe Ile Glu Thr  Thr Arg Leu Glu His  Lys Met Gln
    1655                1660                1665

gat agg  atc aag aaa aat gaa  gat ctc aaa aaa tcg  aag gat atc      5049
Asp Arg  Ile Lys Lys Asn Glu  Asp Leu Lys Lys Ser  Lys Asp Ile
    1670                1675                1680

tac ttt  gaa atc aaa gag gta  act aga ttt tat caa  aca tgc tat      5094
Tyr Phe  Glu Ile Lys Glu Val  Thr Arg Phe Tyr Gln  Thr Cys Tyr
```

```
    1685                1690                1695

gaa tat  gtc aaa agt act gat  tat aag gta aaa gta  ttc ata cta      5139
Glu Tyr  Val Lys Ser Thr Asp  Tyr Lys Val Lys Val  Phe Ile Leu
    1700                1705                1710

cca gcc  aaa tgt atg act caa  aca gat ttt tgc gct  gta tta cag      5184
Pro Ala  Lys Cys Met Thr Gln  Thr Asp Phe Cys Ala  Val Leu Gln
    1715                1720                1725

ggt tca  ttg tta gaa gat aaa  aag tgg aaa tta ata  caa cac ctc      5229
Gly Ser  Leu Leu Glu Asp Lys  Lys Trp Lys Leu Ile  Gln His Leu
    1730                1735                1740

aga cct  gtt act gca ggt gga  cat aaa gga gag gtt  cag ccg gta      5274
Arg Pro  Val Thr Ala Gly Gly  His Lys Gly Glu Val  Gln Pro Val
    1745                1750                1755

gtt tcc  atg gat ttt aaa cta  gca aga gag gcc gta  aat tta tta      5319
Val Ser  Met Asp Phe Lys Leu  Ala Arg Glu Ala Val  Asn Leu Leu
    1760                1765                1770

tgc ttt  ttt act gat tca ttt  ata gac tct aga tat  aga aga gac      5364
Cys Phe  Phe Thr Asp Ser Phe  Ile Asp Ser Arg Tyr  Arg Arg Asp
    1775                1780                1785

ttt ctt  cta aaa gcg tgc gta  gaa atg gct tat aaa  gat agg cct      5409
Phe Leu  Leu Lys Ala Cys Val  Glu Met Ala Tyr Lys  Asp Arg Pro
    1790                1795                1800

atg gtt  aca ttg ata gaa gaa  ata aag aag tca aag  aac cga aca      5454
Met Val  Thr Leu Ile Glu Glu  Ile Lys Lys Ser Lys  Asn Arg Thr
    1805                1810                1815

tct ttc  ttg cca ttc ttg tat  aga att gga gag tta  act caa gaa      5499
Ser Phe  Leu Pro Phe Leu Tyr  Arg Ile Gly Glu Leu  Thr Gln Glu
    1820                1825                1830

gac cta  gat gca tat gat gct  caa aaa gcg gga ggg  aga gta acc      5544
Asp Leu  Asp Ala Tyr Asp Ala  Gln Lys Ala Gly Gly  Arg Val Thr
    1835                1840                1845

tgg aat  cac tgg caa tct aca  aga agc tta aac atg  ggg aag ata      5589
Trp Asn  His Trp Gln Ser Thr  Arg Ser Leu Asn Met  Gly Lys Ile
    1850                1855                1860

gat ttc  caa ata gat aca cat  aaa agt cat ctc cat  att att gga      5634
Asp Phe  Gln Ile Asp Thr His  Lys Ser His Leu His  Ile Ile Gly
    1865                1870                1875

gaa gat  caa caa tta gta ata  gca gag cta aaa att  cct aaa ttg      5679
Glu Asp  Gln Gln Leu Val Ile  Ala Glu Leu Lys Ile  Pro Lys Leu
    1880                1885                1890

aca gca  aat gct atc act caa  gca gga tat aga ctt  tta aat gaa      5724
Thr Ala  Asn Ala Ile Thr Gln  Ala Gly Tyr Arg Leu  Leu Asn Glu
    1895                1900                1905

aag cat  ggg ttt cgg ttt gaa  aca atg aat gag gtt  tta gtc cag      5769
Lys His  Gly Phe Arg Phe Glu  Thr Met Asn Glu Val  Leu Val Gln
    1910                1915                1920

cca aga  aaa tat tat ata aca  tac cag atg aaa tct  aaa aag caa      5814
Pro Arg  Lys Tyr Tyr Ile Thr  Tyr Gln Met Lys Ser  Lys Lys Gln
    1925                1930                1935

tat gtc  tat aaa atc ttt gac  aca gca aca ttg cta  tat gaa aga      5859
Tyr Val  Tyr Lys Ile Phe Asp  Thr Ala Thr Leu Leu  Tyr Glu Arg
    1940                1945                1950

aga aac  ata aag caa tac aca  ggc cga gaa gca aat  ccc ata gta      5904
Arg Asn  Ile Lys Gln Tyr Thr  Gly Arg Glu Ala Asn  Pro Ile Val
    1955                1960                1965

gca gtc  tgc gaa gtt gtt cca  atg gag gag gag gaa  act ccc gct      5949
Ala Val  Cys Glu Val Val Pro  Met Glu Glu Glu Glu  Thr Pro Ala
    1970                1975                1980

tta agc  tta agt gac ata gaa  atg tat aat gct gac  aat gaa tca      5994
```

```
Leu Ser  Leu Ser Asp Ile Glu  Met Tyr Asn Ala Asp  Asn Glu Ser
    1985                 1990                 1995

gtt agc  att tta aaa act tca  ttc aat gag agt gcg  aag atg aga      6039
Val Ser  Ile Leu Lys Thr Ser  Phe Asn Glu Ser Ala  Lys Met Arg
    2000                 2005                 2010

cgt gca  aat ttg tcc aaa atg  caa tat ttt gag act  att ggc gga      6084
Arg Ala  Asn Leu Ser Lys Met  Gln Tyr Phe Glu Thr  Ile Gly Gly
    2015                 2020                 2025

tca atg  ttg aaa att cga ttc  atc aat gtc aac gca  cta atg aaa      6129
Ser Met  Leu Lys Ile Arg Phe  Ile Asn Val Asn Ala  Leu Met Lys
    2030                 2035                 2040

gac aca  act cta atg tcc ctt  aac tat gac aat ttg  gta aat gtc      6174
Asp Thr  Thr Leu Met Ser Leu  Asn Tyr Asp Asn Leu  Val Asn Val
    2045                 2050                 2055

gac ctg  gct aga ttt agc aag  tta ttg gac tgt gac  ggt gat aca      6219
Asp Leu  Ala Arg Phe Ser Lys  Leu Leu Asp Cys Asp  Gly Asp Thr
    2060                 2065                 2070

gaa agt  gtt gaa gat gga ata  ttg tgc ttt tct gat  gac cca atg      6264
Glu Ser  Val Glu Asp Gly Ile  Leu Cys Phe Ser Asp  Asp Pro Met
    2075                 2080                 2085

gaa caa  acc aca aca gaa gag  att gac gcg atc cct  ctc ttc aaa      6309
Glu Gln  Thr Thr Thr Glu Glu  Ile Asp Ala Ile Pro  Leu Phe Lys
    2090                 2095                 2100

gta agc  tac aag ata cct aca  cca gct aga tta aca  tac aag aat      6354
Val Ser  Tyr Lys Ile Pro Thr  Pro Ala Arg Leu Thr  Tyr Lys Asn
    2105                 2110                 2115

gcc att  aga gaa ctg tta agg  agg gaa ata aca agg  ttt atg gat      6399
Ala Ile  Arg Glu Leu Leu Arg  Arg Glu Ile Thr Arg  Phe Met Asp
    2120                 2125                 2130

gct ttt  acc ttt gtt gga cct  tct ttt gat tca cca  gaa aat atg      6444
Ala Phe  Thr Phe Val Gly Pro  Ser Phe Asp Ser Pro  Glu Asn Met
    2135                 2140                 2145

ggg ttc  ata tgc aat ata tgt  tgt ata ata caa ctc  ctc cat aca      6489
Gly Phe  Ile Cys Asn Ile Cys  Cys Ile Ile Gln Leu  Leu His Thr
    2150                 2155                 2160

aac gaa  tgg tct act ata atg  cta aat tgt att cat  atc tgc atg      6534
Asn Glu  Trp Ser Thr Ile Met  Leu Asn Cys Ile His  Ile Cys Met
    2165                 2170                 2175

att tat  ctg gag aaa gac ata  agg ttt cat aaa ttt  tta cta aat      6579
Ile Tyr  Leu Glu Lys Asp Ile  Arg Phe His Lys Phe  Leu Leu Asn
    2180                 2185                 2190

aga ata  ttc ttt gag gga ttg  aat cct gca tct ggg  aaa ttg gat      6624
Arg Ile  Phe Phe Glu Gly Leu  Asn Pro Ala Ser Gly  Lys Leu Asp
    2195                 2200                 2205

tac aaa  aaa atc aaa gaa ttt  gta atc agc ctg aag  gat aga gag      6669
Tyr Lys  Lys Ile Lys Glu Phe  Val Ile Ser Leu Lys  Asp Arg Glu
    2210                 2215                 2220

atg gct  cct tgg aat gag ata  ttt tca aag ttc aag  caa aaa tgt      6714
Met Ala  Pro Trp Asn Glu Ile  Phe Ser Lys Phe Lys  Gln Lys Cys
    2225                 2230                 2235

gtc aca  ttg cta gac aaa gaa  ata aca aga ata gaa  caa aac aca      6759
Val Thr  Leu Leu Asp Lys Glu  Ile Thr Arg Ile Glu  Gln Asn Thr
    2240                 2245                 2250

aac ttt  gaa aat ata cta gct  tta gat gaa agc aca  gat gat cag      6804
Asn Phe  Glu Asn Ile Leu Ala  Leu Asp Glu Ser Thr  Asp Asp Gln
    2255                 2260                 2265

tct gga  ttc ctc ttg ttt gaa  tag                                  6828
Ser Gly  Phe Leu Leu Phe Glu
    2270                 2275
```

<210> SEQ ID NO 6
<211> LENGTH: 2275
<212> TYPE: PRT
<213> ORGANISM: Moissiacense virus (Umbre orthobunyavirus strain Moissiasence)

<400> SEQUENCE: 6

Met Leu Asp Gln Glu Asn Glu Gln Ala Leu Asn Arg Leu Ala Ala Ala
1               5                   10                  15

Val Ala Arg Ala Asn Glu Pro Ala Glu Gly Lys Glu Ala Tyr Asn Ala
            20                  25                  30

Ile Leu Ser Arg Arg His Asp Tyr Phe Gly Gln Val Phe Cys Glu Thr
        35                  40                  45

Ile Gly Ile Pro Tyr Arg Asn Asp Val Arg Leu Glu Asp Ile Leu His
    50                  55                  60

Glu Cys Asp Gln Thr Val Asp Thr Leu Thr Asn Lys Ile Pro Asn Ile
65                  70                  75                  80

Thr Pro Asp Asn Phe Glu Phe Arg Asp Asn Ile Leu Thr Ile Ile Asp
                85                  90                  95

Tyr Lys Val Ala Val Ser Asp Glu Ser Ala Asp Tyr Thr Arg Glu Lys
            100                 105                 110

Tyr Glu Asn Ala Val Asp Ala Ile Lys His Leu Val Asp Phe Pro Ile
        115                 120                 125

Arg Val Cys Ile Val Arg Ile His Pro Tyr Thr Arg Gln Val Thr Tyr
    130                 135                 140

Ser Asp Asp Asn Phe Met Arg Arg Phe Ala His Val Val Tyr Pro Val
145                 150                 155                 160

Asp Phe Thr Arg Tyr Thr Gln Leu Thr Glu Glu Leu Lys Glu Lys Phe
                165                 170                 175

Ala Asp Ser Pro Glu Phe Met Asp Met Ile Ala Tyr Gly Asp Val Thr
            180                 185                 190

Phe Thr Ala Asn Trp Cys Gln Asn Gly Cys Pro Glu Leu Tyr Gly His
        195                 200                 205

Pro Ile Phe Lys Glu Phe Leu Glu Ser Met Pro Leu Lys Tyr Gln Lys
    210                 215                 220

Leu Phe Glu Lys Ser Leu Leu Ser Ser Cys Tyr Thr Ser Glu Arg Trp
225                 230                 235                 240

Asp Ser Asn Leu Lys Glu Val Lys Gly Ala Thr Lys Asp Glu Tyr Glu
                245                 250                 255

Asp Phe Ile Ser Arg Ser Ala Arg Glu Leu Tyr Thr Thr Ser Pro Asp
            260                 265                 270

Tyr Ser Glu Pro Ser Arg Glu Glu Ile Leu Lys Gly Trp Glu Glu Met
        275                 280                 285

Thr Glu Arg Val Lys Glu Gln Arg Glu Val Ser Ser Asn Ile Asn Asp
    290                 295                 300

Gln Lys Pro Ser Ala His Phe Ile Trp Ala Glu Asn Asn Pro Glu Leu
305                 310                 315                 320

Pro Thr Ala Asn Ser Ala Lys Ile Cys Ala Ile Ser Lys Leu Leu Gln
                325                 330                 335

Ser Ile Asn Ile Glu Ser Ser Phe Ala Glu Asp Phe Lys Arg Leu Gly
            340                 345                 350

Lys Leu Phe Asp Phe Ser Glu Asp Ile Pro Gly Tyr Glu Arg His Cys
        355                 360                 365

Glu Gln Leu Lys Arg Gln Ala Arg Ser Asn Pro Gly Gln Ile Lys Asn

```
    370                 375                 380

Lys Lys Leu Asp Pro Lys Lys Ile Gly Asn Ala Leu Val Leu Trp Glu
385                 390                 395                 400

Gln Gln Phe Leu Leu Ser Ala Asp Glu Met Gly Lys Glu Asn Lys Leu
                405                 410                 415

His Leu Leu Lys Asp Phe Phe Gly Ile Gly Lys His Lys Gln Phe Ala
            420                 425                 430

Lys Lys Gly Leu Asp Asp Thr Glu Thr Asp Lys Pro Thr Ile Leu Asp
        435                 440                 445

Phe Asn Asp Thr Glu Val Lys Arg Ser Ala Glu Leu Met Met Gln Arg
    450                 455                 460

Thr Lys Leu Tyr Leu Ser Gly Arg Ser Ser Leu Asn Lys Glu His Pro
465                 470                 475                 480

Val Ala Ser Glu Tyr Leu Asn Glu Ile Lys Lys Cys Asn Asp Glu Thr
                485                 490                 495

His Asn Val Leu Asn Ala Ile Phe Gln Thr Lys Tyr Trp Gln Cys Ile
            500                 505                 510

Thr Asp Ile Ser Met Leu Met Lys Asn Met Leu Ser Val Ser Gln Tyr
        515                 520                 525

Asn Arg Asn Asn Thr Phe Arg Ile Ala Thr Cys Ala Asn Asn Ala Leu
    530                 535                 540

Tyr Gly Leu Ile Phe Pro Ser Ala Asp Ile Lys Thr Lys Asp Ala Ser
545                 550                 555                 560

Ile Val Tyr Cys Ile Ile Ala Ile His Lys Asp Glu Lys Ser Leu Phe
                565                 570                 575

Asn Pro Gly Ala Leu His Ala Thr Phe Lys Val Pro Gly Gly Phe Leu
            580                 585                 590

Ser Ile Ser Lys Ser Met Arg Leu Asp Lys Lys Arg Cys His Arg Ile
        595                 600                 605

Val Thr Ser Pro Gly Ile Phe Leu Thr Ile Ala Thr Met Leu Lys Gly
    610                 615                 620

Asp Asn Pro Thr Ile Ser Leu Asn Asp Val Leu Asn Phe Ser Ile Phe
625                 630                 635                 640

Ala Ser Leu Asn Ile Thr Lys Ser Met Leu Ser Leu Thr Glu Pro Ser
                645                 650                 655

Arg Tyr Met Ile Met Asn Ser Leu Ala Val Ser Ser His Val Arg Glu
            660                 665                 670

Tyr Ile Ser Glu Lys Phe Ser Pro Tyr Thr Lys Thr Leu Phe Ser Val
        675                 680                 685

His Met Val Glu Lys Ile Lys Ala Gly Cys Leu Asn Ala Phe Lys Gln
    690                 695                 700

Arg Glu Lys Ile Lys Thr Arg Asp Ile Tyr Leu Thr Asp Ile Asp Ile
705                 710                 715                 720

Thr Gln Lys Gly Ile Gln Asp Asn Arg Asp Leu Cys Ser Ile Trp Phe
                725                 730                 735

Asp Gly Asn Val Thr Leu Lys Glu Tyr Leu Asn Gln Ile Tyr Ile Val
            740                 745                 750

Phe Tyr Leu Asn Pro Lys Ala Leu His Glu Lys His His Val Met Ile
        755                 760                 765

Asp Leu Leu Lys Thr Val Ile Glu Ile Glu Leu Asp Gln Arg Glu Asn
    770                 775                 780

Val Pro Gln Pro Trp Ser Asp Val Pro Lys Lys Gln Thr Val Asn Leu
785                 790                 795                 800
```

```
Pro Ile Leu Val His Ser Leu Ala Lys Asn Leu Leu Leu Asp Thr Ser
                805                 810                 815

Phe Ala His Phe Leu Arg Ser Arg Ile Glu Ser Arg Asn Asn Phe Arg
            820                 825                 830

Arg Thr Phe Ala Thr Ile Ser Thr Phe Thr Ser Ser Lys Ser Cys Leu
        835                 840                 845

Lys Thr Gly Asn Phe His Glu Phe Lys Ile Lys Gln Cys Gln Arg Leu
    850                 855                 860

Lys Lys Val Asn Thr Ser Glu Ala Lys Lys His Arg Ile Ala Asn Ala
865                 870                 875                 880

Met Phe Val Glu Glu Gln Asp Gln His Leu Glu Val Glu His Ala Asn
                885                 890                 895

Tyr Glu Leu Met Arg Lys Ala Ile Pro Asp Tyr Val Asp Val Leu Ser
            900                 905                 910

Thr Lys Val Phe Asp Arg Leu Tyr Glu Leu Tyr Lys Thr Gly Glu Ile
        915                 920                 925

Asp Asp Ser Pro Val Ile His Gln Ile Phe Ala Thr Met Lys Ser His
    930                 935                 940

Thr Lys Phe Tyr Phe Thr Tyr Phe Asn Lys Gly Gln Lys Thr Ala Lys
945                 950                 955                 960

Asp Arg Glu Ile Phe Val Gly Glu Tyr Glu Ala Lys Met Cys Met Tyr
                965                 970                 975

Leu Val Glu Arg Ile Tyr Lys Glu Arg Ser Lys Val Asn Pro Asp Glu
            980                 985                 990

Met Ile Ser Glu Pro Gly Asp Gly  Lys Leu Arg Val Leu  Glu Arg Lys
        995                 1000                1005

Ala Glu  Gln Glu Ile Arg Phe  Met Val Glu Lys Met  Lys Ala Lys
    1010                 1015                 1020

Asn Asp  Glu Ile Asn Lys Glu  Ile Glu Asp Ala Lys  Asp Asn Tyr
    1025                 1030                 1035

Val Leu  Asn Leu Gly Lys Ile  Ala Ala Leu Gln Ala  Gln Lys Tyr
    1040                 1045                 1050

Lys Ala  Leu Lys Leu Glu Ile  Asn Ala Asp Met Ser  Lys Trp Ser
    1055                 1060                 1065

Ala Gln  Asp Val Phe Phe Lys  Tyr Phe Trp Ser Val  Cys Leu Asp
    1070                 1075                 1080

Pro Ile  Leu Tyr Pro Glu Glu  Lys Glu His Ile Leu  Tyr Phe Phe
    1085                 1090                 1095

Cys Asn  Tyr Met Gln Lys Glu  Leu Val Ile Pro Asp  Glu Val Ile
    1100                 1105                 1110

Cys Asn  Ile Leu Asp Gln Arg  Lys Ala Tyr Pro Asn  Asp Ile Ile
    1115                 1120                 1125

Ser Gln  Ile Thr Asn Gly Leu  Thr Thr Asn His Phe  Asn Val Lys
    1130                 1135                 1140

Arg Asn  Trp Leu Gln Gly Asn  Phe Asn Tyr Met Ser  Ser Tyr Ala
    1145                 1150                 1155

His Ser  Thr Ala Met Ser Val  Phe Lys Asp Val Ile  Lys Arg Ala
    1160                 1165                 1170

Ala Asp  Leu Leu Glu Ala Glu  Val Leu Ile His Ser  Met Val His
    1175                 1180                 1185

Ser Asp  Asp Asn Gln Thr Ser  Val Thr Leu Val Asp  Asn Arg Ile
    1190                 1195                 1200
```

-continued

```
Cys Pro  Lys Gln Phe Thr Ala  Phe Val Ile Asn Thr  Phe Glu Lys
    1205                 1210                 1215

Ile Cys  Leu Thr Phe Gly Cys  Gln Ala Asn Met Lys  Lys Thr Tyr
    1220                 1225                 1230

Ile Thr  Asn His Ile Lys Glu  Phe Val Ser Leu Phe  Asn Leu Tyr
    1235                 1240                 1245

Gly Glu  Pro Phe Ser Ile Tyr  Gly Arg Phe Thr Leu  Thr Ser Val
    1250                 1255                 1260

Gly Asp  Cys Ala Tyr Ile Gly  Pro Tyr Glu Asp Leu  Ala Ser Arg
    1265                 1270                 1275

Ile Ser  Ala Thr Gln Thr Gly  Ile Lys His Gly Cys  Pro Ala Ser
    1280                 1285                 1290

Gln Ala  Trp Leu Ser Ile Thr  Ile Ala Gln Trp Met  Thr Tyr Leu
    1295                 1300                 1305

Thr Tyr  Asn Met Leu Pro Gly  Gln Gln Asn Asp Pro  Trp Pro Ile
    1310                 1315                 1320

Leu Glu  Ile Asp Arg Lys Gln  Leu Pro Leu Glu Leu  Gly Gly Tyr
    1325                 1330                 1335

Ile Ser  Cys Pro Leu Ser Leu  Ile Ala Leu Ala Gly  Leu Glu Ser
    1340                 1345                 1350

Gly Asn  Ile Asp Phe Leu Ile  Lys Leu Val Asn Lys  Tyr Val Asp
    1355                 1360                 1365

Pro Arg  Leu Gln Arg Glu Pro  Ile Gln Asp Gln Cys  Thr Asp Ile
    1370                 1375                 1380

Lys Asn  Trp Asp Ile Ser Arg  Leu Ser Lys Val Glu  Ile Phe Lys
    1385                 1390                 1395

Leu Lys  Val Leu Arg Tyr Leu  Val Leu Asp Ala Glu  Met Asp Asn
    1400                 1405                 1410

Thr Asp  Ile Met Gly Glu Thr  Ser Glu Met Arg Gly  Arg Ser Leu
    1415                 1420                 1425

Leu Thr  Pro Arg Lys Phe Thr  Thr Ala Gly Ser Leu  Arg Lys Leu
    1430                 1435                 1440

Val Ser  Phe Glu Asp Phe Gln  Ala Val Gln Asp Thr  Glu Gln Gly
    1445                 1450                 1455

Val Asp  Val Ile Val Glu Tyr  Met Leu Gln Asn Pro  Ala Leu Leu
    1460                 1465                 1470

Val Thr  Lys Gly Glu Thr Lys  Asp Asp Tyr Met Asn  Thr Val Leu
    1475                 1480                 1485

Tyr Arg  Tyr Asn Ser Lys Lys  Phe Lys Glu Ser Leu  Ser Ile Gln
    1490                 1495                 1500

Asn Pro  Thr Gln Leu Phe Leu  Glu Gln Ile Leu Phe  Ser His Lys
    1505                 1510                 1515

Pro Ile  Val Asp Tyr Thr Gly  Ile Ala Glu Lys Phe  Ser Asn Leu
    1520                 1525                 1530

Asn Asp  Gly Thr Met Leu Glu  Asp Asn Pro Thr Ile  Lys Gly Arg
    1535                 1540                 1545

Met Thr  Phe Thr Asp Ala Phe  Ala Met Ile Lys Lys  Asp Leu Ser
    1550                 1555                 1560

Thr Leu  Lys Ile Thr Asn Glu  Asp Leu Glu Ile Val  Leu Lys Phe
    1565                 1570                 1575

Ile Ile  Leu Asn Asp Pro Leu  Thr Val Thr Ala Ala  Asn Ala His
    1580                 1585                 1590

Ile Leu  His Val Ile Gly His  Ser Gln Pro Arg Leu  Gly Ser Thr
```

```
    1595                1600                1605

Ala Cys  Val Met Pro Glu Phe  Arg Asn Leu Arg Met  Ile Lys His
    1610                1615                1620

Ser Pro  Ala Leu Val Leu Lys  Cys Tyr Ser Lys Asn  Thr Leu Leu
    1625                1630                1635

Leu Pro  Gly Val Gln Glu Arg  Asp Met Glu Arg Asp  Leu Asn His
    1640                1645                1650

Leu Lys  Thr Phe Ile Glu Thr  Thr Arg Leu Glu His  Lys Met Gln
    1655                1660                1665

Asp Arg  Ile Lys Lys Asn Glu  Asp Leu Lys Lys Ser  Lys Asp Ile
    1670                1675                1680

Tyr Phe  Glu Ile Lys Glu Val  Thr Arg Phe Tyr Gln  Thr Cys Tyr
    1685                1690                1695

Glu Tyr  Val Lys Ser Thr Asp  Tyr Lys Val Lys Val  Phe Ile Leu
    1700                1705                1710

Pro Ala  Lys Cys Met Thr Gln  Thr Asp Phe Cys Ala  Val Leu Gln
    1715                1720                1725

Gly Ser  Leu Leu Glu Asp Lys  Lys Trp Lys Leu Ile  Gln His Leu
    1730                1735                1740

Arg Pro  Val Thr Ala Gly Gly  His Lys Gly Glu Val  Gln Pro Val
    1745                1750                1755

Val Ser  Met Asp Phe Lys Leu  Ala Arg Glu Ala Val  Asn Leu Leu
    1760                1765                1770

Cys Phe  Phe Thr Asp Ser Phe  Ile Asp Ser Arg Tyr  Arg Arg Asp
    1775                1780                1785

Phe Leu  Leu Lys Ala Cys Val  Glu Met Ala Tyr Lys  Asp Arg Pro
    1790                1795                1800

Met Val  Thr Leu Ile Glu Glu  Ile Lys Lys Ser Lys  Asn Arg Thr
    1805                1810                1815

Ser Phe  Leu Pro Phe Leu Tyr  Arg Ile Gly Glu Leu  Thr Gln Glu
    1820                1825                1830

Asp Leu  Asp Ala Tyr Asp Ala  Gln Lys Ala Gly Gly  Arg Val Thr
    1835                1840                1845

Trp Asn  His Trp Gln Ser Thr  Arg Ser Leu Asn Met  Gly Lys Ile
    1850                1855                1860

Asp Phe  Gln Ile Asp Thr His  Lys Ser His Leu His  Ile Ile Gly
    1865                1870                1875

Glu Asp  Gln Gln Leu Val Ile  Ala Glu Leu Lys Ile  Pro Lys Leu
    1880                1885                1890

Thr Ala  Asn Ala Ile Thr Gln  Ala Gly Tyr Arg Leu  Leu Asn Glu
    1895                1900                1905

Lys His  Gly Phe Arg Phe Glu  Thr Met Asn Glu Val  Leu Val Gln
    1910                1915                1920

Pro Arg  Lys Tyr Tyr Ile Thr  Tyr Gln Met Lys Ser  Lys Lys Gln
    1925                1930                1935

Tyr Val  Tyr Lys Ile Phe Asp  Thr Ala Thr Leu Leu  Tyr Glu Arg
    1940                1945                1950

Arg Asn  Ile Lys Gln Tyr Thr  Gly Arg Glu Ala Asn  Pro Ile Val
    1955                1960                1965

Ala Val  Cys Glu Val Val Pro  Met Glu Glu Glu Glu  Thr Pro Ala
    1970                1975                1980

Leu Ser  Leu Ser Asp Ile Glu  Met Tyr Asn Ala Asp  Asn Glu Ser
    1985                1990                1995
```

```
Val Ser  Ile Leu Lys Thr Ser  Phe Asn Glu Ser Ala  Lys Met Arg
    2000                 2005                 2010

Arg Ala  Asn Leu Ser Lys Met  Gln Tyr Phe Glu Thr  Ile Gly Gly
    2015                 2020                 2025

Ser Met  Leu Lys Ile Arg Phe  Ile Asn Val Asn Ala  Leu Met Lys
    2030                 2035                 2040

Asp Thr  Thr Leu Met Ser Leu  Asn Tyr Asp Asn Leu  Val Asn Val
    2045                 2050                 2055

Asp Leu  Ala Arg Phe Ser Lys  Leu Leu Asp Cys Asp  Gly Asp Thr
    2060                 2065                 2070

Glu Ser  Val Glu Asp Gly Ile  Leu Cys Phe Ser Asp  Asp Pro Met
    2075                 2080                 2085

Glu Gln  Thr Thr Thr Glu Glu  Ile Asp Ala Ile Pro  Leu Phe Lys
    2090                 2095                 2100

Val Ser  Tyr Lys Ile Pro Thr  Pro Ala Arg Leu Thr  Tyr Lys Asn
    2105                 2110                 2115

Ala Ile  Arg Glu Leu Leu Arg  Arg Glu Ile Thr Arg  Phe Met Asp
    2120                 2125                 2130

Ala Phe  Thr Phe Val Gly Pro  Ser Phe Asp Ser Pro  Glu Asn Met
    2135                 2140                 2145

Gly Phe  Ile Cys Asn Ile Cys  Cys Ile Ile Gln Leu  Leu His Thr
    2150                 2155                 2160

Asn Glu  Trp Ser Thr Ile Met  Leu Asn Cys Ile His  Ile Cys Met
    2165                 2170                 2175

Ile Tyr  Leu Glu Lys Asp Ile  Arg Phe His Lys Phe  Leu Leu Asn
    2180                 2185                 2190

Arg Ile  Phe Phe Glu Gly Leu  Asn Pro Ala Ser Gly  Lys Leu Asp
    2195                 2200                 2205

Tyr Lys  Lys Ile Lys Glu Phe  Val Ile Ser Leu Lys  Asp Arg Glu
    2210                 2215                 2220

Met Ala  Pro Trp Asn Glu Ile  Phe Ser Lys Phe Lys  Gln Lys Cys
    2225                 2230                 2235

Val Thr  Leu Leu Asp Lys Glu  Ile Thr Arg Ile Glu  Gln Asn Thr
    2240                 2245                 2250

Asn Phe  Glu Asn Ile Leu Ala  Leu Asp Glu Ser Thr  Asp Asp Gln
    2255                 2260                 2265

Ser Gly  Phe Leu Leu Phe Glu
    2270                 2275
```

<210> SEQ ID NO 7
<211> LENGTH: 316
<212> TYPE: DNA
<213> ORGANISM: artificial sequence
<220> FEATURE:
<223> OTHER INFORMATION: synthetic polynucleotide (S segment target sequence (partial))

<400> SEQUENCE: 7

```
aaacgcagaa ctgggtagca ctagcattta tccaggatgg ctgattctaa gctcacatac     60

gaggatacac aggatgttag tagaagtact tataacccag cagatgaata cgatacgttt    120

gtgggtgtct acagagaatt tctcacaatt gataacatta gaatcttctt catcaacgct    180

ccaaaggcca aaactgcgat ggctaaactc aagaccgaga cagttgaagt tacatttgga    240

acactcgttg tcaagctggt taataaccat agaattggac aggctcagcg tgaggttgcg    300
```

```
gacgatgagc taactc                                                316


<210> SEQ ID NO 8
<211> LENGTH: 425
<212> TYPE: DNA
<213> ORGANISM: artificial sequence
<220> FEATURE:
<223> OTHER INFORMATION: synthetic polynucleotide (M segment target
      sequence)

<400> SEQUENCE: 8

acaggacaaa tagcactaaa ggtcttgttg ggagacttta actacaagca gtatgctgca     60

aatgtagagg ctgacataga agcaaattgc gttgggtgta caaattgtat aaagggaata    120

acatgtgaaa taaaggtgaa aacagaaatt gaagcatcat gtaaggtaga gcccccatgc    180

ccctcttaca caagtagaat tataataaaa ccaggtagag acacccacac attattgatg    240

aagtgtgaca aaaaaataac gactggtgaa ctagcaataa aaatatgtaa tatgcaaatc    300

caggctcatc tttcaacaat agagagcaat gaccaactag aattgtcgac tggggatcaa    360

tcaacatata tacatgaaga agacctaagg tgttcaacct ggatctgcaw wgtgagagac    420

gaagg                                                            425


<210> SEQ ID NO 9
<211> LENGTH: 457
<212> TYPE: DNA
<213> ORGANISM: artificial sequence
<220> FEATURE:
<223> OTHER INFORMATION: synthetic polynucleotide (L segment target
      sequence)

<400> SEQUENCE: 9

agaattggtt atcccagatg aggttatctg caatatccta gatcagagga aagcataccc     60

taatgacata attagtcaga tcacaaatgg cttgacaacc aaccatttca atgtaaagag    120

aaactggcta caaggcaact tcaattacat gtccagctat gctcacagta cagcaatgtc    180

tgtctttaaa gatgtgataa agcgtgctgc agatttacta gaagctgaag ttctgattca    240

ttctatggtt cactctgatg ataaccagac ctctgtaaca ttggtcgaca acaggatatg    300

cccaaagcaa ttcacagcat ttgtaatcaa tacatttgaa aagatctgcc taacattcgg    360

ctgtcaagct aatatgaaaa aaacctatat caccaaccat ataaaagaat ttgtttcact    420

attcaattta tatggagaac cattttcaat ttatggc                             457


<210> SEQ ID NO 10
<211> LENGTH: 20
<212> TYPE: DNA
<213> ORGANISM: artificial sequence
<220> FEATURE:
<223> OTHER INFORMATION: synthetic oligonucleotide (BunyaCladeS_Fw1)

<400> SEQUENCE: 10

aaacgcagaa ctgggtagca                                             20


<210> SEQ ID NO 11
<211> LENGTH: 20
<212> TYPE: DNA
<213> ORGANISM: artificial sequence
<220> FEATURE:
<223> OTHER INFORMATION: synthetic oligonucleotide (BunyaCladeS_Rv1)

<400> SEQUENCE: 11

gagttagctc atcgtccgca                                             20
```

<210> SEQ ID NO 12
<211> LENGTH: 23
<212> TYPE: DNA
<213> ORGANISM: artificial sequence
<220> FEATURE:
<223> OTHER INFORMATION: synthetic oligonucleotide (BunyaCladeM_Fw1)

<400> SEQUENCE: 12
acaggrcaaa tagcactaaa ggt 23

<210> SEQ ID NO 13
<211> LENGTH: 21
<212> TYPE: DNA
<213> ORGANISM: artificial sequence
<220> FEATURE:
<223> OTHER INFORMATION: synthetic oligonucleotide (BunyaCladeM_Rv1)

<400> SEQUENCE: 13
ccttcrtctc tcactttgca g 21

<210> SEQ ID NO 14
<211> LENGTH: 24
<212> TYPE: DNA
<213> ORGANISM: artificial sequence
<220> FEATURE:
<223> OTHER INFORMATION: synthetic oligonucleotide (BunyaCladeL_Fw1)

<400> SEQUENCE: 14
agaattggtt atcccagatg aggt 24

<210> SEQ ID NO 15
<211> LENGTH: 25
<212> TYPE: DNA
<213> ORGANISM: artificial sequence
<220> FEATURE:
<223> OTHER INFORMATION: synthetic oligonucleotide (BunyaCladeL_Rv1)

<400> SEQUENCE: 15
gccataaatt gaaaatggtt ctcca 25

<210> SEQ ID NO 16
<211> LENGTH: 23
<212> TYPE: DNA
<213> ORGANISM: artificial sequence
<220> FEATURE:
<223> OTHER INFORMATION: synthetic oligonucleotide (BunyaUmbreM_Fw1)

<400> SEQUENCE: 16
ggatagtctc agattggacc aca 23

<210> SEQ ID NO 17
<211> LENGTH: 23
<212> TYPE: DNA
<213> ORGANISM: artificial sequence
<220> FEATURE:
<223> OTHER INFORMATION: synthetic oligonucleotide (BunyaUmbreM_Rv1)

<400> SEQUENCE: 17
tctgtgggtt ttcattgcat ctg 23

<210> SEQ ID NO 18
<211> LENGTH: 22
<212> TYPE: DNA
<213> ORGANISM: artificial sequence
<220> FEATURE:

<223> OTHER INFORMATION: synthetic oligonucleotide (BunyaUmbreM_Fw2)

<400> SEQUENCE: 18
gcttaccacc ctttcacaaa gt 22

<210> SEQ ID NO 19
<211> LENGTH: 20
<212> TYPE: DNA
<213> ORGANISM: artificial sequence
<220> FEATURE:
<223> OTHER INFORMATION: synthetic oligonucleotide (BunyaUmbreM_Rv2)

<400> SEQUENCE: 19
gctgcggcag tcagcattat 20

<210> SEQ ID NO 20
<211> LENGTH: 22
<212> TYPE: DNA
<213> ORGANISM: artificial sequence
<220> FEATURE:
<223> OTHER INFORMATION: synthetic oligonucleotide (BunyaUmbreM_Fw3)

<400> SEQUENCE: 20
acgaaatcat tgctctgcca ac 22

<210> SEQ ID NO 21
<211> LENGTH: 20
<212> TYPE: DNA
<213> ORGANISM: artificial sequence
<220> FEATURE:
<223> OTHER INFORMATION: synthetic oligonucleotide (BunyaUmbreM_Rv3)

<400> SEQUENCE: 21
tgttgtgctt ggctgcattt 20

<210> SEQ ID NO 22
<211> LENGTH: 22
<212> TYPE: DNA
<213> ORGANISM: artificial sequence
<220> FEATURE:
<223> OTHER INFORMATION: synthetic oligonucleotide (BunyaUmbreM_Fw4)

<400> SEQUENCE: 22
aaggaatctg agctaggaca ag 22

<210> SEQ ID NO 23
<211> LENGTH: 23
<212> TYPE: DNA
<213> ORGANISM: artificial sequence
<220> FEATURE:
<223> OTHER INFORMATION: synthetic oligonucleotide (BunyaUmbreM_Rv4)

<400> SEQUENCE: 23
atctgttgtt agcacacaat gtt 23

<210> SEQ ID NO 24
<211> LENGTH: 20
<212> TYPE: DNA
<213> ORGANISM: artificial sequence
<220> FEATURE:
<223> OTHER INFORMATION: synthetic oligonucleotide (BunyaUmbreM_Fw5)

<400> SEQUENCE: 24
ttgcaaagtg ctcgcgaatg 20

<210> SEQ ID NO 25
<211> LENGTH: 20
<212> TYPE: DNA
<213> ORGANISM: artificial sequence
<220> FEATURE:
<223> OTHER INFORMATION: synthetic oligonucleotide (BunyaUmbreM_Rv5)

<400> SEQUENCE: 25
agccccaatt gctggttctt 20

<210> SEQ ID NO 26
<211> LENGTH: 19
<212> TYPE: DNA
<213> ORGANISM: artificial sequence
<220> FEATURE:
<223> OTHER INFORMATION: synthetic oligonucleotide (BunyaUmbreM_Fw6)

<400> SEQUENCE: 26
gagcactgca cagggacat 19

<210> SEQ ID NO 27
<211> LENGTH: 20
<212> TYPE: DNA
<213> ORGANISM: artificial sequence
<220> FEATURE:
<223> OTHER INFORMATION: syntehtic oligonucleotide (BunyaUmbreM_Rv6)

<400> SEQUENCE: 27
cttgtgtaag aggggcatgg 20

<210> SEQ ID NO 28
<211> LENGTH: 19
<212> TYPE: DNA
<213> ORGANISM: artificial sequence
<220> FEATURE:
<223> OTHER INFORMATION: synthetic oligonucleotide (BunyaUmbreM5_Fw)

<400> SEQUENCE: 28
gtttgagatt accatcaag 19

<210> SEQ ID NO 29
<211> LENGTH: 23
<212> TYPE: DNA
<213> ORGANISM: artificial sequence
<220> FEATURE:
<223> OTHER INFORMATION: synthetic oligonucleotide (BunyaUmbreM5_Rv)

<400> SEQUENCE: 29
tgtggtccaa tctgagacta tcc 23

<210> SEQ ID NO 30
<211> LENGTH: 21
<212> TYPE: DNA
<213> ORGANISM: artificial sequence
<220> FEATURE:
<223> OTHER INFORMATION: synthetic oligonucleotide (BunyaUmbreM3_Fw)

<400> SEQUENCE: 30
ctgcaaagtg agagaygaag g 21

<210> SEQ ID NO 31
<211> LENGTH: 17
<212> TYPE: DNA
<213> ORGANISM: artificial sequence
<220> FEATURE:
<223> OTHER INFORMATION: synthetic oligonucleotide (BunyaUmbreM3_Rv)

<400> SEQUENCE: 31
catgactata ccattga 17

<210> SEQ ID NO 32
<211> LENGTH: 22
<212> TYPE: DNA
<213> ORGANISM: artificial sequence
<220> FEATURE:
<223> OTHER INFORMATION: synthetic oligonucleotide (BunyaUmbreL3_Fw)

<400> SEQUENCE: 32
tcctgcatct gggaaattgg at 22

<210> SEQ ID NO 33
<211> LENGTH: 24
<212> TYPE: DNA
<213> ORGANISM: artificial sequence
<220> FEATURE:
<223> OTHER INFORMATION: synthetic oligonucleotide (BunyaUmbreL3_Rv)

<400> SEQUENCE: 33
ctagagagaa tagatgaact cttg 24

<210> SEQ ID NO 34
<211> LENGTH: 20
<212> TYPE: DNA
<213> ORGANISM: artificial sequence
<220> FEATURE:
<223> OTHER INFORMATION: synthetic oligonucleotide (BunyaUmbreL_Fw1)

<400> SEQUENCE: 34
acaggaacga tgttcggcta 20

<210> SEQ ID NO 35
<211> LENGTH: 21
<212> TYPE: DNA
<213> ORGANISM: artificial sequence
<220> FEATURE:
<223> OTHER INFORMATION: synthetic oligonucleotide (BunyaUmbreL_Rv1)

<400> SEQUENCE: 35
tctttgaata tcggatgccc a 21

<210> SEQ ID NO 36
<211> LENGTH: 20
<212> TYPE: DNA
<213> ORGANISM: artificial sequence
<220> FEATURE:
<223> OTHER INFORMATION: synthetic oligonucleotide (BunyaUmbreL_Fw1bis)

<400> SEQUENCE: 36
gttgcgagag caaatgagcc 20

<210> SEQ ID NO 37
<211> LENGTH: 22
<212> TYPE: DNA
<213> ORGANISM: artificial sequence
<220> FEATURE:
<223> OTHER INFORMATION: artificial sequence (BunyaUmbreL_Rv1bis)

<400> SEQUENCE: 37
ttctttgaat atcggatgcc ca 22

<210> SEQ ID NO 38
<211> LENGTH: 23

<212> TYPE: DNA
<213> ORGANISM: artificial sequence
<220> FEATURE:
<223> OTHER INFORMATION: synthetic oligonucleotide (BunyaUmbreL_Fw2)

<400> SEQUENCE: 38
aagaacaaag ggaagtgtcc tca 23

<210> SEQ ID NO 39
<211> LENGTH: 23
<212> TYPE: DNA
<213> ORGANISM: artificial sequence
<220> FEATURE:
<223> OTHER INFORMATION: synthetic oligonucleotide (BunyaUmbreL_Rv2)

<400> SEQUENCE: 39
tctgtttcag tgtcatctaa gcc 23

<210> SEQ ID NO 40
<211> LENGTH: 21
<212> TYPE: DNA
<213> ORGANISM: artificial sequence
<220> FEATURE:
<223> OTHER INFORMATION: synthetic oligonucleotide (BunyaUmbreL_Fw3)

<400> SEQUENCE: 40
ctggcaggtc gtcactcaat a 21

<210> SEQ ID NO 41
<211> LENGTH: 22
<212> TYPE: DNA
<213> ORGANISM: artificial sequence
<220> FEATURE:
<223> OTHER INFORMATION: synthetic oligonucleotide (BunyaUmbreL_Rv3)

<400> SEQUENCE: 41
aatgcattta gacagcctgc tt 22

<210> SEQ ID NO 42
<211> LENGTH: 25
<212> TYPE: DNA
<213> ORGANISM: artificial sequence
<220> FEATURE:
<223> OTHER INFORMATION: synthtetic oligonucleotide (BunyaUmbreL_Fw4)

<400> SEQUENCE: 42
tggtttgatg gtaatgtcac tttga 25

<210> SEQ ID NO 43
<211> LENGTH: 21
<212> TYPE: DNA
<213> ORGANISM: artificial sequence
<220> FEATURE:
<223> OTHER INFORMATION: synthetic oligonucleotide (BunyaUmbreL_Rv4)

<400> SEQUENCE: 43
tcgtctggat tgactttcga t 21

<210> SEQ ID NO 44
<211> LENGTH: 20
<212> TYPE: DNA
<213> ORGANISM: artificial sequence
<220> FEATURE:
<223> OTHER INFORMATION: synthetic oligonucleotide (BunyaUmbreL_Fw5)

<400> SEQUENCE: 44
tgtaggggaa tacgaggcca 20

<210> SEQ ID NO 45
<211> LENGTH: 22
<212> TYPE: DNA
<213> ORGANISM: artificial sequence
<220> FEATURE:
<223> OTHER INFORMATION: synthetic oligonucleotide (BunyaUmbreL_Rv5)

<400> SEQUENCE: 45
agggtatgct ttcctctgat ct 22

<210> SEQ ID NO 46
<211> LENGTH: 20
<212> TYPE: DNA
<213> ORGANISM: artificial sequence
<220> FEATURE:
<223> OTHER INFORMATION: synthetic oligonucleotide (BunyaUmbreL_Fw6)

<400> SEQUENCE: 46
ctgcctaaca ttcggctgtc 20

<210> SEQ ID NO 47
<211> LENGTH: 20
<212> TYPE: DNA
<213> ORGANISM: artificial sequence
<220> FEATURE:
<223> OTHER INFORMATION: synthetic oligonucleotide (BunyaUmbreL_Rv6)

<400> SEQUENCE: 47
tcttgcaccg cttggaaatc 20

<210> SEQ ID NO 48
<211> LENGTH: 22
<212> TYPE: DNA
<213> ORGANISM: artificial sequence
<220> FEATURE:
<223> OTHER INFORMATION: synthetic oligonucleotide (BunyaUmbreL_Fw6bis)

<400> SEQUENCE: 48
actgggacat ttcaaggctt ag 22

<210> SEQ ID NO 49
<211> LENGTH: 22
<212> TYPE: DNA
<213> ORGANISM: artificial sequence
<220> FEATURE:
<223> OTHER INFORMATION: synthetic oligonucleotide (BunyaUmbreL_Rv6bis)

<400> SEQUENCE: 49
gagaactttt ctgcgatacc tg 22

<210> SEQ ID NO 50
<211> LENGTH: 21
<212> TYPE: DNA
<213> ORGANISM: artificial sequence
<220> FEATURE:
<223> OTHER INFORMATION: synthetic oligonucleotide (BunyaUmbreL_Fw7)

<400> SEQUENCE: 50
actgatcaag gtgtggatgt t 21

<210> SEQ ID NO 51
<211> LENGTH: 20
<212> TYPE: DNA
<213> ORGANISM: artificial sequence
<220> FEATURE:
<223> OTHER INFORMATION: synthetic oligonucleotide (BunyaUmbreL_Rv7)

<400> SEQUENCE: 51
cgggcagcaa caaagtgttt 20

<210> SEQ ID NO 52
<211> LENGTH: 25
<212> TYPE: DNA
<213> ORGANISM: artificial sequence
<220> FEATURE:
<223> OTHER INFORMATION: synthetic oligonucleotide (BunyaUmbreL_Fw8)

<400> SEQUENCE: 52
gagcataaaa tgcaagatag gatca 25

<210> SEQ ID NO 53
<211> LENGTH: 20
<212> TYPE: DNA
<213> ORGANISM: artificial sequence
<220> FEATURE:
<223> OTHER INFORMATION: synthetic oligonucleotide (BunyaUmbreL_Rv8)

<400> SEQUENCE: 53
tcaaaccgaa acccatgctt 20

<210> SEQ ID NO 54
<211> LENGTH: 20
<212> TYPE: DNA
<213> ORGANISM: artificial sequence
<220> FEATURE:
<223> OTHER INFORMATION: synthetic oligonucleotide (BunyaUmbreL_Fw9)

<400> SEQUENCE: 54
aagcatgggt ttcggtttga 20

<210> SEQ ID NO 55
<211> LENGTH: 21
<212> TYPE: DNA
<213> ORGANISM: artificial sequence
<220> FEATURE:
<223> OTHER INFORMATION: synthetic oligonucleotide (BunyaUmbreL_Rv9)

<400> SEQUENCE: 55
agccaggtcg acatttacca a 21

<210> SEQ ID NO 56
<211> LENGTH: 22
<212> TYPE: DNA
<213> ORGANISM: artificial sequence
<220> FEATURE:
<223> OTHER INFORMATION: synthetic oligonucleotide (BunyaUmbreL_Fw10)

<400> SEQUENCE: 56
ttggactgtg acggtgatac ag 22

<210> SEQ ID NO 57
<211> LENGTH: 22
<212> TYPE: DNA
<213> ORGANISM: artificial sequence
<220> FEATURE:
<223> OTHER INFORMATION: synthetic oligonucleotide (BunyaUmbreL_Rv10)

<400> SEQUENCE: 57
atccaatttc ccagatgcag ga 22

<210> SEQ ID NO 58
<211> LENGTH: 285
<212> TYPE: PRT
<213> ORGANISM: Moissiacense virus (Umbre orthobunyavirus strain Moissiacense)

<400> SEQUENCE: 58

Gln Ala Thr Ile Arg Cys Phe Ser Gly Gly Ser Lys Ile Met Glu Lys
1 5 10 15

Thr Ser Asn Val Ser Leu Ser Glu Leu Cys Leu Lys Asp Asp Val Ser
20 25 30

Gln Leu Lys Ile Ile Val Asp His Thr Lys Asn Asp Ser Gly Leu Phe
35 40 45

Ser Thr Ala Ser Val Trp Arg Lys Trp Ile Val Ser Asp Trp Thr Thr
50 55 60

Cys Asn Pro Lys Lys Met Ala Leu Gly Thr Ile Ser Val Ile Asp Ile
65 70 75 80

Asp Lys Asn Phe Ile Leu Lys Ser Ser Ser Tyr Ile Cys Asn Lys Glu
85 90 95

Cys Thr Ile Thr Val Asp Lys Glu Arg Ala Gln Val Leu Leu Gln Ser
100 105 110

Asp Gly Leu Asn His Phe Glu Val Ser Gly Thr Thr Leu Ser Ser Gly
115 120 125

Trp Phe Lys Ser Thr Ala Thr Val Thr Leu Asp Gln Thr Cys Glu His
130 135 140

Val Lys Val Ser Cys Gly Gln Lys Ser Met Gln Phe His Ala Cys Phe
145 150 155 160

Lys Asn His Met Ser Cys Ile Arg Phe Leu His Arg Ser Ile Met Pro
165 170 175

Ala Ser Phe Ala Val Ser Ile Cys Gln Asn Ile Glu Leu Ile Leu Met
180 185 190

Thr Thr Phe Thr Leu Ile Ile Phe Leu Leu Leu Ser Ile Leu Thr Lys
195 200 205

Thr Tyr Ile Cys Tyr Ile Leu Leu Pro Ile Phe Ile Pro Phe Ala Tyr
210 215 220

Ala Tyr Gly Phe Val Tyr Asp Lys Thr Cys Lys Lys Cys Ser Leu Cys
225 230 235 240

Gly Leu Ala Tyr His Pro Phe Thr Lys Cys Gly Ile His Cys Val Cys
245 250 255

Gly Cys Arg Phe Glu Asn Ser Asp Ala Met Lys Thr His Arg Glu Lys
260 265 270

Gly Lys Cys Pro Gly Phe Lys Ser Met Arg Ile Ala Arg
275 280 285

<210> SEQ ID NO 59
<211> LENGTH: 174
<212> TYPE: PRT
<213> ORGANISM: Moissiacense virus (Umbre orthobunyavirus strain Moissiacense)

<400> SEQUENCE: 59

Val Leu Cys Lys Ala Lys Gly Ser Ala Phe Ala Leu Ser Val Leu Leu
1 5 10 15

Ala Thr Leu Ala Leu Gly Phe Leu Thr Pro Val Gln Gly Leu Val Leu
20 25 30

Asp Lys Thr Gln Ile Asn Tyr Thr Glu Asp Gln Leu Pro Glu Ser Phe

```
        35                  40                  45

Gln Thr Met Gln Ser Thr Ile Ser Ile Phe Lys Phe Ala Thr Val Met
    50                  55                  60

Asn Ala Gly Trp Thr Tyr Cys Met Phe Leu Val Thr Leu Ala Leu Tyr
65                  70                  75                  80

Ile Ile His Lys Lys Tyr Ala His Arg Leu Leu Ser Tyr Tyr Val Ile
                85                  90                  95

His Cys Arg Glu Cys Asp Met Leu His Asp Lys Ser Gly Leu Lys Tyr
            100                 105                 110

Asn Gly Asp Phe Thr Asn Lys Cys Gly Phe Cys Thr Cys Gly Gln Val
        115                 120                 125

Glu Asp Ala Met Gly Leu Thr Val His Gln Ile Arg Asn His Cys Ser
    130                 135                 140

Ala Asn Tyr Arg Thr Lys Met Val Leu Asn Trp Met Ile Val Leu Leu
145                 150                 155                 160

Leu Ala Thr Leu Ile Lys Asp Ser Ile Met Leu Thr Ala Ala
                165                 170


<210> SEQ ID NO 60
<211> LENGTH: 989
<212> TYPE: PRT
<213> ORGANISM: Moissiacense virus (Umbre orthobunyavirus strain
      Moissiacense)

<400> SEQUENCE: 60

Ala Gly Thr Glu Phe Glu Thr Cys Ile Lys Lys Val Glu Met Thr Pro
1               5                   10                  15

Glu Cys Thr Gly Pro Phe Met Glu Val Gly Ile Cys Asp His Gln Gln
            20                  25                  30

Lys Ser Leu Arg Tyr His Glu Ile Ala Asn Met Leu Leu Gly Lys Gly
        35                  40                  45

Thr Ile Ser Lys Leu Asp Val Asp Ile Ile Asp Ala Leu Pro Asp Arg
    50                  55                  60

Ile Ala Gly Asp Leu Gln Ile Ile Gln Ser Ser Ser Asp Phe His His
65                  70                  75                  80

Gln Gln Met Leu Glu Tyr Val Phe Leu Leu Arg His Cys Asp Tyr Tyr
                85                  90                  95

Ser Ser Phe Val Ser Asp Asn Ser Tyr Ser Gln Ile Leu Trp Gln Thr
            100                 105                 110

Ala Ala Lys Leu Asn Glu Thr Asn Leu Cys Lys His Glu Asn Ser Lys
        115                 120                 125

Lys Ser Cys Lys Cys Leu Lys Ser Asn Ala Asn Cys Gly Glu Ser Glu
    130                 135                 140

Asp Ile Asn Ile Ala Ala Gln Ala Tyr Tyr Lys Asn Lys Glu Ser Glu
145                 150                 155                 160

Leu Gly Gln Asp Leu Thr Thr Ile Met Tyr Ile Leu Lys Lys Met Ile
                165                 170                 175

Pro Gly Ser Gly Tyr Ser Tyr Leu Leu Asn Ala Ala Lys His Asn Lys
            180                 185                 190

Leu Glu Leu Phe Lys Ala Tyr Met Thr Asn Ile Ser Ser Lys Tyr Ser
        195                 200                 205

Asn Asn Lys Lys Leu Lys Asp Phe Met Ala Ile Ile Asn Ala Ile Leu
    210                 215                 220

Ala Asn Leu Ser Ala Leu Ser His Ser Ser Glu Glu Ser Ile Ser Gln
225                 230                 235                 240
```

```
Tyr Lys Gln Ile Asp Phe Ser Ser Leu Val Gly Glu Thr Thr Asp Met
                245                 250                 255

Leu Glu Ala Asn Phe Asn Gln Thr Ile Ser Thr Asp Lys Ile Ile Cys
            260                 265                 270

Glu Asn Pro Lys Val Met Ile Cys Ile Ser Pro Arg Thr Lys Val Ser
        275                 280                 285

Ser Gly Glu Leu Tyr Val Cys Gln Arg Ser Gly Lys Tyr Tyr Ile Ile
    290                 295                 300

Asp Thr Gly Lys Phe Lys Leu Tyr Lys Leu Ile Asp Ala Asp Asn Leu
305                 310                 315                 320

Tyr Cys Ala Ala Asp Ala Gln Cys Arg Tyr Glu Phe Arg Ile Leu Thr
                325                 330                 335

Thr Gly Glu Met Gln Ala Thr Phe Lys Asp Asn Cys Lys Ala Ser Val
            340                 345                 350

His Val Asn Thr Pro Gly Tyr Gln Asn Glu Ala Ile Thr His Cys Lys
        355                 360                 365

Val Leu Ala Asn Gly Lys Cys Lys Tyr Asn Asn Gln Thr Ser Ile Asp
    370                 375                 380

Ile Thr Leu Cys Ala Asn Asn Arg Tyr Tyr Pro Glu Ala Lys Gly Arg
385                 390                 395                 400

Ile Phe Gly Val Asp Pro Glu Asp Leu Cys Phe Asp Lys Thr Cys Thr
                405                 410                 415

Lys Gln Gln Thr Pro Tyr Asn Glu Glu Leu Ile Ser Met Cys Val Trp
            420                 425                 430

Glu Asn Pro Thr Leu Arg Pro Ile Lys Pro Arg Thr Glu Val Ser Met
        435                 440                 445

Thr Phe Gln Glu Tyr Lys Asp Gln Leu Leu Lys Lys Ile Asn Thr Asp
    450                 455                 460

Leu Val Leu His Lys Phe Val Arg Thr Gln Asn Leu Pro Tyr Phe Ile
465                 470                 475                 480

Pro Gln Phe Lys Tyr Ile Thr Ile Gln Gly Thr Ser Thr Thr Asp Gly
                485                 490                 495

Ile Thr Ser Ser Phe Ile Phe Phe Glu Ile Pro Ala Leu Thr Gly Ala
            500                 505                 510

Ser Ala Gly Tyr Lys Val Ile Asn Ser Glu Gly Gln Glu Leu Met Asp
        515                 520                 525

Met Val Val Tyr Ile Lys Thr Ser Lys Thr Ser Ala Lys Tyr Lys Arg
    530                 535                 540

Val Tyr Tyr Thr Gly Pro Thr Ile Ala Ile Asn Thr Lys His Gln Glu
545                 550                 555                 560

His Cys Thr Gly Thr Cys Pro Glu Arg Ile Glu His Asp Glu Gly Trp
                565                 570                 575

Ala Thr Phe Ser Lys Glu Arg Thr Ser Asn Trp Gly Cys Glu Glu Phe
            580                 585                 590

Gly Cys Leu Ala Val Glu Thr Gly Cys Leu Phe Gly Ser Cys Gln Asp
        595                 600                 605

Val Ile Arg Arg Glu Leu Asp Val Phe Ser Lys Leu Glu Glu Asp Lys
    610                 615                 620

Ile Leu Thr Glu Leu Cys Ile Thr Leu Ser His Asp Thr Tyr Cys Val
625                 630                 635                 640

Thr Ile Asp Ser Thr Thr Pro Thr Ile Asn Asp Tyr Phe Glu Ile Gln
                645                 650                 655
```

```
Tyr Lys Thr Val Asp Val Gln Thr Leu Pro Lys Met Ile Gly Val Thr
            660                 665                 670

His His Lys Leu Leu Arg Gly Gln Ile Asn Glu Leu Gly Ser Phe Gly
        675                 680                 685

Lys Phe Cys Gly Asn Ile Gln Val Val Gly Asn Gln Thr Tyr Gly Gln
    690                 695                 700

Ala Ala Val Lys Phe Asp Tyr Ile Cys His Ala Ala Gln Arg Lys Asp
705                 710                 715                 720

Val Val Ile Arg Lys Cys Leu Glu Asn Asn Tyr Gln Ser Cys Lys Leu
                725                 730                 735

Leu Thr His Asp Thr Asp Leu Ile Leu Glu Glu Ser Lys Thr Ser Val
            740                 745                 750

Glu Val Ile Asn Asn Lys Arg Ile Thr Gly Gln Ile Ala Leu Lys Val
        755                 760                 765

Leu Leu Gly Asp Phe Asn Tyr Lys Gln Tyr Ala Ala Asn Val Glu Ala
    770                 775                 780

Asp Ile Glu Ala Asn Cys Val Gly Cys Thr Asn Cys Ile Lys Gly Ile
785                 790                 795                 800

Thr Cys Glu Ile Lys Val Lys Thr Glu Ile Glu Ala Ser Cys Lys Val
                805                 810                 815

Glu Pro Pro Cys Pro Ser Tyr Thr Ser Arg Ile Ile Ile Lys Pro Gly
            820                 825                 830

Arg Asp Thr His Thr Leu Leu Met Lys Cys Asp Lys Lys Ile Thr Thr
        835                 840                 845

Gly Glu Leu Ala Ile Lys Ile Cys Asn Met Gln Ile Gln Ala His Leu
    850                 855                 860

Ser Thr Ile Glu Ser Asn Asp Gln Leu Glu Leu Ser Thr Gly Asp Gln
865                 870                 875                 880

Ser Thr Tyr Ile His Glu Glu Asp Leu Arg Cys Ser Thr Trp Ile Cys
                885                 890                 895

Lys Val Arg Asp Glu Gly Ile Ser Phe Ile Phe Lys Pro Leu Thr Asp
            900                 905                 910

Trp Leu Gly Ser Phe Thr Lys Pro Ile Leu Ile Ala Gly Cys Met Ile
        915                 920                 925

Ile Val Ala Ile Ile Leu Ile Tyr Ile Leu Met Pro Met Cys Ala Arg
    930                 935                 940

Leu Arg Asp Leu Leu Lys Lys Asn Glu Tyr Glu Tyr Leu Gln Asp Thr
945                 950                 955                 960

Lys Val Ile Val Lys Pro Lys Gly Thr Ala Ser Ser Ile Gly Leu Arg
                965                 970                 975

Ser Lys Lys Ile Asn Ile Gln Ser Ser Lys Ala Val Asp
            980                 985
```

<210> SEQ ID NO 61
<211> LENGTH: 920
<212> TYPE: PRT
<213> ORGANISM: artificial sequence
<220> FEATURE:
<223> OTHER INFORMATION: synthetic polypeptide (Gc protein extracellular domain)
<220> FEATURE:
<221> NAME/KEY: VARIANT
<222> LOCATION: (897)..(897)
<223> OTHER INFORMATION: Xaa is Isoleucine or Lysine

<400> SEQUENCE: 61

```
Ala Gly Thr Glu Phe Glu Thr Cys Ile Lys Lys Val Glu Met Thr Pro
```

-continued

```
1               5                   10                  15

Glu Cys Thr Gly Pro Phe Met Glu Val Gly Ile Cys Asp His Gln Gln
            20                  25                  30

Lys Ser Leu Arg Tyr His Glu Ile Ala Asn Met Leu Leu Gly Lys Gly
        35                  40                  45

Thr Ile Ser Lys Leu Asp Val Asp Ile Ile Asp Ala Leu Pro Asp Arg
    50                  55                  60

Ile Ala Gly Asp Leu Gln Ile Ile Gln Ser Ser Ser Asp Phe His His
65                  70                  75                  80

Gln Gln Met Leu Glu Tyr Val Phe Leu Leu Arg His Cys Asp Tyr Tyr
                85                  90                  95

Ser Ser Phe Val Ser Asp Asn Ser Tyr Ser Gln Ile Leu Trp Gln Thr
            100                 105                 110

Ala Ala Lys Leu Asn Glu Thr Asn Leu Cys Lys His Glu Asn Ser Lys
        115                 120                 125

Lys Ser Cys Lys Cys Leu Lys Ser Asn Ala Asn Cys Gly Glu Ser Glu
    130                 135                 140

Asp Ile Asn Ile Ala Ala Gln Ala Tyr Tyr Lys Asn Lys Glu Ser Glu
145                 150                 155                 160

Leu Gly Gln Asp Leu Thr Thr Ile Met Tyr Ile Leu Lys Lys Met Ile
                165                 170                 175

Pro Gly Ser Gly Tyr Ser Tyr Leu Leu Asn Ala Ala Lys His Asn Lys
            180                 185                 190

Leu Glu Leu Phe Lys Ala Tyr Met Thr Asn Ile Ser Ser Lys Tyr Ser
        195                 200                 205

Asn Asn Lys Lys Leu Lys Asp Phe Met Ala Ile Ile Asn Ala Ile Leu
    210                 215                 220

Ala Asn Leu Ser Ala Leu Ser His Ser Ser Glu Glu Ser Ile Ser Gln
225                 230                 235                 240

Tyr Lys Gln Ile Asp Phe Ser Ser Leu Val Gly Glu Thr Thr Asp Met
                245                 250                 255

Leu Glu Ala Asn Phe Asn Gln Thr Ile Ser Thr Asp Lys Ile Ile Cys
            260                 265                 270

Glu Asn Pro Lys Val Met Ile Cys Ile Ser Pro Arg Thr Lys Val Ser
        275                 280                 285

Ser Gly Glu Leu Tyr Val Cys Gln Arg Ser Gly Lys Tyr Tyr Ile Ile
    290                 295                 300

Asp Thr Gly Lys Phe Lys Leu Tyr Lys Leu Ile Asp Ala Asp Asn Leu
305                 310                 315                 320

Tyr Cys Ala Ala Asp Ala Gln Cys Arg Tyr Glu Phe Arg Ile Leu Thr
                325                 330                 335

Thr Gly Glu Met Gln Ala Thr Phe Lys Asp Asn Cys Lys Ala Ser Val
            340                 345                 350

His Val Asn Thr Pro Gly Tyr Gln Asn Glu Ala Ile Thr His Cys Lys
        355                 360                 365

Val Leu Ala Asn Gly Lys Cys Lys Tyr Asn Asn Gln Thr Ser Ile Asp
    370                 375                 380

Ile Thr Leu Cys Ala Asn Asn Arg Tyr Tyr Pro Glu Ala Lys Gly Arg
385                 390                 395                 400

Ile Phe Gly Val Asp Pro Glu Asp Leu Cys Phe Asp Lys Thr Cys Thr
                405                 410                 415

Lys Gln Gln Thr Pro Tyr Asn Glu Glu Leu Ile Ser Met Cys Val Trp
            420                 425                 430
```

```
Glu Asn Pro Thr Leu Arg Pro Ile Lys Pro Arg Thr Glu Val Ser Met
        435                 440                 445

Thr Phe Gln Glu Tyr Lys Asp Gln Leu Leu Lys Lys Ile Asn Thr Asp
    450                 455                 460

Leu Val Leu His Lys Phe Val Arg Thr Gln Asn Leu Pro Tyr Phe Ile
465                 470                 475                 480

Pro Gln Phe Lys Tyr Ile Thr Ile Gln Gly Thr Ser Thr Thr Asp Gly
                485                 490                 495

Ile Thr Ser Ser Phe Ile Phe Phe Glu Ile Pro Ala Leu Thr Gly Ala
            500                 505                 510

Ser Ala Gly Tyr Lys Val Ile Asn Ser Glu Gly Gln Glu Leu Met Asp
        515                 520                 525

Met Val Val Tyr Ile Lys Thr Ser Lys Thr Ser Ala Lys Tyr Lys Arg
    530                 535                 540

Val Tyr Tyr Thr Gly Pro Thr Ile Ala Ile Asn Thr Lys His Gln Glu
545                 550                 555                 560

His Cys Thr Gly Thr Cys Pro Glu Arg Ile Glu His Asp Glu Gly Trp
                565                 570                 575

Ala Thr Phe Ser Lys Glu Arg Thr Ser Asn Trp Gly Cys Glu Glu Phe
            580                 585                 590

Gly Cys Leu Ala Val Glu Thr Gly Cys Leu Phe Gly Ser Cys Gln Asp
        595                 600                 605

Val Ile Arg Arg Glu Leu Asp Val Phe Ser Lys Leu Glu Glu Asp Lys
    610                 615                 620

Ile Leu Thr Glu Leu Cys Ile Thr Leu Ser His Asp Thr Tyr Cys Val
625                 630                 635                 640

Thr Ile Asp Ser Thr Thr Pro Thr Ile Asn Asp Tyr Phe Glu Ile Gln
                645                 650                 655

Tyr Lys Thr Val Asp Val Gln Thr Leu Pro Lys Met Ile Gly Val Thr
            660                 665                 670

His His Lys Leu Leu Arg Gly Gln Ile Asn Glu Leu Gly Ser Phe Gly
        675                 680                 685

Lys Phe Cys Gly Asn Ile Gln Val Val Gly Asn Gln Thr Tyr Gly Gln
    690                 695                 700

Ala Ala Val Lys Phe Asp Tyr Ile Cys His Ala Ala Gln Arg Lys Asp
705                 710                 715                 720

Val Val Ile Arg Lys Cys Leu Glu Asn Asn Tyr Gln Ser Cys Lys Leu
                725                 730                 735

Leu Thr His Asp Thr Asp Leu Ile Leu Glu Glu Ser Lys Thr Ser Val
            740                 745                 750

Glu Val Ile Asn Asn Lys Arg Ile Thr Gly Gln Ile Ala Leu Lys Val
        755                 760                 765

Leu Leu Gly Asp Phe Asn Tyr Lys Gln Tyr Ala Ala Asn Val Glu Ala
    770                 775                 780

Asp Ile Glu Ala Asn Cys Val Gly Cys Thr Asn Cys Ile Lys Gly Ile
785                 790                 795                 800

Thr Cys Glu Ile Lys Val Lys Thr Glu Ile Glu Ala Ser Cys Lys Val
                805                 810                 815

Glu Pro Pro Cys Pro Ser Tyr Thr Ser Arg Ile Ile Ile Lys Pro Gly
            820                 825                 830

Arg Asp Thr His Thr Leu Leu Met Lys Cys Asp Lys Lys Ile Thr Thr
        835                 840                 845
```

```
Gly Glu Leu Ala Ile Lys Ile Cys Asn Met Gln Ile Gln Ala His Leu
    850                 855                 860

Ser Thr Ile Glu Ser Asn Asp Gln Leu Glu Leu Ser Thr Gly Asp Gln
865                 870                 875                 880

Ser Thr Tyr Ile His Glu Glu Asp Leu Arg Cys Ser Thr Trp Ile Cys
                885                 890                 895

Xaa Val Arg Asp Glu Gly Ile Ser Phe Ile Phe Lys Pro Leu Thr Asp
            900                 905                 910

Trp Leu Gly Ser Phe Thr Lys Pro
        915                 920


<210> SEQ ID NO 62
<211> LENGTH: 261
<212> TYPE: PRT
<213> ORGANISM: artificial sequence
<220> FEATURE:
<223> OTHER INFORMATION: synthetic polypeptide (Gc protein N-terminal
      alpha helix region)

<400> SEQUENCE: 62

Leu Arg Tyr His Glu Ile Ala Asn Met Leu Leu Gly Lys Gly Thr Ile
1               5                   10                  15

Ser Lys Leu Asp Val Asp Ile Ile Asp Ala Leu Pro Asp Arg Ile Ala
            20                  25                  30

Gly Asp Leu Gln Ile Ile Gln Ser Ser Ser Asp Phe His His Gln Gln
        35                  40                  45

Met Leu Glu Tyr Val Phe Leu Leu Arg His Cys Asp Tyr Tyr Ser Ser
    50                  55                  60

Phe Val Ser Asp Asn Ser Tyr Ser Gln Ile Leu Trp Gln Thr Ala Ala
65                  70                  75                  80

Lys Leu Asn Glu Thr Asn Leu Cys Lys His Glu Asn Ser Lys Lys Ser
                85                  90                  95

Cys Lys Cys Leu Lys Ser Asn Ala Asn Cys Gly Glu Ser Glu Asp Ile
            100                 105                 110

Asn Ile Ala Ala Gln Ala Tyr Tyr Lys Asn Lys Glu Ser Glu Leu Gly
        115                 120                 125

Gln Asp Leu Thr Thr Ile Met Tyr Ile Leu Lys Lys Met Ile Pro Gly
    130                 135                 140

Ser Gly Tyr Ser Tyr Leu Leu Asn Ala Ala Lys His Asn Lys Leu Glu
145                 150                 155                 160

Leu Phe Lys Ala Tyr Met Thr Asn Ile Ser Ser Lys Tyr Ser Asn Asn
                165                 170                 175

Lys Lys Leu Lys Asp Phe Met Ala Ile Ile Asn Ala Ile Leu Ala Asn
            180                 185                 190

Leu Ser Ala Leu Ser His Ser Ser Glu Glu Ser Ile Ser Gln Tyr Lys
        195                 200                 205

Gln Ile Asp Phe Ser Ser Leu Val Gly Glu Thr Thr Asp Met Leu Glu
    210                 215                 220

Ala Asn Phe Asn Gln Thr Ile Ser Thr Asp Lys Ile Ile Cys Glu Asn
225                 230                 235                 240

Pro Lys Val Met Ile Cys Ile Ser Pro Arg Thr Lys Val Ser Ser Gly
                245                 250                 255

Glu Leu Tyr Val Cys
            260


<210> SEQ ID NO 63
```

```
<211> LENGTH: 431
<212> TYPE: PRT
<213> ORGANISM: artificial sequence
<220> FEATURE:
<223> OTHER INFORMATION: synthetic polypeptide (Gc protein N-terminal
      domain)

<400> SEQUENCE: 63

Gly Thr Glu Phe Glu Thr Cys Ile Lys Lys Val Glu Met Thr Pro Glu
1               5                   10                  15

Cys Thr Gly Pro Phe Met Glu Val Gly Ile Cys Asp His Gln Gln Lys
            20                  25                  30

Ser Leu Arg Tyr His Glu Ile Ala Asn Met Leu Leu Gly Lys Gly Thr
        35                  40                  45

Ile Ser Lys Leu Asp Val Asp Ile Ile Asp Ala Leu Pro Asp Arg Ile
    50                  55                  60

Ala Gly Asp Leu Gln Ile Ile Gln Ser Ser Ser Asp Phe His His Gln
65                  70                  75                  80

Gln Met Leu Glu Tyr Val Phe Leu Leu Arg His Cys Asp Tyr Tyr Ser
                85                  90                  95

Ser Phe Val Ser Asp Asn Ser Tyr Ser Gln Ile Leu Trp Gln Thr Ala
            100                 105                 110

Ala Lys Leu Asn Glu Thr Asn Leu Cys Lys His Glu Asn Ser Lys Lys
        115                 120                 125

Ser Cys Lys Cys Leu Lys Ser Asn Ala Asn Cys Gly Glu Ser Glu Asp
    130                 135                 140

Ile Asn Ile Ala Ala Gln Ala Tyr Tyr Lys Asn Lys Glu Ser Glu Leu
145                 150                 155                 160

Gly Gln Asp Leu Thr Thr Ile Met Tyr Ile Leu Lys Lys Met Ile Pro
                165                 170                 175

Gly Ser Gly Tyr Ser Tyr Leu Leu Asn Ala Ala Lys His Asn Lys Leu
            180                 185                 190

Glu Leu Phe Lys Ala Tyr Met Thr Asn Ile Ser Ser Lys Tyr Ser Asn
        195                 200                 205

Asn Lys Lys Leu Lys Asp Phe Met Ala Ile Ile Asn Ala Ile Leu Ala
    210                 215                 220

Asn Leu Ser Ala Leu Ser His Ser Ser Glu Glu Ser Ile Ser Gln Tyr
225                 230                 235                 240

Lys Gln Ile Asp Phe Ser Ser Leu Val Gly Glu Thr Thr Asp Met Leu
                245                 250                 255

Glu Ala Asn Phe Asn Gln Thr Ile Ser Thr Asp Lys Ile Ile Cys Glu
            260                 265                 270

Asn Pro Lys Val Met Ile Cys Ile Ser Pro Arg Thr Lys Val Ser Ser
        275                 280                 285

Gly Glu Leu Tyr Val Cys Gln Arg Ser Gly Lys Tyr Tyr Ile Ile Asp
    290                 295                 300

Thr Gly Lys Phe Lys Leu Tyr Lys Leu Ile Asp Ala Asp Asn Leu Tyr
305                 310                 315                 320

Cys Ala Ala Asp Ala Gln Cys Arg Tyr Glu Phe Arg Ile Leu Thr Thr
                325                 330                 335

Gly Glu Met Gln Ala Thr Phe Lys Asp Asn Cys Lys Ala Ser Val His
            340                 345                 350

Val Asn Thr Pro Gly Tyr Gln Asn Glu Ala Ile Thr His Cys Lys Val
        355                 360                 365

Leu Ala Asn Gly Lys Cys Lys Tyr Asn Asn Gln Thr Ser Ile Asp Ile
```

```
    370                 375                 380

Thr Leu Cys Ala Asn Asn Arg Tyr Tyr Pro Glu Ala Lys Gly Arg Ile
385                 390                 395                 400

Phe Gly Val Asp Pro Glu Asp Leu Cys Phe Asp Lys Thr Cys Thr Lys
                405                 410                 415

Gln Gln Thr Pro Tyr Asn Glu Glu Leu Ile Ser Met Cys Val Trp
            420                 425                 430


<210> SEQ ID NO 64
<211> LENGTH: 254
<212> TYPE: PRT
<213> ORGANISM: artificial sequence
<220> FEATURE:
<223> OTHER INFORMATION: synthetic polypeptide (fragment of Gc protein
      N-terminal domain)

<400> SEQUENCE: 64

Gly Thr Glu Phe Glu Thr Cys Ile Lys Lys Val Glu Met Thr Pro Glu
1               5                   10                  15

Cys Thr Gly Pro Phe Met Glu Val Gly Ile Cys Asp His Gln Gln Lys
            20                  25                  30

Ser Leu Arg Tyr His Glu Ile Ala Asn Met Leu Leu Gly Lys Gly Thr
        35                  40                  45

Ile Ser Lys Leu Asp Val Asp Ile Ile Asp Ala Leu Pro Asp Arg Ile
    50                  55                  60

Ala Gly Asp Leu Gln Ile Ile Gln Ser Ser Ser Asp Phe His His Gln
65                  70                  75                  80

Gln Met Leu Glu Tyr Val Phe Leu Leu Arg His Cys Asp Tyr Tyr Ser
                85                  90                  95

Ser Phe Val Ser Asp Asn Ser Tyr Ser Gln Ile Leu Trp Gln Thr Ala
            100                 105                 110

Ala Lys Leu Asn Glu Thr Asn Leu Cys Lys His Glu Asn Ser Lys Lys
        115                 120                 125

Ser Cys Lys Cys Leu Lys Ser Asn Ala Asn Cys Gly Glu Ser Glu Asp
    130                 135                 140

Ile Asn Ile Ala Ala Gln Ala Tyr Tyr Lys Asn Lys Glu Ser Glu Leu
145                 150                 155                 160

Gly Gln Asp Leu Thr Thr Ile Met Tyr Ile Leu Lys Lys Met Ile Pro
                165                 170                 175

Gly Ser Gly Tyr Ser Tyr Leu Leu Asn Ala Ala Lys His Asn Lys Leu
            180                 185                 190

Glu Leu Phe Lys Ala Tyr Met Thr Asn Ile Ser Ser Lys Tyr Ser Asn
        195                 200                 205

Asn Lys Lys Leu Lys Asp Phe Met Ala Ile Ile Asn Ala Ile Leu Ala
    210                 215                 220

Asn Leu Ser Ala Leu Ser His Ser Ser Glu Glu Ser Ile Ser Gln Tyr
225                 230                 235                 240

Lys Gln Ile Asp Phe Ser Ser Leu Val Gly Glu Thr Thr Asp
                245                 250


<210> SEQ ID NO 65
<211> LENGTH: 2760
<212> TYPE: DNA
<213> ORGANISM: artificial sequence
<220> FEATURE:
<223> OTHER INFORMATION: synthetic polynucleotide coding for Gc protein
      extracellular domain
```

<400> SEQUENCE: 65

```
gcagggacag aatttgaaac atgcatcaag aaagtagaaa tgacaccgga atgcacagga     60
cctttcatgg aagttggaat ctgtgatcac cagcagaaga gcctaagata ccatgagata    120
gctaatatgt tattgggtaa agggacaatc tcaaaattag atgtggatat tatagatgca    180
ttgcctgaca ggatagctgg agacctccag ataatacagt caagcagtga tttccaccat    240
caacagatgc tggaatatgt gtttctattg cgtcattgtg attattactc aagttttgtt    300
tcggataaca gctactcaca aatcttgtgg caaacagcag caaagttaaa tgaaaccaac    360
ctttgcaaac atgagaattc aaagaaatcc tgcaagtgct taaaatcaaa tgcaaattgt    420
ggagagtcag aagacatcaa catagcagca caggcatact acaaaaataa ggaatctgag    480
ctaggacaag atctaacaac cataatgtac atactcaaaa aaatgattcc aggatcaggt    540
tatagttatc tgctaaatgc agccaagcac aacaaattag aattgttcaa agcttacatg    600
actaatattt cctcaaaata ttcaaataac aaaaaattaa aagatttcat ggcgataata    660
aatgctatac tagcaaatct gtcagctctc tcacatagta gtgaagaatc aatctcacaa    720
tacaaacaga ttgatttttc ttccctagta ggcgaaacaa cagacatgct cgaagcaaat    780
tttaatcaaa cgatcagtac agacaagata atttgtgaaa atcctaaagt aatgatttgc    840
atttcaccca ggacaaaagt ttcatccggt gaattgtatg tctgccaaag atcaggaaag    900
tactacataa tagataccgg caaattcaag ctatataaat taattgacgc agacaatttg    960
tactgtgcag cagatgctca gtgtaggtat gaatttagaa ttttaaccac aggggaaatg   1020
caggcaactt ttaaagataa ttgcaaagca tcagtacatg ttaacacccc aggataccaa   1080
aatgaagcta taactcattg caaagtgctc gcgaatggta aatgtaagta taataatcaa   1140
acttcaatag atataacatt gtgtgctaac aacagatatt atcccgaagc aaaaggcagg   1200
atctttggag ttgatccaga agatctatgc tttgataaga catgtactaa acaacagact   1260
ccatacaacg aagaactaat cagtatgtgt gtttgggaaa atccgacact taggccaatc   1320
aaacccagaa ctgaggtttc tatgactttc caagagtaca aagatcagtt attaaagaaa   1380
atcaacacag acctggtgct gcacaaattt gttagaacac aaaacttacc ttatttcata   1440
ccgcaattca agtatataac tatacaagga acgtcaacaa cagacgggat tacttccagt   1500
tttatattct ttgaaattcc tgcattgaca ggagcatctg ctggatacaa agttataaat   1560
agcgaaggcc aagaattgat ggacatggta gtttatatca aaacatcaaa gactagcgca   1620
aagtacaagc gcgtgtatta tacaggcccc actatagcta taaatacaaa acatcaagag   1680
cactgcacag ggacatgtcc tgaaagaata gaacatgatg aaggttgggc aacattttcg   1740
aaagaaagaa ccagcaattg ggctgtgaa gaatttggtt gtctagctgt tgagactggt    1800
tgtttatttg ggtcatgcca ggatgtaatt agaagagaac ttgatgtttt ttcaaagttg   1860
gaggaagata aaatattgac tgaactctgt ataacattaa gccatgacac ttactgcgtg   1920
acaatcgatt ctacaacacc aacaatcaat gattactttg aaatccaata caaaaacagta   1980
gatgtacaaa cattgccaaa gatgatagga gtcactcatc ataagctatt gcgagggcag   2040
ataaacgaat taggatcatt tggcaaattt tgtggcaaca tacaagtagt tggtaatcaa   2100
acatatgggc aggctgcagt aaagtttgat tacatttgcc atgctgcaca aagaaaagat   2160
gtagttataa gaaagtgctt agaaaataat taccaaagtt gtaagctact gacacatgac   2220
acagacttga tacttgaaga aagtaagacc agtgttgaag tcataaacaa taaaaggatt   2280
acaggacaaa tagcactaaa ggtcttgttg ggagacttta actacaagca gtatgctgca   2340
```

```
aatgtagagg ctgacataga agcaaattgc gttgggtgta caaattgtat aaagggaata   2400

acatgtgaaa taaaggtgaa aacagaaatt gaagcatcat gtaaggtaga gcccccatgc   2460

ccctcttaca caagtagaat tataataaaa ccaggtagag acacccacac attattgatg   2520

aagtgtgaca aaaaaataac gactggtgaa ctagcaataa aaatatgtaa tatgcaaatc   2580

caggctcatc tttcaacaat agagagcaat gaccaactag aattgtcgac tggggatcaa   2640

tcaacatata tacatgaaga agacctaagg tgttcaacct ggatctgcaw wgtgagagac   2700

gaagggataa gcttcatctt taagccatta acagactggc ttggaagctt cacaaagccg   2760
```

```
<210> SEQ ID NO 66
<211> LENGTH: 783
<212> TYPE: DNA
<213> ORGANISM: artificial sequence
<220> FEATURE:
<223> OTHER INFORMATION: synthetic polynucleotide coding fo Gc protein
      N-terminal alpha-helix region

<400> SEQUENCE: 66

ctaagatacc atgagatagc taatatgtta ttgggtaaag ggacaatctc aaaattagat     60

gtggatatta tagatgcatt gcctgacagg atagctggag acctccagat aatacagtca    120

agcagtgatt tccaccatca acagatgctg gaatatgtgt ttctattgcg tcattgtgat    180

tattactcaa gttttgtttc ggataacagc tactcacaaa tcttgtggca aacagcagca    240

aagttaaatg aaaccaacct ttgcaaacat gagaattcaa agaaatcctg caagtgctta    300

aaatcaaatg caaattgtgg agagtcagaa gacatcaaca tagcagcaca ggcatactac    360

aaaaataagg aatctgagct aggacaagat ctaacaacca taatgtacat actcaaaaaa    420

atgattccag gatcaggtta tagttatctg ctaaatgcag ccaagcacaa caaattagaa    480

ttgttcaaag cttacatgac taatatttcc tcaaaatatt caaataacaa aaaattaaaa    540

gatttcatgg cgataataaa tgctatacta gcaaatctgt cagctctctc acatagtagt    600

gaagaatcaa tctcacaata caaacagatt gatttttctt ccctagtagg cgaaacaaca    660

gacatgctcg aagcaaattt taatcaaacg atcagtacag acaagataat ttgtgaaaat    720

cctaaagtaa tgatttgcat ttcacccagg acaaaagttt catccggtga attgtatgtc    780

tgc                                                                  783
```

```
<210> SEQ ID NO 67
<211> LENGTH: 1293
<212> TYPE: DNA
<213> ORGANISM: artificial sequence
<220> FEATURE:
<223> OTHER INFORMATION: synthetic polynucleotide coding for Gc protein
      N-terminal domain

<400> SEQUENCE: 67

gggacagaat ttgaaacatg catcaagaaa gtagaaatga caccggaatg cacaggacct     60

ttcatggaag ttggaatctg tgatcaccag cagaagagcc taagatacca tgagatagct    120

aatatgttat tgggtaaagg gacaatctca aaattagatg tggatattat agatgcattg    180

cctgacagga tagctggaga cctccagata atacagtcaa gcagtgattt ccaccatcaa    240

cagatgctgg aatatgtgtt tctattgcgt cattgtgatt attactcaag ttttgtttcg    300

gataacagct actcacaaat cttgtggcaa acagcagcaa agttaaatga aaccaacctt    360

tgcaaacatg agaattcaaa gaaatcctgc aagtgcttaa aatcaaatgc aaattgtgga    420
```

gagtcagaag acatcaacat agcagcacag gcatactaca aaaataagga atctgagcta 480
ggacaagatc taacaaccat aatgtacata ctcaaaaaaa tgattccagg atcaggttat 540
agttatctgc taaatgcagc caagcacaac aaattagaat tgttcaaagc ttacatgact 600
aatatttcct caaaatattc aaataacaaa aaattaaaag atttcatggc gataataaat 660
gctatactag caaatctgtc agctctctca catagtagtg aagaatcaat ctcacaatac 720
aaacagattg atttttcttc cctagtaggc gaaacaacag acatgctcga agcaaatttt 780
aatcaaacga tcagtacaga caagataatt tgtgaaaatc ctaaagtaat gatttgcatt 840
tcacccagga caaaagtttc atccggtgaa ttgtatgtct gccaaagatc aggaaagtac 900
tacataatag ataccggcaa attcaagcta tataaattaa ttgacgcaga caatttgtac 960
tgtgcagcag atgctcagtg taggtatgaa tttagaattt taaccacagg ggaaatgcag 1020
gcaactttta aagataattg caaagcatca gtacatgtta acaccccagg ataccaaaat 1080
gaagctataa ctcattgcaa agtgctcgcg aatggtaaat gtaagtataa taatcaaact 1140
tcaatagata taacattgtg tgctaacaac agatattatc ccgaagcaaa aggcaggatc 1200
tttggagttg atccagaaga tctatgcttt gataagacat gtactaaaca acagactcca 1260
tacaacgaag aactaatcag tatgtgtgtt tgg 1293

<210> SEQ ID NO 68
<211> LENGTH: 762
<212> TYPE: DNA
<213> ORGANISM: artificial sequence
<220> FEATURE:
<223> OTHER INFORMATION: synthetic polynucleotide coding for fragment of Gc protein N-terminal domain

<400> SEQUENCE: 68
gggacagaat ttgaaacatg catcaagaaa gtagaaatga caccggaatg cacaggacct 60
ttcatggaag ttggaatctg tgatcaccag cagaagagcc taagatacca tgagatagct 120
aatatgttat tgggtaaagg gacaatctca aaattagatg tggatattat agatgcattg 180
cctgacagga tagctggaga cctccagata atacagtcaa gcagtgattt ccaccatcaa 240
cagatgctgg aatatgtgtt tctattgcgt cattgtgatt attactcaag ttttgtttcg 300
gataacagct actcacaaat cttgtggcaa acagcagcaa agttaaatga aaccaacctt 360
tgcaaacatg agaattcaaa gaaatcctgc aagtgcttaa aatcaaatgc aaattgtgga 420
gagtcagaag acatcaacat agcagcacag gcatactaca aaaataagga atctgagcta 480
ggacaagatc taacaaccat aatgtacata ctcaaaaaaa tgattccagg atcaggttat 540
agttatctgc taaatgcagc caagcacaac aaattagaat tgttcaaagc ttacatgact 600
aatatttcct caaaatattc aaataacaaa aaattaaaag atttcatggc gataataaat 660
gctatactag caaatctgtc agctctctca catagtagtg aagaatcaat ctcacaatac 720
aaacagattg atttttcttc cctagtaggc gaaacaacag ac 762

<210> SEQ ID NO 69
<211> LENGTH: 19
<212> TYPE: DNA
<213> ORGANISM: artificial sequence
<220> FEATURE:
<223> OTHER INFORMATION: synthetic oligonucleotide (Koongol virus L segment forward primer)

<400> SEQUENCE: 69
gacccaatac tgtaaacag 19

<210> SEQ ID NO 70
<211> LENGTH: 18
<212> TYPE: DNA
<213> ORGANISM: artificial sequence
<220> FEATURE:
<223> OTHER INFORMATION: synthetic oligonucleotide (Koongol virus L segment reverse primer)

<400> SEQUENCE: 70

```
cgtcagaatg caccattg                                                   18
```

<210> SEQ ID NO 71
<211> LENGTH: 240
<212> TYPE: DNA
<213> ORGANISM: Moissiacense virus (Umbre orthobunyavirus strain Moissiacense)
<220> FEATURE:
<221> NAME/KEY: CDS
<222> LOCATION: (1)..(240)

<400> SEQUENCE: 71

```
atg tta gta gaa gta ctt ata acc cag cag atg aat acg ata cgt ttg       48
Met Leu Val Glu Val Leu Ile Thr Gln Gln Met Asn Thr Ile Arg Leu
1               5                   10                  15

tgg gtg tct aca gag aat ttc tca caa ttg ata aca tta gaa tct tct       96
Trp Val Ser Thr Glu Asn Phe Ser Gln Leu Ile Thr Leu Glu Ser Ser
            20                  25                  30

tca tca acg ctc caa agg cca aaa ctg cga tgg cta aac tca aga ccg      144
Ser Ser Thr Leu Gln Arg Pro Lys Leu Arg Trp Leu Asn Ser Arg Pro
        35                  40                  45

aga cag ttg aag tta cat ttg gaa cac tcg ttg tca agc tgg tta ata      192
Arg Gln Leu Lys Leu His Leu Glu His Ser Leu Ser Ser Trp Leu Ile
    50                  55                  60

acc ata gaa ttg gac agg ctc agc gtg agg ttg cgg acg atg agc taa      240
Thr Ile Glu Leu Asp Arg Leu Ser Val Arg Leu Arg Thr Met Ser
65                  70                  75
```

<210> SEQ ID NO 72
<211> LENGTH: 79
<212> TYPE: PRT
<213> ORGANISM: Moissiacense virus (Umbre orthobunyavirus strain Moissiacense)

<400> SEQUENCE: 72

```
Met Leu Val Glu Val Leu Ile Thr Gln Gln Met Asn Thr Ile Arg Leu
1               5                   10                  15

Trp Val Ser Thr Glu Asn Phe Ser Gln Leu Ile Thr Leu Glu Ser Ser
            20                  25                  30

Ser Ser Thr Leu Gln Arg Pro Lys Leu Arg Trp Leu Asn Ser Arg Pro
        35                  40                  45

Arg Gln Leu Lys Leu His Leu Glu His Ser Leu Ser Ser Trp Leu Ile
    50                  55                  60

Thr Ile Glu Leu Asp Arg Leu Ser Val Arg Leu Arg Thr Met Ser
65                  70                  75
```

<210> SEQ ID NO 73
<211> LENGTH: 714
<212> TYPE: DNA
<213> ORGANISM: moissiacense virus (Umbre orthobunyavirus strain Moissiacense)

<400> SEQUENCE: 73
atggctgatt ctaagctcac atacgaggat acacaggatg ttagtagaag tacttataac 60
ccagcagatg aatacgatac gtttgtgggt gtctacagag aatttctcac aattgataac 120
attagaatct tcttcatcaa cgctccaaag gccaaaactg cgatggctaa actcaagacc 180
gagacagttg aagttacatt tggaacactc gttgtcaagc tggttaataa ccatagaatt 240
ggacaggctc agcgtgaggt tgcggacgat gagctaactc ttcaccgact ttctggctac 300
attgcaaagt acactcttca cctatacaaa aatgcaaaaa aagcaggaga gagagaagca 360
ataataacca agatcgttaa tccaatttct gccaaaatgg gcttccaatg gagtgttggg 420
ccggaaattt atctctcaac gctgccagga accgaaatgt ttctagatac atttaaaatg 480
ttcccattgg cattcatctt gttaagagtt aaaagaggag agatcaaggt ggaaatggca 540
aaaaaagcaa tgcggcagaa gtatggcgac aaagatgcca gtgaatggct gcaggaggac 600
attgagactg taaaaggggc aataaaaaca gttgaaaagc tcaagccaac gctgacagga 660
ttggctgctt caatgactgc tttcctgcaa caacttggta tcaacactaa gtaa 714

<210> SEQ ID NO 74
<211> LENGTH: 24
<212> TYPE: RNA
<213> ORGANISM: artificial sequence
<220> FEATURE:
<223> OTHER INFORMATION: Cal/Bwa group Fw primer (RNA equivalent)

<400> SEQUENCE: 74
gcaaauggau uugauccuga ugca 24

<210> SEQ ID NO 75
<211> LENGTH: 25
<212> TYPE: RNA
<213> ORGANISM: artificial sequence
<220> FEATURE:
<223> OTHER INFORMATION: Cal/Bwa group RV primer (RNA equivalent)

<400> SEQUENCE: 75
uuguuccugu uugcuggaaa augau 25

<210> SEQ ID NO 76
<211> LENGTH: 25
<212> TYPE: RNA
<213> ORGANISM: artificial sequence
<220> FEATURE:
<223> OTHER INFORMATION: Moissiacense virus genomic sequence

<400> SEQUENCE: 76
agaaguacuu auaacccagc agaug 25

<210> SEQ ID NO 77
<211> LENGTH: 25
<212> TYPE: RNA
<213> ORGANISM: artificial sequence
<220> FEATURE:
<223> OTHER INFORMATION: Moissiacense virus genomic sequence

<400> SEQUENCE: 77
cgcugagccu guccaauucu auggu 25

<210> SEQ ID NO 78
<211> LENGTH: 26
<212> TYPE: RNA
<213> ORGANISM: artificial sequence
<220> FEATURE:
<223> OTHER INFORMATION: Bunyamwera group Fw primer (RNA equivalent)

<400> SEQUENCE: 78
cugcuaacac cagcaguacu uuugac 26

<210> SEQ ID NO 79
<211> LENGTH: 28
<212> TYPE: RNA
<213> ORGANISM: artificial sequence
<220> FEATURE:
<223> OTHER INFORMATION: Bunyamwera group Rv primer (RNA equivalent)

<400> SEQUENCE: 79
uggaggguaa gaccaucguc aggaacug 28

<210> SEQ ID NO 80
<211> LENGTH: 26
<212> TYPE: RNA
<213> ORGANISM: artificial sequence
<220> FEATURE:
<223> OTHER INFORMATION: Moissiacense virus genomic sequence

<400> SEQUENCE: 80
aggauguuag uagaaguacu uauaac 26

<210> SEQ ID NO 81
<211> LENGTH: 28
<212> TYPE: RNA
<213> ORGANISM: artificial sequence
<220> FEATURE:
<223> OTHER INFORMATION: Moissiacense virus sequence

<400> SEQUENCE: 81
ugaagaguua gcucaucguc cgcaaccu 28

<210> SEQ ID NO 82
<211> LENGTH: 29
<212> TYPE: RNA
<213> ORGANISM: artificial sequence
<220> FEATURE:
<223> OTHER INFORMATION: Wyeomyia Fw primer (RNA equivalent)

<400> SEQUENCE: 82
augucugaaa uuguauuuga ugauauugg 29

<210> SEQ ID NO 83
<211> LENGTH: 21
<212> TYPE: RNA
<213> ORGANISM: artificial sequence
<220> FEATURE:
<223> OTHER INFORMATION: Wyeomyia Rv primer (RNA equivalent)

<400> SEQUENCE: 83
uauuucgauu ccccggaaag u 21

<210> SEQ ID NO 84
<211> LENGTH: 29
<212> TYPE: RNA
<213> ORGANISM: artificial sequence
<220> FEATURE:
<223> OTHER INFORMATION: Moissiacense virus genomic sequence

<400> SEQUENCE: 84
gauucuaagc ucacauacga ggauacaca 29

<210> SEQ ID NO 85

<211> LENGTH: 21
<212> TYPE: RNA
<213> ORGANISM: artificial sequence
<220> FEATURE:
<223> OTHER INFORMATION: Moissiacense virus genomic sequence

<400> SEQUENCE: 85
gcugagccug uccaauucua u 21

<210> SEQ ID NO 86
<211> LENGTH: 22
<212> TYPE: RNA
<213> ORGANISM: artificial sequence
<220> FEATURE:
<223> OTHER INFORMATION: Oropouche Fw primer (RNA equivalent)

<400> SEQUENCE: 86
ggcccauggu ugaccuuacu uu 22

<210> SEQ ID NO 87
<211> LENGTH: 21
<212> TYPE: RNA
<213> ORGANISM: artificial sequence
<220> FEATURE:
<223> OTHER INFORMATION: Oropouche Rv primer (RNA equivalent)

<400> SEQUENCE: 87
accaaaggga agaaagugaa u 21

<210> SEQ ID NO 88
<211> LENGTH: 22
<212> TYPE: RNA
<213> ORGANISM: artificial sequence
<220> FEATURE:
<223> OTHER INFORMATION: Moissiacense virus genomic sequence

<400> SEQUENCE: 88
ccgagacagu ugaaguuaca uu 22

<210> SEQ ID NO 89
<211> LENGTH: 21
<212> TYPE: RNA
<213> ORGANISM: artificial sequence
<220> FEATURE:
<223> OTHER INFORMATION: Moissiacense virus genomic sequence

<400> SEQUENCE: 89
gccaauggga acauuuuaaa u 21

<210> SEQ ID NO 90
<211> LENGTH: 714
<212> TYPE: DNA
<213> ORGANISM: Umbre orthobunyavirus strain Marna

<400> SEQUENCE: 90
atggctgatt ctaaactcac atacgaggat acgcaggatg ttagtagaag tacttataac 60
ccagcagatg aatacgatac gtttgtgggt gtctacagag aatttctcac aattgataac 120
attagaatct tcttcatcaa cgctccaaag gccaaagctg cgatggctaa actcaagacc 180
gagacagttg aagttacgtt tggaacactc gtcgtcaagc tggttaataa ccatagaatt 240
ggacaggctc agcgtgaggt tgcggacgat gagctaactc ttcaccggct ttctggctac 300
attgcgaagt acactcttca cctatacaag aatgcaaaaa aagcaggaga gagagaagca 360
ataacaacca aaatagttaa tccaatttct gccaaaatgg gcttccaatg gagcgttggg 420

```
ccagaaattt acctttcaac actgccagga actgaaatgt ttctagatac atttaaaatg    480

ttcccattgg cattcatctt ggtgagagtt aagagaggag aaatcaaggt agagatggcg    540

aaaaaagcaa tgcggcagaa atatggcgac aaagatgcca gtgaatggct gcaggaggac    600

attgagactg tgaaaggggc aataaaaaca gttgaaaagc tcaagccaac gctgacagga    660

ttggctgctt caatgaccgc tttcctgcaa caacttggta tcaacactaa gtaa          714
```

<210> SEQ ID NO 91
<211> LENGTH: 4389
<212> TYPE: DNA
<213> ORGANISM: Umbre orthobunyavirus strain Marna

<400> SEQUENCE: 91

```
atggtgatct ttgcattgtt gttgatatta ttggttgggt tcagcaatca agcgactatt     60

cgatgcttct ctggcggctc caaaattatg gaaaaaacat cgaatgtctc attgagtgag    120

ttatgcttga aggatgatgt aagccagcta aaaattatag ttgaccacac taaaaatgac    180

tcaggattgt tttcaactgc cagcgtctgg agaaaatgga tagtttcaga ctggaccaca    240

tgcaacccta aaaaaatggc cttgggaact atatctgtca tagacatcga taagaacttt    300

atcttaaaaa gctccagcta catatgcaat aaagagtgca cgataacagt agataaagaa    360

agggcccaag ttttgctaca gtcggatgga ttaaaccatt ttgaggtttc tggaaccact    420

ttaagttctg gatggtttaa actgacagcc actgttacct tagaccaaac ttgcgagcat    480

gttaaagtgt cttgtggtca aaaatcaatg caattccatg cctgtttcaa gaatcatatg    540

tcatgcatta gattcttgca tagaagtata atgccagcaa gctttgcagt ttccatctgc    600

caaaatatag agttgatatt aatgacaaca tttacactga ttatattttt gctattgagc    660

attttgacca aaacatacat atgctacatt ttgctaccca tatttatacc cttcgcgtac    720

gcatacggat tcatttatga taagacatgc aagaagtgct cattgtgtgg gttggcttat    780

cacccttttta caaagtgtgg gacacactgc gtctgtggat gtagatttga aaattcagat    840

gcaatgaaaa cccacagaga aaaagggaaa tgtccgggat tcaagtcaat gagaactgct    900

agggtactat gtaaggctaa aggttcagct ttcactttat ctgtactatt ggccacatta    960

gcattgggct tcttgacgcc tgtgcaaggg ctagttttag atgagaccca aattagttac   1020

acagaagatc aattaccaga atcatttcag gtgatgcaat caacaatatc catattcaaa   1080

tttgcaacaa ttatgaatgc aggttggact tactgcatgt tcctagttac attggcttta   1140

tatatcatat acaagaagta tgcccacagg ttattaagct attatgtgat acattgcaag   1200

gagtgtgata tgcttcatga caaaagtggg cttaagtata atggtgattt tactaacaaa   1260

tgcgggtttt gcacatgtga gcaagttgaa gatgcaatgg ggctgactgt ccatcaaata   1320

cgaaatcatt gctctgccaa ttatagaact aagttggtgc tgaactggat ggttgtacta   1380

ttattagcta ctctaatcaa gaatagcata atgttgacta ctgcagcagg gacagaattt   1440

gaaacatgca tcaagaaagt agaaatgaca cctgaatgca caggaccttt catggaagtt   1500

ggaatctgta atcaccaaca aaaaagctta agataccacg agatagctaa tatgttattg   1560

ggtaaaggga caatctcaaa attagatgtg gacattatag atgcattgcc tgacaagata   1620

gctggagacc tccaggtaat acaatcaagc agtgatttcc atcatcagca gatgctggag   1680

tatgtgtttc tattacgtca ttgtgattac tactcaagtt ttgtttcaga taacagctac   1740

tcgcaaattt tatggcaaac agcagcaaaa ttaaatgaaa tcaacctttg caaacatgag   1800
```

-continued

```
agttcaaaaa agtcctgcaa gtgcttaaaa tcaaatgcaa attgtggaga gtcagaagac   1860
atcaatacag cagcacaggc atattacaaa aataaagagt ctgagctagg acaggattta   1920
acaaccataa tgtacatact caaaaaaatg attccaggat caggttatag ttatctgcta   1980
aatgcaacta agcacaacaa attagaattg tttaaagctt acatgactaa tatttcttca   2040
aaatatccaa acaacaagaa attaaaagat tttgtggcaa taacaaatgc tatactagca   2100
gatctatcag ctctctcgca tagtagtgaa gaatcaatcc cagaatataa gcagattgac   2160
ttttcttccc tagtaggtga aacaacagac atgcttgaag caaattttaa tcaaacaatc   2220
agcacagaca agatagtttg cgaaaatcct aaagtaatga tttgcatttc accaagagtt   2280
tcatctggtg aattatatgt ctgccaaaaa ttgggaaagt actacataat agatactggc   2340
aggtttaagt tatataaatt ggttgatgca gacaatttgt actgtgcagc agatgctcag   2400
tgcaggtatg aatttagaat tctaaccaca ggagaaatgc aggcaacttt taaagataat   2460
tgtaaagcat caatacatac taacacccca ggatatcaga atgaagctat aactcactgc   2520
aaggtgcttg cgaatgggaa atgtaaatat gacaatcaaa ctttaataga cgtaacattg   2580
tgtgctaaca acagatatta tcccgaagca aagggcagga tttttggagt tgatccagaa   2640
gatctatgct ttgacaagac atgcaccaag ctacaaactc catacaacga agaactcatc   2700
agtatgtgtg tttgggaaaa tccgacactt agaccaatca gacccagaac tgagatttcc   2760
atgactttcc aagagtacaa agatcagtta ctaaaaaaaa tcaacacaga tctggtgctg   2820
cataaatttg ttagaacaca aaacttgcct tatttcatac cgcaatttaa gtacataact   2880
atacaaggaa cgtcaacaac agatgggatt acttccagtt ttatattctt tgaaatccct   2940
gcactgacag ggcatctgc tggatacaaa gttataaata gtgaaggtca agaactaatg   3000
gacatggtag tttatgtcaa aacatcaaaa accagcgcaa agtataagcg catgtactat   3060
acaggcccca ctatagctat aaatgcaaaa catcaagagc actgcacagg cacatgtcct   3120
gaaaggatag aacatgatga cggttgggca acattttcga aagaaagaac cagcaattgg   3180
gggtgtgaag aatttggttg tctagctgtt gagactggtt gtttatttgg gtcatgccag   3240
gatgtaatta gaagagaact cgatgttttt tcaaaattgg aggaagataa aatattgact   3300
gaactctgta taacattaag tcatgacact tactgcgtga caattgactc tacaacacca   3360
acaatcaatg attactttga aattcaatat aaaacagtag atgtacaaac attgccaaag   3420
atgatagggg tcactcatca taagctattg cgagggcaga taaacgaatt agggtcattt   3480
ggcaaatttt gtggcgacat acaagtagtt ggtaatcaaa catatgggca agctgcagtg   3540
aagtttgatt acatctgtca tgctgcacag agaaaagatg tagttataag aaaatgctta   3600
gagaataatt accaaagttg taagctactg acacatgaca cagacttgat mcttgaagaa   3660
agtgagacta gcgttgaagt cataaacaac aaaaggatta caggacaaat agcactaaaa   3720
gtcttgttgg gagactttaa ctacaagcag tatgctgcaa atgtggaagc tgacatagaa   3780
gcaaattgtg ttggatgtac aaattgtata aaagggataa catgtgaaat aaaggtgaaa   3840
acagaaattg aagcatcatg caaagtagag cccccatgtc cttcttacac gaatagaatt   3900
ataataaaac caggtagaga cacccacaca ttgttgatga agtgtgacaa aaaaataatg   3960
actggtgaat tagcaataaa gatatgtaat atgcaaatcc aagctcatct ttcaacaata   4020
gaaagtaatg accaactaga attgtcaact ggggatcaat caacatatat acatgaagaa   4080
gacctaaggt gctcaacctg gatctgcaaa gtgagagatg aagggataag cttcatcttt   4140
aagccattga cagattggct tggaagcttc acaaaaccaa tacttatagc tggctgcata   4200
```

ataattgtcg caattatttt gatttatata ttaatgccta tgtgtgctaa gctcagagat 4260
ttgttaaaaa agaacgagta tgaatatcta caagatacaa aagtgattgt aaagcccaag 4320
gctacagcta gctcaatcgg cttgagatcg aagaaaataa atatccaatc atctaaagca 4380
gttgattaa 4389

<210> SEQ ID NO 92
<211> LENGTH: 6828
<212> TYPE: DNA
<213> ORGANISM: Umbre orthobunyavirus strain Marna

<400> SEQUENCE: 92
atgttggatc aagaaaatga gcaagcttta aatagacttg cagctacagt tgcaagagca 60
aatgagcctg ccgaaggtaa agaagcatat aatgctatac tgagtagaag gcatgactac 120
tttgggcaag ttttttgcga gactataggc ataccatata gaaacgatgt tcggctagaa 180
gatatcctac atgaatgcga ccaaacagtt gacactctaa caaataaaat accaaacata 240
actccagaca atttcgagtt tagagacaat atcctaacta ttatagatta taaagtggca 300
gttagtgatg aaagtgctga ctatactcgt gaaaagtatg aaaatgctgt tgatgctata 360
aagcatttgg ttgacttccc tattagagtg tgtatagtta ggatacatcc atacactaga 420
caagttactt actcagatga caactttatg agacgatttg cccatgtggt ataccctgtt 480
gattttacaa gatacactca attgactgaa gaactcaagg aaaaatttgc agatagccct 540
gagtttatgg atatgatagc atatggcgat gtcactttta ctgcaaactg gtgtcaaaat 600
ggatgccctg agttgtacga gcatccaata tttaaagagt ttttagagag catgccattg 660
aaataccaga aattgtttga aaaatcttta ctaagctctt gctatacttc tgagagatgg 720
gattccaatc ttaaagaagt caaggctgca actaaagatg agtatgaaga tttcatatct 780
cgatctgcaa aacaactcta tacaacatct cctgactatt cagaacctag tcgagaggaa 840
attctaaaag ggtgggaaga aatgacagaa agagtgaaag aacaaaggga agtatcctca 900
aatattaatg accaaaaacc aagtgctcac ttcatatggg ctgaaaacaa tcacgaactg 960
cctactgcaa attctgctaa gatatgtgca atttcaaaac ttctacagtc cattaatata 1020
gaaagctctt ttgctgaaga ttttaaaaga ctaggcaaat tattcgactt ttctgaagat 1080
attcctggat atgagcgaca ttgcgaacaa cttaaaaggc aggctagatc aaatccagga 1140
caaataaaaa ccaaaaaact agacccaaag aaaattggga atgcattagt tttatgggag 1200
caacaatttt tattatctgc agacgaaatg ggaaaagaga ataagctaca cctacttaaa 1260
gacttctttg gcatagggaa acataagcaa tttgcaagaa aaggcctaga tgacaccgaa 1320
acagacaaac caacaatctt agatttcaat gatacagaag tcaaaagatc agcagaatta 1380
atgatgcaaa aaacaaaact ctacttatct ggcaaatcat cactcaataa agagcatcct 1440
atagcatcag aatatcttaa tgaaataaaa aagtgtaatg acgagacata taatgtcctt 1500
aatgcgatct ttcagacaaa gtattggcaa tgtatcacag acattagcat gctaatgaaa 1560
aatatgctat ctgtgtcaca gtataataga aacaatactt tcagaattgc aacatgtgct 1620
aataatgcac tatatggact tatttttcca tcagcagaca ttaaaacaaa ggatgcaagc 1680
attgtatatt gcattattgc aattcacaaa gatgagaagt ctttattcaa tccaggagct 1740
ctgcatgcaa cttttaaagt gccaggtggc tttttatcta tatctaaatc aatgcggctc 1800
gacaagaagc gctgccatag aatagttact agtccaggca tattcttaac aattgccacc 1860

```
atgttgaaag gggacaatcc aaccattagt ctaaacgatg tcttaaattt tagcattttt   1920
gcaagcttga acataactaa gagcatgcta tcattaacag agccttctag gtatatgatc   1980
atgaactcgc tagcagtctc tagtcatgta cgagaatata tctctgagaa attttcacca   2040
tatactaaaa ctctctttag tgtccatatg gttgagaaaa taaaagcagg ttgcctaaat   2100
gcattcaaac aaagagaaaa aatcaagact cgggacatat acttgacaga catagatata   2160
actcaaaaag ggatacaaga taacagagat ctatgtagca tatggtttga tggtaatgtc   2220
actttgaaag aatatctgaa tcagatttat attgtctttt atctgaatcc gaaggcattg   2280
catgaaaagc atcatgtaat gatagatcta cttaaaacag tgatagaaat agaacttgat   2340
caaagggaga atgtccctca accatggtct gatgtcccta aaaagcagac tgtcaagtta   2400
cccattcttg ttcatagcct ggcaaagaat ctactcttgg acacttcatt tgcacatttc   2460
ttaagatcta gaattgaaag tcgcaataat tttagacgca cgtttgcaac aatttcaacc   2520
tttacaagta gtaagagttg cttaaaaaca ggcaatttcc atgaattcaa gattaagcaa   2580
tgtcaaaggc tcaaaaaagt gaatgcgagt gaagcaaaga aacatagaat agcaaatgct   2640
atgtttgtcg aggaacaaga tcaacatttg gaggtggagc atgcaaacta cgaattgatg   2700
aggaaggcaa tcccggatta tgtggatgtc ttatcaacca aggtatttga tagattgtat   2760
gagttataca aaactggaga aatcgacgat agtcctgtta tccaccagat ttttgcgacc   2820
atgaaaagtc acactaaatt ctacttcact tattttaaca agggccaaaa gacagcaaaa   2880
gaccgagaaa tattcgtagg ggaatatgag gccaaaatgt gcatgtacct ggtagaaaga   2940
atatataaag agagatcgaa agtcaatcca gacgagatga tcagtgaacc aggagatggg   3000
aaactcagag tgttagagcg caaagcagag caagagataa gattcatggt tgaaaaaatg   3060
aaagcaaaga atgatgaaat aaataaggaa atcgaggatg caaaagacaa ttatgtctta   3120
aatctaggga aaatagcagc tttgcaagca caaaaaataca aagctttaaa attggaaatc   3180
aatgcagaca tgtcaaagtg gagtgctcag gatgtatttt ttaaatactt ttggtctatc   3240
tgtcttgacc cgattctcta tcctgaagaa aaagaacaca ttttatattt tttttgtaat   3300
tatatgcaaa aagaattggt tatcccagac gaagttatct gtaacatcct agaccagagg   3360
aaagcatacc ctaatgacat aattagccag atcacaaatg gattgacaac taaccatttc   3420
aatgtaaaaa ggaactggct acaaggcaat ttcaattaca tgtccagcta tgctcacagt   3480
acagcaatgt ctgtctttaa agatgtgata aagcgtgctg cagatttact agaagctgaa   3540
gttttgattc attctatggt tcactctgat gataatcaaa cctctgtaac attagttgac   3600
aataggatat gcccaaagca attcacagca tttgtaatca atacatttga aaagatctgc   3660
ctgacatttg gctgtcaagc caatatgaaa aaaacctata tcaccaacca tataaaagaa   3720
tttgtttcat tatttaattt atatggggaa ccattttcaa tttacggcag attcacatta   3780
acatctgttg gagactgtgc atacattgga ccatatgaag acctcgcaag cagaatatca   3840
gcaacacaga ctgggataaa gcatggatgc ccagctagcc aagcctggtt atcaattgct   3900
atcgcccaat ggatgactta tttgacatac aatatgttgc caggccaaca aaatgatccc   3960
cagccaatat tagaaatcga tagaaagcaa ttgccacttg aattgggtgg gtacatttct   4020
tgtcctctat ccttaatagc tttagctgga ttggaatctg gaaacattga tttcctgatc   4080
aaattagtaa acaaatatat cgaccccaga cttcaacgtg aacctattca agaccaatgc   4140
actgatataa agaactggga tatttcaaaa cttagcaaag ttgaaatatt taagctaaaa   4200
gtgctgcgct atttagtttt agatgcagag atggataata ctgacattat gggagaaacc   4260
```

agtgagatga gaggaagatc tctactaaca cccagaaagt tcacaacagc tgggtctttg 4320
aggaaattag tatcttttga agacttccag gcggtccaag attctgaaca aggtgtggat 4380
tctatagttg agtacatgtt gcaaaaccca gcattacttg tgacaaaggg agaaacaaaa 4440
gacgactata tgaacactgt gctctataga tacaactcaa agaaatttaa agaatcatta 4500
tctattcaga accctactca gctcttcttg gaacaaatcc tattctcgca caaacctatt 4560
gttgattata caggtatcgc agaaaaattc tcaaatctta atgatggaac catgcttgaa 4620
gataatccga caataaaagg tagaatgacc ttcacagatg ctttcgcaat gattaagaaa 4680
gatctatcaa cactcagaat cactaatgag gatcttgaaa ttgttctaaa atttataatt 4740
ttgaatgacc ctttaactgt gactgctgct aatgcccata tcttgcatgt aataggccat 4800
tcacaaccca ggcttgggtc aacagcttgt gttatgcctg aatttaggaa tttgagaatg 4860
ataaaacatt cacctgcact agtcttgaag tgttatagta aaaacacttt gttgctgcct 4920
ggggtgcaag aaagggacat ggaaagagac cttaaccatc taaaaacatt tattgagact 4980
acaagattag agcataaaat gcaagataga attaagaaaa atgaagatct caaaaaatca 5040
aaggatattt acttcgaaat caaagaggta accagatttt atcaaacatg ctatgaatat 5100
gtcaaaagta ctgattataa ggtaaaagta ttcatattgc cagccaaatg tatgactcaa 5160
acagattttt gtgctgtatt acagggttca ttattagaag ataaaaagtg gaaattaata 5220
caacacctta gacctgttac tgcaggtggc cataaaggag aggttcaacc agtagtttcc 5280
atggatttta aactagcacg agaggccgtg aatttgttat gtttttcac tgattcattc 5340
atagactcta gatataggag agactttctt ctaaaagcat gcgtagaaat ggcttataaa 5400
gataggccta tggtcacatt gatagaagaa ataaagaagt caaagaacag aacatctttc 5460
ttaccattct tgtatagaat tggtgagtta actcaagaag acctcgatgc atatgatgct 5520
caaaaggctg gggaagagt aacctggaat cactggcagt ccacaagaag tttgaacatg 5580
ggaaagatag attttcaaat agatacacac aaaactcatc tccatattat tggtgaagat 5640
caacaactgg tgatagcaga actaaaaatt cctaagttga cagcaaatgc catcactcaa 5700
gcagggtata gacttttgaa tgaaaagcat gggtttcggt ttgaaacgat gaatgaagtt 5760
ttagtccagc caagaaaata ttatataaca taccagatga aatctaaaaa gcaatatgtc 5820
tataaaatct ttgacacagc gacgttgcta tatgaaagaa gaaatataaa gcaatacaca 5880
ggtcgagaag caaatcccat agtagcagtc tgtgaagttg ttccaatgga ggaggaggaa 5940
actcctgctt taagcctaag cgacatagaa atgtataatg ctgacaacga atcagttagt 6000
attttaaaaa catcatttaa tgagagtgct aagatgagac gtgcaaactt gtccaaaatg 6060
caatattttg agactattgg aggatcaatg ttgaaaattc gattcatcaa tgttaatgca 6120
ctaatgaaag acacaactct aatgtccctt aactatgaca atctggtaaa tgttgatcta 6180
gctagattta gcaagttatt ggactgtgac ggtgacacag aaagtgttga agatggcata 6240
ttgtgctttt ctgatgaccc aatggaacaa accacaacag aagagatcga tgcaattcct 6300
ctctttaaag taagctacaa gatatcagca cctgccagat taacatacaa gaatgccatt 6360
agggaactgt taaggaggga aataacaagg tttatggatg cttttacctt tgttggacct 6420
tcttttgatt ctccagaaaa tatggggttc atatgcaata tatgttgtat aatacaactc 6480
ctccatacaa acgaatggtc tatcataatg ctaaactgta tccacatctg catgatatat 6540
ttggaaaaag acataaggtt ccataaattt ctgctaaata gaatattttt tgaggggttg 6600
aatcctgcat ctggaaaatt ggattacaag aaaattaaag aatttgtaat cagcctgaaa 6660
gatagggaga tggctccttg gaatgagata ttttcaaaat tcaagcaaaa atgtgtcaca 6720
ttgctagata aagaaataac aagaatagaa caaaacacaa actttgaaaa catactagct 6780
ttagatgaaa acacagatga tcagtctgaa ttcctcttgt ttgaatag 6828

<210> SEQ ID NO 93
<211> LENGTH: 237
<212> TYPE: PRT
<213> ORGANISM: Umbre orthobunyavirus strain Marna

<400> SEQUENCE: 93

Met Ala Asp Ser Lys Leu Thr Tyr Glu Asp Thr Gln Asp Val Ser Arg
1               5                   10                  15

Ser Thr Tyr Asn Pro Ala Asp Glu Tyr Asp Thr Phe Val Gly Val Tyr
            20                  25                  30

Arg Glu Phe Leu Thr Ile Asp Asn Ile Arg Ile Phe Phe Ile Asn Ala
        35                  40                  45

Pro Lys Ala Lys Ala Ala Met Ala Lys Leu Lys Thr Glu Thr Val Glu
    50                  55                  60

Val Thr Phe Gly Thr Leu Val Val Lys Leu Val Asn Asn His Arg Ile
65                  70                  75                  80

Gly Gln Ala Gln Arg Glu Val Ala Asp Asp Glu Leu Thr Leu His Arg
                85                  90                  95

Leu Ser Gly Tyr Ile Ala Lys Tyr Thr Leu His Leu Tyr Lys Asn Ala
            100                 105                 110

Lys Lys Ala Gly Glu Arg Glu Ala Ile Thr Thr Lys Ile Val Asn Pro
        115                 120                 125

Ile Ser Ala Lys Met Gly Phe Gln Trp Ser Val Gly Pro Glu Ile Tyr
    130                 135                 140

Leu Ser Thr Leu Pro Gly Thr Glu Met Phe Leu Asp Thr Phe Lys Met
145                 150                 155                 160

Phe Pro Leu Ala Phe Ile Leu Val Arg Val Lys Arg Gly Glu Ile Lys
                165                 170                 175

Val Glu Met Ala Lys Lys Ala Met Arg Gln Lys Tyr Gly Asp Lys Asp
            180                 185                 190

Ala Ser Glu Trp Leu Gln Glu Asp Ile Glu Thr Val Lys Gly Ala Ile
        195                 200                 205

Lys Thr Val Glu Lys Leu Lys Pro Thr Leu Thr Gly Leu Ala Ala Ser
    210                 215                 220

Met Thr Ala Phe Leu Gln Gln Leu Gly Ile Asn Thr Lys
225                 230                 235

<210> SEQ ID NO 94
<211> LENGTH: 90
<212> TYPE: PRT
<213> ORGANISM: Umbre orthobunyavirus strain Marna

<400> SEQUENCE: 94

Met Ile Leu Asn Ser His Thr Arg Ile Arg Arg Met Leu Val Glu Val
1               5                   10                  15

Leu Ile Thr Gln Gln Met Asn Thr Ile Arg Leu Trp Val Ser Thr Glu
            20                  25                  30

Asn Phe Ser Gln Leu Ile Thr Leu Glu Ser Ser Ser Ser Thr Leu Gln
        35                  40                  45

Arg Pro Lys Leu Arg Trp Leu Asn Ser Arg Pro Arg Gln Leu Lys Leu

```
    50                  55                  60

Arg Leu Glu His Ser Ser Ser Ser Trp Leu Ile Thr Ile Glu Leu Asp
65                  70                  75                  80

Arg Leu Ser Val Arg Leu Arg Thr Met Ser
                85                  90


<210> SEQ ID NO 95
<211> LENGTH: 1462
<212> TYPE: PRT
<213> ORGANISM: Umbre orthobunyavirus strain Marna

<400> SEQUENCE: 95

Met Val Ile Phe Ala Leu Leu Leu Ile Leu Leu Val Gly Phe Ser Asn
1               5                   10                  15

Gln Ala Thr Ile Arg Cys Phe Ser Gly Gly Ser Lys Ile Met Glu Lys
            20                  25                  30

Thr Ser Asn Val Ser Leu Ser Glu Leu Cys Leu Lys Asp Asp Val Ser
        35                  40                  45

Gln Leu Lys Ile Ile Val Asp His Thr Lys Asn Asp Ser Gly Leu Phe
    50                  55                  60

Ser Thr Ala Ser Val Trp Arg Lys Trp Ile Val Ser Asp Trp Thr Thr
65                  70                  75                  80

Cys Asn Pro Lys Lys Met Ala Leu Gly Thr Ile Ser Val Ile Asp Ile
                85                  90                  95

Asp Lys Asn Phe Ile Leu Lys Ser Ser Ser Tyr Ile Cys Asn Lys Glu
            100                 105                 110

Cys Thr Ile Thr Val Asp Lys Glu Arg Ala Gln Val Leu Leu Gln Ser
        115                 120                 125

Asp Gly Leu Asn His Phe Glu Val Ser Gly Thr Thr Leu Ser Ser Gly
    130                 135                 140

Trp Phe Lys Leu Thr Ala Thr Val Thr Leu Asp Gln Thr Cys Glu His
145                 150                 155                 160

Val Lys Val Ser Cys Gly Gln Lys Ser Met Gln Phe His Ala Cys Phe
                165                 170                 175

Lys Asn His Met Ser Cys Ile Arg Phe Leu His Arg Ser Ile Met Pro
            180                 185                 190

Ala Ser Phe Ala Val Ser Ile Cys Gln Asn Ile Glu Leu Ile Leu Met
        195                 200                 205

Thr Thr Phe Thr Leu Ile Ile Phe Leu Leu Leu Ser Ile Leu Thr Lys
    210                 215                 220

Thr Tyr Ile Cys Tyr Ile Leu Leu Pro Ile Phe Ile Pro Phe Ala Tyr
225                 230                 235                 240

Ala Tyr Gly Phe Ile Tyr Asp Lys Thr Cys Lys Lys Cys Ser Leu Cys
                245                 250                 255

Gly Leu Ala Tyr His Pro Phe Thr Lys Cys Gly Thr His Cys Val Cys
            260                 265                 270

Gly Cys Arg Phe Glu Asn Ser Asp Ala Met Lys Thr His Arg Glu Lys
        275                 280                 285

Gly Lys Cys Pro Gly Phe Lys Ser Met Arg Thr Ala Arg Val Leu Cys
    290                 295                 300

Lys Ala Lys Gly Ser Ala Phe Thr Leu Ser Val Leu Leu Ala Thr Leu
305                 310                 315                 320

Ala Leu Gly Phe Leu Thr Pro Val Gln Gly Leu Val Leu Asp Glu Thr
                325                 330                 335
```

```
Gln Ile Ser Tyr Thr Glu Asp Gln Leu Pro Glu Ser Phe Gln Val Met
            340                 345                 350

Gln Ser Thr Ile Ser Ile Phe Lys Phe Ala Thr Ile Met Asn Ala Gly
        355                 360                 365

Trp Thr Tyr Cys Met Phe Leu Val Thr Leu Ala Leu Tyr Ile Ile Tyr
    370                 375                 380

Lys Lys Tyr Ala His Arg Leu Leu Ser Tyr Tyr Val Ile His Cys Lys
385                 390                 395                 400

Glu Cys Asp Met Leu His Asp Lys Ser Gly Leu Lys Tyr Asn Gly Asp
                405                 410                 415

Phe Thr Asn Lys Cys Gly Phe Cys Thr Cys Glu Gln Val Glu Asp Ala
            420                 425                 430

Met Gly Leu Thr Val His Gln Ile Arg Asn His Cys Ser Ala Asn Tyr
        435                 440                 445

Arg Thr Lys Leu Val Leu Asn Trp Met Val Val Leu Leu Leu Ala Thr
    450                 455                 460

Leu Ile Lys Asn Ser Ile Met Leu Thr Thr Ala Ala Gly Thr Glu Phe
465                 470                 475                 480

Glu Thr Cys Ile Lys Lys Val Glu Met Thr Pro Glu Cys Thr Gly Pro
                485                 490                 495

Phe Met Glu Val Gly Ile Cys Asn His Gln Gln Lys Ser Leu Arg Tyr
            500                 505                 510

His Glu Ile Ala Asn Met Leu Leu Gly Lys Gly Thr Ile Ser Lys Leu
        515                 520                 525

Asp Val Asp Ile Ile Asp Ala Leu Pro Asp Lys Ile Ala Gly Asp Leu
    530                 535                 540

Gln Val Ile Gln Ser Ser Ser Asp Phe His His Gln Gln Met Leu Glu
545                 550                 555                 560

Tyr Val Phe Leu Leu Arg His Cys Asp Tyr Tyr Ser Ser Phe Val Ser
                565                 570                 575

Asp Asn Ser Tyr Ser Gln Ile Leu Trp Gln Thr Ala Ala Lys Leu Asn
            580                 585                 590

Glu Ile Asn Leu Cys Lys His Glu Ser Ser Lys Lys Ser Cys Lys Cys
        595                 600                 605

Leu Lys Ser Asn Ala Asn Cys Gly Glu Ser Glu Asp Ile Asn Thr Ala
    610                 615                 620

Ala Gln Ala Tyr Tyr Lys Asn Lys Glu Ser Glu Leu Gly Gln Asp Leu
625                 630                 635                 640

Thr Thr Ile Met Tyr Ile Leu Lys Lys Met Ile Pro Gly Ser Gly Tyr
                645                 650                 655

Ser Tyr Leu Leu Asn Ala Thr Lys His Asn Lys Leu Glu Leu Phe Lys
            660                 665                 670

Ala Tyr Met Thr Asn Ile Ser Ser Lys Tyr Pro Asn Asn Lys Lys Leu
        675                 680                 685

Lys Asp Phe Val Ala Ile Thr Asn Ala Ile Leu Ala Asp Leu Ser Ala
    690                 695                 700

Leu Ser His Ser Ser Glu Glu Ser Ile Pro Glu Tyr Lys Gln Ile Asp
705                 710                 715                 720

Phe Ser Ser Leu Val Gly Glu Thr Thr Asp Met Leu Glu Ala Asn Phe
                725                 730                 735

Asn Gln Thr Ile Ser Thr Asp Lys Ile Val Cys Glu Asn Pro Lys Val
            740                 745                 750

Met Ile Cys Ile Ser Pro Arg Val Ser Ser Gly Glu Leu Tyr Val Cys
```

```
        755                 760                 765

Gln Lys Leu Gly Lys Tyr Tyr Ile Ile Asp Thr Gly Arg Phe Lys Leu
    770                 775                 780

Tyr Lys Leu Val Asp Ala Asp Asn Leu Tyr Cys Ala Ala Asp Ala Gln
785                 790                 795                 800

Cys Arg Tyr Glu Phe Arg Ile Leu Thr Thr Gly Glu Met Gln Ala Thr
                805                 810                 815

Phe Lys Asp Asn Cys Lys Ala Ser Ile His Thr Asn Thr Pro Gly Tyr
            820                 825                 830

Gln Asn Glu Ala Ile Thr His Cys Lys Val Leu Ala Asn Gly Lys Cys
        835                 840                 845

Lys Tyr Asp Asn Gln Thr Leu Ile Asp Val Thr Leu Cys Ala Asn Asn
    850                 855                 860

Arg Tyr Tyr Pro Glu Ala Lys Gly Arg Ile Phe Gly Val Asp Pro Glu
865                 870                 875                 880

Asp Leu Cys Phe Asp Lys Thr Cys Thr Lys Leu Gln Thr Pro Tyr Asn
                885                 890                 895

Glu Glu Leu Ile Ser Met Cys Val Trp Glu Asn Pro Thr Leu Arg Pro
            900                 905                 910

Ile Arg Pro Arg Thr Glu Ile Ser Met Thr Phe Gln Glu Tyr Lys Asp
        915                 920                 925

Gln Leu Leu Lys Lys Ile Asn Thr Asp Leu Val Leu His Lys Phe Val
    930                 935                 940

Arg Thr Gln Asn Leu Pro Tyr Phe Ile Pro Gln Phe Lys Tyr Ile Thr
945                 950                 955                 960

Ile Gln Gly Thr Ser Thr Thr Asp Gly Ile Thr Ser Ser Phe Ile Phe
                965                 970                 975

Phe Glu Ile Pro Ala Leu Thr Gly Ala Ser Ala Gly Tyr Lys Val Ile
            980                 985                 990

Asn Ser Glu Gly Gln Glu Leu Met  Asp Met Val Val Tyr  Val Lys Thr
        995                 1000                1005

Ser Lys  Thr Ser Ala Lys Tyr  Lys Arg Met Tyr Tyr  Thr Gly Pro
    1010                1015                1020

Thr Ile  Ala Ile Asn Ala Lys  His Gln Glu His Cys  Thr Gly Thr
    1025                1030                1035

Cys Pro  Glu Arg Ile Glu His  Asp Asp Gly Trp Ala  Thr Phe Ser
    1040                1045                1050

Lys Glu  Arg Thr Ser Asn Trp  Gly Cys Glu Glu Phe  Gly Cys Leu
    1055                1060                1065

Ala Val  Glu Thr Gly Cys Leu  Phe Gly Ser Cys Gln  Asp Val Ile
    1070                1075                1080

Arg Arg  Glu Leu Asp Val Phe  Ser Lys Leu Glu Glu  Asp Lys Ile
    1085                1090                1095

Leu Thr  Glu Leu Cys Ile Thr  Leu Ser His Asp Thr  Tyr Cys Val
    1100                1105                1110

Thr Ile  Asp Ser Thr Thr Pro  Thr Ile Asn Asp Tyr  Phe Glu Ile
    1115                1120                1125

Gln Tyr  Lys Thr Val Asp Val  Gln Thr Leu Pro Lys  Met Ile Gly
    1130                1135                1140

Val Thr  His His Lys Leu Leu  Arg Gly Gln Ile Asn  Glu Leu Gly
    1145                1150                1155

Ser Phe  Gly Lys Phe Cys Gly  Asp Ile Gln Val Val  Gly Asn Gln
    1160                1165                1170
```

Thr Tyr Gly Gln Ala Ala Val Lys Phe Asp Tyr Ile Cys His Ala
1175 1180 1185

Ala Gln Arg Lys Asp Val Val Ile Arg Lys Cys Leu Glu Asn Asn
1190 1195 1200

Tyr Gln Ser Cys Lys Leu Leu Thr His Asp Thr Asp Leu Ile Leu
1205 1210 1215

Glu Glu Ser Glu Thr Ser Val Glu Val Ile Asn Asn Lys Arg Ile
1220 1225 1230

Thr Gly Gln Ile Ala Leu Lys Val Leu Leu Gly Asp Phe Asn Tyr
1235 1240 1245

Lys Gln Tyr Ala Ala Asn Val Glu Ala Asp Ile Glu Ala Asn Cys
1250 1255 1260

Val Gly Cys Thr Asn Cys Ile Lys Gly Ile Thr Cys Glu Ile Lys
1265 1270 1275

Val Lys Thr Glu Ile Glu Ala Ser Cys Lys Val Glu Pro Pro Cys
1280 1285 1290

Pro Ser Tyr Thr Asn Arg Ile Ile Ile Lys Pro Gly Arg Asp Thr
1295 1300 1305

His Thr Leu Leu Met Lys Cys Asp Lys Lys Ile Met Thr Gly Glu
1310 1315 1320

Leu Ala Ile Lys Ile Cys Asn Met Gln Ile Gln Ala His Leu Ser
1325 1330 1335

Thr Ile Glu Ser Asn Asp Gln Leu Glu Leu Ser Thr Gly Asp Gln
1340 1345 1350

Ser Thr Tyr Ile His Glu Glu Asp Leu Arg Cys Ser Thr Trp Ile
1355 1360 1365

Cys Lys Val Arg Asp Glu Gly Ile Ser Phe Ile Phe Lys Pro Leu
1370 1375 1380

Thr Asp Trp Leu Gly Ser Phe Thr Lys Pro Ile Leu Ile Ala Gly
1385 1390 1395

Cys Ile Ile Ile Val Ala Ile Ile Leu Ile Tyr Ile Leu Met Pro
1400 1405 1410

Met Cys Ala Lys Leu Arg Asp Leu Leu Lys Lys Asn Glu Tyr Glu
1415 1420 1425

Tyr Leu Gln Asp Thr Lys Val Ile Val Lys Pro Lys Ala Thr Ala
1430 1435 1440

Ser Ser Ile Gly Leu Arg Ser Lys Lys Ile Asn Ile Gln Ser Ser
1445 1450 1455

Lys Ala Val Asp
1460

<210> SEQ ID NO 96
<211> LENGTH: 2275
<212> TYPE: PRT
<213> ORGANISM: Umbre orthobunyavirus strain Marna

<400> SEQUENCE: 96

Met Leu Asp Gln Glu Asn Glu Gln Ala Leu Asn Arg Leu Ala Ala Thr
1 5 10 15

Val Ala Arg Ala Asn Glu Pro Ala Glu Gly Lys Glu Ala Tyr Asn Ala
20 25 30

Ile Leu Ser Arg Arg His Asp Tyr Phe Gly Gln Val Phe Cys Glu Thr
35 40 45

Ile Gly Ile Pro Tyr Arg Asn Asp Val Arg Leu Glu Asp Ile Leu His

```
    50                  55                  60

Glu Cys Asp Gln Thr Val Asp Thr Leu Thr Asn Lys Ile Pro Asn Ile
65                  70                  75                  80

Thr Pro Asp Asn Phe Glu Phe Arg Asp Asn Ile Leu Thr Ile Ile Asp
                85                  90                  95

Tyr Lys Val Ala Val Ser Asp Glu Ser Ala Asp Tyr Thr Arg Glu Lys
            100                 105                 110

Tyr Glu Asn Ala Val Asp Ala Ile Lys His Leu Val Asp Phe Pro Ile
        115                 120                 125

Arg Val Cys Ile Val Arg Ile His Pro Tyr Thr Arg Gln Val Thr Tyr
    130                 135                 140

Ser Asp Asp Asn Phe Met Arg Arg Phe Ala His Val Val Tyr Pro Val
145                 150                 155                 160

Asp Phe Thr Arg Tyr Thr Gln Leu Thr Glu Glu Leu Lys Glu Lys Phe
                165                 170                 175

Ala Asp Ser Pro Glu Phe Met Asp Met Ile Ala Tyr Gly Asp Val Thr
            180                 185                 190

Phe Thr Ala Asn Trp Cys Gln Asn Gly Cys Pro Glu Leu Tyr Glu His
        195                 200                 205

Pro Ile Phe Lys Glu Phe Leu Glu Ser Met Pro Leu Lys Tyr Gln Lys
    210                 215                 220

Leu Phe Glu Lys Ser Leu Leu Ser Ser Cys Tyr Thr Ser Glu Arg Trp
225                 230                 235                 240

Asp Ser Asn Leu Lys Glu Val Lys Ala Ala Thr Lys Asp Glu Tyr Glu
                245                 250                 255

Asp Phe Ile Ser Arg Ser Ala Lys Gln Leu Tyr Thr Thr Ser Pro Asp
            260                 265                 270

Tyr Ser Glu Pro Ser Arg Glu Glu Ile Leu Lys Gly Trp Glu Glu Met
        275                 280                 285

Thr Glu Arg Val Lys Glu Gln Arg Glu Val Ser Ser Asn Ile Asn Asp
    290                 295                 300

Gln Lys Pro Ser Ala His Phe Ile Trp Ala Glu Asn Asn His Glu Leu
305                 310                 315                 320

Pro Thr Ala Asn Ser Ala Lys Ile Cys Ala Ile Ser Lys Leu Leu Gln
                325                 330                 335

Ser Ile Asn Ile Glu Ser Ser Phe Ala Glu Asp Phe Lys Arg Leu Gly
            340                 345                 350

Lys Leu Phe Asp Phe Ser Glu Asp Ile Pro Gly Tyr Glu Arg His Cys
        355                 360                 365

Glu Gln Leu Lys Arg Gln Ala Arg Ser Asn Pro Gly Gln Ile Lys Thr
    370                 375                 380

Lys Lys Leu Asp Pro Lys Lys Ile Gly Asn Ala Leu Val Leu Trp Glu
385                 390                 395                 400

Gln Gln Phe Leu Leu Ser Ala Asp Glu Met Gly Lys Glu Asn Lys Leu
                405                 410                 415

His Leu Leu Lys Asp Phe Phe Gly Ile Gly Lys His Lys Gln Phe Ala
            420                 425                 430

Arg Lys Gly Leu Asp Asp Thr Glu Thr Asp Lys Pro Thr Ile Leu Asp
        435                 440                 445

Phe Asn Asp Thr Glu Val Lys Arg Ser Ala Glu Leu Met Met Gln Lys
    450                 455                 460

Thr Lys Leu Tyr Leu Ser Gly Lys Ser Ser Leu Asn Lys Glu His Pro
465                 470                 475                 480
```

```
Ile Ala Ser Glu Tyr Leu Asn Glu Ile Lys Lys Cys Asn Asp Glu Thr
                485                 490                 495

Tyr Asn Val Leu Asn Ala Ile Phe Gln Thr Lys Tyr Trp Gln Cys Ile
            500                 505                 510

Thr Asp Ile Ser Met Leu Met Lys Asn Met Leu Ser Val Ser Gln Tyr
        515                 520                 525

Asn Arg Asn Asn Thr Phe Arg Ile Ala Thr Cys Ala Asn Asn Ala Leu
    530                 535                 540

Tyr Gly Leu Ile Phe Pro Ser Ala Asp Ile Lys Thr Lys Asp Ala Ser
545                 550                 555                 560

Ile Val Tyr Cys Ile Ile Ala Ile His Lys Asp Glu Lys Ser Leu Phe
                565                 570                 575

Asn Pro Gly Ala Leu His Ala Thr Phe Lys Val Pro Gly Gly Phe Leu
            580                 585                 590

Ser Ile Ser Lys Ser Met Arg Leu Asp Lys Lys Arg Cys His Arg Ile
        595                 600                 605

Val Thr Ser Pro Gly Ile Phe Leu Thr Ile Ala Thr Met Leu Lys Gly
    610                 615                 620

Asp Asn Pro Thr Ile Ser Leu Asn Asp Val Leu Asn Phe Ser Ile Phe
625                 630                 635                 640

Ala Ser Leu Asn Ile Thr Lys Ser Met Leu Ser Leu Thr Glu Pro Ser
                645                 650                 655

Arg Tyr Met Ile Met Asn Ser Leu Ala Val Ser Ser His Val Arg Glu
            660                 665                 670

Tyr Ile Ser Glu Lys Phe Ser Pro Tyr Thr Lys Thr Leu Phe Ser Val
        675                 680                 685

His Met Val Glu Lys Ile Lys Ala Gly Cys Leu Asn Ala Phe Lys Gln
    690                 695                 700

Arg Glu Lys Ile Lys Thr Arg Asp Ile Tyr Leu Thr Asp Ile Asp Ile
705                 710                 715                 720

Thr Gln Lys Gly Ile Gln Asp Asn Arg Asp Leu Cys Ser Ile Trp Phe
                725                 730                 735

Asp Gly Asn Val Thr Leu Lys Glu Tyr Leu Asn Gln Ile Tyr Ile Val
            740                 745                 750

Phe Tyr Leu Asn Pro Lys Ala Leu His Glu Lys His His Val Met Ile
        755                 760                 765

Asp Leu Leu Lys Thr Val Ile Glu Ile Glu Leu Asp Gln Arg Glu Asn
    770                 775                 780

Val Pro Gln Pro Trp Ser Asp Val Pro Lys Lys Gln Thr Val Lys Leu
785                 790                 795                 800

Pro Ile Leu Val His Ser Leu Ala Lys Asn Leu Leu Leu Asp Thr Ser
                805                 810                 815

Phe Ala His Phe Leu Arg Ser Arg Ile Glu Ser Arg Asn Asn Phe Arg
            820                 825                 830

Arg Thr Phe Ala Thr Ile Ser Thr Phe Thr Ser Ser Lys Ser Cys Leu
        835                 840                 845

Lys Thr Gly Asn Phe His Glu Phe Lys Ile Lys Gln Cys Gln Arg Leu
    850                 855                 860

Lys Lys Val Asn Ala Ser Glu Ala Lys Lys His Arg Ile Ala Asn Ala
865                 870                 875                 880

Met Phe Val Glu Glu Gln Asp Gln His Leu Glu Val Glu His Ala Asn
                885                 890                 895
```

```
Tyr Glu Leu Met Arg Lys Ala Ile Pro Asp Tyr Val Asp Val Leu Ser
            900                 905                 910

Thr Lys Val Phe Asp Arg Leu Tyr Glu Leu Tyr Lys Thr Gly Glu Ile
        915                 920                 925

Asp Asp Ser Pro Val Ile His Gln Ile Phe Ala Thr Met Lys Ser His
    930                 935                 940

Thr Lys Phe Tyr Phe Thr Tyr Phe Asn Lys Gly Gln Lys Thr Ala Lys
945                 950                 955                 960

Asp Arg Glu Ile Phe Val Gly Glu Tyr Glu Ala Lys Met Cys Met Tyr
                965                 970                 975

Leu Val Glu Arg Ile Tyr Lys Glu Arg Ser Lys Val Asn Pro Asp Glu
            980                 985                 990

Met Ile Ser Glu Pro Gly Asp Gly  Lys Leu Arg Val Leu  Glu Arg Lys
        995                 1000                 1005

Ala Glu  Gln Glu Ile Arg Phe  Met Val Glu Lys Met  Lys Ala Lys
    1010                 1015                 1020

Asn Asp  Glu Ile Asn Lys Glu  Ile Glu Asp Ala Lys  Asp Asn Tyr
    1025                 1030                 1035

Val Leu  Asn Leu Gly Lys Ile  Ala Ala Leu Gln Ala  Gln Lys Tyr
    1040                 1045                 1050

Lys Ala  Leu Lys Leu Glu Ile  Asn Ala Asp Met Ser  Lys Trp Ser
    1055                 1060                 1065

Ala Gln  Asp Val Phe Phe Lys  Tyr Phe Trp Ser Ile  Cys Leu Asp
    1070                 1075                 1080

Pro Ile  Leu Tyr Pro Glu Glu  Lys Glu His Ile Leu  Tyr Phe Phe
    1085                 1090                 1095

Cys Asn  Tyr Met Gln Lys Glu  Leu Val Ile Pro Asp  Glu Val Ile
    1100                 1105                 1110

Cys Asn  Ile Leu Asp Gln Arg  Lys Ala Tyr Pro Asn  Asp Ile Ile
    1115                 1120                 1125

Ser Gln  Ile Thr Asn Gly Leu  Thr Thr Asn His Phe  Asn Val Lys
    1130                 1135                 1140

Arg Asn  Trp Leu Gln Gly Asn  Phe Asn Tyr Met Ser  Ser Tyr Ala
    1145                 1150                 1155

His Ser  Thr Ala Met Ser Val  Phe Lys Asp Val Ile  Lys Arg Ala
    1160                 1165                 1170

Ala Asp  Leu Leu Glu Ala Glu  Val Leu Ile His Ser  Met Val His
    1175                 1180                 1185

Ser Asp  Asp Asn Gln Thr Ser  Val Thr Leu Val Asp  Asn Arg Ile
    1190                 1195                 1200

Cys Pro  Lys Gln Phe Thr Ala  Phe Val Ile Asn Thr  Phe Glu Lys
    1205                 1210                 1215

Ile Cys  Leu Thr Phe Gly Cys  Gln Ala Asn Met Lys  Lys Thr Tyr
    1220                 1225                 1230

Ile Thr  Asn His Ile Lys Glu  Phe Val Ser Leu Phe  Asn Leu Tyr
    1235                 1240                 1245

Gly Glu  Pro Phe Ser Ile Tyr  Gly Arg Phe Thr Leu  Thr Ser Val
    1250                 1255                 1260

Gly Asp  Cys Ala Tyr Ile Gly  Pro Tyr Glu Asp Leu  Ala Ser Arg
    1265                 1270                 1275

Ile Ser  Ala Thr Gln Thr Gly  Ile Lys His Gly Cys  Pro Ala Ser
    1280                 1285                 1290

Gln Ala  Trp Leu Ser Ile Ala  Ile Ala Gln Trp Met  Thr Tyr Leu
```

```
    1295                1300                1305

Thr Tyr  Asn Met Leu Pro Gly  Gln Gln Asn Asp Pro  Gln Pro Ile
    1310                1315                1320

Leu Glu  Ile Asp Arg Lys Gln  Leu Pro Leu Glu Leu  Gly Gly Tyr
    1325                1330                1335

Ile Ser  Cys Pro Leu Ser Leu  Ile Ala Leu Ala Gly  Leu Glu Ser
    1340                1345                1350

Gly Asn  Ile Asp Phe Leu Ile  Lys Leu Val Asn Lys  Tyr Ile Asp
    1355                1360                1365

Pro Arg  Leu Gln Arg Glu Pro  Ile Gln Asp Gln Cys  Thr Asp Ile
    1370                1375                1380

Lys Asn  Trp Asp Ile Ser Lys  Leu Ser Lys Val Glu  Ile Phe Lys
    1385                1390                1395

Leu Lys  Val Leu Arg Tyr Leu  Val Leu Asp Ala Glu  Met Asp Asn
    1400                1405                1410

Thr Asp  Ile Met Gly Glu Thr  Ser Glu Met Arg Gly  Arg Ser Leu
    1415                1420                1425

Leu Thr  Pro Arg Lys Phe Thr  Thr Ala Gly Ser Leu  Arg Lys Leu
    1430                1435                1440

Val Ser  Phe Glu Asp Phe Gln  Ala Val Gln Asp Ser  Glu Gln Gly
    1445                1450                1455

Val Asp  Ser Ile Val Glu Tyr  Met Leu Gln Asn Pro  Ala Leu Leu
    1460                1465                1470

Val Thr  Lys Gly Glu Thr Lys  Asp Asp Tyr Met Asn  Thr Val Leu
    1475                1480                1485

Tyr Arg  Tyr Asn Ser Lys Lys  Phe Lys Glu Ser Leu  Ser Ile Gln
    1490                1495                1500

Asn Pro  Thr Gln Leu Phe Leu  Glu Gln Ile Leu Phe  Ser His Lys
    1505                1510                1515

Pro Ile  Val Asp Tyr Thr Gly  Ile Ala Glu Lys Phe  Ser Asn Leu
    1520                1525                1530

Asn Asp  Gly Thr Met Leu Glu  Asp Asn Pro Thr Ile  Lys Gly Arg
    1535                1540                1545

Met Thr  Phe Thr Asp Ala Phe  Ala Met Ile Lys Lys  Asp Leu Ser
    1550                1555                1560

Thr Leu  Arg Ile Thr Asn Glu  Asp Leu Glu Ile Val  Leu Lys Phe
    1565                1570                1575

Ile Ile  Leu Asn Asp Pro Leu  Thr Val Thr Ala Ala  Asn Ala His
    1580                1585                1590

Ile Leu  His Val Ile Gly His  Ser Gln Pro Arg Leu  Gly Ser Thr
    1595                1600                1605

Ala Cys  Val Met Pro Glu Phe  Arg Asn Leu Arg Met  Ile Lys His
    1610                1615                1620

Ser Pro  Ala Leu Val Leu Lys  Cys Tyr Ser Lys Asn  Thr Leu Leu
    1625                1630                1635

Leu Pro  Gly Val Gln Glu Arg  Asp Met Glu Arg Asp  Leu Asn His
    1640                1645                1650

Leu Lys  Thr Phe Ile Glu Thr  Thr Arg Leu Glu His  Lys Met Gln
    1655                1660                1665

Asp Arg  Ile Lys Lys Asn Glu  Asp Leu Lys Lys Ser  Lys Asp Ile
    1670                1675                1680

Tyr Phe  Glu Ile Lys Glu Val  Thr Arg Phe Tyr Gln  Thr Cys Tyr
    1685                1690                1695
```

```
Glu Tyr  Val Lys Ser Thr Asp  Tyr Lys Val Lys Val  Phe Ile Leu
    1700                 1705                 1710

Pro Ala  Lys Cys Met Thr Gln  Thr Asp Phe Cys Ala  Val Leu Gln
    1715                 1720                 1725

Gly Ser  Leu Leu Glu Asp Lys  Lys Trp Lys Leu Ile  Gln His Leu
    1730                 1735                 1740

Arg Pro  Val Thr Ala Gly Gly  His Lys Gly Glu Val  Gln Pro Val
    1745                 1750                 1755

Val Ser  Met Asp Phe Lys Leu  Ala Arg Glu Ala Val  Asn Leu Leu
    1760                 1765                 1770

Cys Phe  Phe Thr Asp Ser Phe  Ile Asp Ser Arg Tyr  Arg Arg Asp
    1775                 1780                 1785

Phe Leu  Leu Lys Ala Cys Val  Glu Met Ala Tyr Lys  Asp Arg Pro
    1790                 1795                 1800

Met Val  Thr Leu Ile Glu Glu  Ile Lys Lys Ser Lys  Asn Arg Thr
    1805                 1810                 1815

Ser Phe  Leu Pro Phe Leu Tyr  Arg Ile Gly Glu Leu  Thr Gln Glu
    1820                 1825                 1830

Asp Leu  Asp Ala Tyr Asp Ala  Gln Lys Ala Gly Gly  Arg Val Thr
    1835                 1840                 1845

Trp Asn  His Trp Gln Ser Thr  Arg Ser Leu Asn Met  Gly Lys Ile
    1850                 1855                 1860

Asp Phe  Gln Ile Asp Thr His  Lys Thr His Leu His  Ile Ile Gly
    1865                 1870                 1875

Glu Asp  Gln Gln Leu Val Ile  Ala Glu Leu Lys Ile  Pro Lys Leu
    1880                 1885                 1890

Thr Ala  Asn Ala Ile Thr Gln  Ala Gly Tyr Arg Leu  Leu Asn Glu
    1895                 1900                 1905

Lys His  Gly Phe Arg Phe Glu  Thr Met Asn Glu Val  Leu Val Gln
    1910                 1915                 1920

Pro Arg  Lys Tyr Tyr Ile Thr  Tyr Gln Met Lys Ser  Lys Lys Gln
    1925                 1930                 1935

Tyr Val  Tyr Lys Ile Phe Asp  Thr Ala Thr Leu Leu  Tyr Glu Arg
    1940                 1945                 1950

Arg Asn  Ile Lys Gln Tyr Thr  Gly Arg Glu Ala Asn  Pro Ile Val
    1955                 1960                 1965

Ala Val  Cys Glu Val Val Pro  Met Glu Glu Glu Glu  Thr Pro Ala
    1970                 1975                 1980

Leu Ser  Leu Ser Asp Ile Glu  Met Tyr Asn Ala Asp  Asn Glu Ser
    1985                 1990                 1995

Val Ser  Ile Leu Lys Thr Ser  Phe Asn Glu Ser Ala  Lys Met Arg
    2000                 2005                 2010

Arg Ala  Asn Leu Ser Lys Met  Gln Tyr Phe Glu Thr  Ile Gly Gly
    2015                 2020                 2025

Ser Met  Leu Lys Ile Arg Phe  Ile Asn Val Asn Ala  Leu Met Lys
    2030                 2035                 2040

Asp Thr  Thr Leu Met Ser Leu  Asn Tyr Asp Asn Leu  Val Asn Val
    2045                 2050                 2055

Asp Leu  Ala Arg Phe Ser Lys  Leu Leu Asp Cys Asp  Gly Asp Thr
    2060                 2065                 2070

Glu Ser  Val Glu Asp Gly Ile  Leu Cys Phe Ser Asp  Asp Pro Met
    2075                 2080                 2085
```

-continued

```
Glu Gln  Thr Thr Thr Glu Glu  Ile Asp Ala Ile Pro  Leu Phe Lys
    2090                 2095                 2100

Val Ser  Tyr Lys Ile Ser Ala  Pro Ala Arg Leu Thr  Tyr Lys Asn
    2105                 2110                 2115

Ala Ile  Arg Glu Leu Leu Arg  Arg Glu Ile Thr Arg  Phe Met Asp
    2120                 2125                 2130

Ala Phe  Thr Phe Val Gly Pro  Ser Phe Asp Ser Pro  Glu Asn Met
    2135                 2140                 2145

Gly Phe  Ile Cys Asn Ile Cys  Cys Ile Ile Gln Leu  Leu His Thr
    2150                 2155                 2160

Asn Glu  Trp Ser Ile Ile Met  Leu Asn Cys Ile His  Ile Cys Met
    2165                 2170                 2175

Ile Tyr  Leu Glu Lys Asp Ile  Arg Phe His Lys Phe  Leu Leu Asn
    2180                 2185                 2190

Arg Ile  Phe Phe Glu Gly Leu  Asn Pro Ala Ser Gly  Lys Leu Asp
    2195                 2200                 2205

Tyr Lys  Lys Ile Lys Glu Phe  Val Ile Ser Leu Lys  Asp Arg Glu
    2210                 2215                 2220

Met Ala  Pro Trp Asn Glu Ile  Phe Ser Lys Phe Lys  Gln Lys Cys
    2225                 2230                 2235

Val Thr  Leu Leu Asp Lys Glu  Ile Thr Arg Ile Glu  Gln Asn Thr
    2240                 2245                 2250

Asn Phe  Glu Asn Ile Leu Ala  Leu Asp Glu Asn Thr  Asp Asp Gln
    2255                 2260                 2265

Ser Glu  Phe Leu Leu Phe Glu
    2270                 2275


<210> SEQ ID NO 97
<211> LENGTH: 10
<212> TYPE: PRT
<213> ORGANISM: artificial sequence
<220> FEATURE:
<223> OTHER INFORMATION: synthetic peptide

<400> SEQUENCE: 97

Gly Gly Trp Ser His Pro Gln Phe Glu Lys
1               5                   10
```

ORTHOBUNYAVIRUS IN HUMAN ENCEPHALITIS AND ITS DIAGNOSTIC AND THERAPEUTIC APPLICATIONS

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Jun. 10, 2022, is named Corrected_seq_listing.txt and is 203,743 bytes in size.

FIELD OF THE INVENTION

The invention relates to methods of diagnosis or detection of Moissiacense virus, a novel orthobunyavirus causing human encephalitis, comprising determining the presence of at least one nucleic acid or protein of said virus or antibodies thereto, in a biological sample. The invention also relates to the various diagnostic agents derived from the viral nucleic acids or proteins, in particular nucleic acid primers and probes, antigens and antibodies, and their use for the diagnosis of Moissiacense virus infection and associated disease, in particular encephalitis. The invention further relates to antigens derived from the viral proteins as vaccine for the prevention of Moissiacense virus infection and associated disease, in particular encephalitis.

BACKGROUND OF THE INVENTION

Human encephalitis is a potentially fatal disease of the central nervous system that is frequently associated with neurological sequelae. The incidence is about 1.5-7 cases/year/100,000 inhabitants. In 20-50% of cases, encephalitis with known etiology is related to infection most often of viral origin (Glaser et al., Clin. Infect. Dis. Off. Publ. Infect. Dis. Soc. Am., 2006, 43, 1565-77). The most frequently implicated viruses belong to the Herpesviridae family (Herpes Simplex virus, Varicella Zoster virus and others), but also arboviruses depending on the geographical area, in particular Japanese encephalitis virus (JEV) in Asia and Tick-borne encephalitis virus (TBEV) in Europe and Northeast Asia.

Encephalitis is one of the most challenging syndromes as its etiology remains unknown in more than one third of the cases, even in countries benefiting from high-performance diagnostic technologies (Venkatesan et al., Clin. Infect. Dis. Off. Publ. Infect. Dis. Soc. Am., 2013, 57, 1114-28).

Indeed, new pathogens provoking encephalitis are recurrently identified (Mailles et al., Clin. Microbiol. Infect. Off. Publ. Eur. Soc. Clin. Microbiol. Infect. Dis., 2017, 23, 607-13). Diagnosis of encephalitis is also challenging because of the geographical spread of neurotropic arboviruses favored by climate change and human migration. In addition, this spread exposes human or animal populations devoid of specific immunity to these newly introduced arboviruses (Tabachnick W J., Annu. Rev. Virol., 2016, 3, 125-45). A recent example is the Usutu virus, a flavivirus of the JEV complex responsible for human encephalitis, which has recently expanded in Europe (Ashraf et al., Viruses, 2015, 7, 219-38).

Etiological diagnosis of encephalitis is essential for appropriate management of patients (Nath A., JAMA Neurol., 2015, 72, 143-144). It is, however, particularly difficult as encephalitis can have autoimmune as well as viral origin (Ashraf et al., Viruses, 2015, 7, 219-38). Inaccurate diagnosis is a main issue as immunosuppressive treatments, in the case of undiagnosed infectious encephalitis, can be deleterious for the patient. In addition, the possibility of an infection underlying an autoimmune reaction renders the situation even more complex (Schein et al., Infection, 2017, 45, 545-9). In this context, identification of new pathogens responsible for encephalitis is critical for improving the scope of targeted diagnostic tests and diagnostic efficiency.

SUMMARY OF THE INVENTION

The inventors have used agnostic metatranscriptomics procedures to analyze the brain tissue from two fatal cases of encephalitis for which a viral etiology had been suspected. This approach led to the identification and the characterization of Moissiacense virus, a novel orthobunyavirus group or species that includes Umbre virus a mosquito orthobunyavirus never described in humans before. This novel orthobunyavirus group or species is related to viruses of the Koongol group, a Glade that had never previously been identified in vertebrates. It is of note that standard approach using PCR consensus assays targeting a broad range of orthobunyaviruses would have missed Moissiacense virus due to sequence variation. Viral sequences of the same Glade were found in *Culex pipiens* mosquitoes captured in Southern France, which suggests that a novel arbovirus Glade with neurotropic potential is present in Europe. Thus, Moissiacense virus should be added to serological tests and to targeted tests in routine diagnosis of brain tissue from encephalitis cases with unidentified etiology.

Therefore, in the various embodiments, the invention relates to methods of diagnosis or detection of Moissiacense virus, a novel orthobunyavirus causing human encephalitis, comprising determining the presence of at least one nucleic acid or protein of said virus or antibodies thereto, in a biological sample. The invention also relates to the various diagnostic agents derived from the viral nucleic acids or proteins, in particular nucleic acid primers and probes, antigens and antibodies, and their use for the diagnosis of Moissiacense virus infection and associated disease, in particular encephalitis. The invention further relates to antigens derived from the viral proteins as vaccine for the prevention of Moissiacense virus infection and associated disease, in particular encephalitis.

DETAILED DESCRIPTION OF THE INVENTION

Methods of Diagnosis or Detection of Moissiacense Virus

The invention relates to methods of diagnosis or detection of Moissiacense virus, comprising determining the presence of at least one nucleic acid or protein of said virus or of antibodies against said virus, in a biological sample.

Moissiacense virus is a new neurotropic arbovirus belonging to orthobunayviruses, a genus of viruses within the family Peribunyaviridae in the order Bunyavirales. Orthobunyaviruses are spherical enveloped virus (80 nm to 120 nm in diameter) comprising a segmented Negative-stranded RNA linear genome encapsulated in a ribonucleocapsid. The L segment (about 6.9 kb) encodes the viral RNA dependent RNA Polymerase or L Protein. The M segment (about 4.51(b) encodes a polyprotein which is cleaved by host protease into Gn, NSm and Gc proteins. The S segment (about ikb) encodes the Nucleocapsid protein (N protein) and a non-structural protein (NSs Protein), by leaky scanning. The type species or prototype of orthobunyavirus is Bunyamwera (BUNV). As used herein, a bunyavirus refers to an orthobunyavirus. Unless otherwise specified herein, "Moissiacense virus", refers to the Moissiacense virus group or species which includes in particular, Moissiacense virus, a new virus identified by the inventors of the present application, as well as the known, Umbre and Little Sussex viruses. The Moissiacense virus group or species includes also the Mama virus, a new virus related to Moissiacense virus identified by the inventors of the present application. Based on the species demarcation criteria of the International Committee on Taxonomy of Viruses (ICTV) for orthobunyaviruses, Moissiacense virus, Mama virus, Umbre virus and Little Sussex virus would belong to the same species (>90% identical AA identity; ICTV report, 30 Nov. 2018 (available from: https://talk.ictyonline.org/ictv-reports/ictv_9th_report/). Therefore, taking the known Umbre virus as a reference, the Moissiacense virus and related Mama virus, newly identified by the inventors, are also designated as strains of Umbre virus or Umbre orthobunyavirus. The Moissiacense virus group is a subset of the Koongol virus group or Glade which does not include Koongol virus. The sequences disclosed herein are those of the newly identified Moissiacense virus and related Mama virus, also named Umbre virus (or Umbre orthobunyavirus) strain Moissiacense and Umbre virus (or Umbre orthobunyavirus) strain Mama, respectively. All the sequences disclosed herein are in the 5' to 3' orientation. According to the standard practice in the field of bunyavirus (negative-sense single stranded RNA virus), viral nucleotide sequences are disclosed as the positive strand or sense strand coding sequences of the S, M, and L segments, in the DNA form. However, the present invention encompasses the RNA equivalent of the DNA sequences herein disclosed as well as their complement (i.e., reverse complement) sequences.

A sample or biological sample refers to any material obtained or derived from living or dead individual (human or animal) that may contain a Moissiacense virus or components thereof such as nucleic acids, proteins or fragments thereof, or antibodies against said Moissiacense virus appropriate for detection by the methods of the invention. Biological sample also includes any material derived or obtained from an arthropod vector that may contain a Moissiacense virus or components thereof such as nucleic acids, proteins or fragments thereof. The source of the sample may be any solid tissue as from fresh, frozen and/or preserved organ or tissue sample or biopsy or aspirate; any body fluid such as whole-blood or any blood constituent (serum, plasma), cerebral spinal fluid (CSF), peritoneal, pleural, synovial or amniotic fluid, urine, lymph and mucosal secretions. The sample may also be primary or cultured cells. The source of the sample can also be a whole vector specimen, a portion thereof or egg(s) thereof. The sample can be derived from any vector capable of transmitting Moissiacense virus, in particular a mosquitoe such as *Culex* sp or *Aedes* sp., or others. Samples include also processed samples that have been treated to disrupt tissue or cell structure, thus releasing intracellular components into a solution which may further contain reagents (buffers, salts, detergents, enzymes and the like) which are used to prepare, using standard methods, a biological sample for analysis. In particular, processed samples include samples that have been treated by standard methods used for the isolation of nucleic acids or proteins from biological samples.

In some embodiments of the methods of the invention, the sample is a clinical sample (i.e., a sample from living or dead individual (human or animal) suspected of having a Moissiacense virus). Preferably, the sample is brain biopsy, cerebral spinal fluid (CSF), whole-blood, plasma or serum. In some other embodiments, the biological sample is an arthropod vector specimen.

Nucleic Acid Detection

In some aspects, the method of diagnosis or detection of Moissiacense virus comprises determining the presence of at least one nucleic acid of said virus in a sample.

In some embodiments, the viral nucleic acid is selected from the group consisting of:

- a first nucleic acid (S segment) comprising a sequence having at least 80% identity with SEQ ID NO: 1 and further including a coding sequence for a Nucleocapsid (N) protein, or its complement;
- a second nucleic acid (M segment) comprising a sequence having at least 80% identity with SEQ ID NO: 3 and further including a coding sequence for a polyprotein M, or its complement; and
- a third nucleic acid (L segment) comprising a sequence having at least 80% identity with SEQ ID NO: 5 and further including a coding sequence for a polymerase (L) protein, or its complement.

The first nucleic acid corresponds to the S segment which codes for the Nucleocapsid (N) protein or Nucleoprotein and for the nonstructural protein NSs. The N protein coding sequence or ORF is from positions 59 to 772 of SEQ ID NO: 1 and has the sequence SEQ ID NO: 73. The NSs protein coding sequence or ORF is from positions 96 to 335 of SEQ ID NO: 1 and has the sequence SEQ ID NO: 71.

The Nucleocapsid (N) protein refers to the protein of SEQ ID NO: 2 or a functional variant thereof. The protein of SEQ ID NO: 2 and its functional variants have the general properties of a bunyavirus nucleocapsid protein, taking as reference Bunyamwera (BUNV-N: GenBank NP 047213.1). The bunyavirus N protein is the major component of the viral nucleocapsid. This protein is thought to interact with the L protein, virus RNA and/or other N proteins.

The NSs protein refers to the protein of SEQ ID NO: 72 or a functional variant thereof. The protein of SEQ ID NO: 72 and its functional variants have the general properties of a bunyavirus NSs protein, taking as reference Bunyamwera (BUNV-NSs: GenBank NP 047214.1). The bunyavirus NSs protein plays a role in the escape of host innate immune response by promoting the degradation of host EIF2AK2/PKR and inhibiting host transcription. Cytoplasmic NSs interacts with host FBXW11 to degrade PKR whereas nuclear pool binds to host FBXO3 to target subunit GTF2H1 for proteasomal degradation.

The second nucleic acid corresponds to the M segment which codes for the two virion glycoproteins, Gn (G2) and Gc (G1), and a nonstructural protein NSm, in the form of a polyprotein precursor (polyprotein M or M polyprotein) which is cotranslationally cleaved. The gene order is 5'Gn-NSm-Gc-3'. The polyprotein M coding sequence or ORF is from positions 1 to 4395 of SEQ ID NO: 3.

The polyprotein M refers to the protein precursor of SEQ ID NO: 4 which is cotranslationally cleaved into the two virion glycoproteins, Gn (G2) and Gc (G1), and nonstructural protein NSm, or a functional variant thereof. Gn is from positions 17 to 301 of SEQ NO: 4 and has the sequence SEQ ID NO: 58; NSm is from positions 302 to 475 of SEQ ID NO: 4 and has the sequence SEQ ID NO: 59, and Gc is from positions 476 to 1464 of SEQ ID NO: 4 and has the sequence SEQ ID NO: 60. The polyprotein of SEQ ID NO: 4, the derived Gn (G2), Gc (G1), and NSm proteins and their functional variants have the general properties of bunyavirus M polyprotein, Gn, Gc and NSm proteins, taking as reference Bunyamwera (BUNV-M: Uniprot P04505-1 or GenBank NP_047212.1). Using BUNV polyprotein M (1433 aa) as reference sequence, Gn is from positions 17 to 302, NSm is from positions 303 to 477, and Gc is from positions 478 to 1433. Glycoprotein N (Gn) and Glycoprotein C (Gc) interact with each other and are present at the surface of the virion. They, are able to attach the virion to a cell receptor and to promote fusion of membranes after endocytosis of the virion. Non-structural protein M (NSm) plays a role in virion budding at Golgi tubes and in subcellular location of Glycoprotein C.

The third nucleic acid corresponds to the L segment which codes for the RNA-dependent or RNA-directed RNA polymerase (L protein) also named as large structural protein, Replicase, Transcriptase or RdRp. The L protein coding sequence or ORF is from positions 1 to 6828 of SEQ ID NO: 5.

The polymerase (L) protein refers to the protein of SEQ ID NO: 6 or a functional variant thereof. The protein of SEQ ID NO: 6 and its functional variants have the general properties of a bunyavirus L protein, taking as reference Bunyamwera (BUNV-L: UniProt P20470-1). The bunyavirus RNA-dependent RNA polymerase (RdRp or L protein) is responsible for replication and transcription of the viral RNA genome using antigenomic RNA as an intermediate. During transcription, it synthesizes subgenomic RNAs and assures their capping by a cap-snatching mechanism. These short capped RNAs are then used as primers for viral transcription. Bunyavirus RdRp have eight conserved motifs (PreA:F, A, H, B, C, D and E) in their central region or core polymerase domain (positions 951 to 1220 of RUN-L). The core polymerase domain of Moissiacense virus RdRP including the eight conserved motifs is from positions 954 to 1246 of SEQ ID NO: 6.

The percent amino acid or nucleotide sequence identity is defined as the percent of amino acid residues or nucleotides in a Compared Sequence that are identical to the Reference Sequence after aligning the sequences and introducing gaps if necessary, to achieve the maximum sequence identity. Alignment for purposes of determining percent amino acid or nucleotide sequence identity can be achieved in various ways known to a person of skill in the art, for instance using publicly available computer software such as the GCG (Genetics Computer Group, Program Manual for the GCG Package, Version 7, Madison, Wisconsin) pileup program, or any of sequence comparison algorithms such as BLAST (Altschul et al., J. Mol. Biol., 1990, 215, 403-10), FASTA or CLUSTALW.

Individual refers to a mammal, including a human or a domestic animal, preferably a human.

As used herein "the diagnosis of Moissiacense virus infection" includes the diagnosis of any Moissiacense virus associated disease, in particular encephalitis.

The terms "a", "an", and "the" include plural referents, unless the context clearly indicates otherwise. For example "a target" as used herein is understood to represent one or more targets. As such, the term "a" (or "an"), "one or more" or "at least one" can be used interchangeably herein.

In some embodiments, the S segment comprises a sequence having at least 85% or more identity with SEQ ID NO: 1 (said sequence may have at least 85%, 86%, 87%, 88%, 89%, 90%, 91%, 92%, 93%, 94%, 95%, 96%, 97%, 98% or 99% identity with SEQ ID NO: 1; or 100%° identity with SEQ ID NO: 1); the M segment comprises a sequence having at least 85% or more identity with SEQ ID NO: 3 (said sequence may have at least 85%, 86%, 87%, 88%, 89%, 90%, 91%, 92%, 93%, 94%, 95%, 96%, 97%, 98% or 99% identity with SEQ ID NO: 3; or 100%° identity with SEQ ID NO: 3); and/or the L segment comprises a sequence having at least 85% or more identity with SEQ ID NO: 5 (said sequence may have at least 85%, 86%, 87%, 88%, 89%, 90%, 91%, 92%, 93%, 94%, 95%, 96%, 97%, 98%, or 99% identity with SEQ ID NO: 5; or 100% identity with SEQ ID NO: 5).

In some embodiments, the nucleocapsid (N) protein has at least 90% identity with SEQ ID NO: 2 (said protein may have at least 90%, 91%, 92%, 93%, 94%, 95%, 96%, 97%, 98%, or 99% identity with SEQ ID NO: 2; or 100% identity with SEQ ID NO: 2°); the polyprotein M has at least 90% identity with SEQ ID NO: 4 (said protein may have at least 90%, 91%, 92%, 93%, 94%, 95%, 96%, 97%, 98%, or 99% identity with SEQ ID NO: 4; or 100% identity with SEQ ID NO: 4) and comprises the Gn protein from positions 17 to 301, the NSm from positions 302 to 475 and the Gc protein from positions 476 to 1464, the indicated positions being determined by alignment with SEQ ID NO: 4; and/or the L polyprotein has at least 90% identity with SEQ ID NO: 6 (said protein may have at least 90%, 91%, 92%, 93%, 94%, 95%, 96%, 97%, 98% or 99% identity with SEQ ID NO: 6; or 100% identity with SEQ ID NO: 6) including at least 90% identity on the core polymerase domain (positions 954 to 1246 of SEQ ID NO: 6). In some preferred embodiments, the nucleocapsid (N) protein has at least 95% identity with SEQ ID NO: 2 (said protein may have at least 95%, 96%, 97%, 98%, or 99% identity with SEQ ID NO: 2; or 100% identity with SEQ ID NO: 2°); the polyprotein M has at least 90% identity with SEQ ID NO: 4 (said protein may have at least 90%, 91%, 92%, 93%, 94%, 95%, 96%, 97%, 98%, or 99% identity with SEQ ID NO: 4; or 100% identity with SEQ ID NO: 4) and comprises the Gn protein from positions 17 to 301, the NSm from positions 302 to 475 and the Gc protein from positions 476 to 1464, the indicated positions being determined by alignment with SEQ ID NO: 4; and the L polyprotein has at least 95% identity with SEQ ID NO: 6 (said protein may have at least 95%, 96%, 97%, 98% or 99% identity with SEQ ID NO: 6; or 100% identity with SEQ ID NO: 6) including at least 90% identity on the core polymerase domain (positions 954 to 1246 of SEQ ID NO: 6).

The method of the invention is used for the detection or diagnosis of any virus of the Moissiacense group or species, in particular Moissiacense virus, Mama virus, Umbre virus, Little Sussex virus or any variant thereof. In some preferred embodiments, said virus is Moissiacense virus, Mama virus or any variant thereof. Moissiacense virus has a S segment comprising SEQ ID NO: 1 which codes for a Nucleocapsid (N) protein of SEQ ID NO: 2 and a NSs protein of SEQ ID NO: 72, a M segment comprising SEQ ID NO: 3 which codes for a polyprotein M of SEQ ID NO: 4, and a L segment comprising SEQ ID NO: 5 which codes for a polymerase protein (L) of SEQ ID NO: 6. Mama virus has a S segment comprising SEQ ID NO: 90 which codes for a Nucleocapsid (N) protein of SEQ ID NO: 93 and a NSs protein of SEQ ID NO: 94, a M segment comprising SEQ ID NO: 91 which codes for a polyprotein M of SEQ ID NO: 95, and a L segment comprising SEQ ID NO: 92 which codes for a polymerase protein (L) of SEQ ID NO: 96. Umbre virus includes the strain IG1424 comprising a S segment having the sequence GenBank accession number KP792685.2 as accessed on Nov. 16, 2016 which codes for a Nucleocapsid (N) protein having the sequence GenBank: AKO90197.1 as accessed on Nov. 16, 2016 and a NSs protein having the sequence GenBank: AKO90198.1 as accessed on Nov. 16, 2016; a M segment having the sequence GenBank accession number KP792686.1 as accessed on Dec. 1, 2015 which codes for a polyprotein M having the sequence GenBank: AKO90182.1 as accessed on Dec. 1, 2015; and a L segment having the sequence GenBank accession number KP792687.1 as accessed on Dec. 1, 2015 which codes for a polymerase protein (L) having the sequence GenBank: AKO90167.1 as accessed on Dec. 1, 2015. Little Sussex virus has a L segment comprising the sequence GenBank accession number KT720483.1 as accessed on Apr. 2, 2016 which codes for a polymerase protein (L) comprising having the sequence GenBank: AMR73388.1 as accessed on Apr. 2, 2016.

The viral nucleic acid or target nucleic acid may be genomic RNA (viral RNA or vRNA), complementary RNA (cRNA) or viral mRNA. Genomic RNA or viral RNA (vRNA) is negative-sense RNA comprising the reverse complement of one of the above-mentioned coding sequences, in the RNA form. Complementary RNA (cRNA) is positive-sense RNA comprising one of the above-mentioned coding sequences, in the RNA form. Viral mRNA comprises one of the above-mentioned coding sequences, in the RNA form. In some preferred embodiments of the methods of the invention, the viral nucleic acid is viral RNA (i.e. Moissiacense virus genomic RNA).

The diagnosis or detection method of the invention comprises the detection of a target sequence of the viral nucleic acid. The target sequence refers to the particular nucleotide sequence of the viral nucleic acid that is to be detected by any appropriate mean such as hybridization with an oligonucleotide probe, amplification with a pair of oligonucleotide primers, sequencing, in particular high-throughput sequencing, or a combination thereof. For example, an amplification product (amplicon) of the target sequence obtained by amplification of viral nucleic acid from the sample may be detected by using a DNA binding dye or labelled primer, or hybridization assay using a labelled oligonucleotide probe. As used herein, the detection of a target sequence of the viral nucleic acid refers to the direct detection and the detection following another step performed on the viral nucleic acid such as a reverse transcription step and an amplification of said viral nucleic acid.

The target sequence includes the sequence to which oligonucleotide probe hybridizes during the nucleic acid detection process and the sequences to which oligonucleotide primers hybridize during the nucleic acid amplification process. The target sequence that is detected directly using an oligonucleotide probe consists usually from a lower limit of 15 to 20 consecutive nucleotides to an upper limit of 45 to 60 consecutive nucleotides of one of the above-mentioned viral nucleic acid sequences. The target sequence that is amplified and detected consists usually of at least 50 consecutive nucleotides, preferably at least 100 or 150 consecutive nucleotides of one of the above-mentioned viral nucleic acid sequences. Preferably, the target sequence consists of 150 to 600 consecutive nucleotides, more preferably 300 to 500 consecutive nucleotides of one of the above-mentioned viral nucleic acid sequences. The target nucleic acid being originally single-stranded, the term target sequence will also refer to the sequence complementary to the target sequence as present in the viral nucleic acid.

The target sequence is a unique sequence which is specific for Moissiacense virus. Thus, the detection of the target sequence indicates the presence of Moissiacense virus in the sample. Therefore, the detection of the target sequence in a sample from the individual is indicative of whether the individual is suffering from Moissiacense virus infection and in particular from a disease caused by Moissiacense virus such as encephalitis.

By comparing the L, M and S segment sequences of Moissiacense virus which are disclosed in the present application with that of other bunyavirus species or other members of the order Bunyavirales which are available in the sequence databases, one skilled in the art can easily identify a unique target sequence which is specific for Moissiacense virus using standard nucleotide sequence analysis softwares that are well-known in the art.

In some embodiments, the method of the invention comprises the detection of at least one target sequence selected from the group consisting of:

a) a sequence SEQ ID NO: 7 situated in the region from positions 23 to position 338 of the S segment sequence SEQ ID NO: 1;
b) a sequence SEQ ID NO: 8 situated in the region from positions 3706 to 4130 of the M segment sequence SEQ ID NO: 3;
c) a sequence SEQ ID NO: 9 situated in the region from positions 3312 to 3768 of the L segment sequence SEQ ID NO: 5;
d) a sequence of at least 15 nucleotides, preferably at least 50, 100, 150, 200 or 300 nucleotides from any one of SEQ ID NO: 7 to 9; and
e) a sequence comprising any one of SEQ ID NO: 7 to 9 and up to 40 consecutive nucleotides, preferably up to 35, 30, 25 or 20 (2, 3, 4, 5, 6, 7, 8, 9, 10, 11, 12, 13, 14, 15, 16, 17, 18, 19 and 20), more preferably up to 15 (2, 3, 4, 5, 6, 7, 8, 9, 10, 11, 12, 13, 14, 15), up to 10 (2, 3, 4, 5, 6, 7, 8, 9, 10) or up to 5 (2, 3, 4, 5) consecutive nucleotides of 5' and/or 3' flanking sequence from said S, M or L segment sequence.

The target sequences listed above are species specific. They allow the detection of viruses of the Moissiacense group or species including at least Moissiacence, Marna, Umbre and Little Sussex viruses. The target sequence consists of or is included, comprised in or contained in the target region. In some preferred embodiment, the target sequence consists of the target region as defined above.

Nucleic acid amplification techniques include target amplification systems, probe amplification systems and signal amplification. Target amplification systems include with no limitations: Polymerase Chain Reaction (PCR) including RT-PCR, nested PCR and multiplex PCR; Nucleic Acid Sequence-Based Amplification (NASBA), Transcription Mediated Amplification (TMA), Strand Displacement Amplification (SDA) and isothermal amplification such as reverse-transcription loop-mediated isothermal amplification (RT-LAMP). Target nucleic acid amplification is performed using any of the various natural or engineered enzymes available for this purpose. For example, PCR can be performed using any thermostable polymerase such as with no limitations: Taq, Vent, Pfu, Tth and variants thereof. Signal amplification includes Branched DNA probes (bDNA) and Hybrid capture assay using anti-DNA-RNA hybrid antibody conjugated to a label such as phosphatase alkaline. Probe amplification includes Ligase Chain Reaction (LCR) and Cleavase Invader (FEN-1 DNA polymerase (cleavase)). Hybridization is preferably sequence-specific hybridization, i.e., hybridization with a nucleic acid probe that specifically hybridizes to a target sequence specific for Moissiacense virus.

Since the viral nucleic acid is RNA, the method of the invention comprise a reverse transcription reaction prior to or concomitantly with the amplification reaction of the target sequence. The reverse transcription reaction is performed using any reverse transcriptase (RT). RT are well-known in the art and include for example Avian Myeloblastosis Virus (AMV) and Moloney Murine Leukemia virus (MMLV) RT. The Reverse transcription and DNA amplification can be performed in the same reaction mixture comprising the DNA polymerase and RT enzymes.

The amplification product is detected using any of the various methods available for this purpose which are well-known in the art. For example, the detection method is fluorescence, bioluminescence, colorimetry or immunoenzymatic detection. The detection may be semi-quantitative or quantitative. The detection may also be real-time detection, wherein the signal resulting from the presence of the amplification product is measured during the course of the nucleic acid amplification reaction to monitor the accumulation of specific amplification products. Fluorescence may use DNA intercaling dyes or fluorescent molecular beacon probes. Immunoassays include Enzyme-linked immunosorbent assays (ELISA) and lateral flow.

In some preferred embodiments, the method of the invention comprises:

subjecting said sample to a nucleic acid amplification reaction using at least one pair of oligonucleotide primers for amplifying a target sequence of said viral nucleic acid, and detecting the presence of an amplification product for said target sequence.

The target amplification reaction is performed using any nucleic acid target amplification techniques as defined above. In some preferred embodiments, target amplification is performed by RT-PCR techniques using suitable enzymes for that purpose as defined above. The amplification product includes monomers and concatemers of the target sequence. The amplification product may be detected using any appropriate means available for that purpose as disclosed above such as by using a labelled primer or probe or a DNA binding dye. In the second step of the method of the invention, the detection of the presence or absence of the amplification product determines the presence or absence of a Moissiacence virus in the sample, and thereby whether or not the individual is infected with Moissiacense virus.

Oligonucleotide refers to a polymer of 5 to 100 nucleotides, preferably from a lower limit of 15 to 20 nucleotides to an upper limit of 45 to 60 nucleotides, wherein the polymer comprise ribonucleotides, deoxyribonucleotides, modified nucleotides or mixtures thereof and may further include modified internucleotide linkages and/or modified 5' and/or 3' termini. For example, the oligonucleotide can be DNA, RNA, PNA or mixed, and may comprise locked nucleic acids (LNA). Oligonucleotides are usually synthesized using any of a variety of well-known enzymatic or chemical methods. Oligonucleotide includes a probe or primer. The oligonucleotide probe or primer according to the invention is substantially complementary to the target sequence. Substantially complementary means that the oligonucleotide is at least 80% identical, preferably at least 85%, 90%, 95%, 96%, 97% 98% or 99% identical to the target sequence. The oligonucleotide may comprise additional sequences (not complementary to the target sequence) at its 5' end. In some embodiments the oligonucleotide comprises a sequence of at least 5, preferably 10 to 15 consecutive nucleotides which is 100% identical to the target sequence. In some more preferred embodiments, the oligonucleotide sequence is 100% identical to the target sequence.

The oligonucleotides which function as probes are capable of hybridizing specifically to the target sequence. They advantageously include a label to detect the target nucleic acid. The oligonucleotides which function as primers are capable of annealing specifically to the target sequence and can be further extended in the presence of a nucleic acid polymerase to specifically amplify the target sequence. At least one oligonucleotide may also function as a probe and further includes a detectable label to detect a target nucleic acid or an amplicon thereof.

The label is any moiety that can be detected directly or indirectly by the production of a detectable signal such as luminescent (radioluminescent, chemiluminescent, bioluminescent, fluorescent or phosphorescent), radioactive, colorimetric, magnetic signal or others. Directly detectable labels include radioisotopes and fluorophores. Indirectly detectable labels are detected by labelling with additional reagents that enable the detection. Indirectly detectable labels include, for example, chemiluminescent agents, enzymes that produce visible or coloured reaction products. Indirectly detectable labels also include ligand-detectable ligand binding partners, for example based on avidin or streptavidin/biotin complex, such as with no limitations a biotinylated oligonucleotide (for nucleic acid detection) or antibody (for protein detection) and streptavidin conjugated with a label (fluorophore or enzyme).

The oligonucleotides are designed by comparing the L, M and S segment sequences of the Moissiacense virus which are disclosed in the present application with that of other bunyaviruses or other members of the order Bunyavirales which are available in sequence databases, using general principles for designing amplification primers or probes that are well-known in the art. The design of the primers may also include specific principles for designing primers for use in specific amplification methods. Appropriate softwares for designing oligonucleotide primers or probes are available in the art. The sequences of the oligonucleotide primers or probe are specific for the target sequence of the Moissiacense virus. This means that they are chosen to hybridize specifically to the target sequence of the Moissiacense virus but not to related target sequences of other bunyaviruses or other members of the order Bunyavirales which infect humans or animals, under the hybridization conditions which are used for the methods of the invention. It is within the skills of one of ordinary skill in the art to choose the sequences of the oligonucleotide probe or primes pair and adapt the hybridization conditions (Temperature, salt concentration) of said oligonucleotide probe or primer pair to permit only hybridization with nucleic acid of Moissiacense virus.

In some embodiments of the above method, the oligonucleotide probe or primers are selected from the group consisting of: the sequences of 5 to 100 nucleotides, preferably 15 to 60 nucleotides having 80% to 100% identity, preferably at least 85%, 90% 95%, 96%, 97%, 98% or 99% identity with any of SEQ ID NO: 1, 3, 5, and 7 to 9 or with a sequence comprising any of SEQ ID NO: 7 to 9 and up to 40 consecutive nucleotides, preferably up to 35, 30, 25 or 20 (2, 3, 4, 5, 6, 7, 8, 9, 10, 11, 12, 13, 14, 15, 16, 17, 18, 19 and 20), more preferably up to 15 (2, 3, 4, 5, 6, 7, 8, 9, 10, 11, 12, 13, 14, 15), up to 10 (2, 3, 4, 5, 6, 7, 8, 9, 10) or up to 5 (2, 3, 4, 5) consecutive nucleotides of 5' and/or 3' flanking sequence from said S, M or L segment sequence, and their complement.

In some preferred embodiments, the oligonucleotide probe or primers are selected from the group consisting of the sequences SEQ ID NO: 10 to 57. The primer pairs are advantageously selected from the group consisting of: SEQ ID NO: 10-11, 12-13, 14-15, 16-17, 18-19, 20-21, 22-23, 24-25, 26-27, 28-29, 30-31, 32-33, 34-35, 36-37, 38-39, 40-41, 42-43, 44-45, 46-47, 48-49, 50-51, 52-53, 54-55, and 56-57. The primer pairs SEQ ID NO: 10-11, 12-13, and/or 14-15 are advantageously used for the detection of any virus of the Moissiacense group, in particular Moissiacense virus, Umbre virus, Little Sussex virus or any variant thereof.

Antigen or Antibody Detection

In some aspects, the method of detection or diagnosis of Moissiacense virus comprises determining the presence of at least one protein of said virus or antibodies thereto in a sample.

The detection or diagnosis is generally performed by immunoassay using an antigen from virus Moissiacense or antibody thereto. Immunoassays are well-known techniques for protein or antibody detection which rely on the detection of antigen-antibody complexes using an appropriate label. The method of the invention may use any immunoassay such as with no limitations, immunoblotting, immunoprecipitation, ELISA, immunocytochemistry or immunohistochemistry, and immunofluorescence like flow cytometry assay, and FACS. The method of the invention may use any appropriate label used in immunoassays such as enzymes, biotin, fluorescent dyes/proteins or others.

In some embodiments, the antigen from Moissiacense virus comprises the amino acid sequence of the N, Gn or Gc protein or a fragment thereof. A fragment refers to a functional fragment, which means a fragment of at least 10 amino acids that is bound by antibodies against Moissiacense virus. In some embodiments, the fragment comprises at least 50, 100, 200, 300 or more amino acids.

In some preferred embodiments, the antigen comprises the N protein amino acid sequence or a fragment thereof, preferably a sequence having 90% to 100% identity with SEQ ID NO: 2, or a fragment of at least 10 amino acids thereof which is bound by antibodies against Moissiacense virus.

In some other preferred embodiments, the antigen comprises an extracellular fragment of Gc protein, preferably chosen from:

- a sequence SEQ ID NO: 61 comprising the extracellular domain (positions 476 to 1395 on the polyprotein M of SEQ ID NO: 4);
- a sequence SEQ ID NO: 62 comprising the N-terminal alpha-helix (positions 510 to 770 on the polyprotein M of SEQ ID NO: 4);
- a sequence SEQ ID NO: 63 comprising the N-terminal domain (positions 477 to 907 on the polyprotein M of SEQ ID NO: 4), and
- a sequence of at least 50 amino acids from any one of SEQ ID NO: 61 to 63, in particular SEQ ID NO: 64 (positions 477 to 730 of SEQ ID NO: 4).

In some embodiments, the method is for the detection or diagnosis of Moissiacense virus, Mama virus or any variant thereof.

An antibody refers to an antibody against a protein of Moissiacense virus, preferably the N, Gn or Gc protein, more preferably an antibody which binds an extracellular epitope of the Gn or Gc protein that is exposed on the surface of virion particles. The antibody according to the invention recognizes specifically said viral protein, in particular Gn or Gc protein on the plasma membrane of infected cells. Such recognition can be determined by standard immunofluorescence assay like flow cytometry assay. The antibody has a relatively high affinity to its epitope of said viral protein, but do not substantially recognize and bind to peptides other than the one(s) of interest. As used herein, the term "relatively high affinity" means a binding affinity between the antibody and the protein of interest of at least $10^{-6}$ M, and preferably of at least about $10^{-7}$ M and even more preferably $10^{-8}$ M to $10^{-10}$ M. Determination of such affinity is preferably conducted under standard competitive binding immunoassay conditions which is common knowledge to the person of ordinary skill in the art. The term "antibody" is meant to encompass a whole antibody or antigen binding fragment thereof, an aggregate, polymer, derivative, or conjugate of antibody. The antibody may be monoclonal, polyclonal, non-recombinant or recombinant, chimeric or humanized.

The antigen or antibody may include an appropriate label for antibody or antigen detection, for example in the form of a fusion protein or conjugate. In some embodiments, the antigen is fused with an enzyme such as luciferase.

The antigen of the invention is prepared by the conventional techniques known to those skilled in the art, in particular by expression from an appropriate recombinant expression vector in a suitable cell system (eukaryotic including mammalian and insect cells or prokaryotic). In particular embodiments, the vector comprises any one of SEQ ID NO: 65 to 68 and 73 or a fragment thereof The antibody of the invention can be produced by the conventional techniques known to those skilled in the art. For example, they may be produced by immunization of an animal with an antigen from virus Moissiacense, in particular a recombinant antigen as define above.

The antigen and antibody are specific for Moissiacense virus and usually do not exhibit substantial cross-reactivity with other pathogens that infect human or animal individuals, under the conditions for antigen-antibody complex formation that are used in the methods of the invention. It is within the skill of a person having ordinary skill in the art to prepare specific antigen and antibodies and adapt the conditions of the method to detect the specific binding of the diagnostic agent (antigen or antibody) to its antibody or antigen counterpart from Moissiacense virus.

In some embodiments, the method of detection or diagnosis of Moissiacense virus comprises the step of:

- incubating an antigen from Moissiacense virus or antibody thereto with the biological sample to form a mixture; and
- detecting antigen-antibody complexes in the mixture.

The sample for anti-Moissiacense virus antibody detection is preferably body fluid from the individual, in particular serum. The sample for viral protein detection may be tissue sample, in particular biopsied tissue such as brain biopsy, or body fluid such as cerebral spinal fluid (CSF), whole-blood or serum.

The antigen or antibody is preferably labeled and the antigen-antibody complexes are detected by measuring the signal from the label by any appropriate means available for that purpose as disclosed above.

In some embodiments, antibody detection is performed by luciferase immunoprecipitation using an antigen fused with luciferase, preferably an antigen comprising SEQ ID NO: 61 or 62.

In some embodiments, antibody detection is performed by ELISA using an antigen comprising SEQ ID NO: 63 or 64.

In some embodiments, the detecting step comprises the determination of the amount of bound antibody or bound antigen in the mixture, and optionally, comparing the amount of bound antibody or bound antigen in the mixture with at least one predetermined value.

The detection of the viral nucleic acid target sequence, protein or antibody thereto in a sample from the individual using the methods of the invention is indicative of whether the individual is suffering from Moissiacense virus infection and in particular from a disease caused by Moissiacense virus such as encephalitis.

Therefore, the above methods of the invention are useful for the diagnosis of Moissiacense virus infection in an individual, in particular the diagnosis of the disease caused by Moissiacense virus, ranging from febrile illness to central nervous system involvement such as encephalitis. In some embodiments, said virus is Moissiacense virus, Marna virus or any variant thereof.

In some embodiments, the above methods comprise the step of deducing therefrom whether the individual is suffering from Moissiacense virus infection and in particular from a disease caused by Moissiacense virus such as encephalitis.

In some embodiments in connection with this aspect of the invention, the above methods comprise a further step of administering an appropriate treatment to the individual depending on whether or not the individual is diagnosed with Moissiacense virus infection and in particular with a disease caused by Moissiacense virus such as encephalitis.

The above methods of the invention are in particular useful for the differential diagnosis of encephalitis, in particular human encephalitis. In some embodiments, in connection with this aspect of the invention, the same biological sample from an individual may be subjected, simultaneously or separately, to a method of detection or diagnosis of at least another pathogen, in particular at least another encephalitis-causing agent such as encephalitis virus. Encephalitis virus includes in particular Herpesvirus such as HSV and VZV, enteroviruses, polyomaviruses, astroviruses, measles virus, mumps virus, and various arboviruses such as without limitation, West Nile, JEV and TBEV.

The above methods of the invention are also useful for the detection of Moissiacense virus in an arthropod vector population to study virus Moissiacense dissemination across geographic areas for epidemiological surveys.

In some preferred embodiments, the above methods of the invention comprise assaying several samples simultaneously, and/or assaying different target sequences, antigens or antibodies simultaneously on the same sample, in parallel in separate reaction mixtures, or in the same reaction mixture and detected independently. In some advantageous embodiments, the methods comprise assaying multiple samples, targets, antigens, and/or antibodies simultaneously in a high-throughput process.

Kits for the Diagnosis or Detection of Moissiacense Virus

Another aspect of the invention is a kit for the diagnosis or detection of Moissiacense virus, comprising at least one oligonucleotide probe or primer, antigen or antibody thereto for the detection of Moissiacense virus nucleic acid, antibody or protein, as defined above, preferably further including a detectable label. In particular, the kit comprises at least one pair of oligonucleotide primers for amplifying said target; preferably wherein at least one oligonucleotide of the pair may comprise a detectable label. In some embodiments, the kit is for the diagnosis or detection of Moissiacense virus, Mama virus or any variant thereof.

In some embodiments, the kit is for the differential diagnosis of encephalitis, in particular human encephalitis. In some particular embodiments, in connection with this aspect of the invention, the kit further comprises at least one oligonucleotide probe or primer, antigen or antibody thereto for the detection of least another encephalitis-causing agent such as encephalitis virus, as defined above. The encephalitis virus is in particular chosen from Herpesvirus such as HSV and VZV, enteroviruses, polyomaviruses, astroviruses, measles virus, mumps virus, and various arboviruses such as without limitation, West Nile, JEV and TBEV. The at least one oligonucleotide probe or primer, antigen or antibody for the detection of said other(s) encephalitis-causing agent(s) preferably further includes a detectable label. In particular, the kit comprises at least one pair of oligonucleotide primers for amplifying a target sequence of the nucleic acid of at least another encephalitis-causing agent such as encephalitis virus as defined above; preferably wherein at least one oligonucleotide of the pair may comprise a detectable label.

The kit optionally comprises reagents for the amplification of the target sequence and/or the detection of the amplification product or antigen/antibody complex. Reagents available for this purpose are well-known in the art and include the DNA polymerases and RT enzymes described above, buffers or substrates for the enzymes, detergents, enhancing agents, nucleic acid binding dyes and probes, preferably labelled probes, secondary antibody conjugated to a label, avidin/streptavidin conjugated to a label. In some preferred embodiments of the kit of the invention, the primers, probe, antigen or antibody, and optional reagents are in lyophilised form to allow ambient storage. The components of the kits are packaged together into any of the various containers suitable for nucleic acid amplification or antigen/antibody complex detection such as plates, slides, wells, dishes, beads, particles, cups, strands, chips, strips and others. The kit optionally includes instructions for performing at least one specific embodiment of the method of the invention. In some advantageous embodiments, the kit comprises micro-well plates or microtubes, preferably in a dried format, i.e., wherein the wells of the plates or microtubes comprise a dried composition containing at least the primers, probe, antigen or antibody, and preferably further comprising all the reagents for the amplification of the target sequence and/or the detection of the amplification product amplification or antigen/antibody complex. In some other advantageous embodiments, the primers, probe, antigen or antibody and optional reagents are included into any of the devices available for nucleic acid amplification or immunoassay including devices further integrating nucleic acid extraction and/or amplification product detection capacities such as microfluidic devices or other devices.

Another aspect of the invention, relates to an oligonucleotide probe or primer, antigen or antibody thereto for the detection of Moissiacense virus nucleic acid, antibody or protein, as defined above. The invention also relates to the use of an oligonucleotide probe or primer, antigen or antibody thereto for the detection of Moissiacense virus nucleic acid, antibody or protein as defined above, as diagnostic agent for the in vitro detection or diagnosis of Moissiacense virus. The invention encompasses combinations of the above diagnostic agents for the detection of Moissiacense virus with other diagnostic agents, in particular oligonucleotide probe(s) or primer(s), antigen(s) or antibodies thereto, for the detection of other encephalitis-causing agent(s) as defined above and their use for the differential diagnosis of encephalitis, in particular human encephalitis. In some embodiments, said virus is Moissiacense virus, Mama virus or any variant thereof.

Immunogenic or Vaccine Compositions

Another aspect of the invention, relates to an immunogenic or vaccine pharmaceutical composition comprising, as active substance an antigen from Moissiacense virus as defined above, in association with at least one pharmaceutically acceptable vehicle.

The pharmaceutical vehicles are those appropriate to the planned route of administration, which are well known in the art.

The pharmaceutical composition may further comprise a carrier and/or adjuvant. Non-limitative examples of carriers suitable for use in the composition of the invention include uni- or multi-lamellar liposomes, ISCOMS, virosomes, viral pseudo-particules, saponin micelles, saccharid (poly(lactide-co-glycolide)) or gold microspheres, and nanoparticules. Non-limitative examples of adjuvants suitable for use in the composition of the invention include: CpG oligodeoxynucleotide, Freund adjuvant, polyI:C (polyinosine-polycytidylic acid), oil emulsion, mineral substances, bacterial extracts, saponin, aluminium salts, monophosphoryl-lipid A and squalene.

The pharmaceutical composition comprises a therapeutically effective amount of the antigen sufficient to induce a protective immune response against Moissiacense virus infection in the individual to whom it is administered. The pharmaceutically effective dose depends upon the composition used, the route of administration, the type of mammal (human or animal) being treated, the physical characteristics of the specific mammal under consideration, concurrent medication, and other factors, that those skilled in the medical arts will recognize.

The invention provides also an antigen according to the invention for use as a medicament.

The invention provides also an antigen or pharmaceutical composition according to the invention for use in the prevention of Moissiacense virus infection and associated disease, in particular encephalitis. In some embodiments, said virus is Moissiacense virus, Mama virus or any variant thereof.

The invention provides also a method for preventing treating Moissiacense virus infection and associated disease, in particular encephalitis in an individual, comprising: administering a therapeutically effective amount of the pharmaceutical composition according to the invention to the individual. In some embodiments, said virus is Moissiacense virus, Mama virus or any variant thereof.

The pharmaceutical composition of the present invention is generally administered according to known procedures, at dosages and for periods of time effective to induce a beneficial effect in the individual. The administration may be by injection.

The practice of the present invention will employ, unless otherwise indicated, conventional techniques which are within the skill of the art. Such techniques are explained fully in the literature.

The invention will now be exemplified with the following examples, which are not limitative, with reference to the attached drawings in which:

FIGURE LEGENDS

Figure 1:
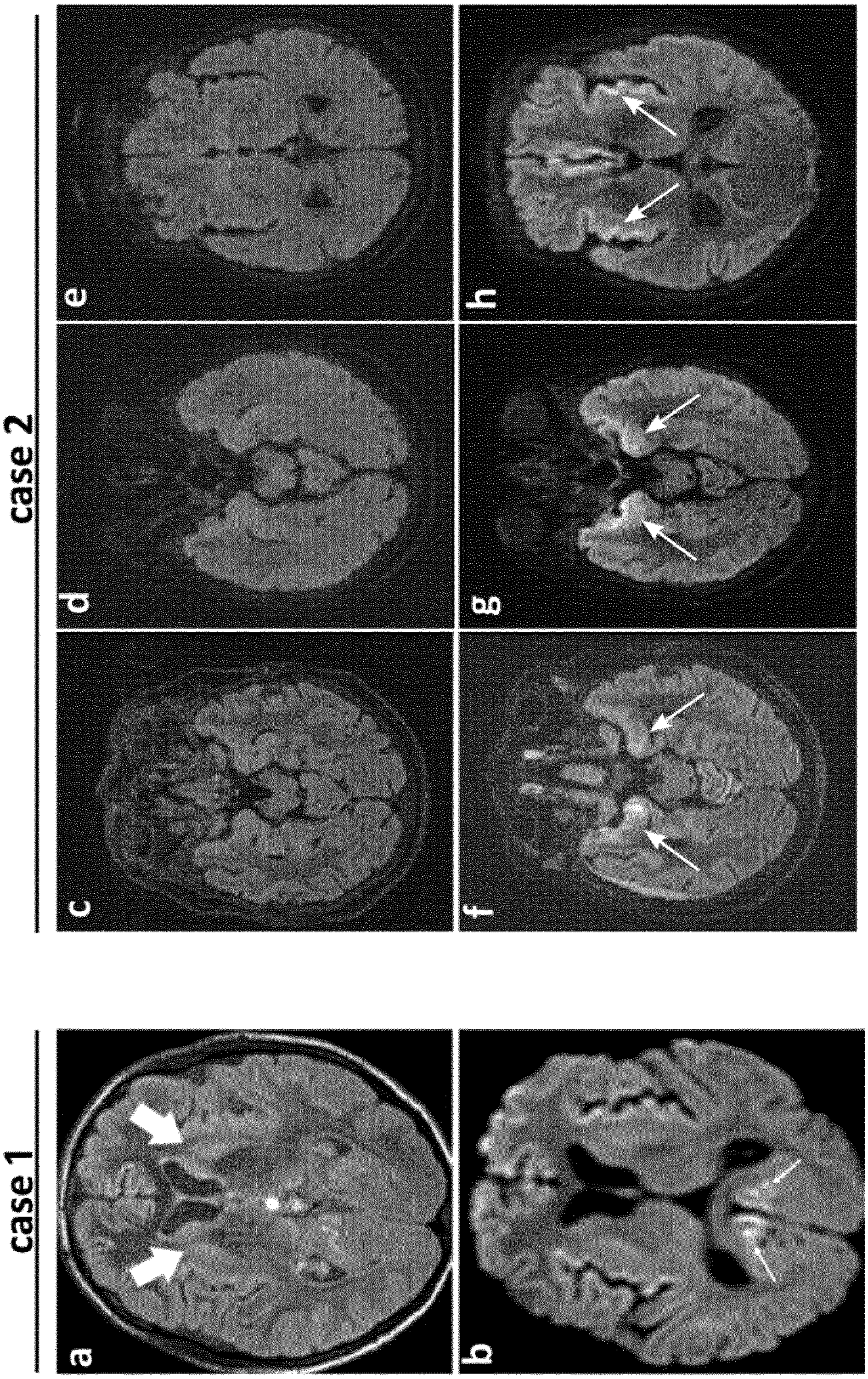

FIG. 1: Brain MRI of the Two Patients with Umbre Virus Encephalitis a & b: case 1. Axial FLAIR (a) and Diffusion-weighted (b) images, revealing mild hyper intensity of both putamina (thick arrows), and of frontal, insular and posterior cingulate cortices (thin arrows). c to h: case 2. Brain MRI at month 1 (c to e) and month 5 (f to h); c & f: axial T2; d & e; g & h: diffusion-weighted images. c, d, e: normal hippocampi and insular cortices at month 1. f, g, h: bilateral hypersignal (arrows) of the hippocampi and insular cortices, with mild bi-hippocampi atrophy.

Figure 2:
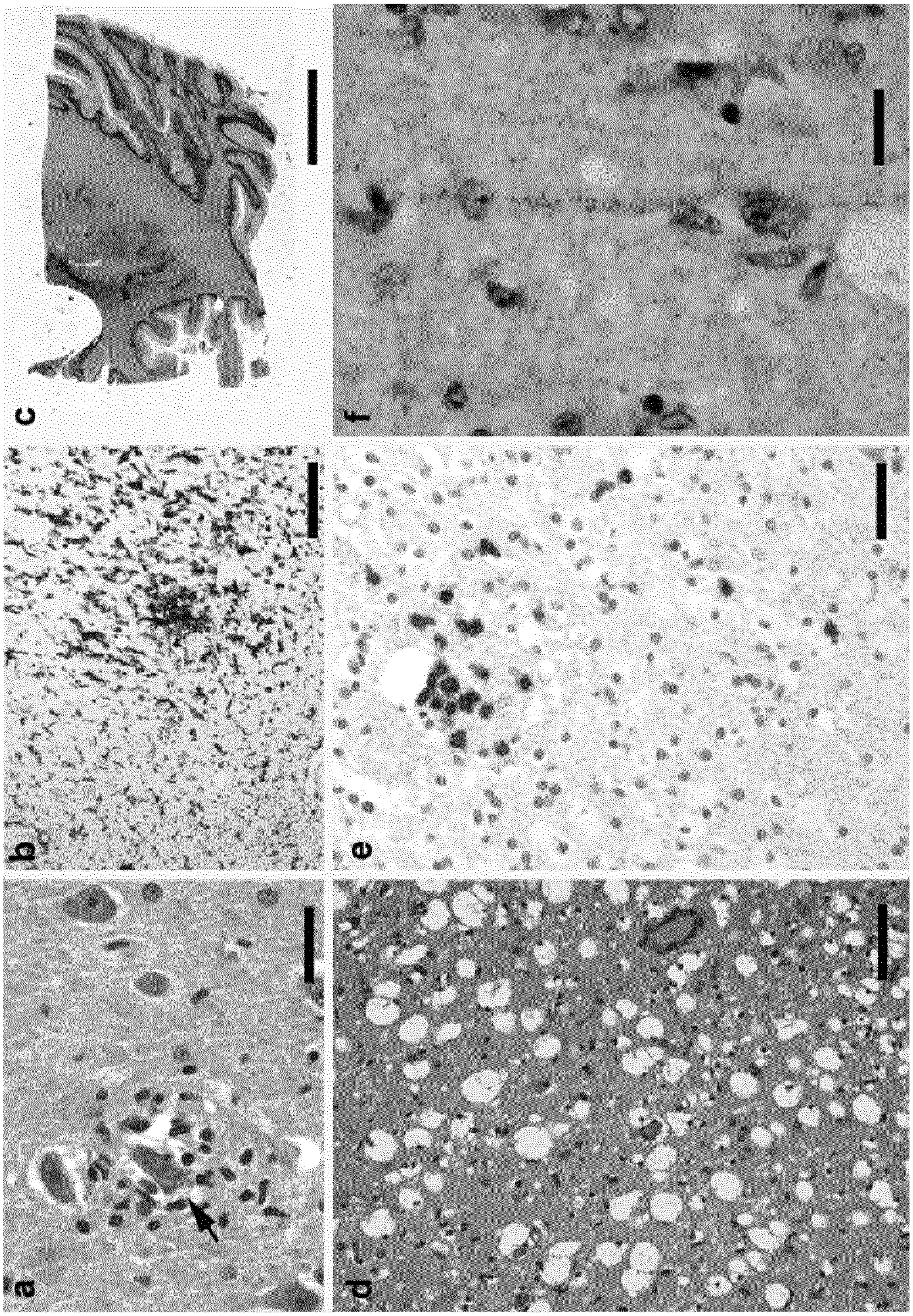

FIG. 2: Histopathology in Case 1 a: Parahippocampal cortex. Haematein-eosin. Microglial cells surrounding a neuron (black arrow), suggesting neuronophagia. b: Dentate nucleus. IBA-1 immunohistochemistry. Diffuse microglial activation and microglial nodule. c: Cerebellum. CD163 immunohistochemistry. Distribution of activated microglia. Enhancement in the dentate nucleus. d: Temporal cortex. Haematein-eosin. Spongiosis. e: Caudate nucleus. CD3 immunohistochemistry. Clusters of T-lymphocytes. f: Frontal cortex. In situ hybridization with a bunyavirus probe. Labeling (red) of the cell body and dendritic shaft of a pyramidal neuron. Scale bars: a & e=50 μm; b & d=100 μm; c=5 mm; f=25 μm.

Figure 3:
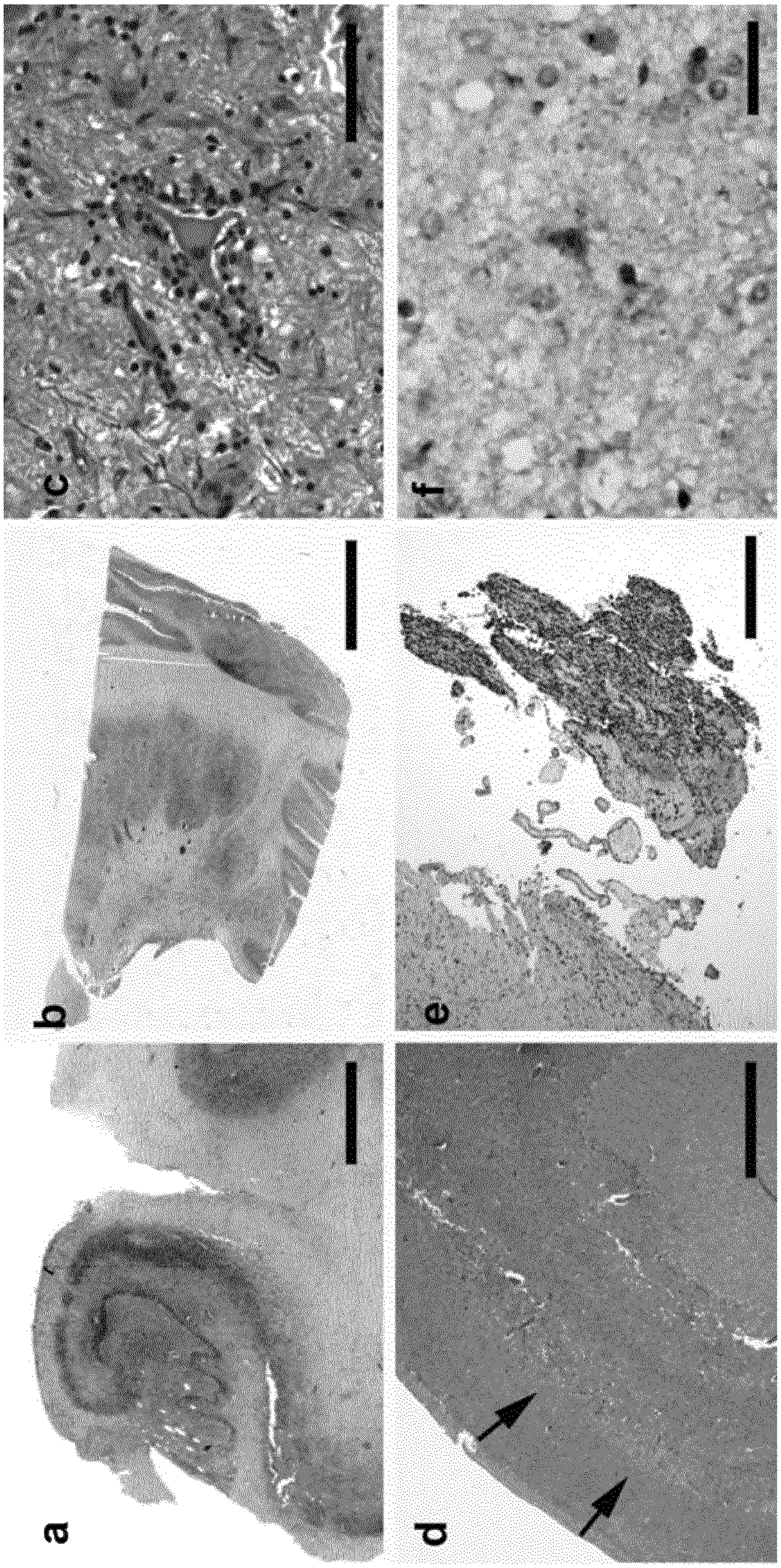

FIG. 3: Histopathology in Case 2 a: Right hippocampus. CD163 immunohistochemistry. Distribution of activated microglia. Enhancement of the dentate gyrus and pyramidal sectors of the cornu Ammonis. b: Cerebellum. CD163 immunohistochemistry. Distribution of activated microglia. Enhancement in the dentate nucleus and cerebellar cortex. c: Anterior horn of the spinal cord. Haematein-eosin. Microglial cells surrounding a neuron, suggesting neuronophagia. d: Right hippocampus. Haematein-eosin. Neuronal loss in CA1 (black arrows). e: Roots of the oculomotor nerve. CD163 immunohistochemistry. Infiltration by macrophages. f: Frontal cortex. In situ hybridization with a bunyavirus probe. Labeling (red) of the cell body of a pyramidal neuron. Scale bars: a & b=5 mm; c=50 μm; d=100 μm; e=500 μm; f=25 μm.

FIG. 4: Phylogenetic Analysis of Orthobunyaviruses.

A) S-segment, B) M-segment, C) L-segment and D) PCR-targeted region on the L-segment. The bootstrap values are given at each branches. Moissiacense virus and the closest relative viral sequences are indicated in red. Serogroups are indicated in black on the right side of each panel. The details of the methods used for the phylogenetic analysis and the list of accession numbers are available in the material and methods section.

Figure 5:
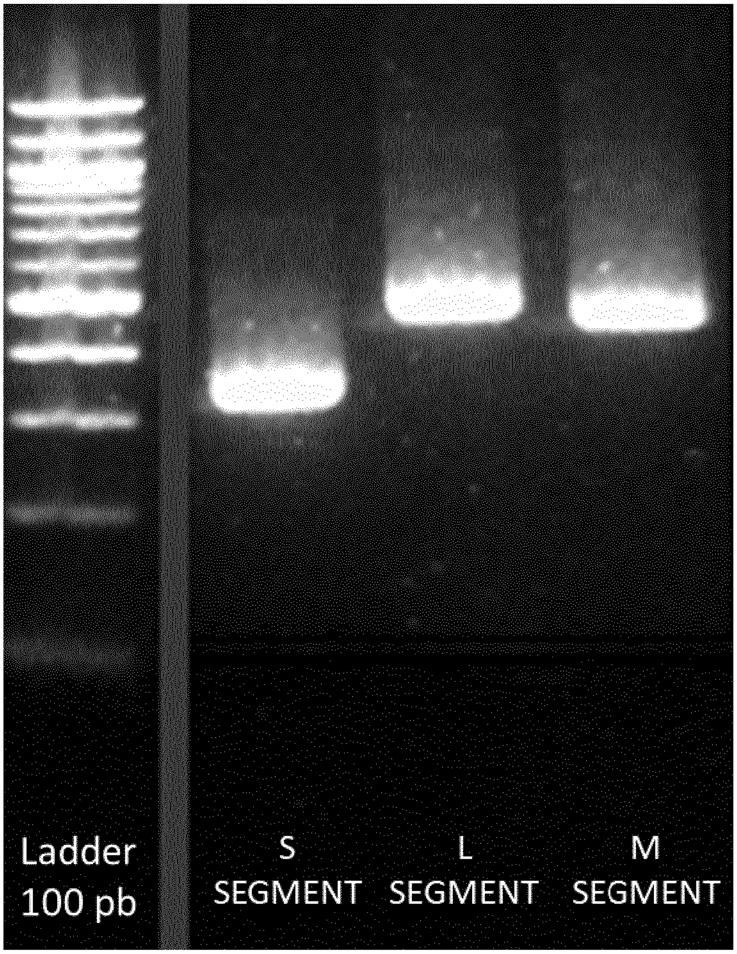

FIG. 5: RT-PCR assay on the patient's brain sample using primer pairs specific for Moissiacense virus species S, L and M segment sequences.

FIG. 6: Comparison of multiplex pan-orthobunyaviruses PCR primers from Lambert A J & Lanciotti R S (J. Clin. Microbiol., 2009, 47, 2398-404) with Moissiacense virus sequence (SEQ ID NO: 74 to 89). Disagreements between the consensus primers and Moissiacense virus sequences are highlighted.

Figure 7:
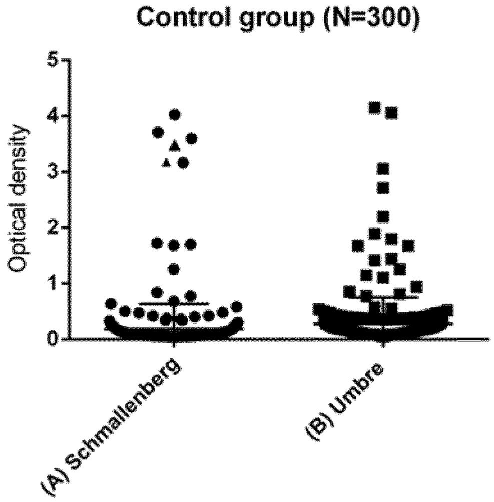

FIG. 7: Distribution of raw optical density values (ELISA immunoassay) using the Gc Head domain of Schmallenberg virus and Umbre virus as antigen on a control population (N=300). Black triangle: Schmallenberg positive serum tested undiluted. Small black triangle: Schmallenberg positive serum tested at a 10-fold dilution.

Figure 8:
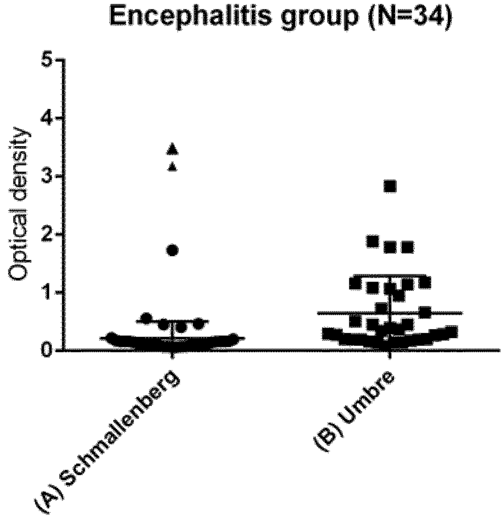

FIG. 8: Distribution of raw optical density values (ELISA immunoassay) using the Gc Head domain of Schmallenberg virus and Umbre virus as antigen on a encephalitis group (N=34). Black triangle: Schmallenberg positive serum tested undiluted. Small black triangle: Schmallenberg positive serum tested at a 10-fold dilution.

EXAMPLES

1. Material and Methods

Metatranscriptomics Analysis

By using untargeted metatranscriptomics, the inventors aimed at identify RNA sequences from bacteria, fungi, viruses or protozoans without prior hypothesis on the involved pathogen. RNA, rather than DNA, is indicative of living microorganisms. For each patient individually, total RNA was extracted from post-mortem brain using a bead based tissue homogenizer (Bertin) and the Trizol procedure (Thermo Fisher Scientific), followed by RNA purification on RNeasy column including a DNAse treatment (Qiagen). RNA Integrity Number (RIN) ranged between 2.9 and 6.9 after extraction, with 18S and 28S rRNA peaks visible. For each sample, a cDNA (NGS) library was prepared with the SMARTer Stranded Total RNA-Seq Kit—Pico Input Mammalian (Takara Bio, kit v.1 for patient 1 and v.2 for patient 2). The libraries of the 2 patients were made independently. The procedure included a random reverse transcription of total RNA into first strand cDNA, a depletion of human ribosomal cDNA, and a final PCR amplification. The cDNA libraries were sequenced independently for the two patients in 1×150 bp on a NextSeq500 instrument (Illumina), using High Output flow cells generating approximately 35 and 116 million reads. A set of reference human transcripts was used as an internal positive control. The inventors have not sequenced the ante-mortem biopsy of Patient #2. The vast majority of raw reads had quality scores (Q scores) above 20. Raw reads were trimmed to remove low quality bases and sequencing adapters at their ends with AlienTrimmer (Criscuolo et al., A, Genomics, 2013, 102, 500-6; version 0.4.0, options-k 10-m 5-1 50-p 80-c 012-q 20). The reads were then assembled with MegaHit (Li et al., Bioinforma Oxf.Engl., 2015, 31, 1674-6; version 1.1.2, with default options). Unassembled reads were kept as singletons. Resulting sequences were aligned after translation in all the six possible reading frames (3 by DNA strand) against a viral protein reference comprehensive database developed by the inventors (RVDB; Bigot et al., F1000Research, 2019, 8, 530) using the DIAMOND program (Buchfink et al., Nat. Methods, 2015, 12, 59-60). Matches with viral sequences were controlled in NCBI NR protein and NCBI NT databases to identify and eliminate false positive. This led to the identification of 168 sequences (22 contigs and 146 singletons) belonging to the Peribunyaviridae family, covering approximately 55% of the closest reference virus genome represented by Umbre virus. No other viral sequence was identified. A search for bacteria or other non-viral pathogen sequences was performed with Kraken2 (Wood et al., Genome Biol., 2014, 15, R46), Centrifuge (Kim D et al., Genome Res [Internet] 2016 [cited 2018 Nov. 30]; Available from: http://genome.cshlp.org/content/early/2016/11/16/gr.210641.116) and Methaphlan2 (Truong et al., Nat. Methods., 2015, 12, 902-3) leading to no other viral or bacterial hit. Full CDS of the S, L and M segments were obtained by a combination of RT-PCR and RACE analysis. Patient 1: S segment (SEQ ID NO: 1); M segment (SEQ ID NO: 3); L segment SEQ ID NO: 5). Patient 2: S segment (SEQ ID NO: 90); M segment (SEQ ID NO: 91); L segment SEQ ID NO: 92.

Phylogenetic Analysis

Alignments of amino acids sequences were done with MAFFT v7.388 (Katoh et al., Nucleic Acids Res., 2002, 30, 3059-66; Katoh et al., Mol. Biol. Evol., 2013, 30, 772-80) and manually adjusted when needed. Identity matrices are given in Tables I to IV. RAxML phylogeny with 100 bootstrap replications was performed in Geneious 11.1.5 (Kearse et al., Bioinforma Oxf Engl., 2012, 28, 1647-9) after initial model selection done in MEGA7 (Kumar et al., Mol. Biol. Evol., 2016, 33, 1870-4). Only complete CDS sequences were kept for phylogenetic analysis of the S, M and L segments (FIG. 4A, B, C). The M segment of Koongol virus was removed from the analysis because of the presence of a large deletion (>300 AA) in the NSn and Gc part of the sequence, which most probably reflects a cell culture passaging artifact as demonstrated for Maguari orthobunyavirus (Pollitt et al., Virology, 2006, 348, 224-32). The M segment of Yacabba virus, and the L segments of Little Sussex virus and Salt Ash virus, were not included in the analysis because of partial CDS sequences. No sequence was available for Little Sussex virus M and S segments. Herbert virus (Family: Peribunyaviridae; Genus: Herbevirus) was used as outgroup. Accession numbers: S segment: Aino virus (NC_018460.1), Akabane virus (NC_009896.1), Batai virus (JX846604.1), Bunyamwera virus (NC_001927.1), Cache Valley virus (KC436108.1), Caraparu virus (KF254789.1), Chatanga virus (EU479697.1), Herbert herbevirus (JQ659258.1), Iaco virus (JN572067.1), Ilesha virus (KF234073.1), Koongol virus (KP792667.1), Kowanyama virus (KT820204.1), La Crosse virus (NC_004110.1), Leanyer virus (HM627177.1), Macaua virus (JN572070.1), Madrid virus (NC_034498.1), Murrumbidgee virus (NC_022597.1), Oropouche virus (NC_005777.1), Oya virus (JX983192.1), Salt ash virus (KF234258.1), Sathuperi orthobunyavirus (NC_018462.1), Simbu orthobunyavirus (NC_018477.1), Sororoca virus (JN572073.1), Tahyna virus (HM036217.1), Umbre virus (KP792685.2), Wyeomyia orthobunyavirus (JN572082.1), Yacaaba virus (KT820210.1). M segment: Aino virus (NC_018459.1), Akabane virus (NC_009895.1), Batai virus (JX846605.1), Bunyamwera virus (NC_001926.1), Cache Valley virus (KC436107.1), Caraparu virus (KF254788.1), Chatanga virus (EU621834.1), Herbert herbevirus (JQ659257.1), Iaco virus (JN572066.1), Ilesha virus (KF234074.1), Kowanyama virus (KT820203.1), La Crosse virus (NC_004109.1), Leanyer virus (HM627176.1), Macaua virus (JN572069.1), Madrid virus (KF254780.1), Murrumbidgee virus (NC_022596.1), Oropouche virus (NC_005775.1), Oya virus (JX983193.1), Salt ash virus (KF234257.1), Sathuperi orthobunyavirus (NC_018466.1), Simbu orthobunyavirus (NC_018478.1), Sororoca virus (JN572072.1), Tahyna virus (HM036218.1), Umbre virus (KP792686.1), Wyeomyia orthobunyavirus (JN572081.1). L segment: Aino virus (NC_018465.1), Akabane virus (NC_009894.1), Batai virus (JX846606.1), Bunyamwera virus (NC_001925.1), Cache Valley virus (KC436106.1), Caraparu virus (KF254793.1), Chatanga virus (EU616903.1), Herbert herbevirus (NC_038714.1), Iaco virus (JN572065.1), Ilesha virus (KF234075.1), Koongol virus (KP792669.1), Kowanyama virus (KT820202.1), La Crosse virus (NC_004108.1), Leanyer virus (HM627178.1), Little Sussex virus (KT720483.1), Macaua virus (JN572068.1), Madrid virus (KF254779.1), Murrumbidgee virus (KF234253.1), Oropouche virus (NC_005776.1), Oya virus (JX983194.1), Salt ash virus (KF234256.1), Schmallenberg virus (NC_043583.1), Simbu orthobunyavirus (HE795108.1), Sororoca virus (JN572071.1), Tahyna virus (HM036219.1), Umbre virus strain IG1424 (KP792687.1), Wyeomyia orthobunyavirus (JN572080.1), Yacaaba virus (KT820208.1).

Umbre orthobunyavirus strain Moissiacense (Moissiacense virus): S segment (SEQ ID NO: 2); M segment (SEQ ID NO: 4); L segment SEQ ID NO: 6.

Umbre orthobunyavirus strain Marna: S segment (SEQ ID NO: 90); M segment (SEQ ID NO: 91); L segment SEQ ID NO: 92.

Neuropathology

The biopsy sample was left overnight in formalin (10% of the commercial formalin solution containing 4% formaldehyde). After autopsy, fresh brain slices were stored frozen at −80° C. prior to nucleic acid extraction. The whole brains were immersion-fixed in formalin 10%. In case 1, only 9 samples were available. In case 2, a systematic protocol was applied. Samples of cerebral neocortex and hippocampus, basal ganglia, brainstem, cerebellum and spinal cord were analyzed.

Immunohistochemistry

The samples were paraffin-embedded. Three μm thick sections were obtained and stained with haematein-eosin, Periodic Acid Schiff (PAS) and Luxol Fast Blue. t. Immunochemistry was performed with various primary antibodies in a Ventana Ultra stainer (Roche) with diaminobenzidine as a brown chromogen. Primary antibodies included a rabbit monoclonal anti-CD3 (clone 2GV6, prediluted, Roche), a mouse monoclonal anti-CD163 (clone MRQ-26, prediluted, Roche) and a polyclonal rabbit anti IBA1 (dilution 1/500, Wako), all incubated 32 min at 37° C. Immunohistochemistry was performed independently for the two patients.

Western Blot

The search for PrPres was performed in the two cases by Western blot according to published protocols (Lasmézas et al., Science, 1997; 275:402-405).

In-Situ Hybridization

ViewRNA ISH Tissue Assay Kit 2-plex (Thermo Fisher Scientific) was used to detect RNA sequences. According to the manufacturer, the technique has a sensitivity of one single copy and is based on branched DNA technology. ViewRNA Probes have a double Z configuration: one side of the Z is complementary to the target sequence and its other side is complementary to the pre-amplifier DNA sequence. A cocktail of 95 custom bDNA probes was designed to target the 3 genomic segments of Umbre orthobunyavirus strain Moissiacense (Moissiacense virus) (15 probes for segment S, 40 probes for segment M, 40 probes for segment L) and was revealed (as the "probe type 1" of the kit) by a red signal. A mix of control probes targeting human GAPDH, ACTB and PPI transcripts was revealed (as the "probe type 6" of the kit) by a blue signal. To unmask RNA targets, the tissue sections (after deparaffinization by xylene and ethanol) were pretreated by heating at 95° C. during 20 min in PBS 1×, cooling at room temperature (RT) during 5 min, washing 2×1 min in distilled water, washing 1 min in PBS 1×, protease digestion during 10 min at 40° C. in a hybridizer Denaturation & Hybridization System (NB-12-0001, Neobrite), and washing 2×1 minute in PBS at room temperature (RT). Tissue sections were fixed 5 min in formaldehyde 4% at RT, then washed 2×1 min in PBS 1×. Probes diluted in Probe Set Diluant QT (ThermoFisher)—a proprietary aqueous solution containing formamide, detergent, and blocker-were added on the tissue section and were hybridized during 2 hours at 40° C. in the hybridizer. The sections were washed 3×2 min in Wash Buffer. During the amplification step, sections were incubated 25 min at 40° C. in PreAmplifier Mix containing the PreAmplifier DNA type 1 and type 6, washed 3×2 min in Wash Buffer, incubated 15 min at 40° C. in Amplifier Mix containing the Amplifier DNA type 1 and type 6, and washed 3×2 min. In order to produce the blue signals, the section were incubated with 6-AP (an alkaline phosphatase binding the amplifier DNA type 6) during 15 min at 40° C. in the hybridizer, washed 3×3 min in Wash Buffer, incubated with Fast Blue solution during 30 min at RT, and washed 3×3 min in Wash Buffer. The 6-AP was quenched by AP STOP QT during 30 min at RT. In order to produce the red signals, the section were incubated with 1-AP (an alkaline phosphatase binding the amplifier DNA type 1) during 15 min at 40° C. in the hybridizer, washed 3×3 min in Wash Buffer, incubated with Fast Red solution during 45 min at 40° C. in the hybridizer, and washed 1 min in PBS. Haematoxylin was used for counterstaining. In-situ hybridization was performed at different times for the two patients, with Patient #1 having secondarily served as a positive control for Patient #2. The five negative controls used for ISH were other encephalitis cases coming from the larger series of brain samples (see section "Context of the study") that have been sequenced with a comparable sequencing depth and that were either negative (3/5) or positive for viruses other than Umbre (2/5).

Mosquito Capture

Approximately 4,000 *Culex pipiens* female mosquitoes were captured in 2015 in the French Rhone Delta region as described in Eiden et al. 2018 (Eiden M, Gil P, Ziegler U, et al. Infect Genet Evol J Mol Epidemiol Evol Genet Infect Dis 2018; 61:151-4) and 133 pools of approximately 30 individuals were made. Mosquito capture was carried for a 24-hour period once a week between June and September. Captures were carried out in the 6 sites in parallel the same days. The June-September period covers most of the mosquito season in the study region. The population of *Culex pipiens* is generally rather low before or after this period (usually less than 10 females per catch). In addition, this period was selected because it includes the population peak for *Culex pipiens* (usually June-July depending on the site) and the peak of prevalence in mosquitoes and clinical cases in vertebrates for *Culex*-borne arboviruses in the region (i.e. September for West Nile and Usutu viruses, e.g. Eiden et al. 2018, precited). 133 pools of approximately 30 individuals were made. In addition, around 100 *Culex pipiens,* 30 *Culex* Sp., 100 *Aedes caspius,* 50 *Aedes detritus,* 10 *Aedes vexans,* 10 *Aedes* Sp., and 20 *Anopheles* mosquitoes were captured in 2017 in Camargue and Languedoc (Southern France) and species-specific pools of 5-20 individuals were made. Of the mosquitoes captured in 2017, no positivity was recorded.

RT-PCR

RT-PCRs were done on the exact same tissue RNA extracts that were used for sequencing. Reverse transcription reactions were performed using the SuperScript IV First-Strand Synthesis System (Thermo Fischer Scientific). Quantitative PCR were done in SYBR Green format with 45 cycles of amplification. Human beta-actin was included in the RT-PCR experiments as a positive control of the cDNA. No Template Control (NTC) wells, validating the absence of cDNA or DNA contaminant into the PCR mix, were also added to the experiment. Positive amplicons after 45 cycles were purified on gel and serial-dilutions were made to generate standard curves. Primer pairs used for detection of Moissiacense virus were: L segment AGAATTGGT-TATCCCAGATGAGGT (forward; SEQ ID NO: 14) and GCCATAAATTGAAAATGGTTCTCCA (reverse; SEQ ID NO: 15); M segment ACAGGR-CAAATAGCACTAAAGGT (forward; SEQ ID NO: 12) and CCTTCRTCTCTCACTTTGCAG (reverse; SEQ ID NO: 13); S segment AAACGCAGAACTGGGTAGCA (forward; SEQ ID NO: 10) and GAGTTAGCTCATCGTCCGCA (reverse; SEQ ID NO: 11). The primer pair used for detection of the Koongol virus L segment was GACC-CAATACTGTAAACAG (forward; SEQ ID NO: 69) and CGTCAGAATGCACCATTG (reverse; SEQ ID NO: 70). PCR performed after omitting the reverse transcription step for samples C2, F2, G2 and C9 were negative, supporting the detection of viral RNA rather than endogenous viral DNA in mosquitoes.

CSF Analysis

RNA extracts from 193 CSFs collected in patients (attending both University hospitals of Montpellier and Nimes, two towns close to the Camargue region) presenting with a meningitis or meningo-encephalitis during the course of a regional arbovirus surveillance program during the peak mosquito activity period from 1st May to 31 Nov. 2016 and 2017 were tested by RT-PCR using primers specific for the S segment of Moissiacense virus (Umbre virus). These 193 CSFs have not been analyzed with the serological assay due to insufficient quantity remaining after RT-PCR.

Serology

Recombinant Protein Preparation

Expression of the Gc Head Domain in Eukaryotic System

The Gc head domains of Umbre orthobunyavirus strain Moissiacense (residues G477-D730 of the polyprotein precursor; SEQ ID NO: 64) and Schmallenberg virus (residues Q465-1702 of the polyprotein precursor (GenBank accession number: CCF55030.1) carrying a C-terminal Strep-tag (GGWSHPQFEK; SEQ ID NO: 97) were produced in recombinant *Drosophila* S2 cells (Gibco) grown at 28° C. in HyClone SFM4Insect medium with L-glutamine (GE Healthcare) supplemented with 25 U/mL penicillin/streptomycin (Gibco). For this purpose, a codon-optimized synthetic gene fragment (Invitrogen) was cloned into the pMT expression vector (Invitrogen) downstream of a BiP secretion signal. The expression plasmid was co-transfected with the selection plasmid pCoPURO (Iwaki et al., BioTechniques 2003; 35:482-484, 486) at a mass ratio of 20:1 using the Effectene transfection reagent (Qiagen) according to the manufacturer's instructions. A polyclonal stable S2 cell line was established by selection with 7.5 μg/mL puromycin (Invivogen), which was added to the medium starting 40 h after transfection. The culture was expanded to 1 L of $10^7$ cells/mL in Erlenmeyer flasks shaking at 100 rpm and at 28° C. Recombinant protein expression was then induced with 500 μM $CuSO_4$. The cell supernatant was harvested 1 week after induction, concentrated to 50 mL on a 10 kDa MWCO PES membrane (Sartorius), pH-adjusted with 0.1M Tris-Cl pH 8.0, cleared from biotin with 15 μg/mL avidin, cleared from precipitate by centrifugation at 4000×g for 15 min at 8° C., and was used for affinity purification on a 5 mL StrepTactin Superflow he column (iba Life Science). The protein was further purified by gel permeation chromatography on a HiLoad Superdex 200 μg column (GE Healthcare) in 20 mM Tris-Cl pH 8.0, 150 mM NaCl. Aliquots were flash-frozen on liquid nitrogen and stored at −80° C.

Expression of then Protein in Prokaryotic System

The N protein (SEQ ID NO: 2) was expressed from a codon-optimized synthetic gene in *E. coli* BL21 with N-terminal Strep- and His-tags. The protein was sequentially purified on a HisTrap column (GE Healthcare), a StrepTactin column (iba) and a Superdex S200 column (GE Healthcare). Peak fractions in 20 mM Tris-Cl pH 8, 150 mM NaCl were frozen.

Serum Samples

Three hundred serum samples randomly collected from patients attending the Montpellier University hospital as part of a collection for seroepidemiological investigation through the Arbosud project (Montpellier University MUSE project) were screened. Additional 34 serum samples from patients with diagnosis of meningitis or meningo-encephalitis were also tested (Institutional review board 2019-IRB-MPT-05-06).

ELISA Serological Assay

Two enzyme linked immuno assays were set up with two recombinant antigens, corresponding to the head domain of the Gc protein for respectively the Umbre virus Moissiacence strain and the Schmallenberg virus used as a negative control. Reactivity of every serum samples was concomitantly tested against each antigen in 96 wells plates. Plates were coated overnight at 4° C. with 1004, of 2 μg/mL of the respective antigens. Plates were subsequently washed 3 times with PBS-tween 0.1% and further blocked with PBS-tween 0.01% plus 2% of bovine serum albumin during 2 hours at room temperature. Plates were washed 3 times before 100 μL of a one hundred dilution of serum samples in blocking solution was added. Serum samples were incubated 3 hours at room temperature. Horseradish peroxidase secondary antibody diluted in blocking solution was added after 3 washes and incubated one hour at 37° C., under agitation. TMB substrate was added and plates remained in dark at room temperature for 20 min before reaction was further stopped with $H_2SO_4$. The 450 nm optical densities were recorded for each sample. Samples giving the highest values were alternatively tested through a commercial pan-species ELISA Schmallenberg virus assay that displays the N protein as targeted antigen, following the manufacturer recommendations (ID Screen Schmallenberg virus indirect Multi-species, IDvet, France).

LIPS Serological Assay

The search for antibodies against Umbre virus are carried out on sera using a Luciferase Immuno-Precipitation System (LIPS) assay as described (Temmam et al., Front Microbiol., 2019, 10, 2315, doi.org/10.3389/fmicb.2019.02315) using the full Gc protein (SEQ ID NO: 60) or the Gc extracellular domain (SEQ ID NO: 61) or the N-terminal Alpha helix (SEQ ID NO: 62) or the N protein (SEQ ID NO: 2). Viral antigens are produced in HEK-293F cells transfected with plasmids expressing the gene for Nanoluc fused to the C-terminus of the viral protein. Recombinant proteins are harvested from the supernatant or cell lysate without any purification step, and incubated with 10 μL of animal serum. The immune complexes are precipitated with protein A/G-coated beads, washed, and the luciferase activity is monitored for example on a Centro $XS^3$ LB 960 luminometer (Berthold Technologies, France). The positivity threshold can be defined as the mean of 10 negative controls (without serum)+five standard deviations.

Serological Survey

The Gc head domain of Schmallenberg virus, an orthobunyavirus of ruminants belonging to the Simbu serogroup, served as a negative control. It was not possible to use the sera of the two Umbre patients as a positive control because of their immunoglobulin deficiency. A positive control was used for the Schmallenberg virus antigen and was tested undiluted and at a 10-fold dilution. Three hundred sera from control patients (the control group) and 34 sera from encephalitis cases (the encephalitis group) were screened. In the control group (N=300), optical densities ranged from 0 to 4 for both antigens (FIG. 7). Because no human cases of Schmallenberg virus infection have been reported (Ducomble et al., Emerg Infect Dis, 2012, 18:1333-1335; Reusken et al., Emerg Infect Dis 2012; 18:1746-1754.) the inventors verified and confirmed the absence of detectable antibodies against the immunodominant nucleocapsid N protein of Schmallenberg virus for samples with the highest densities, using a reference veterinary kit which included a positive control (ID Screen Schmallenberg virus indirect Multi-species, IDvet, France). Since the Gc head domains of Schmallenberg virus and Umbre virus were designed in an orthologous manner and produced under strictly identical conditions, the inventors concluded that optical densities values up to 4 corresponded to background noise. In the encephalitis group (N=34), all optical values were inferior to 3 (FIG. 8). The observed statistical differences were therefore attributed to random background noise and it was concluded that no specific antibody response was recorded.

2. Case Report

Context of the Study

The two cases presented in this study were selected from a larger series of sixty brain samples collected either from autopsy or biopsy, with brain inflammation, in which the inventors performed a molecular screening for the presence of pathogens. Over a period of 2 years, seventeen of these samples were analyzed by high-throughput sequencing with a metatranscriptomics approach. Patient #2 had undergone a brain biopsy followed 10 days later by a diagnostic autopsy. Patient #1 had been included in the National Creutzfeldt-Jakob disease (CJD) surveillance network, coordinated by the neuropathology department of Pitié-Salpêtrière. This network collects the postmortem samples from all cases in France with a diagnosis of "possible" or "likely" CJD, according to the World Health Organization criteria (WHO Recommended surveillance standards WHO/CDS/CSR/99.2). The aim of this network is not only to confirm CJD but also to identify differential diagnoses in cases of rapidly progressive neurological diseases. In a large series of 1572 cases autopsied between 1992 and 2009, the inventors found that 30% of the collected cases were not prion diseases (Peckeu L et al., Euro Surveill Bull Eur Sur Mal Transm Eur Commun Dis Bull, 2017; 22).

Case 1

A 21-year-old man was was admitted to the neurology department of Toulouse Hospital in October 2013 for swallowing impairment and fluctuation of consciousness. He was living in Moissac, in the south-west of France. He had developed behavioral changes suggestive of depression after a party during which he could have used cocaine and *cannabis*. His psychiatrist had prescribed selective serotonin reuptake inhibitors. The clinical state had not improved. He was then referred to the psychiatry department at Toulouse University Hospital. His past condition included Bruton's agammaglobulinemia (Omim #300755), an X-linked immunodeficiency characterized by the absence of circulating B cells and low to undetectable levels of all immunoglobulin isotypes in the serum. He was treated since early childhood by repeated infusion of intravenous immunoglobulins together with an anti-infectious prophylaxis by valaciclovir and sulfamethoxazole/trimethoprim. He also suffered from Crohn's disease, which was treated with mesalazine and azathioprine.

The patient was anorectic and had lost 10 kg during the last weeks. He was afebrile. The diagnosis of catatonia was considered. He did not respond to antidepressants, benzodiazepines and neuroleptics at high doses. Upon admission in the Neurology department, brain MRI, with FLAIR (FLuid-Attenuated Inversion Recovery) sequence and diffusion-weighted imaging, showed a diffuse hypersignal in the insular, posterior cingulate and occipital cortices, and in the caudate nucleus and putamen, bilaterally (FIG. 1, a & b). FDG PET/CT scan showed a diffuse cortical hypofixation, more severe in the left hemisphere and no hypermetabolism outside the brain. Blood cell count showed a decreased number of lymphocytes (500 G/L). There was no anti-thyroglobulin and anti-thyroperoxidase antibody in the serum. Serological tests for *Borrelia burgdorferi, Treponema pallidum*, polyomavirus, HIV, and hepatitis B, C, and E viruses were negative—a negativity that was difficult to interpret in a patient with agammaglobulinemia. The concentration of serum C-reactive protein was increased (150 mg/L; normal value below 6 mg/L). The blood levels of aspartate aminotransferase, and alanine aminotransferase were increased two folds.

Total proteins concentration, glucose level, and cell count were normal in the cerebrospinal fluid (CSF). No oligoclonal bands were detected. CSF PCRs for enteroviruses, herpesviruses, and *Tropheryma whipplei* were negative. The search for Ri/La/Hu, VGCC, NMDA receptor, GABA, ANNA-1, ANNA-2, gangliosides, AQP4, and MOG antibodies was negative. The CSF was positive for the 14-3-3 protein.

The patient died two months and a half after the first symptoms. The rapid course of the disease, the cortical and striatal hyperintensity at MRI, the positivity of 14-3-3 protein in the CSF, and a history of repeated treatment with blood products had raised the diagnostic hypothesis of Creutzfeldt-Jakob disease, either iatrogenic or variant. The diagnosis of encephalitis, by contrast, was thought implausible: the patient had been afebrile during the whole course of the disease and the CSF cell count was normal. The autopsy was limited to the brain. The brain samples were referred to the national neuropathology network for the surveillance of Creutzfeldt-Jakob disease.

Case 2

A 58-year-old woman was referred to the emergency department of Paris Pitié-Salpêtrière Hospital in October 2018 for anorexia and psychomotor slowing, without fever. She had been followed in the immunology department (Saint Louis Hospital, Paris) for a complex immunologic disorder.

The diagnosis of a cutaneous follicular lymphoma had been made 17 years earlier. She had been treated with radiotherapy, surgery and chemotherapy (rituximab-cyclophosphamide-vincristin-prednisone, then rituximab-cyclophosphamide). She had been in complete remission for 9 years. She had developed a humoral immune deficiency characterized by low IgG and undetectable IgM levels in the absence of circulating B cells. She had recurrent bacterial infections for which she had received polyvalent immunoglobulins. She was also suffering from vitiligo and lichen planus. She had been followed for more than 10 years for a severe autoimmune hepatitis requiring immunosuppressive treatment with sirolimus and leading to cirrhosis, for which transplantation was being considered. At admission in the intensive care unit, psychomotor slowing was marked. There were no focal neurological signs. CSF was clear and contained 10 white blood cells/$mm^3$ (N<5), with CD20 negative lymphocytes at various stages of activation and some macrophages. CSF glucose was normal (3.53 mmole/L). The protein level was increased (0.67 g/L, N<0.40). MRI was normal (FIG. 1, c-e). Three months later, the patient was apathetic. The CSF contained 34 white blood cells/mm3 and 4,200 red blood cells/mm3. CSF protein level was 0.47 g/L. Interferon alpha was increased in the CSF (6 kUI/L, N<2), normal in the serum (2 kUI/L). The search for autoantibodies (including NMDAr, Yo, RI, Hu, amphiphysine, CV2, Sox1, GAD, Ma1, Ma2) was negative. CSF PCRs for viruses (EBV, CMV, HSV1 and 2, VZV, HHV6, HHV8, adenovirus, enterovirus, polyomavirus) were all negative. She received intravenous immunoglobulins in the hypothesis of dysimmune encephalitis. Four months later, her neurologic condition worsened. She had lost her balance, had fallen several times and was mute. She was transferred to the neurology department at Pitié-Salpêtrière Hospital. She lived in Paris area (Val-de-Marne). Her relatives indicated that she had traveled extensively, visiting China, Japan, Australia, Spain, Israel and Italy in previous years. They also reported that a few weeks before the onset of the symptoms, she had sojourned in Camargue, south of France, and went on a 10-day Mediterranean cruise. Despite treatment with amoxicillin and aciclovir, she progressed to akinetic mutism within three months. Hyperintensity in the hippocampus, the temporal pole and the insula were observed bilaterally and progressed to atrophy (FIG. 1, f-h). The spinal MRI was normal. Repeated EEG showed slow waves, with pseudo-periodic patterns, similar to those observed in Creutzfeldt-Jakob disease. She became comatose, despite Ig replacement therapy, high dose steroids pulses, and plasma exchange in the hypothesis of autoimmune encephalitis. It was decided to perform a biopsy of the right frontal middle gyms in the absence of focal lesion visible at MM. Nine days after the biopsy, the patient developed acute hepatic failure due to portal venous thrombosis. She died after an evolution of five months and a half. The diagnosis of encephalitis was suspected but its cause remained undetermined. An autopsy was performed.

3. Results

Neuropathology

Case 1

The brain weighed 1200 g. Its external aspect was unremarkable. Microscopic examination showed severe neuronal loss and spongiosis in the cerebral cortex and in the striatum in both hemispheres (FIG. 2, d); the number of Purkinje cells was also severely reduced. The gliosis was marked, made of fibrillar astrocytes with abundant eosinophilic cytoplasm. Microglia-IBA1, CD163 and CD68 positive-were diffusely activated (FIG. 2, *a-c*). Numerous microglial nodules were observed, in particular in the pyramidal layer of the hippocampus and in the dentate nucleus of the cerebellum (FIG. 2, a & b). The nodules sometimes contained a neuron (neuronophagia) (FIG. 2, a). A few T lymphocytes, CD3 and CD8 positive, were diffusely distributed around the vessels and in the parenchyma (FIG. 2, e). CD20 and CD4 immunohistochemistry was negative (FIG. 2, d & e). No viral inclusion was observed. Luxol Fast Blue staining did not show significant demyelination. PrP 12F10 immunohistochemistry was negative as well as the PrPres Western blot.

Case 2 Biopsy

The biopsy sample consisted of 1 $cm^3$ of cerebral cortex comprising leptomeninges, gray and white matter. Microscopic examination showed marked astrogliosis and severe microglial activation, confirmed by CD163 immunochemistry. Some perivascular cuffs were observed, made of CD3 positive, small T-lymphocytes, 80% of them being CD4- and 20%, CD8-positive. There was no granuloma nor multinucleated giant cell.

Case 2 Autopsy

The brain weighed 1055 g. Gross examination showed thinning and softening of the temporal poles, and atrophy of the caudate nucleus and cerebral peduncles, bilaterally. An inflammatory infiltrate of low abundance, made of small CD3 positive T lymphocytes, was observed in the leptomeninges and around the veins in the caudate nucleus and mesencephalon. The arterial walls were not altered; there was no evidence for vasculitis. Severe neuronal loss, astrogliosis, and diffuse microglial activation were observed in the neocortex, hippocampus, striatum and cerebellum on both sides (FIG. 3, a & b). There was a severe loss of pyramidal neurons in CA1 to CA4 sectors (FIG. 3, d). Neurons were replaced by reactive astrocytes with enlarged cytoplasms. The numerical density of the granule neurons of the dentate gyrus was decreased. CD163 immunohistochemistry showed massive microglial activation in the pyramidal sectors of the hippocampus and in the dentate gyrus (FIG. 3, a). In the cerebellum (FIG. 3, b), neuronal loss and microglial activation were severe in the dentate nucleus, as well as in the granular and Purkinje cell layers. The loss of Purkinje cells was complete, underlined by the hypertrophy of Bergmann glia. The neuronal loss was severe in the substantia nigra, locus cœruleus and pontine nuclei. Numerous macrophages were observed in the root of the oculomotor nerve in which axonal and myelin loss was severe (FIG. 3, e). Nodules of neuronophagia were found in the medulla oblongata and in the anterior horns of the spinal cord (FIG. 3, c). The spinal roots were spared.

Identification, Characterization and Quantification of Umbre Virus Sequences from Patients Sample Post-mortem, metatranscriptomics identified viral sequences related to Umbre virus in the brain of patient 1 and in the brain and spinal cord of patient 2. Full coding sequence of the S, L and M segments were obtained by a combination of RT-PCR and Rapid Amplification of cDNA Ends (RACE). Patient 1: SEQ ID NO: 5 (L segment), SEQ ID NO: 3 (M segment) and SEQ ID NO: 1 (S segment). Patient 1: SEQ ID NO: 92 (L segment), SEQ ID NO: 91 (M segment) and SEQ ID NO: 90 (S segment). This novel virus, named Moissiacense virus in reference to the French region where patient 1 was living, is a member of a currently unnamed Glade or serogroup (FIG. 4A, B, C), and is closely related to Umbre virus strain IG1424, isolated in India. 97.6% amino acid sequence identity (AA Id) and 88% nucleotide sequence identity (nt Id) for L segment; 94.3% AA Id and 86% nt Id for M segment; 97.5% AA Id and 92% nt Id for S segment) and to a lesser extend to Koongol virus (70.5%-AA Id and 68% nt Id for L segment; 55.0% AA Id and 66% nt Id for S segment; no data for M segment) (Tables I to III).

The viral sequences found in the two patients were closely related to Umbre virus strain IG1424, isolated in India (97.6%-97.9% amino-acids identity for the L segment), and to a lesser extent to Koongol virus, isolated in Australia (70.5%-71.0% AA Id for L segment) (FIG. 4C; Tables III and IV). According to the species demarcation criteria of the International Committee on Taxonomy of Viruses (ICTV) for orthobunyaviruses (International Committee on Taxonomy of Viruses (ICTV). Available at: https://talk.ictvonline.org/ictv-reports/ictv_9th_report/), the virus strain IG1424 and the two viral strains identified from the two patients belong to the same species and represent different strains of Umbre virus. The inventors therefore gave the names Umbre orthobunyavirus strain Moissiacense (Patient 1) and Umbre orthobunyavirus strain Mama (Patient 2), in reference to the French regions where the patients lived (Moissac and Val-de-Marne, respectively). Moissiacense virus and Mama virus also appears to be very closely related to Little Sussex virus (100.0% AA Id for the 96 AA PCR amplicon on L segment) (Table IV).

PCR primer pairs were designed for the specific detection of Moissiacense virus, Umbre virus and Little Sussex virus (Moissiacense virus species-specific primers): SEQ ID NO: 10-11 (S segment); SEQ ID NO: 12-13 (M segment): SEQ ID NO: 14-15 (L segment). Umbre virus S, L and M segments were detected by RT-PCR on the patient's brain sample using the Moissiacense virus species-specific primers (FIG. 5). *C. pipiens* samples containing related virus sequences were negative by PCR with the Moissiacense virus species-specific primer. These results demonstrate the specificity of the designed PCR primers for Moissiacense virus species (Moissiacense virus, Umbre virus and Little Sussex virus). Determination of viral titer in the patient's brain sample by RT-qPCR indicated approximately $10^6$ to $10^8$ genome copies/gram of tissue for both patients. Patient 2 also tested positive, albeit less strongly, in the liver and lymph nodes with viral genome copies ranging from $10^4$ to $10^6$ per gram of tissue.

No CSF from patient 1 was available. Three CSF samples from patient 2, collected less than three months before death, were tested by RT-PCR for the three segments of Moissiacense virus species (Umbre virus) and were negative. In addition, 193 CSFs from meningo-encephalitis cases collected in Montpellier and Nimes, two southern cities close to the Camargue region were tested by RT-PCR, for the Moissiacense virus species (Umbre virus) S segment. None was positive.

Umbre Virus Infects Brain Neurons

In the absence of commercially available antibody specific to the Moissiacense group of viruses, in-situ hybridization probes were designed to detect the S, M and L segments of Moissiacense virus. In situ hybridization (ISH) was performed on tissue sections from samples of frontal cortex, in which microglial activation was severe. Probes homologous to the S, M and L segments of Umbre virus were positive in the cell body and the apical neurite of pyramidal neurons (FIG. 2, *f* and FIG. 3, *f*), while glial cells, macrophages or lymphocytes were negative. Positive neurons were scattered in case 1 but numerous in case 2. Viral sequences were not found in five biopsy and autopsy samples of control cases with encephalitis of other documented causes. These data indicate that Umbre virus infects and replicates in cortical neurons.

Detection and Prevalence of Viral Sequences Related to Umbre Virus in *Culex pipiens* Captured in France Umbre virus has never been described in Europe. Since this virus is borne by mosquitoes (Dandawate et al., Indian J Med Res, 1969; 57:1420-1426) the inventors attempted to determine if it could be detected in mosquitoes captured in Camargue between 2015 and 2017 (see Material and Methods). Camargue is located between the Mediterranean Sea and the two arms of the Rhone delta. It is a touristic area, in the South of France, inhabited by many species of insects and notoriously by mosquitoes. Patient 2 stayed in Camargue during the weeks preceding the onset of her disease. Patient 1 was living 200 km west of the Rhone delta and had never travelled outside continental France.

All 133 pools of *Culex pipiens* mosquitoes captured in 2015 in Camargue were negative for PCRs targeting the S, M and L segments of Moissiacense virus. However, 4 out of the 133 pools were positive for Koongol L-segment by RT-PCR (samples C2, C9, F2 and G2). PCR performed after omitting the reverse transcription step was negative, supporting the detection of viral RNA rather than endogenous viral DNA. Sanger sequence analysis of the viral amplicons from mosquitoes confirmed the proximity between Koongol virus (82.1-83.2% AA Id), Little Sussex, Umbre and Moissiacense viruses (75.8-76.8% AA Id) (FIG. 4D and Table IV). Of the mosquitoes captured in 2017, none were positive, which might reflect the lower number of mosquitoes tested. Based on the number of positive pools and the size of the pools from the 2015 captures, the prevalence of Koongol-like sequences in *Culex pipiens* was estimated by statistical prediction models to be approximately 0.1% (variances ranging from $10^{-7}$ to $10^{-3}$ depending on the model used), assuming either unknown or perfect sensitivity and specificity values of the PCR (Cowling et al., Prev. Vet. Med., 1999, 39, 211-25).

Serological Survey

Three hundred sera from control patients and 34 sera from encephalitis cases from the South of France including the Camargue region were screened with an ELISA test that the inventors developed to detect Umbre virus antibodies (FIGS. 7-8). No serum gave a positive result.

4. Discussion

Inaccurate diagnosis of encephalitis is a main issue as immunosuppressive treatments can be deleterious in case of viral infection. Metatranscriptomics identified sequences of Umbre virus in brain samples from two immunocompromised patients with clinical and pathological signs of encephalitis. In the two cases, behavioral symptoms preceded neurological signs caused by involvement of the basal ganglia (extrapyramidal syndrome) and of the brainstem (swallowing difficulties). There was no fever. The CSF was normal or with a mild hypercytosis. Pathologically, microglial activation, perivascular cuffing by mononucleated cells including T-lymphocytes, neuronal loss and neuronophagia ascertained the diagnosis of encephalitis. The relative scarcity of lymphocytes, contrasting with the abundance of microglial activation, and the frequency of neuronophagia were noticeable in the two cases. The changes predominated in the grey matter (cerebral cortex, striatum, cerebellar cortex and dentate nucleus). At least in case 2, there was a severe involvement of the brainstem and spinal cord. Although never isolated previously in cases of human or animal encephalitis, Umbre virus may be taken as causal in the two reported cases because of the high number of recovered genomes (around $10^8$ genome copies/gram) and the demonstration that Umbre virus infected the neurons of the two patients as seen by in situ hybridization, a key feature of arboviruses responsible for encephalitis (Salimi et al., Neurother J Am Soc Exp Neurother, 2016, 13:514-534.) In addition, no other pathogen was found.

The work is original because it deals with the damaged brain tissue obtained from a brain biopsy or autopsy and analyzed by confirmed neuropathologists and the analysis is done without a priori, by methods of very deep sequencing (High Troughput sequencing or NGS), followed by a comparison of the sequences with viral and general nucleotide and protein data bases. The originality of the work is strengthened by the fact that PCR consensus assays targeting a broad range of orthobunyaviruses (Lambert A J, Lanciotti R S, J. Clin. Microbiol., 2009, 47, 2398-404) would have missed Moissiacense virus due to sequence variation (FIG. 6).

Within the genus Orthobunyavirus, Umbre virus, Little Sussex virus and Koongol virus belong to the Koongol group of viruses, a group that is yet to be classified by the ICTV but that is distinct from other Orthobunyavirus groups such as the California encephalitis, Bunyamwera, Simbu and Wyeomyia groups. Within the order Bunyavirales, members of the California serogroup (genus Orthobunyavirus, family Peribunyaviridae) and the Rift Valley Fever virus (genus Phlebovirus, family Phenuiviridae) can be responsible for human encephalitis. Regarding viruses related to the Koongol group, however, their pathogenic potential remains unknown.

Based on the species demarcation criteria of the International Committee on Taxonomy of Viruses (ICTV) for orthobunyaviruses, Moissiacense virus, Umbre virus and Little Sussex virus would belong to the same species (>90% identical AA identity; ICTV report, 30 Nov. 2018 (available from https://talk.ictvonline.org/ictv-reports/ictv_9th_report/), Previously, Umbre, Little Sussex and Koongol viruses have been identified in *Culex* sp. in India, Australia and New Guinea (Dandawate et al., Indian J. Med. Res., 1969, 57, 1420-6; Doherty et al., Aust. J. Exp. Biol. Med. Sci., 1979, 57, 509-20; Doherty et al., Aust. J. Exp. Biol. Med. Sci., 1963, 41, 17-39; Karabatsos, edited by N. International catalogue of arboviruses, including certain other viruses of vertebrates [Internet]. 3rd ed. San Antonio, Texas: American Society of Tropical Medicine and Hygiene for The Subcommittee on Information Exchange of the American Committee on Arthropod-borne Viruses; 1985. Available from: https://catalysy.library.jhu.edu/catalog/bib_66192).

Umbre virus (genus Orthobunyavirus, family Peribunyaviridae) was first identified in *Culex* sp. mosquitoes in India in the 1950s and was catalogued as an arthropod borne (arbo-) virus after successful disease transmission experiments in mice (Dandawate et al., Indian J Med Res 1969; 57:1420-1426). In the 1970s, related viruses named Little Sussex and Koongol were identified in *Culex* sp. in Queensland, Australia (Doherty et al., Aust J Exp Biol Med Sci 1979; 57:509-520; Doherty et al., Aust J Exp Biol Med Sci 1963; 41:17-39.). The pathogenic potential, in human, of viruses related to the Umbre/Koongol group, however, remained uncertain despite that they are classified by the Center for Disease Control and Prevention (CDC) as 'Probable Arbovirus'. Serological surveys based on hemagglutination assay have suggested that members of the Umbre/Koongol group could infect several mammals, but this has not been confirmed with a more specific technique such as seroneutralization (Shchetinin et al., Viruses, 2015; 7:5987-6008). Only recently, a partially characterized orthobunyavirus closely related to Umbre virus, causing severe kidney disease in broiler chickens, has been reported in Malaysia (Palya et al., Emerg Infect Dis., 2019; 25:1110-1117). The inventors now report the first human cases leading to brain infection with a virus from the Umbre/Koongol group.

In this study, the origin of the two Umbre virus strains could not be elucidated. No Umbre virus could be traced by RT-PCR in pools of mosquitoes isolated in Camargue. Sequences from Koongol virus could however be identified in a small number of mosquitoes, indicating the presence of still unidentified orthobunyaviruses, close to Umbre virus, in the south of France. The inventors concluded that the two patients were possibly infected by mosquito bites—a finding that should stimulate more comprehensive epidemiological studies of the virome of mosquitoes in this area.

Diagnosis of orthobunyavirus encephalitis is based on antibody testing (Miller A et al., Hosp. Pediatr., 2012, 2, 235-242). The inventors have tested the prevalence of antibodies binding the Gc head domain protein of Umbre virus in a first series of control (N=300) and encephalitis (N=34) cases but did not find any positive case. It is noteworthy that, because of the hypo- or agammaglobulinemia status of the two patients, the absence of human serum that can serve as a positive control complicated the methodology. The observations of the inventors nevertheless suggest that the prevalence of infection in the general population is low or that the virus is unable to infect most individuals with a normal immune system. The actual risk of disease transmission in immunocompromised individuals may be different and remains unknown. Immune deficit—and particularly the deficit in neutralizing antibodies (Hellert et al., Nat Commun 2019; 10:879)—may have played a crucial role in the development of the encephalitis in a way that remains to be investigated.

As for other major arboviruses, like JEV, Umbre virus seems to be hardly detectable in the CSF after the onset of the disease (Dubot-Pérès et al., Lancet Infect. Dis., 2015, 15, 1376-7; Touch et al., Trop. Med. Int. Health TM IH, 2009, 14, 1365-73). (three CSFs from P2 tested negative, and none of the 193 CSFs taken from suspected cases of meningoencephalitis in two southern cities close to the Camargue region tested positive). Similarly, negative PCR-testing of the CSF was also recorded for Cache Valley virus, another orthobunyavirus identified recently in the brain of an immunodeficient patient (Wilson et al., Ann. Neurol., 2017, 82, 105-14). This suggests that in immunodeficient patients, especially patients without circulating B cells, persistent neurological symptoms should evoke a viral encephalitis that only a brain biopsy can confirm at an early stage.

In conclusion, the convergence of virological and epidemiological data shows that the inventors have identified Umbre virus as a new neurotropic arbovirus in Europe, belonging to the orthobunyaviruses. Another close species was identified in *Culex pipiens* mosquitoes from the same region. Thus, members of the Moissiacense group or species of viruses (i.e. Umbre virus strains), should be added to targeted tests in routine diagnosis of brain tissue from encephalitis cases with unidentified etiology, in particular in a context of immune suppression. The negativity of the CSF in such cases raises the question of brain biopsy at an early stage in the management of encephalitis of unknown etiology.

TABLE I

Amino acids identity matrix on the S segment (see accession numbers in Phylogenetic analysis)

| | Aino virus | Simbu orthobunyavirus | Akabane virus | Schmallenberg virus | Oropouche virus | Oya virus | Leanyer virus | Batai virus | Bunyamwera virus | Ilesha virus |
|---|---|---|---|---|---|---|---|---|---|---|
| Aino virus | | 83.3 | 82.9 | 79.9 | 69.2 | 65.0 | 54.7 | 42.8 | 41.5 | 41.5 |
| Simbu orthobunyavirus | 83.3 | | 81.6 | 80.3 | 72.2 | 64.5 | 51.3 | 41.5 | 41.1 | 40.7 |
| Akabane virus | 82.9 | 81.6 | | 79.9 | 68.4 | 62.4 | 53.4 | 39.8 | 39.4 | 39.4 |
| Schmallenberg virus | 79.9 | 80.3 | 79.9 | | 70.1 | 62.0 | 52.5 | 40.7 | 40.3 | 39.8 |
| Oropouche virus | 69.2 | 72.2 | 68.4 | 70.1 | | 74.4 | 52.1 | 43.6 | 41.9 | 42.3 |
| Oya virus | 65.0 | 64.5 | 62.4 | 62.0 | 74.4 | | 50.8 | 39.8 | 38.1 | 38.6 |
| Leanyer virus | 54.7 | 51.3 | 53.4 | 52.5 | 52.1 | 50.8 | | 42.4 | 40.8 | 41.2 |
| Batai virus | 42.8 | 41.5 | 39.8 | 40.7 | 43.6 | 39.8 | 42.4 | | 90.6 | 88.5 |
| Bunyamwera virus | 41.5 | 41.1 | 39.4 | 40.3 | 41.9 | 38.1 | 40.8 | 90.6 | | 94.4 |
| Ilesha virus | 41.5 | 40.7 | 39.4 | 39.8 | 42.3 | 38.6 | 41.2 | 88.5 | 94.4 | |
| Cache Valley virus | 41.1 | 41.9 | 41.1 | 40.3 | 42.3 | 40.3 | 42.0 | 90.2 | 90.6 | 90.6 |
| Iaco virus | 44.9 | 43.2 | 43.2 | 44.1 | 41.5 | 39.0 | 41.6 | 63.2 | 65.4 | 66.7 |
| Sororoca virus | 43.6 | 42.8 | 42.8 | 43.2 | 40.6 | 39.0 | 37.8 | 65.0 | 66.7 | 65.4 |
| Wyeomyia orthobunyavirus | 42.8 | 42.4 | 43.6 | 43.6 | 40.6 | 41.5 | 40.8 | 60.7 | 63.2 | 64.1 |
| Macaua virus | 39.4 | 39.8 | 39.8 | 41.1 | 39.3 | 39.0 | 38.2 | 62.4 | 62.4 | 61.5 |
| Chatanga virus | 44.3 | 43.5 | 43.9 | 44.3 | 43.2 | 42.2 | 42.7 | 44.9 | 44.5 | 45.3 |
| Tahyna virus | 43.9 | 43.5 | 44.3 | 43.9 | 43.2 | 42.6 | 43.1 | 44.1 | 44.5 | 45.3 |
| La Crosse virus | 44.3 | 42.6 | 43.5 | 43.9 | 41.9 | 43.0 | 42.7 | 44.9 | 43.2 | 44.9 |
| Kowanyama virus | 40.7 | 39.8 | 41.1 | 40.3 | 38.3 | 39.8 | 43.3 | 43.8 | 41.7 | 42.1 |
| Yacaaba virus | 37.0 | 36.2 | 38.3 | 37.9 | 36.4 | 39.5 | 39.9 | 44.2 | 43.8 | 44.6 |
| Caraparu virus | 39.7 | 40.1 | 38.8 | 40.1 | 41.5 | 38.0 | 42.0 | 41.2 | 43.3 | 42.0 |
| Madrid virus | 39.7 | 40.1 | 40.5 | 41.4 | 41.1 | 38.8 | 41.6 | 41.2 | 41.6 | 40.3 |
| Murrumbidgee virus | 40.2 | 40.2 | 39.7 | 39.3 | 38.1 | 38.1 | 38.8 | 37.7 | 36.8 | 37.7 |
| Salt ash virus | 37.5 | 37.9 | 37.9 | 36.7 | 38.3 | 35.0 | 37.3 | 37.1 | 35.8 | 36.7 |
| Koongol virus | 31.9 | 32.8 | 31.5 | 33.2 | 31.9 | 33.6 | 33.5 | 33.3 | 32.1 | 32.1 |
| Umbre orthobunyavirus strain Marna (Case #2) | 35.3 | 36.6 | 32.8 | 34.9 | 34.0 | 33.2 | 34.7 | 34.5 | 35.3 | 35.3 |
| Umbre orthobunyavirus strain Moissiacense (Case #1) | 35.3 | 36.1 | 32.8 | 34.9 | 34.0 | 33.2 | 34.7 | 34.9 | 35.7 | 35.7 |
| Umbre virus strain IG1424 | 36.1 | 37.4 | 33.6 | 35.3 | 34.5 | 33.6 | 34.3 | 34.9 | 35.7 | 35.7 |
| Herbert virus | 19.7 | 19.7 | 19.3 | 18.5 | 19.8 | 18.5 | 20.3 | 20.4 | 20.4 | 20.0 |

| | Cache Valley virus | Iaco virus | Sororoca virus | Wyeomyia orthobunyavirus | Macaua virus | Chatanga virus | Tahyna virus | La Crosse virus | Kowanyama virus | Yacaaba virus |
|---|---|---|---|---|---|---|---|---|---|---|
| Aino virus | 41.1 | 44.9 | 43.6 | 42.8 | 39.4 | 44.3 | 43.9 | 44.3 | 40.7 | 37.0 |
| Simbu orthobunyavirus | 41.9 | 43.2 | 42.8 | 42.4 | 39.8 | 43.5 | 43.5 | 42.6 | 39.8 | 36.2 |
| Akabane virus | 41.1 | 43.2 | 42.8 | 43.6 | 39.8 | 43.9 | 44.3 | 43.5 | 41.1 | 38.3 |
| Schmallenberg virus | 40.3 | 44.1 | 43.2 | 43.6 | 41.1 | 44.3 | 43.9 | 43.9 | 40.3 | 37.9 |
| Oropouche virus | 42.3 | 41.5 | 40.6 | 40.6 | 39.3 | 43.2 | 43.2 | 41.9 | 38.3 | 36.4 |
| Oya virus | 40.3 | 39.0 | 39.0 | 41.5 | 39.0 | 42.2 | 42.6 | 43.0 | 39.8 | 39.5 |
| Leanyer virus | 42.0 | 41.6 | 37.8 | 40.8 | 38.2 | 42.7 | 43.1 | 42.7 | 43.3 | 39.9 |
| Batai virus | 90.2 | 63.2 | 65.0 | 60.7 | 62.4 | 44.9 | 44.1 | 44.9 | 43.8 | 44.2 |
| Bunyamwera virus | 90.6 | 65.4 | 66.7 | 63.2 | 62.4 | 44.5 | 44.5 | 43.2 | 41.7 | 43.8 |
| Ilesha virus | 90.6 | 66.7 | 65.4 | 64.1 | 61.5 | 45.3 | 45.3 | 44.9 | 42.1 | 44.6 |
| Cache Valley virus | | 65.0 | 65.0 | 63.7 | 62.8 | 43.6 | 43.6 | 43.6 | 42.1 | 43.0 |
| Iaco virus | 65.0 | | 77.4 | 75.6 | 72.2 | 47.5 | 47.0 | 47.9 | 44.3 | 46.3 |
| Sororoca virus | 65.0 | 77.4 | | 73.9 | 68.8 | 42.8 | 43.2 | 43.6 | 42.6 | 42.1 |
| Wyeomyia orthobunyavirus | 63.7 | 75.6 | 73.9 | | 74.8 | 47.9 | 46.6 | 47.5 | 44.3 | 41.7 |
| Macaua virus | 62.8 | 72.2 | 68.8 | 74.8 | | 44.9 | 44.5 | 44.1 | 43.0 | 42.6 |
| Chatanga virus | 43.6 | 47.5 | 42.8 | 47.9 | 44.9 | | 90.7 | 89.4 | 54.4 | 50.0 |
| Tahyna virus | 43.6 | 47.0 | 43.2 | 46.6 | 44.5 | 90.7 | | 86.0 | 54.4 | 50.4 |
| La Crosse virus | 43.6 | 47.9 | 43.6 | 47.5 | 44.1 | 89.4 | 86.0 | | 54.0 | 50.0 |
| Kowanyama virus | 42.1 | 44.3 | 42.6 | 44.3 | 43.0 | 54.4 | 54.4 | 54.0 | | 62.8 |
| Yacaaba virus | 43.0 | 46.3 | 42.1 | 41.7 | 42.6 | 50.0 | 50.4 | 50.0 | 62.8 | |
| Caraparu virus | 41.6 | 41.6 | 39.1 | 40.3 | 38.7 | 44.8 | 44.8 | 42.3 | 42.9 | 42.6 |
| Madrid virus | 40.8 | 39.9 | 37.8 | 39.1 | 40.3 | 44.8 | 44.8 | 42.3 | 43.7 | 43.4 |
| Murrumbidgee virus | 37.2 | 37.2 | 35.1 | 38.5 | 38.1 | 41.3 | 40.8 | 41.3 | 43.9 | 39.2 |
| Salt ash virus | 35.8 | 38.3 | 37.5 | 38.8 | 37.1 | 45.6 | 43.2 | 43.2 | 43.8 | 38.2 |

TABLE I-continued

Amino acids identity matrix on the S segment (see accession numbers in Phylogenetic analysis)

| | | | | | | | | | | |
|---|---|---|---|---|---|---|---|---|---|---|
| Koongol virus | 33.8 | 33.8 | 34.2 | 33.3 | 31.6 | 40.8 | 41.2 | 39.9 | 39.7 | 36.6 |
| Umbre orthobunyavirus strain Marna (Case #2) | 36.1 | 38.7 | 38.2 | 39.5 | 37.0 | 38.7 | 38.2 | 38.7 | 36.1 | 35.2 |
| Umbre orthobunyavirus strain Moissiacense (Case #1) | 36.6 | 38.2 | 38.2 | 39.5 | 37.0 | 38.2 | 37.8 | 38.2 | 35.7 | 34.8 |
| Umbre virus strain IG1424 | 36.6 | 39.1 | 38.7 | 39.9 | 37.4 | 39.5 | 39.1 | 39.5 | 36.1 | 35.2 |
| Herbert virus | 19.6 | 21.6 | 20.4 | 19.6 | 19.6 | 19.4 | 19.8 | 19.4 | 20.4 | 16.0 |

| | Caraparu virus | Madrid virus | Murrumbidgee virus | Salt ash virus | Koongol virus | Umbre orthobunya-virus strain Marna (Case #2) | Umbre orthobunya-virus strain Moissiacense (Case #1) | Umbre virus strain IG1424 | Herbert virus |
|---|---|---|---|---|---|---|---|---|---|
| Aino virus | 39.7 | 39.7 | 40.2 | 37.5 | 31.9 | 35.3 | 35.3 | 36.1 | 19.7 |
| Simbu orthobunyavirus | 40.1 | 40.1 | 40.2 | 37.9 | 32.8 | 36.6 | 36.1 | 37.4 | 19.7 |
| Akabane virus | 38.8 | 40.5 | 39.7 | 37.9 | 31.5 | 32.8 | 32.8 | 33.6 | 19.3 |
| Schmallenberg virus | 40.1 | 41.4 | 39.3 | 36.7 | 33.2 | 34.9 | 34.9 | 35.3 | 18.5 |
| Oropouche virus | 41.5 | 41.1 | 38.1 | 38.3 | 31.9 | 34.0 | 34.0 | 34.5 | 19.8 |
| Oya virus | 38.0 | 38.8 | 38.1 | 35.0 | 33.6 | 33.2 | 33.2 | 33.6 | 18.5 |
| Leanyer virus | 42.0 | 41.6 | 38.8 | 37.3 | 33.5 | 34.7 | 34.7 | 34.3 | 20.3 |
| Batai virus | 41.2 | 41.2 | 37.7 | 37.1 | 33.3 | 34.5 | 34.9 | 34.9 | 20.4 |
| Bunyamwera virus | 43.3 | 41.6 | 36.8 | 35.8 | 32.1 | 35.3 | 35.7 | 35.7 | 20.4 |
| Ilesha virus | 42.0 | 40.3 | 37.7 | 36.7 | 32.1 | 35.3 | 35.7 | 35.7 | 20.0 |
| Cache Valley virus | 41.6 | 40.8 | 37.2 | 35.8 | 33.8 | 36.1 | 36.6 | 36.6 | 19.6 |
| Iaco virus | 41.6 | 39.9 | 37.2 | 38.3 | 33.8 | 38.7 | 38.2 | 39.1 | 21.6 |
| Sororoca virus | 39.1 | 37.8 | 35.1 | 37.5 | 34.2 | 38.2 | 38.2 | 38.7 | 20.4 |
| Wyeomyia orthobunyavirus | 40.3 | 39.1 | 38.5 | 38.8 | 33.3 | 39.5 | 39.5 | 39.9 | 19.6 |
| Macaua virus | 38.7 | 40.3 | 38.1 | 37.1 | 31.6 | 37.0 | 37.0 | 37.4 | 19.6 |
| Chatanga virus | 44.8 | 44.8 | 41.3 | 45.6 | 40.8 | 38.7 | 38.2 | 39.5 | 19.4 |
| Tahyna virus | 44.8 | 44.8 | 40.8 | 43.2 | 41.2 | 38.2 | 37.8 | 39.1 | 19.8 |
| La Crosse virus | 42.3 | 42.3 | 41.3 | 43.2 | 39.9 | 38.7 | 38.2 | 39.5 | 19.4 |
| Kowanyama virus | 42.9 | 43.7 | 43.9 | 43.8 | 39.7 | 36.1 | 35.7 | 36.1 | 20.4 |
| Yacaaba virus | 42.6 | 43.4 | 39.2 | 38.2 | 36.6 | 35.2 | 34.8 | 35.2 | 16.0 |
| Caraparu virus | | 94.1 | 34.0 | 36.8 | 36.3 | 40.2 | 40.2 | 40.2 | 18.3 |
| Madrid virus | 94.1 | | 34.9 | 37.2 | 36.3 | 38.1 | 38.1 | 38.1 | 18.7 |
| Murrumbidgee virus | 34.0 | 34.9 | | 67.8 | 34.3 | 31.3 | 30.8 | 32.1 | 17.4 |
| Salt ash virus | 36.8 | 37.2 | 67.8 | | 32.1 | 30.3 | 30.3 | 31.1 | 18.3 |
| Koongol virus | 36.3 | 36.3 | 34.3 | 32.1 | | 55.0 | 55.0 | 54.6 | 16.0 |
| Umbre orthobunyavirus strain Marna (Case #2) | 40.2 | 38.1 | 31.3 | 30.3 | 55.0 | | 98.7 | 97.9 | 15.4 |
| Umbre orthobunyavirus strain Moissiacense (Case #1) | 40.2 | 38.1 | 30.8 | 30.3 | 55.0 | 98.7 | | 97.5 | 15.4 |
| Umbre virus strain IG1424 | 40.2 | 38.1 | 32.1 | 31.1 | 54.6 | 97.9 | 97.5 | | 15.8 |
| Herbert virus | 18.3 | 18.7 | 17.4 | 18.3 | 16.0 | 15.4 | 15.4 | 15.8 | |

TABLE II

Amino acids identity matrix on the M segment (see accession numbers in Phylogenetic analysis)

| | Aino virus | Schmallenberg virus | Simbu orthobunyavirus | Oropouche virus | Oya virus | Leanyer virus | Akabane virus | Batai virus | Bunyamwera virus | Cache Valley virus |
|---|---|---|---|---|---|---|---|---|---|---|
| Aino virus | | 57.2 | 51.7 | 36.7 | 37.2 | 32.1 | 35.0 | 32.1 | 32.0 | 32.2 |
| Schmallenberg virus | 57.2 | | 51.4 | 35.1 | 36.7 | 31.4 | 35.6 | 30.7 | 31.5 | 31.9 |
| Simbu orthobunyavirus | 51.7 | 51.4 | | 37.0 | 37.2 | 33.0 | 36.8 | 31.5 | 32.6 | 32.2 |
| Oropouche virus | 36.7 | 35.1 | 37.0 | | 51.0 | 35.7 | 32.4 | 31.8 | 32.9 | 33.2 |
| Oya virus | 37.2 | 36.7 | 37.2 | 51.0 | | 36.3 | 34.1 | 32.7 | 33.5 | 32.9 |
| Leanyer virus | 32.1 | 31.4 | 33.0 | 35.7 | 36.3 | | 31.0 | 31.3 | 31.1 | 31.4 |
| Akabane virus | 35.0 | 35.6 | 36.8 | 32.4 | 34.1 | 31.0 | | 28.9 | 29.1 | 29.1 |
| Batai virus | 32.1 | 30.7 | 31.5 | 31.8 | 32.7 | 31.3 | 28.9 | | 78.6 | 64.4 |
| Bunyamwera virus | 32.0 | 31.5 | 32.6 | 32.9 | 33.5 | 31.1 | 29.1 | 78.6 | | 64.0 |
| Cache Valley virus | 32.2 | 31.9 | 32.2 | 33.2 | 32.9 | 31.4 | 29.1 | 64.4 | 64.0 | |
| Ilesha virus | 32.9 | 31.7 | 31.8 | 32.5 | 33.0 | 30.5 | 28.6 | 64.7 | 63.4 | 69.3 |
| Iaco virus | 30.9 | 30.4 | 30.5 | 31.9 | 33.5 | 30.7 | 28.2 | 51.5 | 51.2 | 51.1 |
| Sororoca virus | 30.8 | 30.3 | 30.0 | 31.8 | 33.1 | 31.0 | 29.1 | 51.0 | 51.4 | 50.0 |

TABLE II-continued

Amino acids identity matrix on the M segment (see accession numbers in Phylogenetic analysis)

| | | | | | | | | | | |
|---|---|---|---|---|---|---|---|---|---|---|
| Macaua virus | 31.5 | 30.3 | 30.8 | 32.4 | 33.5 | 30.9 | 29.1 | 52.4 | 51.2 | 52.5 |
| Wyeomyia orthobunyavirus | 31.9 | 30.3 | 31.3 | 32.3 | 33.2 | 30.2 | 28.9 | 51.4 | 50.8 | 51.1 |
| Chatanga virus | 30.8 | 31.5 | 30.3 | 31.2 | 32.2 | 29.7 | 28.1 | 42.2 | 41.6 | 43.0 |
| La Crosse virus | 30.8 | 31.5 | 30.6 | 31.1 | 31.7 | 30.1 | 28.7 | 42.2 | 42.3 | 42.4 |
| Tahyna virus | 30.6 | 31.6 | 30.3 | 30.6 | 31.9 | 30.1 | 27.5 | 42.4 | 41.8 | 42.7 |
| Kowanyama virus | 29.2 | 29.9 | 28.6 | 32.9 | 32.0 | 28.8 | 28.5 | 37.9 | 37.4 | 38.2 |
| Umbre orthobunyavirus strain Marna (Case #2) | 29.7 | 29.4 | 29.8 | 30.6 | 29.3 | 28.0 | 27.8 | 38.5 | 37.8 | 38.3 |
| Umbre orthobunyavirus strain Moissiacense (Case #1) | 30.0 | 29.1 | 29.7 | 30.7 | 29.5 | 28.1 | 27.4 | 38.8 | 37.9 | 38.6 |
| Umbre virus strain IG1424 | 29.4 | 28.7 | 30.1 | 30.6 | 29.6 | 27.8 | 27.3 | 38.6 | 38.0 | 38.6 |
| Caraparu virus | 29.6 | 28.8 | 28.8 | 30.5 | 32.5 | 29.0 | 28.7 | 33.4 | 33.3 | 34.1 |
| Madrid virus | 29.5 | 29.0 | 29.4 | 30.7 | 33.2 | 29.1 | 27.9 | 34.3 | 34.0 | 34.1 |
| Murrumbidgee virus | 29.1 | 27.7 | 28.2 | 27.8 | 28.7 | 27.4 | 27.9 | 31.2 | 31.5 | 32.8 |
| Salt ash virus | 30.3 | 28.1 | 30.1 | 29.7 | 30.4 | 29.9 | 28.7 | 33.3 | 33.2 | 33.9 |
| Herbert virus | 11.3 | 12.2 | 12.4 | 11.9 | 10.7 | 11.0 | 12.4 | 9.7 | 10.2 | 10.4 |

| | Ilesha virus | Iaco virus | Sororoca virus | Macaua virus | Wyeomyia orthobunyavirus | Chatanga virus | La Crosse virus | Tahyna virus | Kowanyama virus |
|---|---|---|---|---|---|---|---|---|---|
| Aino virus | 32.9 | 30.9 | 30.8 | 31.5 | 31.9 | 30.8 | 30.8 | 30.6 | 29.2 |
| Schmallenberg virus | 31.7 | 30.4 | 30.3 | 30.3 | 30.3 | 31.5 | 31.5 | 31.6 | 29.9 |
| Simbu orthobunyavirus | 31.8 | 30.5 | 30.0 | 30.8 | 31.3 | 30.3 | 30.6 | 30.3 | 28.6 |
| Oropouche virus | 32.5 | 31.9 | 31.8 | 32.4 | 32.3 | 31.2 | 31.1 | 30.6 | 32.9 |
| Oya virus | 33.0 | 33.5 | 33.1 | 33.5 | 33.2 | 32.2 | 31.7 | 31.9 | 32.0 |
| Leanyer virus | 30.5 | 30.7 | 31.0 | 30.9 | 30.2 | 29.7 | 30.1 | 30.1 | 28.8 |
| Akabane virus | 28.6 | 28.2 | 29.1 | 29.1 | 28.9 | 28.1 | 28.7 | 27.5 | 28.5 |
| Batai virus | 64.7 | 51.5 | 51.0 | 52.4 | 51.4 | 42.2 | 42.2 | 42.4 | 37.9 |
| Bunyamwera virus | 63.4 | 51.2 | 51.4 | 51.2 | 50.8 | 41.6 | 42.3 | 41.8 | 37.4 |
| Cache Valley virus | 69.3 | 51.1 | 50.0 | 52.5 | 51.1 | 43.0 | 42.4 | 42.7 | 38.2 |
| Ilesha virus | | 51.4 | 50.5 | 51.2 | 50.2 | 42.0 | 42.1 | 42.2 | 38.4 |
| Iaco virus | 51.4 | | 79.7 | 71.2 | 70.4 | 41.5 | 42.4 | 42.3 | 37.5 |
| Sororoca virus | 50.5 | 79.7 | | 70.1 | 69.8 | 42.5 | 42.9 | 42.8 | 37.4 |
| Macaua virus | 51.2 | 71.2 | 70.1 | | 85.9 | 41.8 | 41.6 | 41.9 | 36.3 |
| Wyeomyia orthobunyavirus | 50.2 | 70.4 | 69.8 | 85.9 | | 40.7 | 40.7 | 41.6 | 36.9 |
| Chatanga virus | 42.0 | 41.5 | 42.5 | 41.8 | 40.7 | | 88.1 | 81.9 | 39.6 |
| La Crosse virus | 42.1 | 42.4 | 42.9 | 41.6 | 40.7 | 88.1 | | 79.5 | 39.9 |
| Tahyna virus | 42.2 | 42.3 | 42.8 | 41.9 | 41.6 | 81.9 | 79.5 | | 39.9 |
| Kowanyama virus | 38.4 | 37.5 | 37.4 | 36.3 | 36.9 | 39.6 | 39.9 | 39.9 | |
| Umbre orthobunyavirus strain Marna (Case #2) | 37.0 | 36.9 | 37.2 | 35.9 | 35.4 | 40.6 | 39.9 | 39.7 | 36.4 |
| Umbre orthobunyavirus strain Moissiacense (Case #1) | 37.1 | 36.7 | 37.0 | 35.7 | 35.2 | 40.9 | 39.9 | 39.9 | 36.0 |
| Umbre virus strain IG1424 | 36.9 | 37.2 | 37.1 | 35.5 | 35.3 | 40.2 | 39.9 | 39.7 | 36.4 |
| Caraparu virus | 32.5 | 31.8 | 32.1 | 32.5 | 32.0 | 32.6 | 33.0 | 32.5 | 31.8 |
| Madrid virus | 32.5 | 32.9 | 33.4 | 33.8 | 32.8 | 32.8 | 33.1 | 33.3 | 32.2 |
| Murrumbidgee virus | 32.4 | 31.6 | 32.8 | 31.6 | 32.0 | 31.3 | 32.4 | 31.8 | 31.4 |
| Salt ash virus | 32.9 | 32.6 | 33.1 | 32.6 | 32.1 | 33.4 | 33.3 | 33.2 | 34.3 |
| Herbert virus | 10.7 | 10.2 | 9.9 | 10.2 | 10.1 | 10.8 | 11.0 | 10.7 | 10.2 |

| | Umbre orthobunyavirus strain Marna (Case #2) | Umbre orthobunyavirus strain Moissiacense (Case #1) | Umbre virus strain IG1424 | Caraparu virus | Madrid virus | Murrumbidgee virus | Salt ash virus | Herbert virus |
|---|---|---|---|---|---|---|---|---|
| Aino virus | 29.7 | 30.0 | 29.4 | 29.6 | 29.5 | 29.1 | 30.3 | 11.3 |
| Schmallenberg virus | 29.4 | 29.1 | 28.7 | 28.8 | 29.0 | 27.7 | 28.1 | 12.2 |
| Simbu orthobunyavirus | 29.8 | 29.7 | 30.1 | 28.8 | 29.4 | 28.2 | 30.1 | 12.4 |
| Oropouche virus | 30.6 | 30.7 | 30.6 | 30.5 | 30.7 | 27.8 | 29.7 | 11.9 |
| Oya virus | 29.3 | 29.5 | 29.6 | 32.5 | 33.2 | 28.7 | 30.4 | 10.7 |
| Leanyer virus | 28.0 | 28.1 | 27.8 | 29.0 | 29.1 | 27.4 | 29.9 | 11.0 |
| Akabane virus | 27.8 | 27.4 | 27.3 | 28.7 | 27.9 | 27.9 | 28.7 | 12.4 |
| Batai virus | 38.5 | 38.8 | 38.6 | 33.4 | 34.3 | 31.2 | 33.3 | 9.7 |
| Bunyamwera virus | 37.8 | 37.9 | 38.0 | 33.3 | 34.0 | 31.5 | 33.2 | 10.2 |
| Cache Valley virus | 38.3 | 38.6 | 38.6 | 34.1 | 34.1 | 32.8 | 33.9 | 10.4 |
| Ilesha virus | 37.0 | 37.1 | 36.9 | 32.5 | 32.5 | 32.4 | 32.9 | 10.7 |
| Iaco virus | 36.9 | 36.7 | 37.2 | 31.8 | 32.9 | 31.6 | 32.6 | 10.2 |
| Sororoca virus | 37.2 | 37.0 | 37.1 | 32.1 | 33.4 | 32.8 | 33.1 | 9.9 |
| Macaua virus | 35.9 | 35.7 | 35.5 | 32.5 | 33.8 | 31.6 | 32.6 | 10.2 |

TABLE II-continued

| Amino acids identity matrix on the M segment (see accession numbers in Phylogenetic analysis) | | | | | | | | |
|---|---|---|---|---|---|---|---|---|
| Wyeomyia orthobunyavirus | 35.4 | 35.2 | 35.3 | 32.0 | 32.8 | 32.0 | 32.1 | 10.1 |
| Chatanga virus | 40.6 | 40.9 | 40.2 | 32.6 | 32.8 | 31.3 | 33.4 | 10.8 |
| La Crosse virus | 39.9 | 39.9 | 39.9 | 33.0 | 33.1 | 32.4 | 33.3 | 11.0 |
| Tahyna virus | 39.7 | 39.9 | 39.7 | 32.5 | 33.3 | 31.8 | 33.2 | 10.7 |
| Kowanyama virus | 36.4 | 36.0 | 36.4 | 31.8 | 32.2 | 31.4 | 34.3 | 10.2 |
| Umbre orthobunyavirus strain Marna (Case #2) | | 96.1 | 94.5 | 32.2 | 32.4 | 29.4 | 31.2 | 11.0 |
| Umbre orthobunyavirus strain Moissiacense (Case #1) | 96.1 | | 94.3 | 31.9 | 32.5 | 29.7 | 31.2 | 11.1 |
| Umbre virus strain IG1424 | 94.5 | 94.3 | | 32.1 | 32.0 | 29.5 | 30.9 | 10.9 |
| Caraparu virus | 32.2 | 31.9 | 32.1 | | 82.1 | 30.7 | 31.8 | 11.0 |
| Madrid virus | 32.4 | 32.5 | 32.0 | 82.1 | | 29.9 | 31.4 | 11.0 |
| Murrumbidgee virus | 29.4 | 29.7 | 29.5 | 30.7 | 29.9 | | 48.8 | 11.0 |
| Salt ash virus | 31.2 | 31.2 | 30.9 | 31.8 | 31.4 | 48.8 | | 11.6 |
| Herbert virus | 11.0 | 11.1 | 10.9 | 11.0 | 11.0 | 11.0 | 11.6 | |

TABLE III

Amino acids identity matrix on the L segment (see accession numbers in Phylogenetic analysis)

| | Aino virus | Akabane virus | Schmallenberg virus | Simbu orthobunyavirus | Oropouche virus | Oya virus | Leanyer virus | Caraparu virus | Madrid virus | Batai virus |
|---|---|---|---|---|---|---|---|---|---|---|
| Aino virus | | 68.0 | 68.8 | 71.1 | 58.7 | 57.9 | 55.3 | 49.6 | 49.7 | 48.3 |
| Akabane virus | 68.0 | | 70.9 | 70.1 | 58.4 | 57.5 | 54.3 | 50.6 | 50.6 | 48.8 |
| Schmallenberg virus | 68.8 | 70.9 | | 70.0 | 57.6 | 56.8 | 54.5 | 49.4 | 49.5 | 48.1 |
| Simbu orthobunyavirus | 71.1 | 70.1 | 70.0 | | 58.3 | 57.6 | 55.0 | 49.7 | 49.2 | 48.4 |
| Oropouche virus | 58.7 | 58.4 | 57.6 | 58.3 | | 66.2 | 58.8 | 52.6 | 52.7 | 50.2 |
| Oya virus | 57.9 | 57.5 | 56.8 | 57.6 | 66.2 | | 58.0 | 52.8 | 52.4 | 48.6 |
| Leanyer virus | 55.3 | 54.3 | 54.5 | 55.0 | 58.8 | 58.0 | | 50.7 | 50.8 | 49.0 |
| Caraparu virus | 49.6 | 50.6 | 49.4 | 49.7 | 52.6 | 52.8 | 50.7 | | 94.4 | 50.6 |
| Madrid virus | 49.7 | 50.6 | 49.5 | 49.2 | 52.7 | 52.4 | 50.8 | 94.4 | | 50.3 |
| Batai virus | 48.3 | 48.8 | 48.1 | 48.4 | 50.2 | 48.6 | 49.0 | 50.6 | 50.3 | |
| Bunyamwera virus | 48.8 | 49.4 | 48.8 | 48.4 | 49.9 | 48.5 | 48.4 | 51.4 | 51.4 | 82.8 |
| Ilesha virus | 47.7 | 49.3 | 47.9 | 48.3 | 49.9 | 48.6 | 48.1 | 50.5 | 50.7 | 81.9 |
| Cache Valley virus | 48.6 | 49.3 | 48.5 | 48.7 | 49.8 | 48.2 | 48.2 | 51.2 | 51.2 | 80.6 |
| Iaco virus | 49.0 | 49.5 | 48.5 | 48.4 | 49.9 | 49.3 | 49.2 | 51.0 | 51.2 | 67.2 |
| Sororoca virus | 48.1 | 49.1 | 48.0 | 47.1 | 49.1 | 48.3 | 48.2 | 50.2 | 50.4 | 65.5 |
| Macaua virus | 48.5 | 49.1 | 48.1 | 48.9 | 49.0 | 48.9 | 49.2 | 51.1 | 51.3 | 66.7 |
| Wyeomyia orthobunyavirus | 47.8 | 49.0 | 48.0 | 47.6 | 48.7 | 48.8 | 48.8 | 50.4 | 50.6 | 66.6 |
| Chatanga virus | 49.4 | 49.8 | 49.8 | 48.8 | 51.4 | 50.5 | 50.4 | 50.7 | 50.7 | 54.4 |
| La Crosse virus | 49.2 | 50.5 | 50.1 | 49.3 | 51.5 | 50.6 | 50.6 | 50.9 | 51.2 | 55.0 |
| Tahyna virus | 49.4 | 49.9 | 50.2 | 48.9 | 51.1 | 50.5 | 50.3 | 50.8 | 50.8 | 54.0 |
| Kowanyama virus | 47.8 | 49.8 | 49.3 | 48.4 | 49.8 | 49.5 | 49.3 | 49.2 | 49.1 | 52.1 |
| Yacaaba virus | 49.4 | 50.9 | 49.3 | 49.5 | 50.4 | 50.1 | 48.4 | 50.6 | 50.6 | 51.6 |
| Koongol virus | 45.3 | 45.1 | 44.7 | 44.6 | 46.5 | 46.4 | 46.2 | 46.2 | 46.3 | 47.6 |
| Umbre orthobunyavirus strain Marna (Case #2) | 44.1 | 44.3 | 44.6 | 44.5 | 45.8 | 45.9 | 45.0 | 46.5 | 46.6 | 48.3 |
| Umbre orthobunyavirus strain Moissiacense (Case #1) | 44.2 | 44.4 | 44.7 | 44.6 | 45.7 | 45.9 | 45.1 | 46.5 | 46.6 | 48.4 |
| Umbre virus strain IG1424 | 44.0 | 44.1 | 44.7 | 44.5 | 45.9 | 45.9 | 44.8 | 46.4 | 46.5 | 48.0 |
| Murrumbidgee virus | 45.5 | 45.3 | 45.6 | 45.5 | 46.1 | 45.2 | 46.8 | 47.3 | 46.9 | 48.8 |
| Herbert virus | 24.5 | 24.1 | 24.6 | 24.5 | 25.0 | 23.6 | 24.1 | 25.0 | 25.0 | 25.3 |

| | Bunyamwera virus | Ilesha virus | Cache Valley virus | Iaco virus | Sororoca virus | Macaua virus | Wyeomyia orthobunyavirus | Chatanga virus | La Crosse virus | Tahyna virus |
|---|---|---|---|---|---|---|---|---|---|---|
| Aino virus | 48.8 | 47.7 | 48.6 | 49.0 | 48.1 | 48.5 | 47.8 | 49.4 | 49.2 | 49.4 |
| Akabane virus | 49.4 | 49.3 | 49.3 | 49.5 | 49.1 | 49.1 | 49.0 | 49.8 | 50.5 | 49.9 |
| Schmallenberg virus | 48.8 | 47.9 | 48.5 | 48.5 | 48.0 | 48.1 | 48.0 | 49.8 | 50.1 | 50.2 |
| Simbu orthobunyavirus | 48.4 | 48.3 | 48.7 | 48.4 | 47.1 | 48.9 | 47.6 | 48.8 | 49.3 | 48.9 |
| Oropouche virus | 49.9 | 49.9 | 49.8 | 49.9 | 49.1 | 49.0 | 48.7 | 51.4 | 51.5 | 51.1 |
| Oya virus | 48.5 | 48.6 | 48.2 | 49.3 | 48.3 | 48.9 | 48.8 | 50.5 | 50.6 | 50.5 |
| Leanyer virus | 48.4 | 48.1 | 48.2 | 49.2 | 48.2 | 49.2 | 48.8 | 50.4 | 50.6 | 50.3 |
| Caraparu virus | 51.4 | 50.5 | 51.2 | 51.0 | 50.2 | 51.1 | 50.4 | 50.7 | 50.9 | 50.8 |
| Madrid virus | 51.4 | 50.7 | 51.2 | 51.2 | 50.4 | 51.3 | 50.6 | 50.7 | 51.2 | 50.8 |
| Batai virus | 82.8 | 81.9 | 80.6 | 67.2 | 65.5 | 66.7 | 66.6 | 54.4 | 55.0 | 54.0 |

TABLE III-continued

Amino acids identity matrix on the L segment (see accession numbers in Phylogenetic analysis)

| | | | | | | | | | | |
|---|---|---|---|---|---|---|---|---|---|---|
| Bunyamwera virus | | 91.6 | 82.1 | 67.9 | 65.8 | 67.4 | 67.0 | 55.4 | 55.9 | 55.0 |
| Ilesha virus | 91.6 | | 81.1 | 67.6 | 65.3 | 67.2 | 66.9 | 54.4 | 55.0 | 54.3 |
| Cache Valley virus | 82.1 | 81.1 | | 67.7 | 66.1 | 66.3 | 67.2 | 54.5 | 55.4 | 54.6 |
| Iaco virus | 67.9 | 67.6 | 67.7 | | 86.1 | 80.2 | 80.0 | 54.1 | 54.3 | 54.0 |
| Sororoca virus | 65.8 | 65.3 | 66.1 | 86.1 | | 78.3 | 77.6 | 53.6 | 53.6 | 53.2 |
| Macaua virus | 67.4 | 67.2 | 66.3 | 80.2 | 78.3 | | 84.9 | 55.1 | 55.4 | 54.5 |
| Wyeomyia orthobunyavirus | 67.0 | 66.9 | 67.2 | 80.0 | 77.6 | 84.9 | | 54.7 | 55.1 | 54.5 |
| Chatanga virus | 55.4 | 54.4 | 54.5 | 54.1 | 53.6 | 55.1 | 54.7 | | 93.7 | 89.7 |
| La Crosse virus | 55.9 | 55.0 | 55.4 | 54.3 | 53.6 | 55.4 | 55.1 | 93.7 | | 89.5 |
| Tahyna virus | 55.0 | 54.3 | 54.6 | 54.0 | 53.2 | 54.5 | 54.5 | 89.7 | 89.5 | |
| Kowanyama virus | 52.7 | 52.5 | 52.4 | 51.2 | 50.9 | 50.9 | 51.0 | 57.1 | 57.8 | 57.9 |
| Yacaaba virus | 52.0 | 52.0 | 51.8 | 51.9 | 52.0 | 52.0 | 51.6 | 56.4 | 57.0 | 56.6 |
| Koongol virus | 47.1 | 47.2 | 47.8 | 48.6 | 48.6 | 49.4 | 49.2 | 51.4 | 51.6 | 51.8 |
| Umbre orthobunyavirus strain Marna (Case #2) | 47.7 | 47.4 | 47.9 | 47.9 | 47.5 | 48.2 | 48.2 | 52.3 | 52.0 | 51.4 |
| Umbre orthobunyavirus strain Moissiacense (Case #1) | 47.6 | 47.3 | 47.9 | 48.0 | 47.6 | 48.3 | 48.2 | 52.2 | 51.9 | 51.4 |
| Umbre virus strain IG1424 | 47.4 | 47.1 | 47.5 | 47.8 | 47.6 | 48.2 | 48.0 | 52.1 | 51.8 | 51.5 |
| Murrumbidgee virus | 48.4 | 48.5 | 48.5 | 48.7 | 47.9 | 48.8 | 48.1 | 49.6 | 49.7 | 49.9 |
| Herbert virus | 24.9 | 24.5 | 25.1 | 24.9 | 24.0 | 24.6 | 24.8 | 25.0 | 25.0 | 24.7 |

| | Kowanyama virus | Yacaaba virus | Koongol virus | Umbre orthobunya-virus strain Marna (Case #2) | Umbre orthobunya-virus strain Moissiacense (Case #1) | Umbre virus strain IG1424 | Murrumbidgee virus | Herbert virus |
|---|---|---|---|---|---|---|---|---|
| Aino virus | 47.8 | 49.4 | 45.3 | 44.1 | 44.2 | 44.0 | 45.5 | 24.5 |
| Akabane virus | 49.8 | 50.9 | 45.1 | 44.3 | 44.4 | 44.1 | 45.3 | 24.1 |
| Schmallenberg virus | 49.3 | 49.3 | 44.7 | 44.6 | 44.7 | 44.7 | 45.6 | 24.6 |
| Simbu orthobunyavirus | 48.4 | 49.5 | 44.6 | 44.5 | 44.6 | 44.5 | 45.5 | 24.5 |
| Oropouche virus | 49.8 | 50.4 | 46.5 | 45.8 | 45.7 | 45.9 | 46.1 | 25.0 |
| Oya virus | 49.5 | 50.1 | 46.4 | 45.9 | 45.9 | 45.9 | 45.2 | 23.6 |
| Leanyer virus | 49.3 | 48.4 | 46.2 | 45.0 | 45.1 | 44.8 | 46.8 | 24.1 |
| Caraparu virus | 49.2 | 50.6 | 46.2 | 46.5 | 46.5 | 46.4 | 47.3 | 25.0 |
| Madrid virus | 49.1 | 50.6 | 46.3 | 46.6 | 46.6 | 46.5 | 46.9 | 25.0 |
| Batai virus | 52.1 | 51.6 | 47.6 | 48.3 | 48.4 | 48.0 | 48.8 | 25.3 |
| Bunyamwera virus | 52.7 | 52.0 | 47.1 | 47.7 | 47.6 | 47.4 | 48.4 | 24.9 |
| Ilesha virus | 52.5 | 52.0 | 47.2 | 47.4 | 47.3 | 47.1 | 48.5 | 24.5 |
| Cache Valley virus | 52.4 | 51.8 | 47.8 | 47.9 | 47.9 | 47.5 | 48.5 | 25.1 |
| Iaco virus | 51.2 | 51.9 | 48.6 | 47.9 | 48.0 | 47.8 | 48.7 | 24.9 |
| Sororoca virus | 50.9 | 52.0 | 48.6 | 47.5 | 47.6 | 47.6 | 47.9 | 24.0 |
| Macaua virus | 50.9 | 52.0 | 49.4 | 48.2 | 48.3 | 48.2 | 48.8 | 24.6 |
| Wyeomyia orthobunyavirus | 51.0 | 51.6 | 49.2 | 48.2 | 48.2 | 48.0 | 48.1 | 24.8 |
| Chatanga virus | 57.1 | 56.4 | 51.4 | 52.3 | 52.2 | 52.1 | 49.6 | 25.0 |
| La Crosse virus | 57.8 | 57.0 | 51.6 | 52.0 | 51.9 | 51.8 | 49.7 | 25.0 |
| Tahyna virus | 57.9 | 56.6 | 51.8 | 51.4 | 51.4 | 51.5 | 49.9 | 24.7 |
| Kowanyama virus | | 65.9 | 47.8 | 47.4 | 47.4 | 47.6 | 48.1 | 25.0 |
| Yacaaba virus | 65.9 | | 49.2 | 48.8 | 48.9 | 48.9 | 46.9 | 25.6 |
| Koongol virus | 47.8 | 49.2 | | 71.0 | 70.5 | 70.8 | 44.8 | 24.7 |
| Umbre orthobunyavirus strain Marna (Case #2) | 47.4 | 48.8 | 71.0 | | 98.8 | 97.9 | 45.3 | 24.4 |
| Umbre orthobunyavirus strain Moissiacense (Case #1) | 47.4 | 48.9 | 70.5 | 98.8 | | 97.6 | 45.2 | 24.5 |
| Umbre virus strain IG1424 | 47.6 | 48.9 | 70.8 | 97.9 | 97.6 | | 45.2 | 24.3 |
| Murrumbidgee virus | 48.1 | 46.9 | 44.8 | 45.3 | 45.2 | 45.2 | | 24.0 |
| Herbert virus | 25.0 | 25.6 | 24.7 | 24.4 | 24.5 | 24.3 | 24.0 | |

TABLE IV

Amino acids identity matrix on PCR-targeted region on the L segment (See accession numbers in phylogenetic analysis)

| | Aino virus | Akabane virus | Schmallenberg virus | Simbu ortho-bunya-virus | Oropouche virus | Oya virus | Leanyer virus | Batai virus | Bunyamwera virus | Ilesha virus | Cache Valley virus | Iaco virus |
|---|---|---|---|---|---|---|---|---|---|---|---|---|
| Aino virus | | 75.8 | 81.1 | 76.8 | 69.5 | 64.2 | 66.3 | 67.4 | 68.4 | 66.3 | 62.1 | 62.1 |
| Akabane virus | 75.8 | | 81.1 | 73.7 | 67.4 | 66.3 | 62.1 | 63.2 | 63.2 | 63.2 | 61.1 | 58.9 |
| Schmallenberg virus | 81.1 | 81.1 | | 78.9 | 71.6 | 68.4 | 73.7 | 64.2 | 66.3 | 63.2 | 63.2 | 60.0 |
| Simbu orthobunyavirus | 76.8 | 73.7 | 78.9 | | 70.5 | 68.4 | 66.3 | 64.2 | 66.3 | 66.3 | 62.1 | 57.9 |
| Oropouche virus | 69.5 | 67.4 | 71.6 | 70.5 | | 71.6 | 68.4 | 61.1 | 61.1 | 62.1 | 62.1 | 57.9 |
| Oya virus | 64.2 | 66.3 | 68.4 | 68.4 | 71.6 | | 65.3 | 64.2 | 57.9 | 60.0 | 58.9 | 57.9 |
| Leanyer virus | 66.3 | 62.1 | 73.7 | 66.3 | 68.4 | 65.3 | | 63.2 | 63.2 | 64.2 | 63.2 | 63.2 |
| Batai virus | 67.4 | 63.2 | 64.2 | 64.2 | 61.1 | 64.2 | 63.2 | | 80.0 | 83.2 | 82.1 | 71.6 |
| Bunyamwera virus | 68.4 | 63.2 | 66.3 | 66.3 | 61.1 | 57.9 | 63.2 | 80.0 | | 92.6 | 82.1 | 68.4 |
| Ilesha virus | 66.3 | 63.2 | 63.2 | 66.3 | 62.1 | 60.0 | 64.2 | 83.2 | 92.6 | | 85.3 | 67.4 |
| Cache Valley virus | 62.1 | 61.1 | 63.2 | 62.1 | 62.1 | 58.9 | 63.2 | 82.1 | 82.1 | 85.3 | | 66.3 |
| Iaco virus | 62.1 | 58.9 | 60.0 | 57.9 | 57.9 | 57.9 | 63.2 | 71.6 | 68.4 | 67.4 | 66.3 | |
| Sororoca virus | 62.1 | 58.9 | 61.1 | 55.8 | 57.9 | 57.9 | 61.1 | 69.5 | 68.4 | 67.4 | 66.3 | 89.5 |
| Macaua virus | 58.9 | 55.8 | 58.9 | 61.1 | 58.9 | 54.7 | 65.3 | 64.2 | 72.6 | 71.6 | 66.3 | 84.2 |
| Wyeomyia orthobunyavirus | 61.1 | 61.1 | 62.1 | 58.9 | 56.8 | 61.1 | 66.3 | 68.4 | 70.5 | 68.4 | 70.5 | 82.1 |
| Chatanga virus | 65.3 | 60.0 | 68.4 | 65.3 | 66.3 | 61.1 | 67.4 | 70.5 | 70.5 | 69.5 | 71.6 | 62.1 |
| La Crosse virus | 65.3 | 64.2 | 68.4 | 64.2 | 68.4 | 60.0 | 67.4 | 68.4 | 71.6 | 71.6 | 70.5 | 62.1 |
| Tahyna virus | 65.3 | 62.1 | 68.4 | 64.2 | 68.4 | 61.1 | 66.3 | 69.5 | 71.6 | 70.5 | 72.6 | 64.2 |
| Culex pipiens France (C2) | 52.6 | 57.9 | 57.9 | 55.8 | 57.9 | 55.8 | 50.5 | 57.9 | 51.6 | 53.7 | 52.6 | 57.9 |
| Culex pipiens France (F2) | 52.6 | 57.9 | 57.9 | 55.8 | 57.9 | 55.8 | 50.5 | 57.9 | 51.6 | 53.7 | 52.6 | 57.9 |
| Culex pipiens France (G2) | 52.6 | 57.9 | 57.9 | 55.8 | 57.9 | 55.8 | 50.5 | 57.9 | 51.6 | 53.7 | 52.6 | 57.9 |
| Culex pipiens France (C9) | 51.6 | 56.8 | 56.8 | 55.8 | 56.8 | 54.7 | 50.5 | 56.8 | 51.6 | 53.7 | 52.6 | 56.8 |
| Koongol virus | 54.7 | 62.1 | 58.9 | 52.6 | 57.9 | 57.9 | 52.6 | 63.2 | 54.7 | 56.8 | 56.8 | 58.9 |
| Little Sussex virus | 61.1 | 61.1 | 64.2 | 62.1 | 57.9 | 57.9 | 52.6 | 62.1 | 57.9 | 58.9 | 55.8 | 56.8 |
| Umbre virus strain IG1424 | 61.1 | 61.1 | 64.2 | 62.1 | 57.9 | 57.9 | 52.6 | 62.1 | 57.9 | 58.9 | 55.8 | 56.8 |
| Umbre orthobunyavirus strain Marna (Case #2) | 61.1 | 61.1 | 64.2 | 62.1 | 57.9 | 57.9 | 52.6 | 62.1 | 57.9 | 58.9 | 55.8 | 56.8 |
| Umbre orthobunyavirus strain Moissiacense (Case #1) | 61.1 | 61.1 | 64.2 | 62.1 | 57.9 | 57.9 | 52.6 | 62.1 | 57.9 | 58.9 | 55.8 | 56.8 |
| Kowanyama virus | 67.4 | 64.2 | 72.6 | 67.4 | 71.6 | 61.1 | 67.4 | 66.3 | 66.3 | 64.2 | 65.3 | 61.1 |
| Yacaaba virus | 69.5 | 68.4 | 74.7 | 72.6 | 70.5 | 64.2 | 64.2 | 61.1 | 63.2 | 61.1 | 61.1 | 62.1 |
| Caraparu virus | 61.1 | 62.1 | 67.4 | 62.1 | 61.1 | 63.2 | 66.3 | 61.1 | 60.0 | 61.1 | 62.1 | 56.8 |
| Madrid virus | 62.1 | 62.1 | 67.4 | 64.2 | 62.1 | 62.1 | 66.3 | 60.0 | 61.1 | 62.1 | 61.1 | 55.8 |
| Murrumbidgee virus | 51.6 | 50.5 | 53.7 | 53.7 | 47.4 | 49.5 | 50.5 | 56.8 | 51.6 | 52.6 | 50.5 | 52.6 |
| Salt ash virus | 58.9 | 54.7 | 53.7 | 55.8 | 51.6 | 52.6 | 50.5 | 53.7 | 54.7 | 54.7 | 52.6 | 55.8 |
| Herbert virus | 45.8 | 47.9 | 51.0 | 47.9 | 44.8 | 43.8 | 41.7 | 44.8 | 44.8 | 46.9 | 42.7 | 40.6 |

| | Sororoca virus | Macaua virus | Wyeomyia ortho-bunya-virus | Chatanga virus | La Crosse virus | Tahyna virus | Culex pipiens France (C2) | Culex pipiens France (F2) | Culex pipiens France (G2) | Culex pipiens France (C9) | Koongol virus |
|---|---|---|---|---|---|---|---|---|---|---|---|
| Aino virus | 62.1 | 58.9 | 61.1 | 65.3 | 65.3 | 65.3 | 52.6 | 52.6 | 52.6 | 51.6 | 54.7 |
| Akabane virus | 58.9 | 55.8 | 61.1 | 60.0 | 64.2 | 62.1 | 57.9 | 57.9 | 57.9 | 56.8 | 62.1 |
| Schmallenberg virus | 61.1 | 58.9 | 62.1 | 68.4 | 68.4 | 68.4 | 57.9 | 57.9 | 57.9 | 56.8 | 58.9 |
| Simbu orthobunyavirus | 55.8 | 61.1 | 58.9 | 65.3 | 64.2 | 64.2 | 55.8 | 55.8 | 55.8 | 55.8 | 52.6 |
| Oropouche virus | 57.9 | 58.9 | 56.8 | 66.3 | 68.4 | 68.4 | 57.9 | 57.9 | 57.9 | 56.8 | 57.9 |
| Oya virus | 57.9 | 54.7 | 61.1 | 61.1 | 60.0 | 61.1 | 55.8 | 55.8 | 55.8 | 54.7 | 57.9 |
| Leanyer virus | 61.1 | 65.3 | 66.3 | 67.4 | 67.4 | 66.3 | 50.5 | 50.5 | 50.5 | 50.5 | 52.6 |
| Batai virus | 69.5 | 64.2 | 68.4 | 70.5 | 68.4 | 69.5 | 57.9 | 57.9 | 57.9 | 56.8 | 63.2 |
| Bunyamwera virus | 68.4 | 72.6 | 70.5 | 70.5 | 71.6 | 71.6 | 51.6 | 51.6 | 51.6 | 51.6 | 54.7 |
| Ilesha virus | 67.4 | 71.6 | 68.4 | 69.5 | 71.6 | 70.5 | 53.7 | 53.7 | 53.7 | 53.7 | 56.8 |
| Cache Valley virus | 66.3 | 66.3 | 70.5 | 71.6 | 70.5 | 72.6 | 52.6 | 52.6 | 52.6 | 52.6 | 56.8 |
| Iaco virus | 89.5 | 84.2 | 82.1 | 62.1 | 62.1 | 64.2 | 57.9 | 57.9 | 57.9 | 56.8 | 58.9 |
| Sororoca virus | | 80.0 | 80.0 | 64.2 | 64.2 | 66.3 | 54.7 | 54.7 | 54.7 | 53.7 | 62.1 |
| Macaua virus | 80.0 | | 85.3 | 63.2 | 64.2 | 65.3 | 52.6 | 52.6 | 52.6 | 52.6 | 53.7 |
| Wyeomyia orthobunyavirus | 80.0 | 85.3 | | 67.4 | 66.3 | 69.5 | 55.8 | 55.8 | 55.8 | 54.7 | 56.8 |
| Chatanga virus | 64.2 | 63.2 | 67.4 | | 92.6 | 93.7 | 57.9 | 57.9 | 57.9 | 56.8 | 58.9 |
| La Crosse virus | 64.2 | 64.2 | 66.3 | 92.6 | | 92.6 | 58.9 | 58.9 | 58.9 | 57.9 | 61.1 |
| Tahyna virus | 66.3 | 65.3 | 69.5 | 93.7 | 92.6 | | 58.9 | 58.9 | 58.9 | 57.9 | 58.9 |
| Culex pipiens France (C2) | 54.7 | 52.6 | 55.8 | 57.9 | 58.9 | 58.9 | | 100.0 | 100.0 | 98.9 | 83.2 |
| Culex pipiens France (F2) | 54.7 | 52.6 | 55.8 | 57.9 | 58.9 | 58.9 | 100.0 | | 100.0 | 98.9 | 83.2 |

TABLE IV-continued

Amino acids identity matrix on PCR-targeted region on the L segment (See accession numbers in phylogenetic analysis)

| | | | | | | | | | | | |
|---|---|---|---|---|---|---|---|---|---|---|---|
| Culex pipiens France (G2) | 54.7 | 52.6 | 55.8 | 57.9 | 58.9 | 58.9 | 100.0 | 100.0 | | 98.9 | 83.2 |
| Culex pipiens France (C9) | 53.7 | 52.6 | 54.7 | 56.8 | 57.9 | 57.9 | 98.9 | 98.9 | 98.9 | | 82.1 |
| Koongol virus | 62.1 | 53.7 | 56.8 | 58.9 | 61.1 | 58.9 | 83.2 | 83.2 | 83.2 | 82.1 | |
| Little Sussex virus | 55.8 | 55.8 | 60.0 | 60.0 | 60.0 | 60.0 | 76.8 | 76.8 | 76.8 | 75.8 | 77.9 |
| Umbre virus strain IG1424 | 55.8 | 55.8 | 60.0 | 60.0 | 60.0 | 60.0 | 76.8 | 76.8 | 76.8 | 75.8 | 77.9 |
| Umbre orthobunyavirus strain Marna (Case #2) | 55.8 | 55.8 | 60.0 | 60.0 | 60.0 | 60.0 | 76.8 | 76.8 | 76.8 | 75.8 | 77.9 |
| Umbre orthobunyavirus strain Moissiacense (Case #1) | 55.8 | 55.8 | 60.0 | 60.0 | 60.0 | 60.0 | 76.8 | 76.8 | 76.8 | 75.8 | 77.9 |
| Kowanyama virus | 62.1 | 62.1 | 62.1 | 73.7 | 74.7 | 74.7 | 60.0 | 60.0 | 60.0 | 58.9 | 61.1 |
| Yacaaba virus | 63.2 | 65.3 | 65.3 | 67.4 | 69.5 | 70.5 | 57.9 | 57.9 | 57.9 | 56.8 | 57.9 |
| Caraparu virus | 55.8 | 61.1 | 62.1 | 63.2 | 63.2 | 64.2 | 51.6 | 51.6 | 51.6 | 51.6 | 53.7 |
| Madrid virus | 54.7 | 62.1 | 61.1 | 62.1 | 64.2 | 63.2 | 52.6 | 52.6 | 52.6 | 52.6 | 54.7 |
| Murrumbidgee virus | 51.6 | 51.6 | 48.4 | 52.6 | 53.7 | 53.7 | 54.7 | 54.7 | 54.7 | 54.7 | 53.7 |
| Salt ash virus | 56.8 | 52.6 | 50.5 | 54.7 | 56.8 | 56.8 | 53.7 | 53.7 | 53.7 | 52.6 | 56.8 |
| Herbert virus | 40.6 | 39.6 | 39.6 | 44.8 | 44.8 | 45.8 | 43.8 | 43.8 | 43.8 | 43.8 | 40.6 |

| | Little Sussex virus | Umbre virus strain IG1424 | Umbre orthobunyavirus strain Marna (Case #2) | Umbre orthobunyavirus strain Moissiacense (Case #1) | Kowanyama virus | Yacaaba virus | Caraparu virus | Madrid virus | Murrumbidgee virus | Salt ash virus | Herbert virus |
|---|---|---|---|---|---|---|---|---|---|---|---|
| Aino virus | 61.1 | 61.1 | 61.1 | 61.1 | 67.4 | 69.5 | 61.1 | 62.1 | 51.6 | 58.9 | 45.8 |
| Akabane virus | 61.1 | 61.1 | 61.1 | 61.1 | 64.2 | 68.4 | 62.1 | 62.1 | 50.5 | 54.7 | 47.9 |
| Schmallenberg virus | 64.2 | 64.2 | 64.2 | 64.2 | 72.6 | 74.7 | 67.4 | 67.4 | 53.7 | 53.7 | 51.0 |
| Simbu orthobunyavirus | 62.1 | 62.1 | 62.1 | 62.1 | 67.4 | 72.6 | 62.1 | 64.2 | 53.7 | 55.8 | 47.9 |
| Oropouche virus | 57.9 | 57.9 | 57.9 | 57.9 | 71.6 | 70.5 | 61.1 | 62.1 | 47.4 | 51.6 | 44.8 |
| Oya virus | 57.9 | 57.9 | 57.9 | 57.9 | 61.1 | 64.2 | 63.2 | 62.1 | 49.5 | 52.6 | 43.8 |
| Leanyer virus | 52.6 | 52.6 | 52.6 | 52.6 | 67.4 | 64.2 | 66.3 | 66.3 | 50.5 | 50.5 | 41.7 |
| Batai virus | 62.1 | 62.1 | 62.1 | 62.1 | 66.3 | 61.1 | 61.1 | 60.0 | 56.8 | 53.7 | 44.8 |
| Bunyamwera virus | 57.9 | 57.9 | 57.9 | 57.9 | 66.3 | 63.2 | 60.0 | 61.1 | 51.6 | 54.7 | 44.8 |
| Ilesha virus | 58.9 | 58.9 | 58.9 | 58.9 | 64.2 | 61.1 | 61.1 | 62.1 | 52.6 | 54.7 | 46.9 |
| Cache Valley virus | 55.8 | 55.8 | 55.8 | 55.8 | 65.3 | 61.1 | 62.1 | 61.1 | 50.5 | 52.6 | 42.7 |
| Iaco virus | 56.8 | 56.8 | 56.8 | 56.8 | 61.1 | 62.1 | 56.8 | 55.8 | 52.6 | 55.8 | 40.6 |
| Sororoca virus | 55.8 | 55.8 | 55.8 | 55.8 | 62.1 | 63.2 | 55.8 | 54.7 | 51.6 | 56.8 | 40.6 |
| Macaua virus | 55.8 | 55.8 | 55.8 | 55.8 | 62.1 | 65.3 | 61.1 | 62.1 | 51.6 | 52.6 | 39.6 |
| Wyeomyia orthobunyavirus | 60.0 | 60.0 | 60.0 | 60.0 | 62.1 | 65.3 | 62.1 | 61.1 | 48.4 | 50.5 | 39.6 |
| Chatanga virus | 60.0 | 60.0 | 60.0 | 60.0 | 73.7 | 67.4 | 63.2 | 62.1 | 52.6 | 54.7 | 44.8 |
| La Crosse virus | 60.0 | 60.0 | 60.0 | 60.0 | 74.7 | 69.5 | 63.2 | 64.2 | 53.7 | 56.8 | 44.8 |
| Tahyna virus | 60.0 | 60.0 | 60.0 | 60.0 | 74.7 | 70.5 | 64.2 | 63.2 | 53.7 | 56.8 | 45.8 |
| Culex pipiens France (C2) | 76.8 | 76.8 | 76.8 | 76.8 | 60.0 | 57.9 | 51.6 | 52.6 | 54.7 | 53.7 | 43.8 |
| Culex pipiens France (F2) | 76.8 | 76.8 | 76.8 | 76.8 | 60.0 | 57.9 | 51.6 | 52.6 | 54.7 | 53.7 | 43.8 |
| Culex pipiens France (G2) | 76.8 | 76.8 | 76.8 | 76.8 | 60.0 | 57.9 | 51.6 | 52.6 | 54.7 | 53.7 | 43.8 |
| Culex pipiens France (C9) | 75.8 | 75.8 | 75.8 | 75.8 | 58.9 | 56.8 | 51.6 | 52.6 | 54.7 | 52.6 | 43.8 |
| Koongol virus | 77.9 | 77.9 | 77.9 | 77.9 | 61.1 | 57.9 | 53.7 | 54.7 | 53.7 | 56.8 | 40.6 |
| Little Sussex virus | | 100.0 | 100.0 | 100.0 | 60.0 | 56.8 | 55.8 | 56.8 | 54.7 | 54.7 | 40.6 |
| Umbre virus strain IG1424 | 100.0 | | 100.0 | 100.0 | 60.0 | 56.8 | 55.8 | 56.8 | 54.7 | 54.7 | 40.6 |
| Umbre orthobunyavirus strain Marna (Case #2) | 100.0 | 100.0 | | 100.0 | 60.0 | 56.8 | 55.8 | 56.8 | 54.7 | 54.7 | 40.6 |
| Umbre orthobunyavirus strain Moissiacense (Case #1) | 100.0 | 100.0 | 100.0 | | 60.0 | 56.8 | 55.8 | 56.8 | 54.7 | 54.7 | 40.6 |
| Kowanyama virus | 60.0 | 60.0 | 60.0 | 60.0 | | 72.6 | 65.3 | 66.3 | 52.6 | 55.8 | 47.9 |
| Yacaaba virus | 56.8 | 56.8 | 56.8 | 56.8 | 72.6 | | 62.1 | 62.1 | 55.8 | 54.7 | 46.9 |
| Caraparu virus | 55.8 | 55.8 | 55.8 | 55.8 | 65.3 | 62.1 | | 97.9 | 50.5 | 53.7 | 43.8 |
| Madrid virus | 56.8 | 56.8 | 56.8 | 56.8 | 66.3 | 62.1 | 97.9 | | 50.5 | 53.7 | 43.8 |
| Murrumbidgee virus | 54.7 | 54.7 | 54.7 | 54.7 | 52.6 | 55.8 | 50.5 | 50.5 | | 61.3 | 37.5 |
| Salt ash virus | 54.7 | 54.7 | 54.7 | 54.7 | 55.8 | 54.7 | 53.7 | 53.7 | 61.3 | | 43.8 |
| Herbert virus | 40.6 | 40.6 | 40.6 | 40.6 | 47.9 | 46.9 | 43.8 | 43.8 | 37.5 | 43.8 | |

The invention claimed is:

1. A method of detection of Moissiacense virus nucleic acid in a sample, comprising determining the presence of at least one viral nucleic acid selected from the group consisting of:

a first nucleic acid (S segment) comprising a sequence having at least 80% identity with SEQ ID NO: 1 or the complement thereof, wherein the sequence having at least 80% identity with SEQ ID NO: 1 encodes a Nucleocapsid (N) protein having at least 90% identity with SEQ ID NO: 2;

a second nucleic acid (M segment) comprising a sequence having at least 80% identity with SEQ ID NO: 3 or the complement thereof, wherein the sequence having at least 80% identity with SEQ ID NO: 3 encodes a polyprotein M having at least 90% identity with SEQ ID NO: 4; and a third nucleic acid (L segment) comprising a sequence having at least 80% identity with SEQ ID NO: 5 or the complement thereof, wherein the sequence having at least 80% identity with SEQ ID NO: 5 encodes a polymerase (L) protein having at least 90% identity with SEQ ID NO: 6 including at least 90% identity in the core polymerase domain.

2. The method according to claim 1, wherein said Moissiacense virus comprises: a S segment sequence of SEQ ID NO: 1 coding for a nucleocapsid (N) protein of SEQ ID NO: 2, a M segment sequence of SEQ ID NO: 3 coding for a polyprotein M of SEQ ID NO: 4 and a L segment sequence of SEQ ID NO: 5 coding for a polymerase (L) protein of SEQ ID NO: 6, or a S segment sequence of SEQ ID NO: 90 coding for a nucleocapsid (N) protein of SEQ ID NO: 93, a M segment sequence of SEQ ID NO: 91 coding for a polyprotein M of SEQ ID NO: 95, and a L segment sequence of SEQ ID NO: 92 coding for a polymerase (L) protein of SEQ ID NO: 96.

3. The method according to claim 1, which comprises the detection of at least one specific target sequence of the viral nucleic acid by a process of hybridization with an oligonucleotide probe, amplification with a pair of oligonucleotide primers, sequencing, or a combination thereof.

4. The method according to claim 1, which comprises the detection of at least one specific target sequence of the viral nucleic acid chosen from the sequences SEQ ID NO: 7, 8, 9; the sequences of at least 15 nucleotides from any one of SEQ ID NO: 7 to 9, and the sequences comprising any one of SEQ ID NO: 7 to 9 and up to 40 consecutive nucleotides of 5' and/or 3' flanking sequence from the S, M or L segment sequence.

5. The method according to claim 1, which comprises the detection of at least one specific target sequence of the viral nucleic acid using oligonucleotide probe or primers selected from the group consisting of: the sequences of 5 to 100 nucleotides, preferably 15 to 60 nucleotides having 80% to 100% identity with any of SEQ ID NO: 1, 3, 5, and 7 to 9, which are specific for Moissiacense virus; and their complement.

6. The method according to claim 1, which comprises the detection of at least one specific target sequence of the viral nucleic acid using an oligonucleotide probe selected from the group consisting of the sequences SEQ ID NO: 10 to 57 or the pair of oligonucleotide primers is selected from the group consisting of: SEQ ID NO: 10-11, 12-13, 14-15, 16-17, 18-19, 20-21, 22-23, 24-25, 26-27, 28-29, 30-31, 32-33, 34-35, 36-37, 38-39, 40-41, 42-43, 44-45, 46-47, 48-49, 50-51, 52-53, 54-55, and 56-57.

7. A method of detection of Moissiacense virus antigen or antibody in a sample, comprising:

-incubating an antigen from Moissiacense virus or antibody thereto with the sample to form a mixture; and -detecting antigen-antibody complexes in the mixture.

8. The method according to claim 7, wherein the antigen from Moissiacense virus comprises an amino acid sequence selected from the group consisting of:

a sequence having 90 to 100% with SEQ ID NO: 2 or a fragment of at least 10 amino acids of said sequence which is bound by antibodies against Moissiacense virus;

a sequence having 90 to 100% identity with SEQ ID NO: 58 or 60 or a fragment of at least 10 amino acids of said sequence which is bound by antibodies against Moissiacense virus; and an extracellular fragment of the sequence SEQ ID NO: 58 which is of at least 10 amino acids of said sequence and which is bound by antibodies against Moissiacense virus.

9. The method according to claim 7, which comprises an immunoprecipitation, ELISA or immunohistochemistry assay.

10. The method according to claim 7, wherein the antigen from Moissiacense virus comprises an amino acid sequence chosen from the sequences SEQ ID NO: 61 to 64.

11. The method according to claim 1, wherein the sample is brain biopsy, cerebral spinal fluid, whole-blood, plasma or serum.

12. The method according to claim 1, wherein the same biological sample from an individual is subjected to a method of detection of at least another encephalitis virus such as herpesvirus, enterovirus, polyomavirus, astrovirus, measles virus, mumps virus, or arbovirus.

13. The method according to claim 1, which is for the diagnosis of encephalitis, in particular in humans, specifically for the differential diagnosis of human encephalitis.

14. The method according to claim 7, wherein the sample is brain biopsy, cerebral spinal fluid, whole-blood, plasma or serum.

15. The method according to claim 7, wherein the same biological sample from an individual is subjected to a method of detection of at least another encephalitis virus such as herpesvirus, enterovirus, polyomavirus, astrovirus, measles virus, mumps virus, or arbovirus.

16. The method according to claim 7, which is for the diagnosis of encephalitis, in particular in humans, specifically for the differential diagnosis of human encephalitis.

17. A kit for the detection of Moissiacense virus nucleic acid, comprising:

at least one oligonucleotide probe or primer selected from the group consisting of: the sequences of 5 to 100 nucleotides, preferably 15 to 60 nucleotides having 80% to 100% identity with any of SEQ ID NO: 1, 3, 5, and 7 to 9, which are specific for Moissiacense virus; and their complement, and reagents for the amplification of a target sequence and/or the detection of an amplification product.

18. A kit for the detection of Moissiacense virus antigen or antibody, comprising:

a) at least an antigen from Moissiacense virus or an antibody thereto, wherein the antigen comprises an amino acid sequence selected from the group consisting of:

a sequence having 90 to 100% with SEQ ID NO: 2 or a fragment of at least 10 amino acids of said sequence which is bound by antibodies against Moissiacense virus;

a sequence having 90 to 100% identity with SEQ ID NO: 58 or 60 or a fragment of at least 10 amino acids of said sequence which is bound by antibodies against Moissiacense virus;

an extracellular fragment of the sequence SEQ ID NO: 58 which is of at least 10 amino acids of said sequence and which is bound by antibodies against Moissiacense virus; and a fragment having the sequence of any of SEQ ID NO: 61 to 64, which is bound by antibodies against Moissiacense virus, and b) reagents for the amplification of a target sequence and/or the detection of an amplification product.

19. The method of claim 1, which comprises the detection of Moissiacense virus nucleic acid in arthropod vector population for epidemiological survey.

20. An immunogenic or vaccine pharmaceutical composition comprising, as active substance an antigen from Moissiacense virus comprising an amino acid sequence selected from the group consisting of:

a sequence having 90 to 100% with SEQ ID NO: 2 or a fragment of at least 10 amino acids of said sequence which is bound by antibodies against Moissiacense virus;

a sequence having 90 to 100% identity with SEQ ID NO: 58 or 60 or a fragment of at least 10 amino acids of said sequence which is bound by antibodies against Moissiacense virus;

an extracellular fragment of the sequence SEQ ID NO: 58 which is of at least 10 amino acids of said sequence and which is bound by antibodies against Moissiacense virus; and a fragment consisting of the sequence of any of SEQ ID NO: 61 to 64, which is bound by antibodies against Moissiacense virus, wherein the composition further comprises at least one pharmaceutically acceptable adjuvant.

* * * * *